US011357755B2

(12) United States Patent
Telser et al.

(10) Patent No.: US 11,357,755 B2
(45) Date of Patent: Jun. 14, 2022

(54) COMPOUNDS FOR CONTROLLING ARTHROPODS

(71) Applicant: Bayer Animal Health GmbH, Leverkusen (DE)

(72) Inventors: Joachim Telser, Wuppertal (DE); Ursula Krenz, Leichlingen (DE); Kirsten Boerngen, Cologne (DE); Andreas Turberg, Haan (DE); Klein Sofia, Cologne (DE); Franziska Schmidt, Duesseldorf (DE)

(73) Assignee: Bayer Animal Health GmbH, Leverkusen (DE)

( * ) Notice: Subject to any disclaimer, the term of this patent is extended or adjusted under 35 U.S.C. 154(b) by 0 days.

(21) Appl. No.: 17/256,867

(22) PCT Filed: Jun. 27, 2019

(86) PCT No.: PCT/EP2019/067165

§ 371 (c)(1),
(2) Date: Dec. 29, 2020

(87) PCT Pub. No.: WO2020/007704

PCT Pub. Date: Jan. 9, 2020

(65) Prior Publication Data

US 2022/0008391 A1 Jan. 13, 2022

(30) Foreign Application Priority Data

Jul. 5, 2018 (EP) .................................... 18181950

(51) Int. Cl.

| | |
|---|---|
| ***C07C 69/96*** | (2006.01) |
| ***C07D 231/12*** | (2006.01) |
| ***A61K 31/4155*** | (2006.01) |
| ***A61P 33/14*** | (2006.01) |
| ***A61K 9/00*** | (2006.01) |
| ***A61K 31/415*** | (2006.01) |

(52) U.S. Cl.

CPC ........ *A61K 31/4155* (2013.01); *A61K 9/0019* (2013.01); *A61K 31/415* (2013.01); *A61P 33/14* (2018.01); *C07C 69/96* (2013.01); *C07D 231/12* (2013.01)

(58) Field of Classification Search

CPC .... C07D 231/12; C07C 69/96; A61K 31/415; A61P 33/14

See application file for complete search history.

(56) References Cited

U.S. PATENT DOCUMENTS

| | | | |
|---|---|---|---|
| 2015/0353500 | A1 | 12/2015 | Maue et al. |
| 2016/0278379 | A1 | 9/2016 | Hallenbach et al. |
| 2016/0297765 | A1 | 10/2016 | Hallenbach et al. |
| 2017/0217899 | A1 | 8/2017 | Maue et al. |

FOREIGN PATENT DOCUMENTS

| | | | |
|---|---|---|---|
| EP | 1911751 | A1 | 4/2008 |
| WO | 2012069366 | A1 | 5/2012 |
| WO | 2012080376 | A1 | 6/2012 |
| WO | 2012107434 | A1 | 8/2012 |
| WO | 2012175474 | A1 | 12/2012 |
| WO | 2014122083 | A1 | 8/2014 |
| WO | 2015067647 | A1 | 5/2015 |
| WO | 2016174052 | A1 | 3/2016 |
| WO | 2016020441 | A1 | 11/2016 |

OTHER PUBLICATIONS

International Search Report for Application No. PCT/EP2019/067165 dated Jul. 29, 2019.

Jarkko Rautio, et al., "Prodrugs: design and clinical applications," Nature Reviews Drug Discovery, (2008), vol. 7, No. 3 : 255-270.

Valentino J., Stella and Kwame W. Nti-Addae, "Prodrug strategies to overcome poor water solubility," Advanced Drug Delivery Reviews, (2007), vol. 59, No. 7 : 677-694.

Chunjian Liu, et al., "Synthesis and evaluation of carbamoylmethylene linked prodrugs of BMS-582949, a clinical p38α inhibitor," Bioorganic & Medicinal Chemistry Letters, (2013), vol. 23, No. 10 : 3028-3033.

Ernst Binderup, et al., "EB1627: a soluble prodrug of the potent anticancer cyanoguanidine CHS828," Bioorganic & Medicinal Chemistry Letters, (2005, vol. 15, No. 10 : 2491-2494.

*Primary Examiner* — Kamal A Saeed

(74) *Attorney, Agent, or Firm* — McBee Moore & Vanik IP, LLC; Susan McBee

(57) ABSTRACT

The present invention relates to novel halogen-substituted compounds, to processes for their preparation and to their use for controlling animal pests, in particular arthropods and especially insects and arachnids.

24 Claims, No Drawings

COMPOUNDS FOR CONTROLLING ARTHROPODS

CROSS-REFERENCE TO RELATED APPLICATIONS

This application is the National Stage entry of International Application No. PCT/EP2019/067165, filed 27 Jun. 2019, which claims priority to European Patent Application No. 18181950.9, filed 5 Jul. 2018.

BACKGROUND

Field

The present invention relates to novel halogen-substituted compounds, to processes for their preparation and to their use for controlling animal pests, in particular arthropods and especially insects and arachnids.

Description of Related Art

Ectoparasiticides

Halogenated carboxamides with insecticidal and ectoparasiticidal activity are described in EP 1911751, WO 2012/069366, WO 2012/080376, WO 2012/107434, WO 2012/175474, WO2014/122083 and WO2015/067647. Combinations of halogenated carboxamides for the treatment of animal pests have been described in WO 2016/174052.

Besides the aforementioned classes also other compounds with ectoparasiticidal activity are well-known in the art. Common to these molecules of a number of different molecular modes of action is that none of them exerts a broad arthropodicidal effect over a period of more than three months. Commercial use of prolonged broad arthropodicidal activity can only be found in constant release approaches as used in collars (e.g. deltamethrin in Scalibor® or flumethrin/imidacloprid in Seresto®). A convenient one-time parenteral application with broad arthropod control is not marketed or shown to work in practice to date. Reasons for failure in that area can be found in short halflife, low solubility, low bioavailability, insufficient stability, incomplete arthropod parasite spectrum, local and systemic side effects. A multitude of these parameters need to be improved to lead to a successful approach to fulfil the need of a systemic treatment of ectoparasites with an extended term of efficacy.

Prodrugs

In cases where the efficacy of a drug is limited by its physicochemical properties, a prodrug concept may be used. Prodrugs are defined as bioreversible derivatives of the corresponding parent drugs. This means that the prodrug carries a cleavable group, a so called pro-moiety. This group facilitates administration, absorption into the body and distribution in the treated animal or human. The pro-moiety is cleaved by biological or chemical transformations in the patient's body liberating the parent drug once the prodrug has been absorbed. A general overview of prodrug concepts can be found, for instance, in a review article by J. Rautio, H. Kumpulainen, T. Heimbach, R. Oliyai, D. Oh, T. Järvinen, J. Savolainen, *Nature Reviews Drug Discovery* 2008, 255-270. In many cases, the administration of a drug is limited by its poor aqueous solubility which can impact both oral and, even more so, parenteral administration. Prodrugs have been described for both oral and intravenous applications of drugs whereas little is known about prodrugs for subcutaneous use (see V. J. Stella, K. W. Nti-Addae,

*Advanced Drug Delivery Reviews* 2007, 59, 677-694). Many prodrugs use an attachment group of the parent drug to link the pro-moiety via a linker group and optionally spacer groups. Attachment points are usually functional groups of the parent drug which allow the bioreversible chemical modification, for instance hydroxyl groups, carboxylic acid groups, amino groups, amides or other. A recent example of carbamate linkers attached to an amide group can be found in C. Liu, J. Lin, G. Everlof, C. Gesenberg, H. Zhang, P. H. Marathe, M. Malley, M. A. Gallella, M. McKinnon, J. H. Dodd, J. C. Barrish, G. L. Schieven, K. Leftheris, *Bioorg. Med. Chem. Lett.* 2013, 23, 3028-3033.

Besides carbamates, also carbonate esters are occasionally described as linkers in the prodrug literature, e.g. for the modification of a pyridyl group (see E. Binderup, F. Björkling, P. V. Hjranaa, S. Latini, B. Balther, M. Carlsen, L. Binderup, *Bioorg. Med. Chem. Lett.* 2005, 15, 2491-2494).

SUMMARY

It was thus an object of the present invention to provide novel compounds with high insecticidal and ectoparasiticidal systemic activity and enhanced solubility. A further object of the present invention was to provide novel compounds with high ectoparasiticidal, in particular insecticidal and/or acaricidal, systemic activity and improved bioavailability compared to known compounds. It was a further object of the present invention to provide novel compounds with high ectoparasiticidal, in particular insecticidal and/or acaricidal, systemic activity having sufficient stability in formulations for pharmaceutical administration. It was a further object of the present invention to provide novel compounds with high insecticidal and ectoparasiticidal systemic activity with optimum balance of stability in formulations for pharmaceutical administration and systemic release properties to release the active principle of the novel compounds under systemic conditions in the body. In a further object of the present invention the systemic release of the active principle of the novel compounds should occur at a suitable point of time or over a suitable time period to achieve improved systemic activity in the treatment. A further object of the present invention was to provide novel compounds with high insecticidal and ectoparasiticidal systemic activity and enhanced solubility in formulations for subcutaneous administration. The novel compounds should also not be toxic or release toxic groups upon administration.

The inventors of the present invention now surprisingly found that with the new compounds of the present invention the disadvantages of the prior art can be avoided and the objects described above can be solved.

Accordingly, the new compounds further exhibit and can therefore be employed particularly well in the animal health sector.

DETAILED DESCRIPTION OF A PREFERRED EMBODIMENT

The present invention can be described in particular by the following embodiments:

[1] In a first aspect the invention relates to compounds of formula (I)

(I)

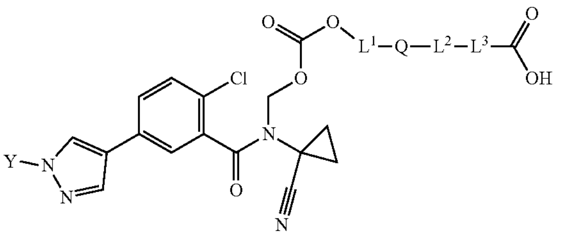

wherein

Q is O or absent;

$L^1$ is linear $C_2$-$C_4$ alkanediyl, which is optionally substituted with one or more groups independently selected from halogen, $C_1$-$C_4$ alkyl and $C_3$-$C_6$ cycloalkyl, wherein two $C_1$-$C_4$-alkyl substituents may form a ring together with the carbon atom to which they are bonded; or is a moiety $(CH_2)_n$—X—$(CH_2)_m$ wherein n and m are independently 0, 1 or 2 and X is $C_3$-$C_7$-cycloalkanediyl, which is optionally substituted with $C_1$-$C_4$ alkyl; or $L^1$ is absent;

with the proviso that in the case of $L^1$ being absent, Q is also absent;

$L^2$ is C═O or absent, $L^3$ is linear $C_1$-$C_4$ alkanediyl, which is optionally substituted with one or more groups independently selected from $C_1$-$C_4$ alkyl, $C_3$-$C_6$ cycloalkyl and halogen, wherein two $C_1$-$C_4$-alkyl substituents may form a ring together with the carbon atom to which they are bonded; or is a group $(CH_2)_n$—(CH═CH)—$CH_2)_m$, which is optionally substituted with up to 2 groups independently selected from $C_1$-$C_4$ alkyl, $C_3$-$C_5$ cycloalkyl and halogen, wherein n and m are independently 0, 1 or 2; or is $C_3$-$C_7$-cycloalkanediyl, which is optionally substituted with one or more groups independently selected from $C_1$-$C_4$-alkyl and halogen;

Y is selected from a group $T^1$ $T^1$

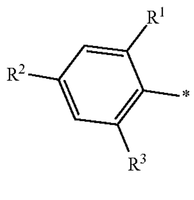

wherein $R^1$, $R^2$ and $R^3$ are each independently selected from hydrogen, halogen, cyano, nitro, linear or branched $C_1$-$C_6$-alkyl, $C_3$-$C_6$-cycloalkyl, $C_1$-$C_6$-alkoxy, linear or branched halogen-substituted $C_1$-$C_6$-alkyl, halogen-substituted $C_1$-$C_6$-alkoxy, halogen substituted $C_3$-$C_6$-cycloalkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, N—$C_1$-$C_3$-alkoxy-$C_1$-$C_4$-alkylamino and 1-pyrrolidinyl or a group $T^2$ $T^2$

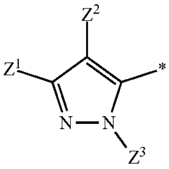

wherein $Z^1$ and $Z^2$ are each independently selected from hydrogen, halogen, cyano, nitro, linear or branched $C_1$-$C_6$-alkyl, $C_3$-$C_6$-cycloalkyl, $C_1$-$C_6$-alkoxy, $C_1$-$C_6$-alkylcarbonyl, halogen-substituted linear or branched $C_1$-$C_6$-alkyl, halogen-substituted $C_1$-$C_6$-alkoxy, halogen substituted $C_3$-$C_6$-cycloalkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, N—$C_1$-$C_3$-alkoxy-$C_1$-$C_4$-alkylamino and 1-pyrrolidinyl; and $Z^3$ represents hydrogen or linear $C_1$-$C_6$-alkyl, $C_3$-$C_6$-cycloalkyl, $C_2$-$C_6$-alkenyl, $C_2$-$C_6$-alkynyl, aryl or hetaryl, which may independently of one another be substituted with 1 to 5 substituents selected from hydroxy, halogen, cyano, nitro, amino, $C_1$-$C_3$-alkyl, $C_1$-$C_3$-alkoxy, hydroxycarbonyl, alkoxycarbonyl, alkylcarbamoyl, cycloalkylcarbamoyl and phenyl and to the salts thereof.

[2] In a further aspect the invention relates to compounds of formula (I) as defined in [1]

wherein

Q is O;

$L^2$ is C═O;

$L^3$ is a group $(CH_2)_n$—(CH═CH)—$CH_2)_m$, which is optionally substituted with up to 2 groups independently selected from $C_1$-$C_4$ alkyl, $C_3$-$C_5$ cycloalkyl and halogen, wherein n and m are independently 0, 1 or 2; and $L^1$ has the meaning as defined in [1];

and the salts thereof.

[3] In a further aspect the invention relates to compounds of formula (I) as defined in [1] or [2]

wherein

Q is O;

$L^2$ is C═O;

$L^3$ is a group $(CH_2)_n$—(CH═CH)—$CH_2)_m$, wherein n and m are 0; and $L^1$ has the meaning as defined in [1];

and the salts thereof.

[4] In a further aspect the invention relates to compounds of formula (I) as defined in [1]

wherein

Q is O $L^2$ is C═O $L^3$ is linear $C_1$-$C_4$ alkanediyl, which is optionally substituted with one or more groups independently selected from $C_1$-$C_4$ alkyl, $C_3$-$C_6$ cycloalkyl and halogen, wherein two $C_1$-$C_4$-alkyl substituents may form a ring together with the carbon atom to which they are bonded; and $L^1$ has the meaning as defined in [1];

and the salts thereof.

[5] In a further aspect the invention relates to compounds of formula (I) as defined in [1]

wherein

Q is O;

$L^2$ is absent;

$L^3$ is linear $C_1$-$C_4$ alkanediyl, which is optionally substituted with one or more groups independently selected from $C_1$-$C_4$ alkyl, $C_3$-$C_6$ cycloalkyl and halogen, wherein two $C_1$-$C_4$-alkyl substituents may form a ring together with the carbon atom to which they are bonded; and $L^1$ has the meaning as defined in [1];

and the salts thereof.

[6] In a further aspect the invention relates to compounds of formula (I) as defined in [1]

wherein $L^1$, $L^2$ and Q are absent; and $L^3$ has the meaning as defined in [1];

and the salts thereof.

[7] In a further aspect the invention relates to compounds of formula (I) as defined in any one of the preceding aspects [1] to [6]

wherein

Q is O or absent;

$L^1$ is linear $C_2$-$C_4$ alkanediyl, which is optionally substituted with one or more groups independently selected from $C_1$-$C_4$ alkyl and $C_3$-$C_6$ cycloalkyl, wherein two $C_1$-$C_4$-alkyl substituents may form a ring together with the carbon atom to which they are bonded; or is a moiety $(CH_2)_n$—X—$(CH_2)_m$ wherein n and m are 0 and X is $C_5$- or $C_6$-cycloalkanediyl, which is optionally substituted with $C_1$-$C_4$ alkyl; or $L^1$ is absent;

with the proviso that in the case of $L^1$ being absent, Q is also absent;

$L^2$ is C═O or absent, $L^3$ is linear $C_1$-$C_4$ alkanediyl, which is optionally substituted with one or more groups independently selected from $C_1$-$C_4$ alkyl, $C_3$-$C_6$ cycloalkyl and halogen, wherein two $C_1$-$C_4$-alkyl substituents may form a ring together with the carbon atom to which they are bonded; or is a group $(CH_2)_n$—(CH═CH)—$CH_2)_m$, which is optionally substituted with up to 2 groups independently selected from $C_1$-$C_4$ alkyl, $C_3$-$C_5$ cycloalkyl and halogen, wherein n and m are 0; or is $C_3$-$C_7$-cycloalkanediyl, which is optionally substituted with one or more groups independently selected from $C_1$-$C_4$-alkyl and halogen;

and the salts thereof.

[8] In a further aspect the invention relates to compounds of formula (I) as defined in any one of the preceding aspects [1] to [7]

wherein.

Q is O or absent;

$L^1$ is selected from 1,2-ethanediyl, 1,3-propanediyl, dimethyl-propanediyl, cyclopentanediyl, cyclohexanediyl; or $L^1$ is absent;

with the proviso that in the case of $L^1$ being absent, Q is also absent;

$L^2$ is C═O or absent, $L^3$ has the meaning as defined in [1];

and the salts thereof.

[9] In a further aspect the invention relates to compounds of formula (I) as defined in any one of the preceding aspects [1] to [8]

wherein

Q is O or absent;

$L^2$ is C═O or absent;

$L^3$ is selected from methylene, 1,2-ethanediyl, 1,3-propanediyl, dimethyl-ethanediyl, ethene-1,2-diyl, and cyclohexanediyl or a group

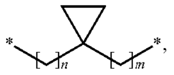

wherein n and m are independently 0, 1, 2;

$L^1$ has the meaning as defined in [1];

and the salts thereof.

[10] In a further aspect the invention relates to compounds of formula (I) as defined in any one of the preceding aspects [1] to [9]

wherein

Q is O;

and the salts thereof.

[11] In a further aspect the invention relates to compounds of formula (I) as defined in any one of the preceding aspects [1] to [10]

wherein $L^1$ is linear $C_2$-$C_4$ alkanediyl, which is optionally substituted with one or more $C_1$-$C_4$ alkyl groups, wherein two $C_1$-$C_4$-alkyl substituents may form a ring together with the carbon atom to which they are bonded and the salts thereof.

[12] In a further aspect the invention relates to compounds of formula (I) as defined in any one of the preceding aspects [1] to [11]

wherein $L^2$ is C═O and the salts thereof.

[13] In a further aspect the invention relates to compounds of formula (I) as defined in any one of the preceding aspects [1] to [12]

wherein $L^3$ is a group $(CH_2)_n$—(CH═CH)—$CH_2)_m$, which is optionally substituted with up to 2 groups independently selected from $C_1$-$C_4$ alkyl, $C_3$-$C_5$ cycloalkyl and halogen, wherein n and m are independently 0, 1 or 2, preferably n and m are 0;

and the salts thereof.

[14] In a further aspect the invention relates to compounds of formula (I) as defined in any one of the preceding aspects [1] to [13]

wherein

Y is selected from a group $T^1$ $T^1$

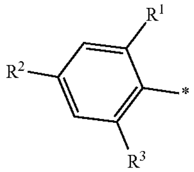

wherein $R^1$, $R^2$ and $R^3$ are each independently selected from hydrogen, halogen, linear or branched $C_1$-$C_3$-alkyl, $C_3$-$C_6$-cycloalkyl, $C_1$-$C_3$-alkoxy, linear or branched halogen-substituted $C_1$-$C_3$-alkyl, halogen-substituted $C_1$-$C_3$-alkoxy, halogen substituted $C_3$-$C_6$-cycloalkyl, and 1-pyrrolidinyl or a group $T^2$ $T^2$

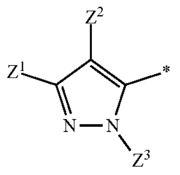

wherein $Z^1$ represents linear or branched $C_1$-$C_3$-alkyl, $C_3$-$C_6$-cycloalkyl, $C_1$-$C_3$-alkoxy, which may independently of one another be substituted with 1 to 5 substituents selected from ˆ hydroxy, halogen, cyano, nitro, $C_1$-$C_3$-alkyl, and $C_1$-$C_3$-alkoxy, $Z^2$ represents halogen, cyano, nitro, amino, or linear or branched $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, which may independently of one another be substituted with 1 to 5 substituents selected from hydroxy, halogen, cyano, nitro, $C_1$-$C_3$-alkyl, and $C_1$-$C_3$-alkoxy; and $Z^3$ represents hydrogen or linear or branched $C_1$-$C_6$-alkyl, $C_3$-$C_6$-cycloalkyl, $C_2$-$C_6$-alkenyl, $C_2$-$C_6$-alkynyl, aryl or hetaryl, which may independently of one another be substituted with 1 to 5 substituents selected from hydroxy, halogen, cyano, nitro, $C_1$-$C_3$-alkyl, and $C_1$-$C_3$-alkoxy; and the salts thereof.

[15] In a further aspect the invention relates to compounds of formula (I) as defined in any one of the preceding aspects [1] to [14]

wherein

Y is selected from a group $T^1$ $T^1$

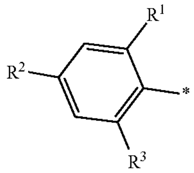

wherein $R^1$, $R^2$ and $R^3$ are each independently selected from halogen, linear or branched halogen-substituted $C_1$-$C_3$-alkyl, and halogen-substituted $C_1$-$C_3$-alkoxy;

or a group $T^2$ $T^2$

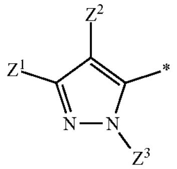

wherein $Z^1$ represents linear or branched $C_1$-$C_3$-alkyl or $C_3$-$C_6$-cycloalkyl, which may independently of one another be substituted with 1 to 5 halogen substituents, $Z^2$ represents linear or branched $C_1$-$C_3$-alkyl, which may be substituted with 1 to 5 halogen substituents, preferably with 1 to 3 halogen substituents, more preferably trifluoromethyl, or $Z^2$ represents nitro, methylsulphanyl, methylsulphinyl, methylsulphonyl, fluorine, chlorine, bromine, iodine; and $Z^3$ represents hydrogen or linear or branched $C_1$-$C_6$-alkyl which may be substituted with 1 to 5 substituents selected from hydroxy, halogen, $C_1$-$C_3$-alkyl, and $C_1$-$C_3$-alkoxy; and the salts thereof.

[16] In a further aspect the invention relates to compounds of formula (I) as defined in any one of the preceding aspects [1] to [15]

wherein

Y is selected from a group $T^1$ $T^1$

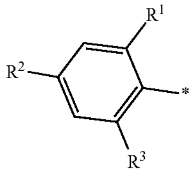

wherein $R^1$ is halogen;

$R^2$ is linear or branched $C_1$-$C_3$-alkyl substituted with 1 to 7 halogen and $R^3$ is $C_1$-$C_3$-alkoxy substituted with 1 to 3 halogen;

or a group $T^2$ $T^2$

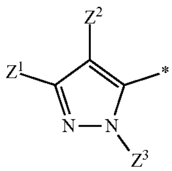

wherein $Z^1$ represents linear or branched $C_1$-$C_3$-alkyl or $C_3$-$C_6$-cycloalkyl, substituted with 1 to 5 halogen substituents, $Z^2$ represents linear or branched $C_1$-$C_3$-alkyl substituted with 1 to 3 halogen substituents, or $Z^2$ represents nitro, methylsulphanyl, methylsulphinyl, methylsulphonyl, fluorine, chlorine, bromine, iodine; and $Z^3$ represents hydrogen or linear or branched $C_1$-$C_6$-alkyl; and the salts thereof.

[17] In a further aspect the invention relates to compounds of formula (I) as defined in any one of the preceding aspects [1] to [16]

wherein

Y is selected from a group $T^1$ $T^1$

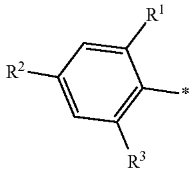

wherein $R^1$ is fluorine, bromine or chlorine, preferably chlorine;

$R^2$ is linear or branched $C_1$-$C_3$-alkyl substituted with 1 to 7 fluorine and $R^3$ is $C_1$-$C_3$-alkoxy substituted with 1 to 3 fluorine;

or a group $T^2$ $T^2$

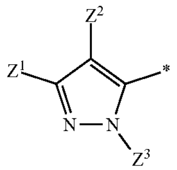

wherein $Z^1$ represents trifluoromethyl, 1-chlorocyclopropyl, 1-fluorocyclopropyl or pentafluoroethyl;

$Z^2$ represents linear or branched $C_1$-$C_3$-alkyl substituted with 1 to 3 fluorine; and $Z^3$ represents linear or branched $C_1$-$C_6$-alkyl;

and the salts thereof.

[18] In a further aspect the invention relates to compounds of formula (I) as defined in any one of the preceding aspects [1] to [17]

wherein

Y is selected from a group $T^1$ $T^1$

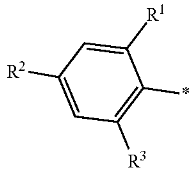

wherein $R^1$ is chlorine;

$R^2$ is $CF_3$, $C_2F_5$ or $C_3F_7$ and $R^3$ is $OCF_3$, $OC_2F_5$ or $OC_3F_7$;

or a group $T^2$ $T^2$

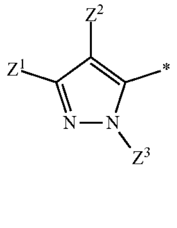

wherein $Z^1$ represents trifluoromethyl or pentafluoroethyl;

$Z^2$ represents trifluoromethyl; and $Z^3$ represents hydrogen, methyl, ethyl, or n-propyl;

and the salts thereof.

[19] In a further aspect the invention relates to compounds of formula (I) as defined in any one of the preceding aspects [1] to [18]

wherein T1 is represented by the following group T1-1:

T1-1

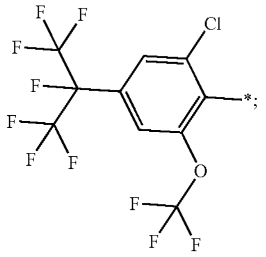

and the salts thereof.

[20] In a further aspect the invention relates to compounds of formula (I) as defined in any one of the preceding aspects [1] to [18]

wherein T1 is represented by the following group T1-2:

T1-2

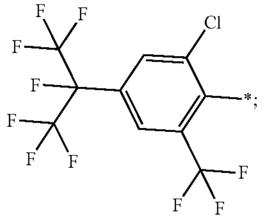

and the salts thereof.

[21] In a further aspect the invention relates to compounds of formula (I) as defined in any one of the preceding aspects [1] to [18]

wherein T1 is represented by the following group T2-1:

T2-1

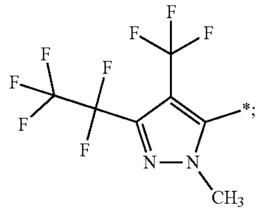

and the salts thereof.

[22] In a further aspect the invention relates to compounds of formula (I) as defined in any one of the preceding aspects wherein Y is T1 as defined in any of the aspects [1] to [20]; and the salts thereof.

[23] In a further aspect the invention relates to compounds of formula (I) as defined in any one of the preceding aspects [1] to [22], which are in the form of salts, solvates, N-oxides and tautomeric forms thereof.

[24] In a further aspect the invention relates to compounds of formula (I) as defined in any one of the preceding aspects [1] to [23], which are selected from (11E)-1-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-1,5,10-trioxo-4,6,9-trioxa-2-azatridec-11-en-13-oic acid, (12E)-1-(2-Chloro-5-{1-[2-chloro-4-(1,1,1,2,3,3,3-heptafluoropropan-2-yl)-6-(trifluoromethoxy)phenyl]-1H- pyrazol-4-yl}phenyl)-2-(1-cyanocyclopropyl)-1,5,11-tri-oxo-4,6,10-trioxa-2-azatetradec-12-en-14-oic acid,
1-(2-Chloro-5-{1-[2-chloro-4-(1,1,1,2,3,3,3-heptafluoro-propan-2-yl)-6-(trifluoromethoxy)phenyl]-1H-pyrazol-4-yl}phenyl)-2-(1-cyanocyclopropyl)-1,5,10-trioxo-4,6,9-trioxa-2-azatridecan-13-oic acid,
(12E)-1-(2-chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-8,8-dimethyl-1,5,11-trioxo-4,6,10-trioxa-2-azatetradec-12-en-14-oic acid,
1-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-8,8-dimethyl-1,5,11-trioxo-4,6,10-trioxa-2-azatetradecan-14-oic acid,
(2E)-4-({(rel 1R,2S)-2-[({[(2-chloro-5-{1-[2-chloro-4-(1,1,1,2,3,3,3-heptafluoropropan-2-yl)-6-(tri-fluoromethoxy)phenyl]-1H-pyrazol-4-yl}benzoyl)(1-cyanocyclopropyl)amino]methoxy}carbonyl)oxy]cyclopentyl}oxy)-4-oxobut-2-enoic acid,
4-({(rel 1R,2S)-2-[({[(2-chloro-5-{1-[2-chloro-4-(1,1,1,2,3,3,3-heptafluoropropan-2-yl)-6-(trifluoro-methoxy)phenyl]-1H-pyrazol-4-yl}benzoyl)(1-cyanocyclopropyl)amino]methoxy}carbonyl)oxy]cyclopentyl}oxy)-4-oxobutanoic acid,
1-(2-chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-11,11-dimethyl-1,5-dioxo-4,6,9-trioxa-2-aza-dodecan-12-oic acid,
1-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-12,12-dimethyl-1,5,10-trioxo-4,6,9-trioxa-2-azatridecan-13-oic acid,
(2E)-4-({(1S,2S)-2-[({[(2-chloro-5-{1-[2-chloro-4-(1,1,1,2,3,3,3-heptafluoropropan-2-yl)-6-(trifluoro-methoxy)phenyl]-1H-pyrazol-4-yl}benzoyl)(1-cyanocyclopropyl)amino]methoxy}carbonyl)-oxy]cyclopentyl}oxy)-4-oxobut-2-enoic acid,
4-{(1S,2S)-2-[({[(2-chloro-5-{1-[2-chloro-4-(1,1,1,2,3,3,3-heptafluoropropan-2-yl)-6-(trifluoro-methoxy)phenyl]-1H-pyrazol-4-yl}benzoyl)(1-cyanocyclopropyl)amino]methoxy}carbonyl)-oxy]cyclopentyl}oxy)-4-oxobutanoic acid,
1-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-1,5,10-trioxo-4,6,9-trioxa-2-azatetradecan-14-oic acid,
1-[10-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-9-(1-cyanocyclopropyl)-6,10-dioxo-2,5,7-trioxa-9-azadecanan-1-oyl]cyclopropane-1-carboxylic acid,
(2E)-4-({cis-4-[({[(2-chloro-5-{1-[2-chloro-4-(1,1,1,2,3,3,3-heptafluoropropan-2-yl)-6-(trifluoro-methoxy)phenyl]-1H-pyrazol-4-yl}benzoyl)(1-cyanocyclopropyl)amino]methoxy}carbonyl)-oxy]cyclohexyl}oxy)-4-oxobut-2-enoic acid,
4-({cis-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexyl}oxy)-4-oxobutanoic acid,
(2E)-4-({trans-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]-methoxy}carbonyl)oxy]cyclohexyl}oxy)-4-oxobut-2-enoic acid,
cis-4-[({[(2-Chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]-methoxy}carbonyl)oxy]cyclohexane-1-carboxylic acid,
trans-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]-methoxy}carbonyl)oxy]cyclohexane-1-carboxylic acid,
[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino] methoxy}carbonyl)oxy]acetic acid;
and the salts solvates, N-oxides and tautomeric forms thereof.

[25] In a further aspect the invention relates to compounds of formula (I) as defined in any one of the preceding aspects [1] to [24], which are for use as medicaments.

[26] In a further aspect the invention relates to pharmaceutical compositions comprising at least one compound according to any of the preceding aspects [1] to [25].

[27] In a further aspect the invention relates to pharmaceutical compositions according to aspect [26], comprising at least one further component selected from auxiliaries, excipients and/or solvents.

[28] In a further aspect the invention relates to pharmaceutical compositions according to aspect [26] or [27], comprising at least one additional pharmaceutically active agent.

[29] In a further aspect the invention relates to pharmaceutical compositions according to aspect [28], wherein the at least one additional pharmaceutically active agent is selected from the group of active agents with ectoparasiticidal activity, in particular with insecticidal and/or acaricidal activity, or from the group of antigens for vaccination purposes.

[30] In a further aspect the invention relates to pharmaceutical compositions according to any of the preceding aspects [26] to [29], which are in the form of an injectable formulation.

[31] In a further aspect the invention relates to pharmaceutical compositions according to any of the preceding aspects [26] to [29], which are in the form of a formulation for oral administration.

[32] In a further aspect the invention relates to the compounds or the pharmaceutical compositions according to any of the preceding aspects for subcutaneous application.

[33] In a further aspect the invention relates to the compounds or the pharmaceutical compositions according to any of the preceding aspects for oral application.

[33] In a further aspect the invention relates to the compounds or the pharmaceutical compositions according to any of the preceding aspects for treating animals.

[34] In a further aspect the invention relates to the compounds or the pharmaceutical compositions according to aspect [34], wherein the animals to be treated are selected from companion animals.

[36] In a further aspect the invention relates to the compounds or the pharmaceutical compositions according to aspect [34] or [35], wherein the companion animals are selected from cats and dogs, preferably from dogs.

[37] In a further aspect the invention relates to the use of the compounds or the pharmaceutical compositions according to any one of the preceding aspects for controlling insects and arachnids.

[38] In a further aspect the invention relates to the use according to aspect [37], wherein the insects and arachnids are selected from the group of Chelicerata.

[39] In a further aspect the invention relates to the use according to aspect [37] or [38], wherein the insects and arachnids are selected from the group consisting of ticks, lice, mosquitoes, flies, fleas, acari and mites.

[40] In a further aspect the invention relates to the use of the compounds as defined in any one of the preceding aspects for preparing pharmaceutical compositions for controlling parasites on animals.

[41] In a further aspect the invention relates to the use of the compounds or the pharmaceutical compositions according to any one of the preceding aspects with treatment intervals of 3 months to two years, preferably 4 months to one year.

[42] In a further aspect the invention relates to the use of the compounds or the pharmaceutical compositions according to aspect [41], wherein the treatment intervals are 6 months to one year, preferably 9 months to one year.

[43] In a further aspect the invention relates to the use of the compounds or the pharmaceutical compositions according to any of the preceding aspects, wherein the total amount of the compounds as defined in any one of the preceding aspects to be administered is in the range of from 0.01 to 200 mg/kg body weight per application, preferably in the range of from 0.1 to 100 mg/kg body weight per application, more preferably of from 0.5 to 75 mg/kg body weight per application, more preferably in the range of from 1.0 to 50 mg/kg body weight per application, most preferably in the range of from 2.0 to 20 mg/kg body weight per application.

[44] In a further aspect the invention relates to a process for preparing the compounds according to any of the preceding aspects comprising the step of reacting a compound (A)

(A)

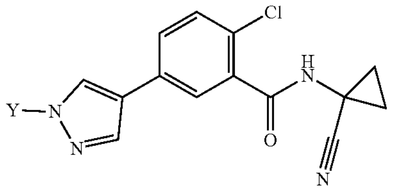

with a group (B)

(B)

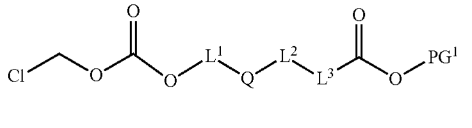

wherein

Y, Q, $L^1$, $L^2$ and $L^3$ have the meaning as defined in any one of the preceding aspects and wherein PG represents a protecting group or hydrogen to form the compounds according to formula (I), and wherein in cases wherein $PG^1$ is not hydrogen, deprotection is carried out to form the compounds (I).

[45] In a further aspect the invention relates to the process according to aspect [44] further comprising the preliminary step of preparing the group (B) by i) reacting a compound (IIa) with a compound (IIIa) to form compound (Va), wherein $PG^2$ is a protecting group or hydrogen, and wherein in cases wherein $PG^2$ is not hydrogen (Va) is obtained by selectively cleaving $PG^2$:

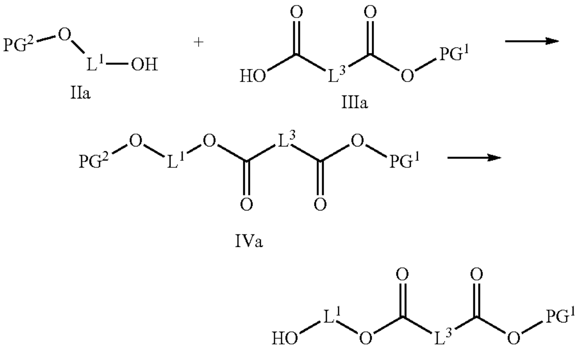

IIa IIIa IVa Va wherein $L^1$ and $L^3$ have the meaning as defined in any one of the preceding aspects and wherein PG represents a protecting group or hydrogen;

or ii) reacting a compound (VI) with compound (IIIb) to form compound (Vb), wherein $PG^2$ is a protecting group or hydrogen, and wherein in cases wherein $PG^2$ is not hydrogen (Vb) is obtained by selectively cleaving $PG^2$:

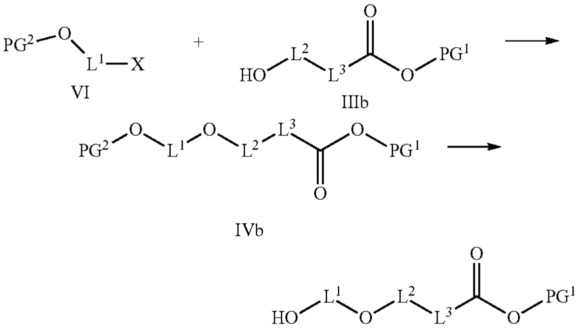

VI IIIb IVb Vb wherein $L^1$, $L^2$ and $L^3$ have the meaning as defined in any one of the preceding aspects and wherein PG represents a protecting group or hydrogen.

[46] In a further aspect the invention relates to intermediate compounds according to formula (B), (B)

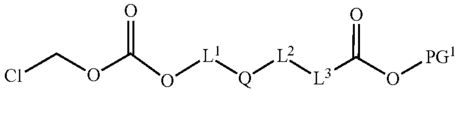

wherein

Q is O;

$L^2$ is C═O;

$L^1$ and $L^3$ have the meaning as defined in any one of the preceding aspects and $PG^1$ represents a tert-butyl group.

[47] In a further aspect the invention relates to intermediate compounds according to formula (C), (C)

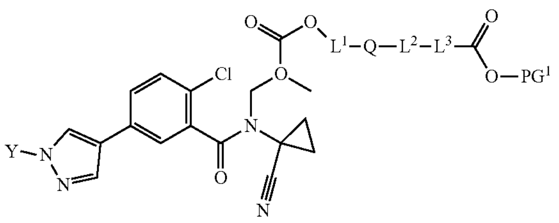

wherein Y, Q, $L^1$, $L^2$ and $L^3$ have the meaning as defined in any one of the preceding aspects and wherein $PG^1$ represents a tert-butyl group.

[48] In a further aspect the invention relates to intermediate compounds selected from tert-Butyl-2-{[(chloromethoxy)carbonyl]oxy}ethyl-(2E)-but-2-enedioate (Intermediate 3A);

tert-Butyl-2-[({[(2-chloro-5-{1-[2-chloro-4-(1,1,2,3,3,3-heptafluorpropane-2-yl)-6-(trifluormethoxy)phenyl]-1H-pyrazol-4-yl}benzoyl)(1-cyanocyclopropyl)amino]methoxy}carbonyl)oxy]ethyl-(2E)-but-2-enedioate (Intermediate 4A);

tert-butyl 3-{[(chloromethoxy)carbonyl]oxy}propyl (2E)-but-2-enedioate (Intermediate 6A);

tert-Butyl 3-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]propyl (2E)-but-2-enedioate (Intermediate 7A);

tert-Butyl 2-{[(chloromethoxy)carbonyl]oxy}ethyl butanedioate (Intermediate 9A);

tert-Butyl 2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]ethyl butanedioate (Intermediate 10A);

tert-Butyl 3-{[(chloromethoxy)carbonyl]oxy}-2,2-dimethylpropyl (2E)-but-2-enedioate (Intermediate 12A);

tert-Butyl 3-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-2,2-dimethylpropyl (2E)-but-2-enedioate (Intermediate 13A);

tert-Butyl 3-{[(chloromethoxy)carbonyl]oxy}-2,2-dimethylpropyl butanedioate (Intermediate 14A);

tert-Butyl 3-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-2,2-dimethylpropyl butanedioate (Intermediate 15A);

tert-Butyl (rel 1S,2R)-2-{[(chloromethoxy)carbonyl]oxy}cyclopentyl (2E)-but-2-enedioate (Intermediate 17A);

tert-Butyl (rel 1R,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl (2E)-but-2-enedioate (Intermediate 18A);

tert-Butyl (rel 1S,2R)-2-{[(chloromethoxy)carbonyl]oxy}cyclopentyl butanedioate (Intermediate 19A);

tert-Butyl (rel 1R,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl butanedioate (Intermediate 20A);

tert-Butyl 3-[2-(benzyloxy)ethoxy]-2,2-dimethylpropanoate (Intermediate 21A);

tert-Butyl 3-(2-hydroxyethoxy)-2,2-dimethylpropanoate (Intermediate 22A);

tert-Butyl 3-(2-{[(chloromethoxy)carbonyl]oxy}ethoxy)-2,2-dimethylpropanoate (Intermediate 23A);

tert-Butyl 1-(2-chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-11,11-dimethyl-1,5-dioxo-4,6,9-trioxa-2-azadodecan-12-oate (Intermediate 24A);

1-tert-Butyl 4-(2-hydroxyethyl) 2,2-dimethylsuccinate (Intermediate 28A)

1-tert-Butyl 4-(2-{[(chloromethoxy)carbonyl]oxy}ethyl) 2,2-dimethylbutanedioate (Intermediate 29A);

1-tert-Butyl 4-{2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]ethyl} 2,2-dimethylbutanedioate (Intermediate 30A);

tert-Butyl (1S,2S)-2-hydroxycyclopentyl (2E)-but-2-enedioate (Intermediate 31A);

tert-Butyl (1S,2S)-2-{[(chloromethoxy)carbonyl]oxy}cyclopentyl (2E)-but-2-enedioate (Intermediate 32A);

tert-Butyl (1S,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl (2E)-but-2-enedioate (Intermediate 33A);

tert-Butyl (1S,2S)-2-{[(chloromethoxy)carbonyl]oxy}cyclopentyl butanedioate (Intermediate 34A);

tert-Butyl (1S,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl butanedioate (Intermediate 35A);

tert-Butyl 2-hydroxyethyl pentanedioate (Intermediate 36A);

tert-Butyl 2-{[(chloromethoxy)carbonyl]oxy}ethyl pentanedioate (Intermediate 37A);

tert-Butyl 2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]ethyl pentanedioate (Intermediate 38A);

1-tert-Butyl 1-(2-hydroxyethyl) cyclopropane-1,1-dicarboxylate (Intermediate 39A);

1-tert-Butyl 1-(2-{[(chloromethoxy)carbonyl]oxy}ethyl) cyclopropane-1,1-dicarboxylate (Intermediate 40A);

1-tert-Butyl 1-{2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]ethyl}cyclopropane-1,1-dicarboxylate (Intermediate 41A);

tert-Butyl-4-hydroxycyclohexyl (2E)-but-2-enedioate (Mixture of diastereomers) (Intermediate 42A);

tert-Butyl cis-4-hydroxycyclohexyl (2E)-but-2-enedioate Intermediate 43A);

tert-Butyl trans-4-hydroxycyclohexyl (2E)-but-2-enedioate (Intermediate 44A);

tert-Butyl cis-4-{[(chloromethoxy)carbonyl]oxy}cyclohexyl (2E)-but-2-enedioate (Intermediate 45A);

tert-Butyl cis-4-[({[(2-chloro-5-{1-[2-chloro-4-(1,1,1,2,3,3,3-heptafluoropropan-2-yl)-6-(trifluoromethoxy)phenyl]-

1H-pyrazol-4-yl}benzoyl)(1-cyanocyclopropyl)amino]methoxy}carbonyl)oxy]cyclohexyl (2E)-but-2-enedioate (Intermediate 46A);

tert-Butyl cis-4-hydroxycyclohexyl butanedioate (Intermediate 47A);

tert-Butyl cis-4-{[(chloromethoxy)carbonyl]oxy}cyclohexyl butanedioate (Intermediate 48A);

tert-Butyl cis-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexyl butanedioate (Intermediate 49A);

tert-Butyl trans-4-{[(chloromethoxy)carbonyl]oxy}cyclohexyl (2E)-but-2-enedioate (Intermediate 50A);

tert-butyl trans-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexyl (2E)-but-2-enedioate (Intermediate 51A);

tert-Butyl cis-4-{[(chloromethoxy)carbonyl]oxy}cyclohexane-1-carboxylate (Intermediate 52A);

tert-Butyl cis-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexane-1-carboxylate (Intermediate 53A);

tert-Butyl trans-4-{[(chloromethoxy)carbonyl]oxy}cyclohexane-1-carboxylate (Intermediate 54A);

tert-Butyl trans-4-[({[(2-chloro-5-{1-[2-chloro-4-(1,1,1,2,3,3,3-heptafluoropropan-2-yl)-6-(trifluoromethoxy)phenyl]-1-pyrazol-4-yl}benzoyl)(1-cyanocyclopropyl)amino]methoxy}carbonyl)oxy]cyclohexane-1-carboxylate (Intermediate 55A);

tert-Butyl [({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]acetate (Intermediate 57A).

Definitions

“Arachnids” are a class (Arachnida) of joint-legged invertebrate animals (arthropods), in the subphylum Chelicerata. A preferred subclass of the arachnids are acari (or acarina) which comprise in particular mites and ticks.

The term “substituted” means that one or more hydrogen atoms on the designated atom or group are replaced with a selection from the indicated group, provided that the designated atom’s normal valency under the existing circumstances is not exceeded. Combinations of substituents and/or variables are permissible.

The term “optionally substituted” means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term “one or more”, e.g. in the definition of the substituents of the compounds of general formula (I) of the present invention, means “1, 2, 3, 4 or 5, particularly 1, 2, 3 or 4, more particularly 1, 2 or 3, even more particularly 1 or 2”.

As used herein, the position via which a respective substituent is connected to the rest of the molecule may in a drawn structure be depicted by a star sign [*] in said substituent.

The term “comprising” when used in the specification includes “consisting of”.

If within the present text any item is referred to as “as mentioned herein”, it means that it may be mentioned anywhere in the present text.

The terms as mentioned in the present text have the following meanings:

The term “halogen atom” means a fluorine, chlorine, bromine or iodine atom, particularly a fluorine, chlorine or bromine atom, more particularly chlorine and/or fluorine.

The term “$C_1$-$C_4$-alkanediyl” represents a divalent straight-chained (linear) or branched alkanediyl radical having from 1 to 4, preferably 1, 2 or 3, more preferably 2 or 3, carbon atoms. The term “$C_2$-$C_4$-alkanediyl” represents a divalent straight-chained (linear) or branched alkanediyl radical having from 2 to 4, preferably 2 or 3 carbon atoms. The following may be mentioned as preferred examples: methylene, 1,2-ethanediyl, ethane-1,1-diyl, 1,3-propylene (1,3-propanediyl), propane-1,1-diyl, propane-1,2-diyl, propane-2,2-diyl, 1,4-butylene (1,4-butanediyl), butane-1,2-diyl, butane-1,3-diyl, butane-2,3-diyl. Preferred are methylene, 1,2-ethanediyl and 1,3-propylene (1,3-propanediyl), more preferred are 1,2-ethanediyl and 1,3-propylene (1,3-propanediyl).

In the present invention a linear $C_1$-$C_4$-alkanediyl group or a $C_2$-$C_4$-alkanediyl group may be substituted with one or more groups independently selected from halogen (as defined above), $C_1$-$C_4$ alkyl and $C_3$-$C_6$ cycloalkyl. In the present invention a linear $C_1$-$C_4$-alkanediyl group or a $C_2$-$C_4$-alkanediyl group, which is substituted with one or more groups selected from $C_1$-$C_4$ alkyl comprises in particular a 1,2-dimethyl-ethanediyl group and a 2,2-dimethyl-1,3-propanediyl group.

In the case of a $C_1$-$C_4$-alkanediyl group or a $C_2$-$C_4$-alkanediyl group which may be substituted with one or more $C_1$-$C_4$ alkyl substituents, it is also possible that two $C_1$-$C_4$-alkyl substituents form a ring together with the carbon atom to which they are bonded. Respective groups comprise in particular the following groups:

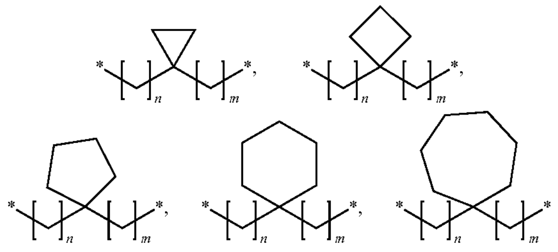

Preferably a respective group is

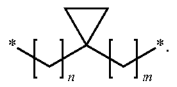

Therein n and m are independently 0, 1, 2 or 3. Preferably n and m are independently 0, 1 or 2. More preferably one of n and m is 0 and the other one is 1.

The term "$C_1$-$C_6$-alkyl", comprises linear and branched, saturated, monovalent hydrocarbon group having 1, 2, 3, 4, 5 or 6 carbon atoms. The term "$C_1$-$C_4$-alkyl" comprises linear and branched, saturated, monovalent hydrocarbon group having 1, 2, 3, or 4 carbon atoms. The term "$C_1$-$C_3$-alkyl" comprises linear and branched, saturated, monovalent hydrocarbon group having 1, 2 or 3 carbon atoms. Examples of the respective alkyl-groups are a methyl, ethyl, n-propyl, isopropyl, n-butyl, sec-butyl, isobutyl, a tert-butyl group etc., or an isomer thereof. Most preferred are methyl, ethyl, and n-propyl The term "$C_3$-$C_7$-cycloalkyl" means a saturated, monovalent, monocyclic hydrocarbon ring which contains 3, 4, 5, 6 or 7 carbon atoms. The term "$C_3$-$C_6$-cycloalkyl" means a saturated, monovalent, monocyclic hydrocarbon ring which contains 3, 4, 5 or 6 carbon atoms. The term "$C_3$-$C_5$-cycloalky" means a saturated, monovalent, monocyclic hydrocarbon ring which contains 3, 4 or 5 carbon atoms. Said $C_3$-$C_7$-cycloalkyl groups are for example, a monocyclic hydrocarbon ring, e.g. a cyclopropyl, cyclobutyl, cyclopentyl, cyclohexyl or cycloheptyl group. Particularly, said cycloalkyl group contains 3, 5 or 6 carbon atoms and is e.g. cyclopropyl, cyclopentyl or cyclohexyl.

The term "$C_3$-$C_7$-cycloalkanediyl" represents a divalent monocyclic hydrocarbon radical having from 3 to 7, preferably from 3 to 6 ring carbon atoms. Examples are the following groups:

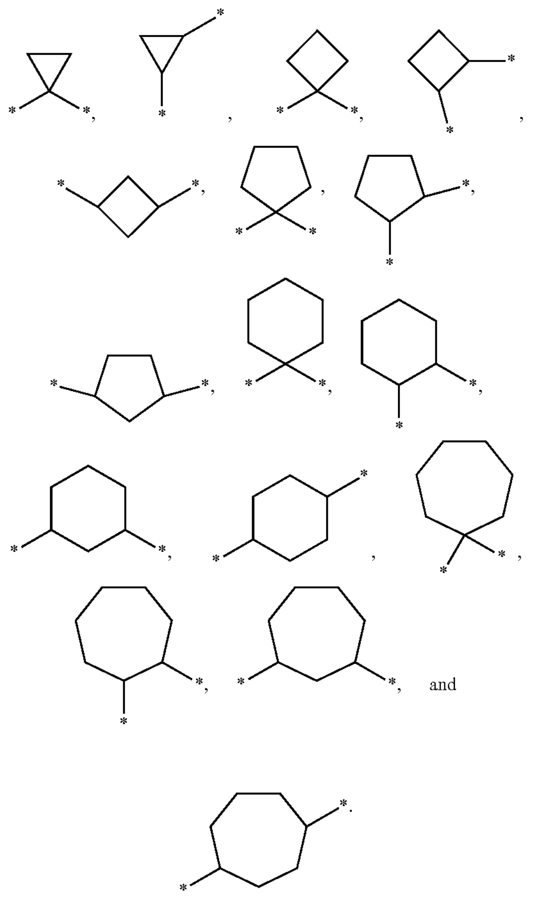

Therein, the following groups are preferred:

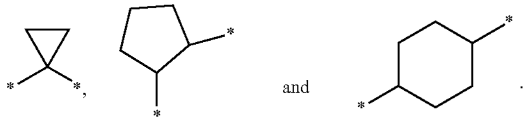

Said $C_3$-$C_7$-cycloalkanediyl groups may be substituted with one or more groups independently selected from $C_1$-$C_4$-alkyl and halogen, each as defined above.

In the present invention the substituent $L^1$ may be a moiety $(CH_2)_n$—X—$(CH_2)_m$ wherein n and m are independently 0, 1 or 2 and wherein X is a $C_3$-$C_7$-cycloalkanediyl group as defined above. Therein, the groups $(CH_2)_n$ and $(CH_2)_m$ are bound to the $C_3$-$C_7$-cycloalkanediyl groups at the positions indicated with * in the formulae supra. In the case of n and m both being 0 the respective moiety corresponds to a $C_3$-$C_7$-cycloalkanediyl group as defined above. Particular examples of said moiety comprise:

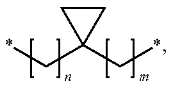

with one of n or m being 1 and the other one being 0 and

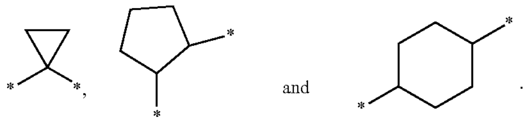

wherein in each case n and m are both 0.

In the present invention the substituent $L^3$ may be a moiety $(CH_2)_n$—(CH═CH)—$CH_2)_m$ wherein n and m are independently 0, 1 or 2. Examples comprise ethene-1,1-diyl, ethene-1,2-diyl, propene-1,1-diyl, propene-1,2-diyl, propene-1,3-diyl, but-1-ene-1,4-diyl, but-1-ene-1,3-diyl, but-2-ene-1,4-diyl, buta-1,3-diene-1,4-diyl, pent-2-ene-1,5-diyl, hex-3-ene-1,6-diyl and hexa-2,4-diene-1,6-diyl. Preferably n and m are both 0, i.e. an ethene-1,1-diyl group.

Said $(CH_2)_n$—(CH═CH)—$CH_2)_m$ groups may be substituted with one or more groups independently selected from $C_1$-$C_4$-alkyl, $C_3$-$C_5$-cycloalkyl and halogen, each as defined above.

The term "$C_1$-$C_6$-alkoxy" represents a straight-chain or branched O-alkyl having 1 to 6 carbon atoms, for example methoxy, ethoxy, n-propoxy, isopropoxy, n-butoxy, isobutoxy, s-butoxy and t-butoxy. Preference is also given to alkoxy groups having 1 to 4 carbon atoms. The inventive alkoxy groups may be substituted by one or more identical or different radicals.

The term "$C_1$-$C_6$-alkylsulphanyl" represents straight-chain or branched S-alkyl having 1 to 6 carbon atoms, for example methylthio, ethylthio, n-propylthio, isopropylthio, n-butylthio, isobutylthio, s-butylthio and t-butylthio. Preference is also given to alkylsulphanyl groups having 1 to 4 carbon atoms. The inventive alkylsulphanyl groups may be substituted by one or more identical or different radicals.

The term "$C_1$-$C_6$-alkylsulphinyl" represents straight-chain or branched alkylsulphinyl having 1 to 6 carbon atoms, for example methylsulphinyl, ethylsulphinyl, n-propylsulphinyl, isopropylsulphinyl, n-butylsulphinyl, isobutylsulphinyl, s-butylsulphinyl and t-butylsulphinyl. Preference is also given to alkylsulphinyl groups having 1 to 4 carbon atoms. The inventive alkylsulphinyl groups may be substituted by one or more identical or different radicals.

The term "alkylsulphonyl" represents straight-chain or branched alkylsulphonyl having 1 to 6 carbon atoms, for example methylsulphonyl, ethylsulphonyl, n-propylsulphonyl, isopropylsulphonyl, n-butylsulphonyl, isobutylsulphonyl, s-butylsulphonyl and t-butylsulphonyl. Preference is also given to alkylsulphonyl groups having 1 to 4 carbon atoms. The inventive alkylsulphonyl groups may be substituted by one or more identical or different radicals.

The terms "halogen-substituted $C_1$-$C_6$-alkyl", "halogen-substituted $C_1$-$C_6$-alkoxy" and "halogen-substituted $C_3$-$C_6$-cycloalkyl" represent $C_1$-$C_6$-alkyl, $C_1$-$C_6$-alkoxy and $C_3$-$C_6$-cycloalkyl groups as defined above, which are mono- or polysubstituted by halogen up to the maximum possible number of substituents. Such groups are also referred to as halo groups (for example haloalkyl). In the case of polysubstitution by halogen, the halogen atoms may be the same or different, and may all be bonded to one carbon atom or may be bonded to a plurality of carbon atoms. Halogen is especially fluorine, chlorine, bromine or iodine, preferably fluorine, chlorine or bromine and more preferably fluorine. More particularly, halogen-substituted groups are monohalocycloalkyl such as 1-fluorocyclopropyl, 2-fluorocyclopropyl or 1-fluorocyclobutyl, monohaloalkyl such as 2-chloroethyl, 2-fluoroethyl, 1-chloroethyl, 1-fluoroethyl, chloromethyl, or fluoromethyl; perhaloalkyl such as trichloromethyl or trifluoromethyl or $CF_2CF_3$, polyhaloalkyl such as difluoromethyl, 2-fluoro-2-chloroethyl, dichloromethyl, 1,1,2,2-tetrafluoroethyl or 2,2,2-trifluoroethyl. Further examples of haloalkyls are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl, 3,3,3-trifluoropropyl and pentafluoro-t-butyl. Preference is given to haloalkyls having 1 to 4 carbon atoms and 1 to 9, preferably 1 to 5, identical or different halogen atoms selected from fluorine, chlorine and bromine, preferably from fluorine. Particular preference is given to haloalkyls having 1 or 2 carbon atoms and 1 to 5 identical or different halogen atoms selected from fluorine and chlorine, such as, inter alia, difluoromethyl, trifluoromethyl or 2,2-difluoroethyl. Further examples of halogen-substituted compounds are haloalkoxy such as $OCF_3$, $OCHF_2$, $OCH_2F$, $OCF_2CF_3$, $OCH_2CF_3$, $OCH_2CHF_2$ and $OCH_2CH_2Cl$, haloalkylsulphanyls such as difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio, haloalkylsulphinyls such as difluoromethylsulphinyl, trifluoromethylsulphinyl, trichloromethylsulphinyl, chlorodifluoromethylsulphinyl, 1-fluoroethylsulphinyl, 2-fluoroethylsulphinyl, 2,2-difluoroethylsulphinyl, 1,1,2,2-tetrafluoroethylsulphinyl, 2,2,2-trifluoroethylsulphinyl and 2-chloro-1,1,2-trifluoroethylsulphinyl, haloalkylsulphinyls such as difluoromethylsulphinyl, trifluoromethylsulphinyl, trichloromethylsulphinyl, chlorodifluoromethylsulphinyl, 1-fluoroethylsulphinyl, 2-fluoroethylsulphinyl, 2,2-difluoroethylsulphinyl, 1,1,2,2-tetrafluoroethylsulphinyl, 2,2,2-trifluoroethylsulphinyl and 2-chloro-1,1,2-trifluoroethylsulphinyl, haloalkylsulphonyl groups such as difluoromethylsulphonyl, trifluoromethylsulphonyl, trichloromethylsulphonyl, chlorodifluoromethylsulphonyl, 1-fluoroethylsulphonyl, 2-fluoroethylsulphonyl, 2,2-difluoroethylsulphonyl, 1,1,2,2-tetrafluoroethylsulphonyl, 2,2,2-trifluoroethylsulphonyl and 2-chloro-1,1,2-trifluoroethylsulphonyl. Most preferred fluorinated alkyl groups are $CF_3$, $C_2F_5$ and $C_3F_7$ and most preferred fluorinated alkoxy groups are $OCF_3$, $OC_2F_5$ and $OC_3F_7$.

The terms "N—$C_1$-$C_6$-alkylamino", "N,N-di-$C_1$-$C_6$-alkylamino", and "N—$C_1$-$C_3$-alkoxy-$C_1$-$C_4$-alkylamino" represent an amino group substituted with one or two $C_1$-$C_6$-groups or an amino group substituted with one $C_1$-$C_3$-alkoxy group and one $C_1$-$C_4$-alkyl group, each as defined above.

The term "$C_1$-$C_6$-alkylcarbonyl" represents straight-chain or branched alkyl-C(═O) having 2 to 7 carbon atoms such as methylcarbonyl, ethylcarbonyl, n-propylcarbonyl, isopropylcarbonyl, s-butylcarbonyl and t-butylcarbonyl. Preference is also given to alkylcarbonyls having 1 to 4 carbon atoms. The inventive alkylcarbonyls may be substituted by one or more identical or different radicals.

The term "$C_2$-$C_6$-alkenyl" represents straight-chain or branched hydrocarbons preferably having 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preference is also given to alkenyls having 2 to 4 carbon atoms such as, inter alia, 2-propenyl, 2-butenyl or 1-methyl-2-propenyl. The inventive alkenyls may be substituted by one or more identical or different radicals.

The term "$C_2$-$C_6$-alkynyl" represents straight-chain or branched hydrocarbons preferably having 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Preference is also given to alkynyls having 2 to 4 carbon atoms such as, inter alia, ethynyl, 2-propynyl or 2-butynyl-2-propenyl. The inventive alkynyls may be substituted by one or more identical or different radicals.

The term "aryl" represents a mono-, bi- or polycyclic aromatic system having preferably 6 to 14, especially 6 to 10, ring carbon atoms, for example phenyl, naphthyl, anthryl, phenanthrenyl, preferably phenyl. In addition, aryl also represents polycyclic systems such as tetrahydronaphthyl, indenyl, indanyl, fluorenyl, biphenyl, where the bonding site is on the aromatic system. The inventive aryl groups may be substituted by one or more identical or different radicals.

The term "hetaryl" or "heteroaryl" represents heteroaromatic compounds, i.e. completely unsaturated aromatic heterocyclic compounds having at least one ring in which at least one carbon atom is replaced by a heteroatom, preferably by a heteroatom from the group consisting of N, O, S, P, B, Si, Se, and which may be unsubstituted or substituted, where the bonding site is on a ring atom. Unless defined differently, the heteroaryl ring contains preferably 3 to 9 ring atoms, especially 3 to 6 ring atoms, more preferably 5 to 7 ring atoms, and one or more, preferably 1 to 4, especially 1, 2 or 3, heteroatoms in the heteroaryl ring, preferably from the group consisting of N, O, and S, although no two oxygen atoms should be directly adjacent. The heteroaryl rings usually contain not more than 4 nitrogen atoms and/or not more than 2 oxygen atoms and/or not more than 2 sulphur atoms. Particular preference is given to 5- to 7-membered rings having 1 to 3, preferably 1 or 2, identical or different heteroatoms from the group above. Inventive heteroaryls are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The inventive heteroaryl groups may also be substituted by one or more identical or different radicals Preferred substituents of the aryl and heteroaryl groups are selected from hydroxy, halogen, cyano, nitro, amino, $C_1$-$C_3$-alkyl, $C_1$-$C_3$-alkoxy, hydroxycarbonyl, alkoxycarbonyl, alkylcarbamoyl, cycloalkylcarbamoyl and phenyl.

Preferably the substituents Y, Q, $L^1$, $L^2$ and $L^3$ have the meaning as defined above in the various aspects of the present invention.

In a particularly preferred aspect of the invention the substituent Y in the compounds of formula (I) as defined anywhere herein is selected from a group $T^1$ as defined herein, in particular a group T1-1 or T1-2, each as defined anywhere herein.

Particularly preferred Examples of the present invention are listed in aspect [24] above and as shown in the Examples below. Preferred compounds according to formula (I) of the present invention are those of Examples 1, 2, 3, 4, 5, 6, 7, 9, 10, 11, 12, 13, 14, 15, and 16. More preferred compounds according to formula (I) of the present invention are those of Examples 1, 2, 4, 6, 10, 14, and 16.

Salts of the inventive compounds that are suitable in accordance with the invention, for example salts with bases, are all customary non-toxic salts, preferably agriculturally and/or physiologically acceptable salts. Preference is given to salts with inorganic bases, for example alkali metal salts (e.g. sodium, potassium or caesium salts), alkaline earth metal salts (e.g. calcium or magnesium salts), ammonium salts or salts with organic bases, in particular with organic amines, for example triethylammonium, dicyclohexylammonium, N,N'-dibenzylethylenediammonium, pyridinium, picolinium or ethanolammonium salts. Preferably salts of the compounds of the present invention are pharmaceutically acceptable salts.

Furthermore, the present invention includes all possible crystalline forms, or polymorphs, of the compounds of the present invention, either as single polymorph, or as a mixture of more than one polymorph, in any ratio.

The compounds of the present invention and their salts—to the extent applicable—can exist as a hydrate, or as a solvate, wherein the compounds of the present invention contain water or polar solvents (for example methanol or ethanol), respectively, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates of the compounds and their salts, to the extent applicable.

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers, tautomers or geometric isomers. Accordingly, the invention encompasses both pure stereoisomers and any mixtures of these isomers.

The novel compounds according to the present invention are particularly suitable for the use as medicaments, in particular for the use as medicaments for the treatment of animals. The novel compounds according to the present invention are particularly suitable for the use as medicaments to act against animal parasites, especially ectoparasites, such as insects and arachnids or else. Ectoparasites are typically and preferably arthropods, especially insects such as flies (biting and licking), parasitic fly larvae, sucking lice, biting lice, fleas and the like; or acari such as ticks, for example hard ticks or soft ticks, or mites such as scab mites, bird mites and the like, and also aquatic ectoparasites such as copepods. The novel compounds of the present invention are particularly suitable to act against ticks, fleas, lice, flies and mites.

The novel compounds of the formula (I) having favourable homeotherm toxicity are suitable for controlling parasites which occur in animal breeding and animal husbandry in livestock including aquaculture, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals (also indicated as companion animals) include, for example, mammals, such as hamsters, guinea pigs, rats, mice, chinchillas, ferrets, and particularly dogs, cats, cage birds, reptiles, amphibians and aquarium fish. Preferred companion animals are cats and dogs.

In a preferred embodiment, the compounds of the formula (I) are administered to mammals.

In a preferred embodiment the compounds of formula (I) are administered to cats.

In a preferred embodiment the compounds of formula (I) are administered to dogs.

Use of the compounds of the formula (I) for the control of animal parasites is intended to reduce or prevent illness, cases of deaths and reductions in performance (in the case of meat, milk, wool, hides, eggs, honey and the like), such that more economical and simpler animal keeping is enabled and better animal well-being is achievable.

In relation to the animal health field, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

These parasites include:

From the order of the Anoplurida, for example, *Haematopinus* spp., *Linognathus* spp., *Pediculus* spp., *Phthirus* spp., *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example, *Aedes* spp., *Anopheles* spp., *Culex* spp., *Simulium* spp., Eusimulium spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;*

From the order of the Siphonapterida, for example, *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica* and *Supella* spp. (e.g. *Suppella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) calceratus, *Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;*

From the order of the Actinedida (Prostigmata) and Acaridida (Astigmata), for example, *Acarapis* spp., *Cheyletiella* spp., *Ornithocheyletia* spp., Myobia spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

From the subclass of the copepods with the order of the Siphonostomatoida in particular the genera *Lepeophtheirus* and *Caligus*; the species *Lepeophtheirus salmonis, Caligus elongatus* and *Caligus clemensi* may be mentioned by way of example and with particular preference.

According to a preferred embodiment the parasites are selected from the following group of ectoparsite species:

Fleas: *Ctenocephalides* spp.;

Ticks: *Amblyomma* spp., *Dermacentor* spp., *Rhipicephalus* spp., *Ixodes* spp., *Haemaphysalis* spp., *Hyalomma* spp.;

Mites: *Demodex* spp., *Otodectes* spp., *Sarcoptes* spp.; and

Lice: *Linognathus* spp.

More particularly the parasites are selected from:

Fleas: *Ctenocephalides felis, Ctenocephalides canis;*

Ticks: *Ixodes scapularis, Ixodes ricinus, Dermacentor variabilis, Amblyomma americanum, Rhipicephalus sanguineus, Dermacentor reticulatus, Ixodes holocyclus, Ixodes hexagonus, Haemaphysalis longicornis;*

Mites: *Otodectes cynotis, Sarcoptes scabiei, Demodex canis*; and

Lice: *Linognathus setosus.*

In general, the inventive active ingredients can be employed directly when they are used for the treatment of animals. They are preferably employed (administered) in the form of pharmaceutical compositions which may comprise pharmaceutically acceptable excipients, solvents and/or auxiliaries known in the prior art.

The novel active compounds of the present invention may be administered in a known manner, by enteral administration in the form of, for example, tablets, capsules, portions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of moulded articles containing the active ingredient, such as collars, earmarks, tailmarks, limb bands, halters, marking devices, etc. Preferably the novel compounds of the present invention are administered by subcutaneous or oral administration, more preferably by subcutaneous administration (injection).

The novel active compounds of the present invention can be formulated in any suitable administration form for oral and subcutaneous (injectable) administration known in the prior art.

Based upon standard laboratory techniques known to evaluate compounds useful for controlling parasites on animals, by standard toxicity tests and by standard pharmacological assays for the determination of treatment of the conditions identified above in animals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the subject treated, and the nature and extent of the condition treated.

The content of the novel active compounds of the present invention in formulations for the use (unit dosage) according to the present invention may vary within wide limits. The active compound concentration of the application forms may be from 0.00000001 to 98% by weight of active compound, preferably from 0.00001 to 98% by weight, more preferably from 0.001 to 98% by weight. More preferably, the pharmaceutical compositions of the present invention may comprise the novel compounds of the invention in amounts from 0.01 to 98% by weight of active compound, preferably from 0.1 to 98% by weight, more preferably from 0.5 to 90% by weight. The pharmaceutical compositions of the present invention may comprise the novel compounds of the invention in amounts from 0.001 to 95% by weight of active compound, preferably from 0.01 to 95% by weight, preferably from 0.1 to 50% by weight, more preferably from 5 to 30% by weight.

The total amount of the active ingredient to be administered will generally range from about 0.01 to 200 mg/kg body weight per application, preferably in the range of from 0.1 to 100 mg/kg body weight per application, more preferably of from 0.5 to 75 mg/kg body weight per application, more preferably in the range of from 1.0 to 50 mg/kg body weight and most preferably in the range of from 2.0 to 20 mg/kg body weight per application.

In particular, the average dosage for administration by infusion techniques or by injection, including intravenous, intramuscular, and in particular subcutaneous injections will preferably be within the aforesaid ranges.

The average dosage for oral administration will preferably be within the aforesaid ranges.

Clinically useful dosing or administration intervals will range from one application per month to one application every two years, preferably the treatment interval is from one application every three months to one application every two years, more preferred treatment intervals are from one application every six months to one application every two years. Further preferred dosing or administration intervals will range from one application per month to one application every year, preferably one application every three months to one application every year, more preferably one application every four months to one application every year, in particular one application every six months to one application every year. According to a further embodiment the application interval may be from one application every nine months to one application per year.

In addition, it is possible for "drug holidays", in which a subject is not dosed with a drug for a certain period of time, to be beneficial to the overall balance between pharmacological effect and tolerability.

Of course the specific initial and continuing dosage regimen, administered amount of active compound and the particular dosing interval will vary for each subject according to the nature and severity of the condition as determined by the attending diagnostician, the activity of the specific compound employed, the age and general condition of the subject, time of administration, route of administration, rate of excretion of the drug, drug combinations, and the like. The desired mode of treatment and number of doses of a compound of the present invention or a pharmaceutically acceptable salt or composition thereof can be ascertained by those skilled in the art using conventional treatment tests.

In order to broaden the spectrum of activity, the novel active compounds of the present invention can be used in combination with suitable synergists, repellents or other active ingredients, for example acaricides, insecticides, anthelmintics, anti-protozoal agents.

For example the compounds of the present invention can be used in combination with chloride channel activators or modulators from the class of the macrocylic lactones, in particular avermectins/milbemycins, e.g. abamectin, doramectin, emamectin benzoate, eprinomectin, ivermectin, latidectin, lepimectin, milbemycin oxime, milbemectin, moxidectin and selamectin, particular preference is given here, for applications against ectoparasites, to doramectin, eprinomectin, ivermectin, milbemycin oxime, moxidectin or selamectin.

Further, the the compounds of the present invention can be used in combination with antigens for vaccination purposes. Examples for vaccines which may be combined with the compounds of the present invention are against leptospirosis, infectious tracheobronchitis, leishmaniasis or lyme borreliosis (lyme disease).

Process for Preparing the Novel Compounds of Formula (I)

The novel compounds (I) according to the present invention can be synthesised according to general Schemes 1 to 3 as shown below. Generally, the synthesis can be divided into two stages.

In the first stage, a protected pro-moiety is built up with a terminal alcohol function that will become part of the carbonate ester linker in the novel compounds of the invention.

In the second stage, the terminal alcohol group of the pro-moiety is converted into a chloromethyl carbonate ester that is then coupled to a halogenated amide group of an active compound moiety and eventually deprotected to give a free carboxylic acid.

The first stage of the synthesis differs depending on the meaning of the substituents $L^1$, $L^2$ and Q in the compounds of formula (I) whereas the second stage is common for all compounds of the present invention.

First Stage of the Process—Building Up the Pro-Moiety

Synthesis Route (a) for Compounds (I) Wherein $L^2$ is C═O and Q is O

The following Scheme 1 describes the synthesis of the protected pro-moiety of the above mentioned first stage of the process of the present invention for preparing compounds (I) wherein $L^1$ and $L^3$ have the meaning as defined anywhere above and wherein $L^2$ is selected to be C═O and Q is selected to be O.

Scheme 1

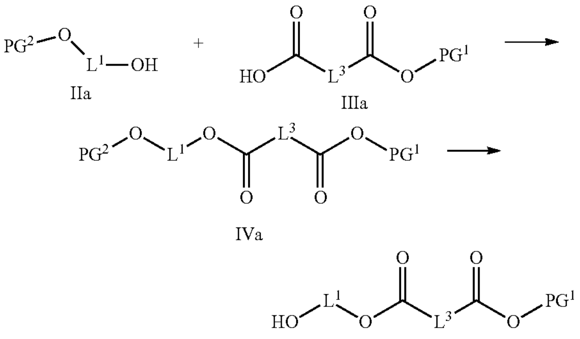

IIa IIIa IVa Va

Therein, $PG^1$ is a protecting group. Protecting groups suitable for the protection of carboxylic acids together with methods for deprotection are described in P. G. Wuts, *Greene's Protective Groups in Organic Synthesis*, Wiley 2014. In a preferred case of the present invention, $PG^1$ is a tert-butyl group.

$PG^2$ is a protecting group suitable for the protection of alcohols or $PG^2$ is hydrogen. In the case of $PG^2$ being hydrogen, the step (IVa) in the above shown Scheme 1 is obsolete as then the compound (IIIa) is directly reacted to form compound (Va).

In a preferred case of the present invention, $PG^2$ is hydrogen and no deprotection step (IVa→Va) is necessary.

In the above shown Scheme 1 for preparing the protected pro-moiety in the first stage of the process of the present invention, a compound of formula (IIa) is reacted with an acid of formula (IIIa). To this end, the acid (IIIa) is first activated by converting it into an acid chloride or into an activated ester using a coupling agent such as HATU, TBTU. Suitable coupling methods are known e.g. from C. A. G. N. Montalbetti, V. Falque, *Tetrahedron* 2005, 61, 10827-10852. In a second step, the activated acid is reacted with compound (IIa) in the presence of a base.

In a preferred case, acid (IIIa) is activated by converting it into the acid chloride using oxalic chloride in the presence of a catalytic amount of DMF in dichloromethane and is then reacted with (IIa) in the presence of an amine base, e.g. DIPEA, TEA in a polar aprotic solvent, e.g. DMF, THF, acetonitrile. Optionally, a catalytic amount of DMAP may be used to facilitate this reaction.

In cases where $PG^2$ is not hydrogen, compound (Va) is obtained by selectively cleaving $PG^2$ from the compound (IVa) in the presence of $PG^1$.

Synthesis Route (b for Compounds (I) Wherein $L^2$ is Absent and Q is O

The following Scheme 2 describes the synthesis of the protected pro-moiety of the above mentioned first stage of the process of the present invention for preparing compounds (I) wherein $L^1$ and $L^3$ have the meaning as defined anywhere above and wherein $L^2$ is absent and Q is selected to be O.

Scheme 2

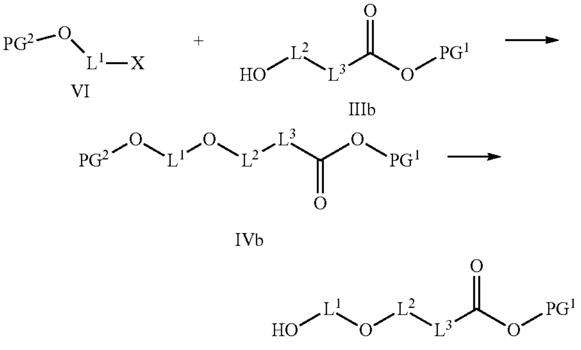

VI IIIb IVb Vb

Therein, X is a leaving group and may be Cl, Br, I, or a sulfonate ester such as triflate, mesylate or para-toluenesulfonate ester. X may also be OH. In a preferred case, X is a halogen selected from Cl, Br or I.

$PG^2$ is a protecting group suitable for the protection of alcohols or $PG^2$ is hydrogen. In the case of $PG^2$ being hydrogen, the step (IVb) in the above shown Scheme 2 is obsolete as then the compound (IIIb) is directly reacted to form compound (Vb).

In a preferred case of the present invention, $PG^2$ is a benzyl ether group or a substituted benzyl ether group.

In the above shown Scheme 2 for preparing the protected pro-moiety in the first stage of the process of the present invention, in a first step, compound (VI) is reacted with compound (IIIb) under the conditions of a Williamson ether synthesis. This requires to treat a solution of (IIIb) with a base, then add compound (VI) and let the reaction proceed at room temperature or above. Strong bases can be used, for instance hydride bases, bis(trimethyldisilyl)amide (HMDS) bases, amidine bases or phosphazene bases.

In a preferred case, sodium hydride or sodium bis(trimethyldisilyl)amide is used. Preferred solvents are polar aprotic solvents, e.g. THF or DMF.

The ether products (IVb) are converted into alcohols (Vb) by removal of the protecting group $PG^2$.

In a preferred case, $PG^2$ is a benzyl group and removal is accomplished by hydrogenation in the presence of palladium on charcoal in a protic solvent such as methanol, ethanol, acetic acid or mixtures of these solvents.

Synthesis Route (c) for Compounds (I) Wherein Q is Absent

The following Scheme 3 describes the synthesis of the protected pro-moiety of the above mentioned first stage of the process of the present invention for preparing compounds (I) wherein $L^1$, $L^2$ and $L^3$ have the meaning as defined anywhere above and wherein Q is absent and thus, no bond between $L^1$-Q or $L^2$-Q or $L^3$-Q needs to be formed.

Scheme 3

Vc

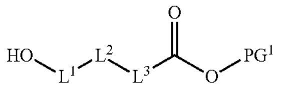

$PG^1$ is a protecting group suitable for the protection of carboxylic acids. By preference, $PG^1$ is a tert-butyl group. Compounds of formula (Vc) can be obtained commercially or synthesized according to methods described in the well-known literature.

Second Stage of the Process—Preparation of Compounds (I)

The second stage of the process of the present invention is shown in Scheme 4.

Scheme 4

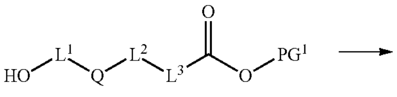

V

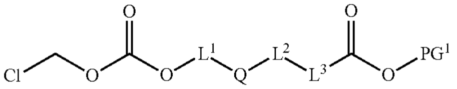

VII

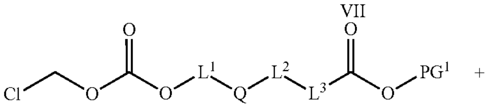

VII

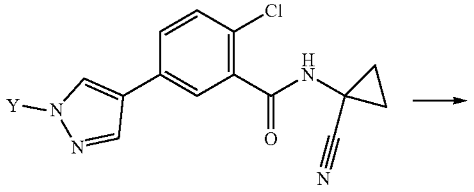

VIII

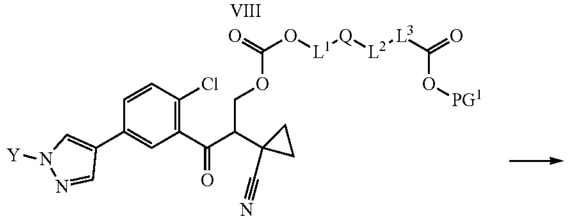

IX

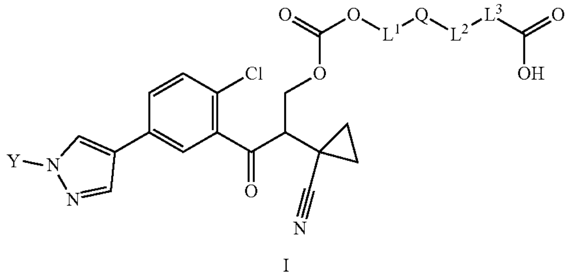

I

Therein, $L^1$, $L^2$, $L^3$, Q, R and $PG^1$ are defined as described above.

This second stage of the synthesis of the invention may be carried out starting from any intermediate (Va), (Vb) and (Vc), resulting from the first stage of the process as described above. Said starting intermediates are herein generally designated as intermediate (V).

In a first step of the second stage of the process, intermediate compounds (V) are treated with chloromethyl carbonochloridate leading to chloromethyl esters (VII). The reaction is carried out in a solvent in the presence of a base. Dipolar aprotic solvents such as DMF, THF, acetonitrile, or pyridine can be used. The base may be an amine base like e.g. DIPEA, TEA, DMAP. In a preferred case, pyridine serves both as the solvent and the base.

In the next step of the second stage of the process, an amide of formula (VIII) is treated with a base and then reacted with a chlorocarbonate ester of formula (VII). Strong bases can be used, for instance tert-butylates, hydride bases, amide bases, bis(trimethyldisilyl)amide (HMDS) bases, amidine bases or phosphazene bases. In a preferred case, sodium hydride or NaHMDS is used. The reaction is generally carried out in a solvent, usually in a polar aprotic solvent such as THF, diethyl ether, DMF or a mixture of a polar aprotic solvent and other solvents.

The protecting group $PG^1$ can be cleaved to provide the compound (I) of the present invention. In a preferred case, $PG^1$ is a tert-butyl group and is removed by treating compound (IX) with a solution of hydrochloric acid in 1,4 dioxane or with a solution of TFA in dichloromethane.

EXAMPLES

List of Abbreviations

AA *Amblyomma americanus* (parasitology)
abs. Absolute
Ac Acetyl
aq. Aqueous, aqueous solution
AUC Area under the curve (in Pharmacokinetics)
cat. Catalytic
CF *Ctenocephalides felis* (parasitology)
CI Chemical ionisation (mass spectroscopy)
conc Concentrated
d Doublet (NMR)
d Day(s)
dd Doublet of doublet (NMR)
DCM Dichloromethane
DIPEA N,N,-diisopropylethylamine (Hünig's base)
DMAP 4-Dimethylaminopyridine
DMF N,N-dimethylformamide
DMSO Dimethylsulfoxide
dt Doublet of triplet (NMR)
DV *Dermacentor variabilis* (parasitology)
ent Enantiomeric
eq. Equivalent(s)
ESI Electrospray-ionisation (mass spectroscopy)
F Bioavailability (in Pharmacokinetics)
GC Gas chromatography
GC/MS Gas chromatography coupled to mass spectroscopy
h Hour(s)
HATU O-(7-Azabenzotriazol-1-yl)-N,N,N',N'-tetramethyluronium-hexafluorophosphate
HMDS Bis(trimethyldisilyl)amide formerly also referred to as hexamethyldisilazide, counterion in strongly basic salts such as LiHMDS, NaHMDS, KHMDS
HPLC High pressure liquid chromatography
iPr Isopropyl IR *Ixodes* rhicinus (parasitology)
iv Intravenous (PK)
KHMDS Potassium bis(trimethyldisilyl)amide
LC Liquid chromatography
LC-MS Liquid chromatography coupled to mass spectroscopy
LiHMDS Lithium bis(trimethyldisilyl)amide
Lit. Literature
m Multiplet (NMR)
Me Methyl
min Minute(s)
MS Mass spectroscopy
MTBE tert-Butyl methyl ether
NaHMDS Sodium bis(trimethyldisilyl)amide
NMP N-Methyl-2-pyrrolidone
NMR Nuclear magnetic resonance spectroscopy
PBS Phosphate buffered saline
PEG Polyethylene glycol
PK Pharmacokinetics
Pr Propyl
q (or quart) Quartet (NMR)
qd Quartet of doublet (NMR)
quant. quantitative (referring to chemical yield)
quint Quintet (NMR)
rac racemic
RP reverse phase (for liquid chromatography)
RS *Rhipicephalus sanguineus* (parasitology)
$R_t$ Retention time (chromatography)
s Singulet (NMR)
Sc Subcutaneous (PK and pharmacology)
SD Study day
sept Septet (NMR)
t Triplet (NMR)
t Time point (during an experiment)
$t_0$ Time point at beginning of an experiment
TBTU O-(Benzotriazol-1-yl)-N,N,N,N'-tetramethyluronium-tetrafluoroborate
tBu tert.-Butyl
td Triplett of doublett (NMR)
TEA triethylamine
TFA Trifluoro acetic acid
THF Tetrahydrofuran
UV Ultraviolett-spectroscopy Analytical Methods Method 1 (HPLC-MS)

Instrument: Agilent MS Quad 6150; HPLC: Agilent 1290; Column: Waters Acquity UPLC HSS T3 1.8 μm 50×2.1 mm; Eluent A: 1 l water+0.25 ml 99% ige Formic acid, Eluent B: 1 l Acetonitrile+0.25 ml 99% ige Formic acid; Gradient: 0.0 min 90% A→0.3 min 90% A→1.7 min 5% A→3.0 min 5% A Column temperature: 50° C.; Flow: 1.20 ml/min; UV-Detektion: 205-305 nm.

Method 2 (HPLC-MS)

Instrument: Waters ACQUITY SQD UPLC System; Column: Waters Acquity UPLC HSS T3 1.8 μm 50×1 mm; eluent A: 1 l water+0.25 ml 99% ige formic acid, eluent B: 1 L acetonitrile+0.25 ml 99% formic acid; gradient: 0.0 min 90% A→1.2 min 5% A→2.0 min 5% A column temperature: 50° C.; flow: 0.40 ml/min; UV-detection: 210 nm.

Method 3 (HPLC-MS)

Instrument MS: Thermo Scientific FT-MS; instrument UHPLC+: Thermo Scientific UltiMate 3000; Column: Waters, HSST3, 2.1×75 mm, C18 1.8 μm; eluent A: 1 L water+0.01% formic acid; eluent B: 1 L acetonitrile+0.01% formic acid; gradient: 0.0 min 10% B→2.5 min 95% B→3.5 min 95% B; column temperature: 50° C.; flow: 0.90 ml/min; UV-detection: 210 nm/Optimum Integration Path 210-300 nm Method 4 (HPLC-MS)

Instrument: Waters ACQUITY SQD UPLC System; Column: Waters Acquity UPLC HSS T3 1.8 μm 50×1 mm; eluent A: 1 L water+0.25 ml 99% formic acid, eluent B: 1 L acetonitrile+0.25 ml 99% formic acid; gradient: 0.0 min 95% A→6.0 min 5% A→7.5 min 5% A column temperature: 50° C.; flow: 0.35 ml/min; UV-Detection: 210 nm.

Method 5 (HPLC-MS)

The column used was a Shim-pack XR-ODS, 2.2 μm, 3.0×50 mm. A linear gradient was applied, starting at 95% A (A: 0.05% TFA in water) and ending at 100% B (B: 0.05% TFA in acetonitrile) over 4.70 min with a total run time of 5.00 min. The column temperature was at 45° C. with the flow rate of 1.20 mL/min.

Method 6 (HPLC-MS)

The column used was a Shim-pack XR-ODS, 2.2 μm, 3.0×50 mm. A linear gradient was applied, starting at 95% A (A: 0.05% TFA in water) and ending at 100% B (B: 0.05% TFA in acetonitrile) over 1.70 min with a total run time of 2.00 min. The column temperature was at 40° C. with the flow rate of 1.20 mL/min.

Method 7 (HPLC-MS)

The column used was a Kinetex EVO C18 100A, 2.6 μm, 3.0×50 mm. A linear gradient was applied, starting at 90% A (A: 0.03% $NH_3H_2O$ in water) and ending at 95% B (B: acetonitrile) over 1.70 min with a total run time of 2.00 min. The column temperature was at 40° C. with the flow rate of 1.20 mL/min.

Method 8 (HPLC)

Instrument: HP 1260 Infinity HPLC System with G4212B diode array detector; column: Kromasil 100 C18ec 5 μm 250×4 mm; eluent A: 1 L water+1.0 mL TFA, eluent B: 1 L acetonitrile+1.0 mL TFA; 20 gradient: 0.0 min 98% A→1.0 min 98% A→8.0 min 30% A→16.0 min 30% A→19.0 min 2% A→20.0 min 2% A→23.0 min 98% A→25.0 min 30% A, column temperature: 37° C.; flow: 1.5 mL/min; UV-Detection: 214 nm, injection volume 10 μL.

Method 9 (HPLC-MS)

Instrument: HP 1200 Infinity HPLC System with G1315B diode array detector; Waters MS QuattroMicro (ESI+/ESI−) column: Kromasil 100 C18ec 5 μm 250×4 mm; eluent A: 1 L water+0.5 mL 50% HCOOH, eluent B: 1 L acetonitrile+0.5 mL 50% HCOOH; gradient: 0.0 min 98% A→1.0 min 98% A→8.0 min 30% A→16.0 min 30% A→19.0 min 2% A→20.0 min 2% A→23.0 min 98% A→25.0 min 30% A, column temperature: 37° C.; flow: 1.5 mL/min; UV-Detection: 214 nm, injection volume 10 μL Synthesis of Starting Materials 2-Chlor-5-{1-[2-chlor-4-(1,1,1,2,3,3,3-heptafluorpropan-2-yl)-6-(trifluormethoxy)phenyl]-1H-pyrazol-4-yl}-N-(1-cyanocyclopropyl)benzamide (CAS-RN 1771742-44-9) was synthesised as described in WO 2015/067646 A1.

(2E)-4-tert-Butoxy-4-oxobut-2-enic acid (CAS RN 135355-96-3) was synthesised according to the method published by P. A. Clarke, R. L. Davie S. Peace, *Tetrahedron Lett.* 2002, 43, 2753-2756.

tert-Butyl 3-hydroxy-2,2-dimethylpropanoate (CAS RN 25307-76-0) was prepared as described in WO2007/116922 (page 51).

tert-Butyl cis-4-hydroxycyclohexanecarboxylate (CAS-RN 931110-79-1) was prepared according to a procedure described in WO 2009/081195.

tert-Butyl trans-4-hydroxycyclohexanecarboxylate (CAS-RN 869193-57-7) was prepared according to a procedure described in 2010126030.

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (CAS-RN 1621436-41-6) was prepared according to procedures described in WO 2014/122083 A1, WO 2015/078846 A1 and WO 2015/181139 A1.

SYNTHESIS OF INTERMEDIATES

Intermediate 1A

Tert-Butyl-(2E)-4-chloro-4-oxobut-2-enoate

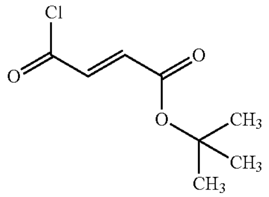

(2E)-4-tert-Butoxy-4-oxobut-2-enic acid (172 mg, 1.00 mmol) and DMF (5 μL) were dissolved in DCM (2.0 mL) and cooled to 0° C. Oxalic chloride (1.0 ml, 2.0 M, 2.0 mmol) was added dropwise under stirring. Stirring was continued until the evolution of gas ceased. Then, the solvent was distilled and the residue was used without purification in the next step. Yield: 191 mg (quant.).

Intermediate 2A

Tert-Butyl-2-hydroxyethyl-(2E)-but-2-enedioate

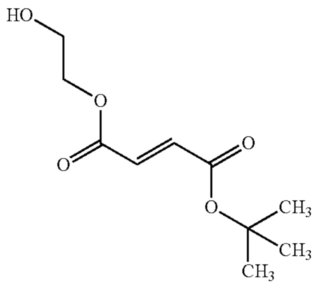

Ethylene glycol (1.1 ml, 20 mmol) and DIPEA (520 μl, 3.0 mmol) were dissolved in DCM (2.0 ml) and a solution of tert-Butyl-(2E)-4-chloro-4-oxobut-2-enoate (Intermediate 1A, 191 mg, 1.00 mmol) in DCM (3.0 mL) was slowly added. The mixture was stirred at ambient temperature for 16 h. Then, water was added, the mixture was extracted with 3 portions of DCM and the combined organic extracts were dried over anhydrous sodium sulfate and evaporated. The solution was purified by chromatography on silica gel (cyclohexane/ethyl acetate 1:1). The title compound (166 mg, 77% of theory) was obtained LC-MS (method 1): $R_t$=1.02 min; MS (ESIpos): m/z=217 $[M+H]^+$ $^{1}$H-NMR (400 MHz, DMSO-$d^6$) δ [ppm]: 1.467 (16.00), 3.607 (0.69), 3.618 (0.75), 4.144 (0.83), 4.157 (0.96), 4.169 (0.75), 4.875 (0.72), 6.690 (1.30), 6.698 (1.32).

Intermediate 3A

Tert-Butyl-2-{[(chloromethoxy)carbonyl]oxy}ethyl-(2E)-but-2-enedioate

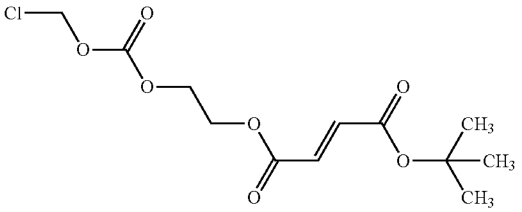 [SMILES: CC(C)(C)OC(=O)/C=C/C(=O)OCCOC(=O)OCCl]

tert-Butyl-2-hydroxyethyl-(2E)-but-2-enedioate (intermediate 2A, 164 mg, 758 μmol) was dissolved in pyridine (3.0 mL) and the solution was cooled to 0° C. Chloromethyl carbonochloridate (100 μl, 1.2 mmol) was added at once and the mixture was stirred at room temperature for 45 min. The solvent was evaporated. The residue was redissolved in ethyl acetate (100 mL) washed with water (30 mL) and brine (30 mL) dried over anhydrous sodium sulfate and evaporated. The crude product was purified by chromatography on silica gel (cyclohexane/ethyl acetate 3:1) to give 174 mg (74% of theory) of the title compound.

LC-MS (method 2): $R_t$=0.98 min; MS (ESIpos): m/z=143 $[M+H-C_6H_{12}ClO_7]^+$ $^{1}$H-NMR (400 MHz, DMSO-$d^6$) δ [ppm]: 1.461 (16.00), 4.402 (0.63), 4.411 (0.64), 4.416 (0.79), 4.452 (0.80), 4.456 (0.64), 4.466 (0.64), 5.906 (3.88), 6.674 (3.58).

Intermediate 4A

Tert-Butyl-2-[({[(2-chloro-5-{1-[2-chloro-4-(1,1,1,2,3,3,3-heptafluorpropane-2-yl)-6-(trifluormethoxy)phenyl]-1H-pyrazol-4-yl}benzoyl)(1-cyanocyclopropyl)amino]methoxy}carbonyl)oxy]ethyl-(2E)-but-2-enedioate

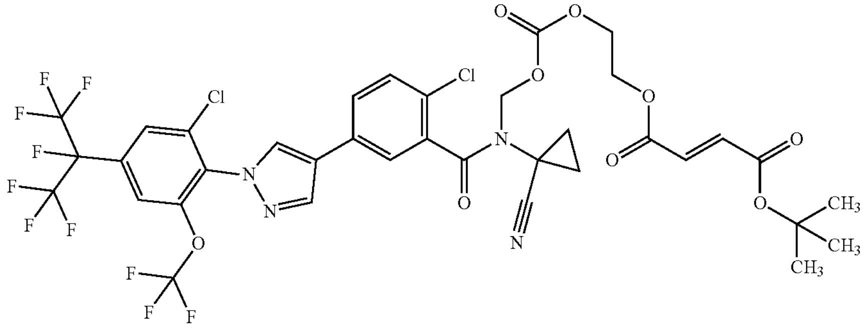 [SMILES: CC(C)(C)OC(=O)/C=C/C(=O)OCCOC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (162 mg, 250 μmol) was dissolved in dry THF (8.0 mL) This solution was cooled to −45° C. on an acetone-dry ice bath. Potassium bis(trimethylsilyl)amide (800 μl, 0.50 M solution in toluene, 400 μmol) was added dropwise and the mixture was stirred 30 min. at −45° C. Then, sodium iodide (19 mg, 125 μmol) and a solution of tert-butyl-2-{[(chlormethoxy)carbonyl]oxy}ethyl-(2E)-but-2-enedioate (intermediate 3A, 116 mg, 375 μmol) in THF (2.0 mL) was added, the dry ice bath was removed and the mixture was stirred at room temperature for 60 min. The reaction mixture was poured into water (30 mL) and extracted with 3 portions of ethyl acetate. The combined organic extracts were dried over anhydrous sodium sulfate, filtered and evaporated. The crude product was purified by preparative HPLC (RP C-18 10 μm water-acetonitrile gradient with 0.01% TFA in both eluents, 90:10->5:95). 210 mg (91% of theory) of the title compound were obtained.

LC-MS (method 3): $R_t$=2.70 min; MS (ESIpos): m/z=943 $[M+Na]^+$ $^1$H-NMR (400 MHz, DMSO-$d^6$) δ [ppm]: −0.008 (0.76), 0.008 (0.80), 1.356 (0.69), 1.443 (16.00), 4.308 (0.69), 6.647 (3.15), 7.801 (0.59), 7.927 (0.68), 8.201 (0.73), 8.436 (0.70), 8.765 (0.47).

Intermediate 5A

Tert-Butyl 3-hydroxypropyl (2E)-but-2-enedioate

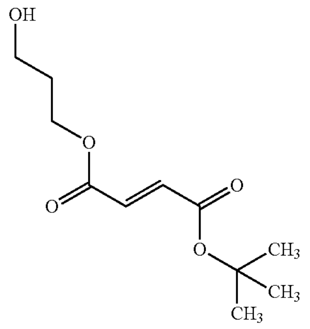 [SMILES: CC(C)(C)OC(=O)/C=C/C(=O)OCCCO]

Propane-1,3-diol (7.2 ml, 100 mmol) and DIPEA (2.6 mL, 15.0 mmol) were dissolved in DCM (25 ml) and a solution of tert-Butyl-(2E)-4-chloro-4-oxobut-2-enoate (intermediate 1A, 953 mg, 5.0 mmol) in DCM (15 mL) was slowly added. The mixture was stirred for a few minutes and then quenched with water. The mixture was extracted with 3 portions of DCM and the combined organic extracts were dried over anhydrous sodium sulfate and evaporated. The crude product was purified by chromatography on silica gel (cyclohexane/ethyl acetate 1:1) to give title compound (800 mg, 69% of theory).

LC-MS (method 3): $R_t$=1.51 min; MS (ESIpos): m/z=175 $[M+H-C_4H_8]^+$ $^1$H-NMR (500 MHz, DMSO-$d^6$) δ [ppm]: 1.464 (16.00), 1.755 (0.65), 1.768 (1.00), 1.781 (0.66), 3.476 (0.80), 3.486 (0.81), 4.197 (0.69), 4.210 (1.44), 4.223 (0.66), 4.529 (0.43), 4.539 (0.89), 4.550 (0.40), 6.658 (2.00), 6.665 (1.99).

Intermediate 6A

Tert-butyl 3-{[(chloromethoxy)carbonyl]oxy}propyl (2E)-but-2-enedioate

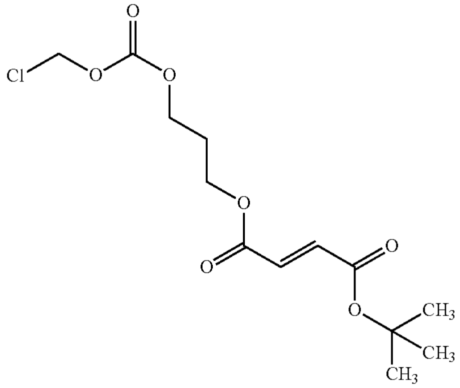 [SMILES: CC(C)(C)OC(=O)/C=C/C(=O)OCCCOC(=O)OCCl]

tert-Butyl 3-hydroxypropyl (2E)-but-2-enedioate (intermediate 5A, 800 mg, 3.47 mmol) was dissolved in pyridine (13 mL) and the solution was cooled to 0° C. Chloromethyl carbonochloridate (460 μl, 5.2 mmol) was added at once and the mixture was stirred at room temperature for 45 min. The solvent was evaporated. The residue was redissolved in ethyl acetate (250 mL) washed with water (30 mL) and brine (30 mL) dried over anhydrous sodium sulfate and evaporated. The crude product was purified by chromatography on silica gel (cyclohexane->cyclohexane/ethyl acetate 85:15) to give 1.13 g (quant.) of the title compound.

$^1$H-NMR (500 MHz, DMSO-$d^6$) δ [ppm]: 1.465 (16.00), 1.761 (1.01), 2.007 (0.54), 2.020 (0.80), 2.032 (0.55), 3.602 (0.83), 4.213 (0.61), 4.225 (1.23), 4.238 (0.58), 4.283 (0.64), 4.296 (1.34), 4.308 (0.61), 5.889 (4.18), 6.673 (4.59).

Intermediate 7A

Tert-Butyl 3-[({[(2-chloro-5-{1-[2-chloro-4-(1,1,1,2,3,3,3-heptafluoropropan-2-yl)-6-(trifluorometh-oxy)phenyl]-1H-pyrazol-4-yl}benzoyl)(1-cyanocyclopropyl)amino]methoxy}carbonyl)oxy]propyl (2E)-but-2-enedioate

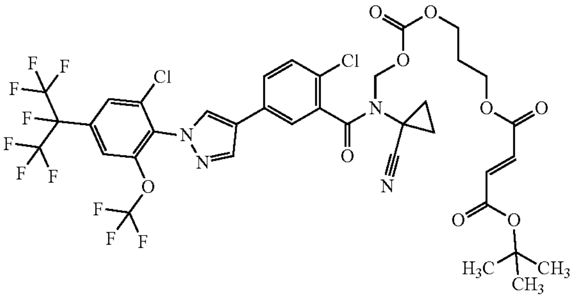 [SMILES: CC(C)(C)OC(=O)/C=C/C(=O)OCCCOC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (195 mg, 300 μmol) was dissolved in dry THF (9.6 mL) This solution was cooled to −45° C. on an acetone-dry ice bath. Potassium bis(trimethylsilyl)amide (960 µl, 0.50 M solution in toluene, 480 µmol) was added dropwise and the mixture was stirred 30 min. at −45° C. Then, sodium iodide (23 mg, 150 µmol) and a solution of tert-butyl 3-{[(chloromethoxy)carbonyl]oxy}propyl (2E)-but-2-enedioate (intermediate 6A, 145 mg, 450 µmol) in THF (2.0 mL) was added, the dry ice bath was removed and the mixture was stirred at room temperature for 60 min. The reaction mixture was poured into water (30 mL) and extracted with 3 portions of ethyl acetate. The combined organic extracts were dried over anhydrous sodium sulfate, filtered and evaporated. The crude product was purified by preparative HPLC (RP C-18 10 µm, water-acetonitrile gradient with 0.01% TFA in both eluents, 90:10->5:95). 195 mg (69% yield) of the title compound were obtained.

LC-MS (method 2): $R_t$=1.51 min; MS (ESIpos): m/z=935 $[M+H]^+$ $^1$H-NMR (500 MHz, DMSO-$d^6$) δ [ppm]: −0.007 (0.99), 0.006 (0.67), 1.356 (0.48), 1.446 (16.00), 6.643 (1.46), 7.925 (0.48), 8.200 (0.54), 8.203 (0.52).

Intermediate 8A

Tert-Butyl 2-hydroxyethyl Butanedioate

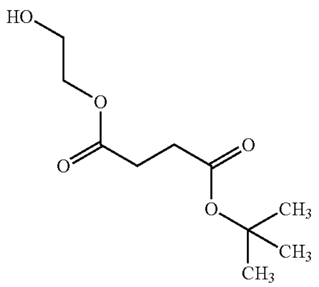

tert-Butyl 2-hydroxyethyl (2E)-but-2-enedioate (intermediate 2A, 345 mg, 1.60 mmol) was dissolved in ethanol (35 mL) under an argon atmosphere. 10% Palladium on charcoal (84.9 mg, 79.8 µmol) was added and the mixture was hydrogenated for 30 min at ambient pressure at room temperature. The catalyst was then removed by filtration over a layer of diatomaceous earth and the solvent was distilled. 347 mg (quant.) of the title compound were obtained.

$^1$H-NMR (400 MHz, DMSO-$d^6$) δ [ppm]: 1.385 (16.00), 2.450 (0.68), 2.455 (0.60), 2.465 (0.86), 2.467 (0.93), 3.532 (0.41), 3.545 (0.87), 3.558 (0.98), 3.571 (0.47), 4.003 (0.86), 4.016 (1.07), 4.029 (0.77), 4.778 (0.68).

Intermediate 9A

Tert-Butyl 2-{[(chloromethoxy)carbonyl]oxy}ethyl butanedioate

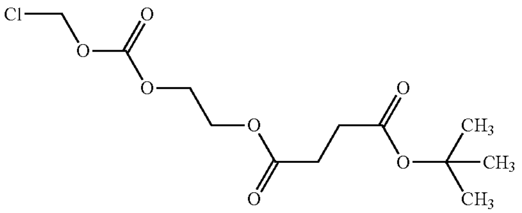 [SMILES: CC(C)(C)OC(=O)CCC(=O)OCCOC(=O)OCCl]

tert-Butyl 2-hydroxyethyl butanedioate (intermediate 8A, 170 mg, 779 µmol) was dissolved in pyridine (5.0 mL) and the solution was cooled to 0° C. Chloromethyl carbonochloridate (100 µl, 1.2 mmol) was added at once and the mixture was stirred at room temperature for 45 min. The solvent was evaporated. The residue was redissolved in ethyl acetate (100 mL) washed with water (30 mL) and brine (30 mL) dried over anhydrous sodium sulfate and evaporated. The crude product was purified by chromatography on silica gel (gradient cyclohexane-cyclohexane/ethyl acetate 7:3) to give 189 mg (78% of theory) of the title compound.

$^1$H-NMR (400 MHz, DMSO-$d^6$) δ [ppm]: 1.381 (16.00), 2.449 (0.71), 2.455 (0.58), 2.465 (0.79), 2.467 (0.83), 2.516 (0.86), 4.252 (0.57), 4.263 (0.73), 4.269 (0.55), 4.275 (0.87), 4.373 (0.90), 4.378 (0.56), 4.385 (0.74), 4.388 (0.54), 4.395 (0.59), 5.905 (3.70).

Intermediate 10A

Tert-Butyl 2-[({[(2-chloro-5-{1-[2-chloro-4-(1,1,1,2,3,3,3-heptafluoropropan-2-yl)-6-(trifluorometh-oxy)phenyl]-1H-pyrazol-4-yl}benzoyl)(1-cyanocyclopropyl)amino]methoxy}carbonyl)oxy]ethyl Butanedioate

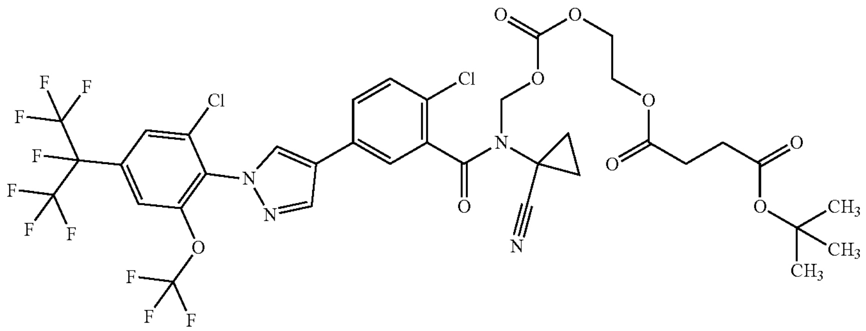 [SMILES: CC(C)(C)OC(=O)CCC(=O)OCCOC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chlor-5-{1-[2-chlor-4-(1,1,1,2,3,3,3-heptafluorpropan-2-yl)-6-(trifluormethoxy)phenyl]-1H-pyrazol-4-yl}-N-(1-cyanocyclopropyl)benzamide (258 mg, 397 µmol) was dissolved in dry THF (13 mL) This solution was cooled to −45° C. on an acetone-dry ice bath. Potassium bis(trimethylsilyl)amide (1.3 mL, 0.50 M solution in toluene, 640 µmol) was added dropwise and the mixture was stirred for 30 min. at −45° C. Then, sodium iodide (30 mg, 198 µmol) and a solution of tert-butyl 2-{[(chloromethoxy)carbonyl]

oxy}ethyl butanedioate (intermediate 9A, 185 mg, 595 μmol) in THF (2.0 mL) was added, the dry ice bath was removed and the mixture was stirred at room temperature for 30 min. The reaction mixture was poured into water (30 mL) and extracted with 3 portions of ethyl acetate. The combined organic extracts were dried over anhydrous sodium sulfate, filtered and evaporated. The crude product was purified by preparative HPLC (RP C-18 10 μm, water-acetonitrile gradient with 0.01% TFA in both eluents, 90:10->5:95). 272 mg (100% purity, 74% yield) of the title compound were obtained.

LC-MS (method 3): $R_t$=2.67 min; MS (ESIpos): m/z=923 $[M+H]^+$ $^1$H-NMR (400 MHz, DMSO-$d^6$) δ [ppm]: −0.008 (1.00), 0.008 (0.86), 1.353 (16.00), 1.758 (0.64), 2.073 (0.70), 2.414 (0.92), 2.430 (1.07), 2.459 (0.86), 2.475 (0.91), 2.524 (0.56), 4.184 (0.90), 7.612 (0.44), 7.798 (0.77), 7.826 (0.46), 7.935 (1.11), 8.208 (1.25), 8.444 (1.01), 8.770 (0.84).

Intermediate 11A

Tert-Butyl 3-hydroxy-2,2-dimethylpropyl (2E)-but-2-enedioate

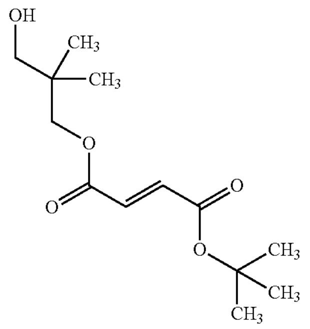 [SMILES: CC(C)(CO)COC(=O)/C=C/C(=O)OC(C)(C)C]

2,2-dimethylpropane-1,3-diol (3.12 g, 30.0 mmol) and N,N-diisopropylethylamine (3.1 mL, 18 mmol) were dissolved in DCM (30 mL) and a solution of tert-butyl (2E)-4-chloro-4-oxobut-2-enoate (intermediate 1A, 1.14 g, 6.00 mmol) in DCM (15 mL) was slowly added. The mixture was stirred at ambient temperature for 30 min. Then, water was added, the mixture was extracted with 3 portions of DCM and the combined organic extracts were dried over anhydrous sodium sulfate and evaporated. The solution was purified by chromatography on silica gel (gradient cyclohexane-cyclohexane/ethyl acetate 3:1). 1.35 g (98% purity, 85% yield) of the title compound was obtained.

$^1$H-NMR (400 MHz, DMSO-$d^6$) δ [ppm]: 0.851 (9.22), 1.469 (16.00), 3.189 (1.31), 3.202 (1.33), 3.929 (2.93), 4.641 (0.79), 6.663 (1.97), 6.676 (1.95).

Intermediate 12A

Tert-Butyl 3-{[(chloromethoxy)carbonyl]oxy}-2,2-dimethylpropyl (2E)-but-2-enedioate

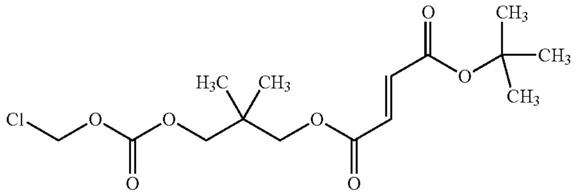 [SMILES: CC(C)(COC(=O)/C=C/C(=O)OC(C)(C)C)COC(=O)OCCl]

tert-Butyl 3-hydroxy-2,2-dimethylpropyl (2E)-but-2-enedioate (intermediate 11A, 675 mg, 2.61 mmol) was dissolved in pyridine (30 mL) and the solution was cooled to 0° C. Chloromethyl carbonochloridate (350 μl, 3.9 mmol) was added at once and the mixture was stirred at room temperature for 60 min. The solvent was evaporated. The residue was redissolved in ethyl acetate (250 mL) washed with water (20 mL) and brine (20 mL) dried over anhydrous sodium sulfate and evaporated. The crude product was purified by chromatography on silica gel (gradient cyclohexane-cyclohexane/ethyl acetate 8:2). 782 mg (98% purity, 84% yield) of the title compound were isolated.

$^1$H-NMR (400 MHz, DMSO-$d^6$) δ [ppm]: 0.962 (8.32), 1.470 (16.00), 3.979 (2.70), 4.073 (2.62), 5.891 (3.77), 6.692 (3.31).

Intermediate 13A

Tert-Butyl 3-[({[(2-chloro-5-{1-[2-chloro-4-(1,1,1,2,3,3,3-heptafluoropropan-2-yl)-6-(trifluorometh-oxy)phenyl]-1H-pyrazol-4-yl}benzoyl)(1-cyanocyclopropyl)amino]methoxy}carbonyl)oxy]-2,2-dimethylpropyl(2E)-but-2-enedioate

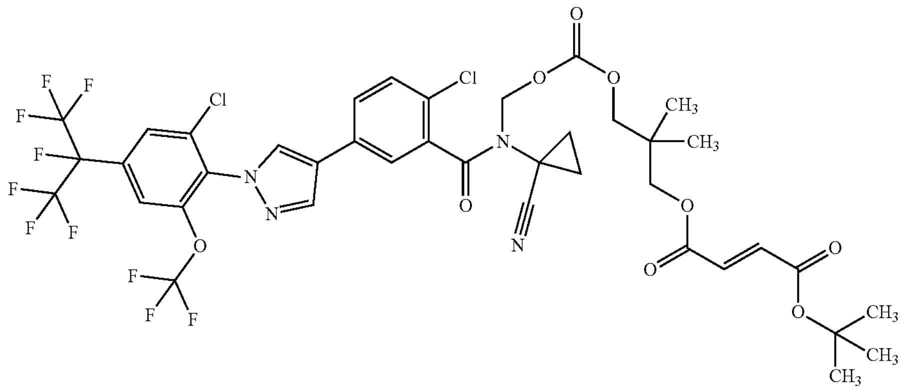 [SMILES: CC(C)(COC(=O)/C=C/C(=O)OC(C)(C)C)COC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (301 mg, 463 μmol) was dissolved in dry THF (8 mL) This solution was cooled to −45° C. on an acetone-dry ice bath. Potassium bis(trimethylsilyl)amide (1.2 mL, 0.50 M solution in toluene, 600 μmol) was added dropwise and the mixture was stirred for 30 min. at −45° C. Then, sodium iodide (35 mg, 232 μmol) and a solution of tert-butyl 3-{[(chloromethoxy)carbonyl]oxy}-2,2-dimethylpropyl (2E)-but-2-enedioate (intermediate 12A, 195 mg, 556 μmol) in THF (4.0 mL) was added, the dry ice bath was removed and the mixture was stirred at room temperature for 30 min. The reaction mixture was poured into water (30 mL) and extracted with 3 portions of ethyl acetate. The combined organic extracts were dried over anhydrous sodium sulfate, filtered and evaporated. The crude product was purified by preparative HPLC (RP C-18 10 μm, water-acetonitrile gradient with 0.01% TFA in both eluents, 90:10->5:95). 303 mg (68% yield) of the title compound were obtained.

catalyst was then removed by filtration over a layer of diatomaceous earth and the solvent was distilled. 385 mg (93% purity, 92% yield) of the title compound were obtained.

$^1$H-NMR (400 MHz, DMSO-d$^6$) δ [ppm]: 0.924 (8.41), 1.355 (0.62), 1.378 (16.00), 2.459 (0.44), 2.463 (0.69), 2.470 (0.79), 2.478 (1.07), 2.480 (1.14), 2.515 (0.83), 2.523 (0.76), 3.848 (2.59), 4.021 (2.73), 5.896 (3.77).

Intermediate 15A

Tert-Butyl 3-[({[(2-chloro-5-{1-[2-chloro-4-(1,1,1,2,3,3,3-heptafluoropropan-2-yl)-6-(trifluorometh-oxy)phenyl]-1H-pyrazol-4-yl}benzoyl)(1-cyanocyclopropyl)amino]methoxy}carbonyl)oxy]-2,2-dimethylpropyl Butanedioate

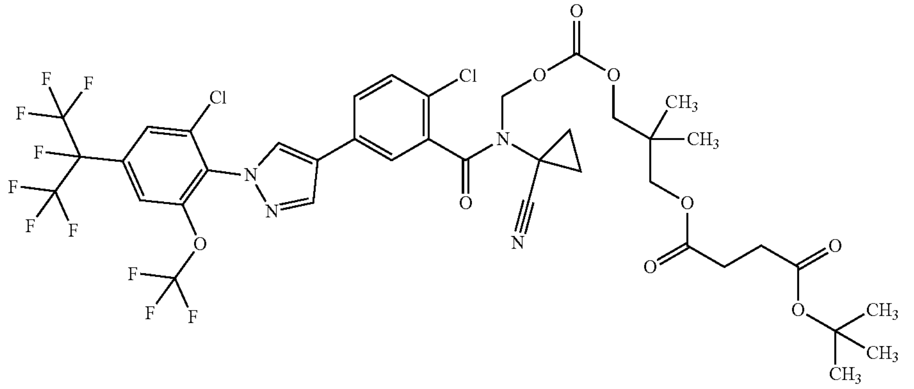

LC-MS (method 4): $R_t$=5.54 min; MS (ESIpos): m/z=963 [M+H]$^+$ $^1$H-NMR (400 MHz, DMSO-d$^6$) δ [ppm]: 0.883 (2.25), 1.448 (16.00), 1.464 (0.51), 2.524 (0.93), 3.911 (1.10), 6.656 (1.25), 7.800 (0.60), 7.929 (0.60), 8.203 (0.70), 8.436 (0.53), 8.753 (0.43).

Intermediate 14A

Tert-Butyl 3-{[(chloromethoxy)carbonyl]oxy}-2,2-dimethylpropyl Butanedioate

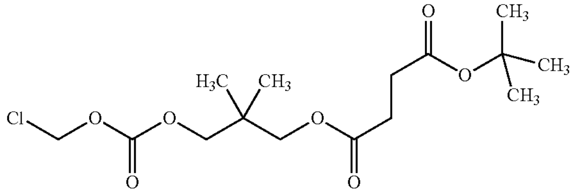 [SMILES: CC(C)(COC(=O)CCC(=O)OC(C)(C)C)COC(=O)OCCl]

tert-Butyl 3-{[(chloromethoxy)carbonyl]oxy}-2,2-dimethylpropyl (2E)-but-2-enedioate (intermediate 12A, 390 mg, 1.11 mmol) was dissolved in THF (20 mL) under an argon atmosphere. 10% Palladium on charcoal (87.9 mg, 111 μmol) was added and the mixture was hydrogenated for 40 min at ambient pressure at room temperature. The 2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (301 mg, 463 μmol) was dissolved in dry THF (8 mL). This solution was cooled to −45° C. on an acetone-dry ice bath. Potassium bis(trimethylsilyl)amide (1.2 mL, 0.50 M solution in toluene, 600 μmol) was added dropwise and the mixture was stirred 30 min. at −45° C. Then, a solution of sodium iodide (35 mg, 232 μmol) and tert-butyl 3-{[(chloromethoxy)carbonyl]oxy}-2,2-dimethylpropyl butanedioate (intermediate 14A, 196 mg, 556 μmol) in THF (4.0 mL) was added, the dry ice bath was removed and the mixture was stirred at room temperature for 90 min. The reaction mixture was poured into water (30 mL) and extracted with 3 portions of ethyl acetate. The combined organic extracts were dried over anhydrous sodium sulfate, filtered and evaporated. The crude product was purified by preparative HPLC (RP C-18 10 μm, water-acetonitrile gradient with 0.01% TFA in both eluents, 90:10->5:95). 303 mg (68% yield) of the title compound were obtained.

LC-MS (method 4): $R_t$=5.41 min; MS (ESIpos): m/z=965 [M+H]$^+$ $^1$H-NMR (400 MHz, DMSO-d$^6$) δ [ppm]: 0.008 (0.62), 0.849 (3.68), 1.352 (16.00), 1.753 (0.56), 2.327 (0.54), 2.442 (0.99), 2.670 (0.56), 3.784 (1.09), 3.866 (0.68), 7.803 (1.05), 7.936 (0.96), 8.213 (1.17), 8.442 (0.88), 8.758 (0.80).

Intermediate 16A

Tert-Butyl (rel 1S,2R)-2-hydroxycyclopentyl (2E)-but-2-enedioate

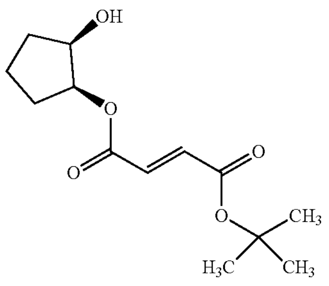 [SMILES: CC(C)(C)OC(=O)/C=C/C(=O)O[C@H]1CCC[C@H]1O]

cis-Cyclopentane-1,2-diol (2.68 g, 26.2 mmol) and N,N-diisopropylethylamine (2.7 mL, 16 mmol) were dissolved in DCM (25 mL). Then, a solution of tert-butyl (2E)-4-chloro-4-oxobut-2-enoate (intermediate 1A, 1.00 g, 5.25 mmol) in DCM (5 mL) was added dropwise at room temperature. The mixture was stirred for 16 h. The reaction was then quenched with concentrated aqueous ammonium chloride and extracted with 3 portions of MTBE. Water was stripped off by filtration over a Chromabond PTS device and the solvent was distilled. The residue was purified by flash chromatography on silica gel (gradient cyclohexane/ethyl acetate 9:1-1:1) 1.09 g (81% yield) of the title compound was isolated.

$^1$H-NMR (400 MHz, DMSO-d$^6$) δ [ppm]: 1.469 (16.00), 4.746 (0.91), 4.760 (0.88), 6.680 (1.91), 6.694 (1.92).

Intermediate 17A

Tert-Butyl (rel 1S,2R)-2-{[(chloromethoxy)carbonyl]oxy}cyclopentyl (2E)-but-2-enedioate

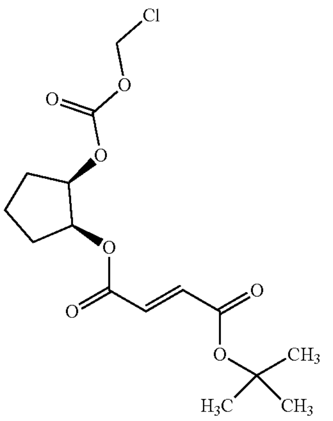 [SMILES: CC(C)(C)OC(=O)/C=C/C(=O)O[C@H]1CCC[C@H]1OC(=O)OCCl]

tert-Butyl (rel 1S,2R)-2-hydroxycyclopentyl (2E)-but-2-enedioate (intermediate 16A, 700 mg, 2.73 mmol) was dissolved in pyridine (30 mL) and the solution was cooled to 0° C. Chloromethyl carbonochloridate (364 μl, 4.1 mmol) was added at once and the mixture was stirred at room temperature for 90 min. Then, the mixture was poured into water, the pH was adjusted to 4 by addition of 1M hydrochloric acid and the mixture was extracted with 3 portions of DCM. The combined organic layers were washed with 1M hydrochloric acid, water and brine. Residual water was stripped by filtration over a Chromabond PTS device, the solvent was distilled. The title compound (900 mg, 94% yield) was used without further purification.

$^1$H-NMR (400 MHz, DMSO-d$^6$) δ [ppm]: 1.453 (16.00), 1.465 (0.48), 1.820 (0.42), 5.220 (0.43), 5.833 (0.76), 5.849 (1.28), 5.893 (1.30), 5.910 (0.77), 6.626 (3.81).

Intermediate 18A

Tert-Butyl (rel 1R,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl (2E)-but-2-enedioate

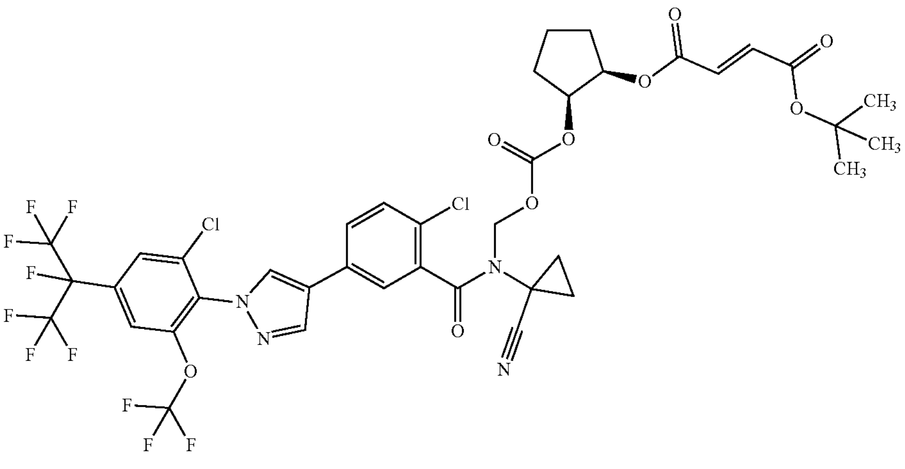 [SMILES: CC(C)(C)OC(=O)/C=C/C(=O)O[C@@H]1CCC[C@@H]1OC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (475 mg, 732 μmol) was dissolved in dry THF (8 mL) This solution was cooled to −45° C. on an acetone-dry ice bath. Potassium bis(trimethylsilyl)amide (2.3 mL, 0.50 M solution in toluene, 1.2 mmol) was added dropwise and the mixture was stirred 30 min. at −45° C. Then, a solution of sodium iodide (55 mg, 366 μmol) and tert-butyl (rel 1S,2R)-2-{[(chloromethoxy)carbonyl]oxy}cyclopentyl (2E)-but-2-enedioate (intermediate 17A, 383 mg, 1.10 mmol) in THF (4.0 mL) was added, the dry ice bath was removed and the mixture was stirred at room temperature for 4 h. The reaction mixture was poured into concentrated aqueous ammonium chloride solution and extracted with 3 portions of ethyl acetate. The combined organic extracts were dried passing them over a Chromabond PTS device and evaporated. The crude product was purified by flash chromatography (silica gel, gradient DCM-DCM/ethyl acetate 1:1) and subsequently by preparative HPLC (RP C-18 10 μm, water-acetonitrile gradient with 0.01% TFA in both eluents, 90:10->5:95). 460 mg (100% purity, 65% yield) of the title compound were obtained.

LC-MS (method 3): $R_t$=2.79 min; MS (ESIneg): m/z=1005 $[M-H+CHOOH]^-$ $^1$H-NMR (400 MHz, DMSO-$d^6$) δ [ppm]: −0.008 (0.66), 0.008 (0.58), 1.437 (16.00), 1.553 (0.48), 1.740 (1.41), 1.958 (0.49), 5.117 (0.49), 6.608 (2.79), 7.590 (0.53), 7.788 (1.06), 7.818 (0.61), 7.935 (1.45), 8.210 (1.58), 8.427 (1.74), 8.739 (0.99).

Intermediate 19A

Tert-Butyl (rel 1S,2R)-2-{[(chloromethoxy)carbonyl]oxy}cyclopentyl Butanedioate

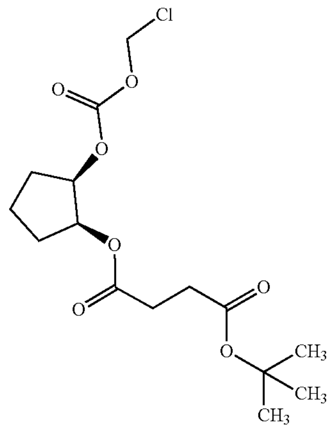 [SMILES: CC(C)(C)OC(=O)CCC(=O)O[C@H]1CCC[C@H]1OC(=O)OCCl]

tert-Butyl (rel 1S,2R)-2-{[(chloromethoxy)carbonyl]oxy}cyclopentyl (2E)-but-2-enedioate (intermediate 17A, 450 mg, 1.29 mmol) was dissolved in THF (20 mL) under an argon atmosphere. 10% Palladium on charcoal (28 mg, 26 μmol) was added and the mixture was hydrogenated for 16 h at ambient pressure at room temperature. The catalyst was then removed by filtration over a layer of diatomaceous earth and the solvent was distilled. 430 mg (95% yield) of the title compound were isolated.

$^1$H-NMR (400 MHz, DMSO-$d^6$) δ [ppm]: 1.381 (16.00), 2.474 (0.49), 5.071 (0.45), 5.883 (1.66), 5.891 (1.67).

Intermediate 20A

Tert-Butyl (rel 1R,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl Butanedioate

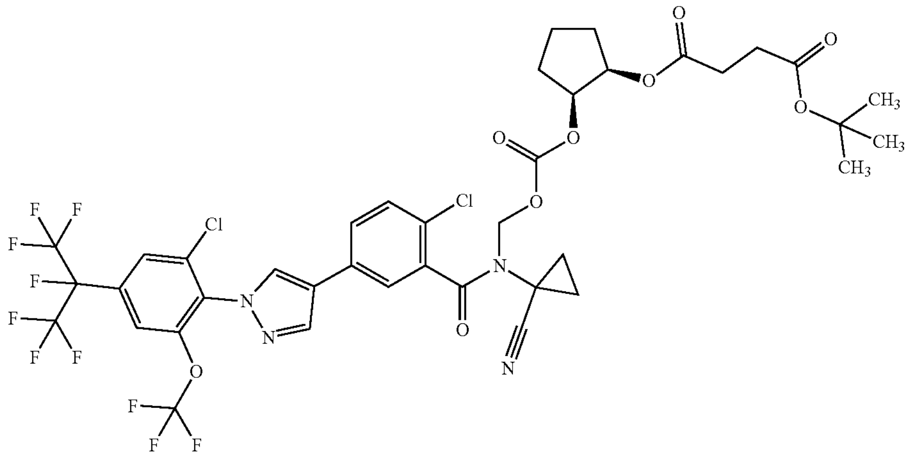 [SMILES: CC(C)(C)OC(=O)CCC(=O)O[C@@H]1CCC[C@@H]1OC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (531 mg, 817 μmol) was dissolved in dry THF (8 mL) This solution was cooled to −45° C. on an acetone-dry ice bath. Potassium bis(trimethylsilyl)amide (2.6 mL, 0.50 M solution in toluene, 1.3 mmol) was added dropwise and the mixture was stirred for 30 min. at −45° C. Then, a solution of sodium iodide (61 mg, 409 μmol) and tert-butyl (rel 1S,2R)-2-{[(chloromethoxy)carbonyl]oxy}cyclopentyl butanedioate (intermediate 19A, 430 mg, 1.23 mmol) in THF (4.0 mL) was added, the dry ice bath was removed and the mixture was stirred at room temperature for 4 h. The reaction mixture was poured into concentrated aqueous ammonium chloride solution and extracted with 3 portions of ethyl acetate. The combined organic extracts were dried passing them over a Chromabond PTS device and evaporated. The crude product was purified by flash chromatography (silica gel, gradient DCM-DCM/ethyl acetate 1:1) and subsequently by preparative HPLC (RP C-18 10 μm, water-acetonitrile gradient with 0.01% TFA in both eluents, 90:10->5:95). 520 mg (98% purity, 64% yield) of the title compound were obtained.

LC-MS (method 3): $R_t$=2.76 min; MS (ESIpos): m/z=963 $[M+H]^+$ $^1$H-NMR (400 MHz, DMSO-d$^6$) δ [ppm]: 1.333 (16.00), 1.356 (4.31), 1.507 (0.70), 1.757 (1.39), 1.898 (0.71), 2.184 (0.44), 2.367 (2.00), 4.885 (0.53), 4.998 (0.61), 7.587 (0.66), 7.608 (0.79), 7.805 (2.03), 7.824 (1.01), 7.937 (2.06), 8.212 (2.29), 8.445 (1.64), 8.756 (1.57).

Intermediate 21A

Tert-Butyl 3-[2-(benzyloxy)ethoxy]-2,2-dimethylpropanoate

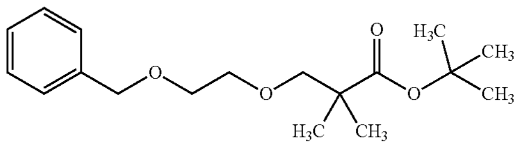 [SMILES: CC(C)(C)OC(=O)C(C)(C)COCCOCc1ccccc1]

tert-Butyl 3-hydroxy-2,2-dimethylpropanoate (CAS RN 25307-76-0, 871 mg, 5.00 mmol) was dissolved in THF (25 mL) and cooled to −20° C. Sodium bis(trimethylsilyl)amide (3.0 mL, 2.0 M in THF, 6.0 mmol) was added in small portions and the mixture was stirred at −20° C. for 30 min. Then, [(2-iodoethoxy)methyl]benzene (3.93 g, 15.0 mmol) was added and the mixture was first stirred at room temperature over night and was then heated to reflux for 16 h. The reaction mixture was poured into water, extracted with ethyl acetate and the organic layer was dried over anhydrous sodium sulfate. The solvent was distilled and the residue was purified by chromatography on silica gel (gradient DCM-DCM/ethyl acetate 9:1). 305 mg (20% yield) of the title compound were obtained.

$^1$H-NMR (400 MHz, DMSO-d6) δ[ppm]: 1.054 (9.88), 1.361 (16.00), 3.378 (3.21), 3.541 (3.94), 4.490 (2.46), 7.316 (1.28), 7.321 (1.60), 7.337 (0.52), 7.339 (0.59).

Intermediate 22A

Tert-Butyl 3-(2-hydroxyethoxy)-2,2-dimethylpropanoate

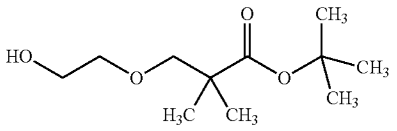

tert-Butyl 3-[2-(benzyloxy)ethoxy]-2,2-dimethylpropanoate (intermediate 21A, 303 mg, 982 μmol) was dissolved in glacial acetic acid (15 mL), 10% palladium on charcoal (105 mg, 98.2 μmol) was added and the mixture was hydrogenated at ambient pressure and room temperature for 3 h. Another portion of 10% palladium on charcoal (105 mg, 98.2 μmol) was added and hydrogenation was continued for another 3 h. The catalyst was filtered off and the solvent was distilled. The crude product was dissolved in DCM, washed with concentrated aqueous sodium carbonate solution, dried over anhydrous sodium sulfate and evaporated again. 198 mg (92% yield) of the title compound were obtained.

$^1$H-NMR (400 MHz, DMSO-d$^6$) δ [ppm]: 1.047 (9.81), 1.380 (16.00), 3.362 (3.22), 3.379 (0.40), 3.392 (1.07), 3.405 (0.94), 3.449 (0.48), 3.461 (0.95), 3.475 (0.70), 4.483 (0.45), 4.496 (0.90), 4.509 (0.41).

Intermediate 23A

Tert-Butyl 3-(2-{[(chloromethoxy)carbonyl]oxy}ethoxy)-2,2-dimethylpropanoate

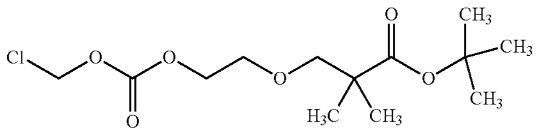 [SMILES: CC(C)(C)OC(=O)C(C)(C)COCCOC(=O)OCCl]

tert-Butyl 3-(2-hydroxyethoxy)-2,2-dimethylpropanoate (intermediate 22A, 95 mg, 435 μmol) was dissolved in pyridine (5.0 mL) under an argon atmosphere and cooled to 0° C. Chloromethyl carbonochloridate (58 μl, 650 μmol) was added at once and the mixture was stirred at room temperature for 45 min. The solvent was distilled, the residue was taken up into ethyl acetate (50 mL), washed consecutively with water, and brine, dried over anhydrous sodium sulfate and evaporated. The crude product was purified by chromatography on silica gel (gradient cyclohexane-cyclohexane ethyl acetate 82.5:17.5) to yield 103 mg (76% of theory) of the title compound.

$^1$H-NMR (400 MHz, DMSO-d$^6$) δ [ppm]: 1.040 (9.89), 1.374 (16.00), 3.377 (3.16), 3.607 (0.73), 3.615 (0.58), 3.619 (0.81), 3.623 (0.61), 3.630 (0.79), 4.273 (0.79), 4.279 (0.60), 4.284 (0.81), 4.288 (0.62), 4.295 (0.75), 5.893 (4.01).

Intermediate 24A

Tert-Butyl 1-(2-chloro-5-{1-[2-chloro-4-(1,1,1,2,3,3,3-heptafluoropropan-2-yl)-6-(trifluorometh-oxy)phenyl]-1H-pyrazol-4-yl}phenyl)-2-(1-cyanocyclopropyl)-11,11-dimethyl-1,5-dioxo-4,6,9-trioxa-2-azadodecan-12-oate

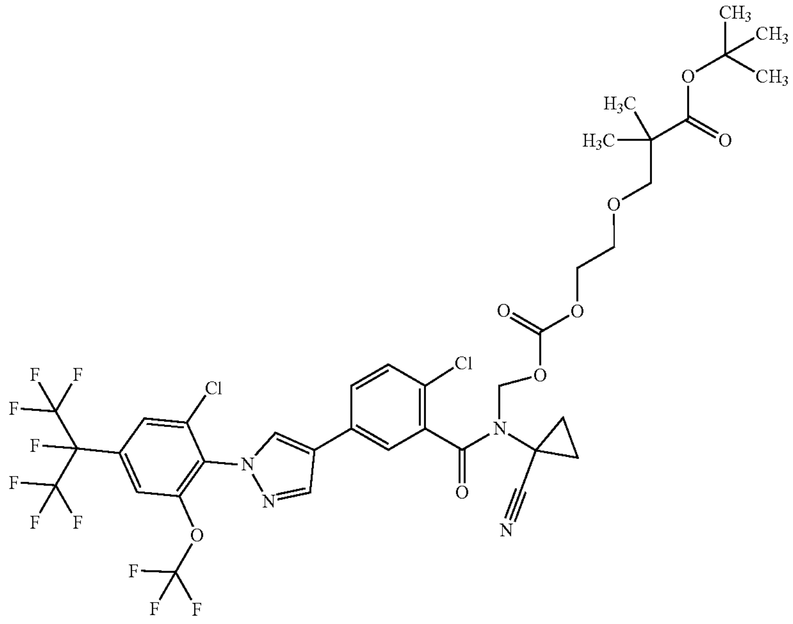 [SMILES: CC(C)(C)OC(=O)C(C)(C)COCCOC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (179 mg, 276 μmol) was dissolved in dry THF (8 mL) This solution was cooled to −45° C. on an acetone-dry ice bath. Potassium bis(trimethylsilyl)amide (720 μL, 0.50 M solution in toluene, 331 μmol) was added dropwise and the mixture was stirred 30 min. at −45° C. Then, a solution of sodium iodide (21 mg, 138 μmol) and tert-butyl 3-(2-{[(chloromethoxy)carbonyl]oxy}ethoxy)-2,2-dimethylpropanoate (intermediate 23A, 103 mg, 331 μmol) in THF (2.0 mL) was added, the dry ice bath was removed and the mixture was stirred at room temperature for 90 min. The reaction mixture was poured into water and extracted with 3 portions of ethyl acetate. The combined organic extracts were dried over anhydrous sodium sulfate. The crude product was purified by flash chromatography (silica gel, gradient DCM-DCM/ethyl acetate 1:1) and subsequently by preparative HPLC (RP C-18 10 μm, water-acetonitrile gradient with 0.01% TFA in both eluents, 90:10->5:95). 200 mg (78% yield) of the title compound were obtained.

LC-MS (method 4): $R_t$=5.47 min; MS (ESIpos): m/z=923 $[M+H]^+$ $^1$H-NMR (400 MHz, DMSO-d$^6$) δ [ppm]: −0.008 (1.22), 0.008 (1.08), 0.997 (11.12), 1.235 (0.47), 1.331 (16.00), 1.754 (1.15), 2.328 (0.74), 2.332 (0.55), 2.366 (0.48), 2.523 (1.67), 2.670 (0.78), 2.710 (0.50), 3.326 (2.99), 3.535 (1.49), 4.113 (0.84), 7.590 (0.68), 7.612 (0.81), 7.780 (1.11), 7.804 (0.91), 7.825 (0.81), 7.936 (1.99), 8.210 (2.27), 8.440 (1.72), 8.763 (1.49).

Intermediate 25A

4-Ethoxy-2,2-dimethyl-4-oxobutanoic Acid

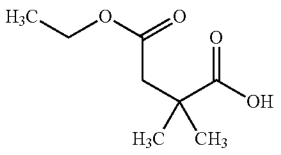

A solution of 3,3-dimethyl-dihydrofuran-2,5-dione, 70.0 g (0.55 mol) in ethanol (400 mL) was stirred at 50° C. over night. After cooling down to room temperature, the solvent was removed under vacuum and the residue was triturated with hexane at −50° C. The precipitated solid was collected to afford the title compound (60.0 g, 63% of theory) as a white solid.

LC-MS (method 6): $R_t$=0.89 min, MS (ESIpos): m/z=175 $[M+H]^+$.

Intermediate 26A 1-tert-Butyl 4-ethyl 2,2-dimethylsuccinate

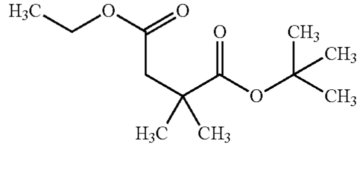 [SMILES: CCOC(=O)CC(C)(C)C(=O)OC(C)(C)C]

4-Ethoxy-2,2-dimethyl-4-oxobutanoic acid (intermediate 25A, 110 g, 0.63 mol), magnesium sulfate (304 g, 2.53 mol), and tert-butanol (330 mL), was dissolved in DCM (2.6 L) Sulfuric acid (93.0 g (0.95 mol), was added dropwise slowly at 0° C. The resulting mixture was stirred at room temperature over night. The reaction mixture was poured into saturated aqueous sodium bicarbonate solution. DCM was added to extract the desired product, and the organic phase was washed with brine, dried over anhydrous sodium sulfate, and concentrated to afford 70.0 g (37%) of the product as colorless oil.

LC-MS (method 7): $R_t$=1.26 min, MS (ESIpos): m/z=253 $[M+Na]^+$.

Intermediate 27A 4-tert-Butoxy-3,3-dimethyl-4-oxobutanoic Acid

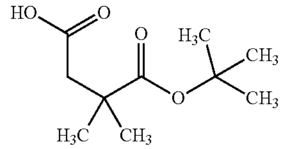

To a solution of 1-tert-butyl 4-ethyl 2,2-dimethylsuccinate, (intermediate 26A, 70.0 g, 0.3 mol) in ethanol (1.4 L) and water (700 mL), potassium hydroxide (85.3 g, 1.52 mol) was added at room temperature. The reaction mixture was stirred at room temperature for 2 hours. The pH of the reaction mixture was adjusted to 3-4 by adding 1M hydrochloric acid. The resulting solution was extracted with ether 3 times, and the combined ether phases were dried over sodium sulfate and concentrated to afford the title compound (37.0 g, 68% of theory) as a yellow solid LC-MS (method 7): $R_t$=0.36 min, MS (ESIpos): m/z=201 [M−H]

Intermediate 28A 1-tert-Butyl 4-(2-hydroxyethyl) 2,2-dimethylsuccinate

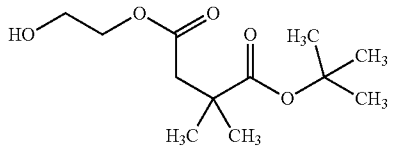 [SMILES: CC(C)(C)OC(=O)C(C)(C)CC(=O)OCCO]

A mixture of 4-tert-butoxy-3,3-dimethyl-4-oxobutanoic acid, (intermediate 27A, 35.0 g 173.1 mmol) and potassium carbonate, 120 g (0.87 mol) in DMF (1.0 L) was stirred at room temperature for 1 hour. 2-bromoethanol, 42.90 g (346.1 mmol), was added and the resulting mixture was stirred over night. The solvent was removed under vacuum. The residue was purified with silica gel column chromatograph (hexane/tert-butyl methyl ether 1:1) to give the title compound (22.6 g, 52% of theory) as yellow oil. LC-MS (method 5): $R_t$=1.39 min, MS (ESIpos): m/z=269 $[M+Na]^+$.

$^1$H-NMR (400 MHz, $CD_3OD$): δ [ppm]=1.21 (s, 6H), 1.43 (s, 9H), 2.59 (s, 2H), 3.73 (t, 2H), 4.11 (t, 2H).

Intermediate 29A 1-tert-Butyl 4-(2-{[(chloromethoxy)carbonyl]oxy}ethyl) 2,2-dimethylbutanedioate

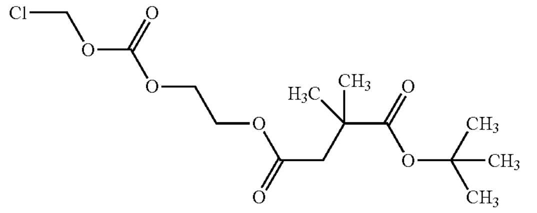 [SMILES: CC(C)(C)OC(=O)C(C)(C)CC(=O)OCCOC(=O)OCCl]

1-tert-Butyl 4-(2-hydroxyethyl) 2,2-dimethylbutanedioate (intermediate 28A, 246 mg, 1.00 mmol) was dissolved in pyridine (5.0 mL) under an argon atmosphere and cooled to 0° C. Chloromethyl carbonochloridate (130 μl, 1.5 mmol) was added at once and the mixture was stirred at room temperature for 45 min. The solvent was distilled, the residue was taken up into ethyl acetate (50 mL), washed consecutively with water, and brine, dried over anhydrous sodium sulfate and evaporated. The crude product was purified by chromatography on silica gel (gradient cyclohexane-cyclohexane ethyl acetate 3:1) to yield 228 mg (66% yield) of the title compound.

Intermediate 30A 1-tert-Butyl 4-{2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-ethyl} 2,2-dimethylbutanedioate

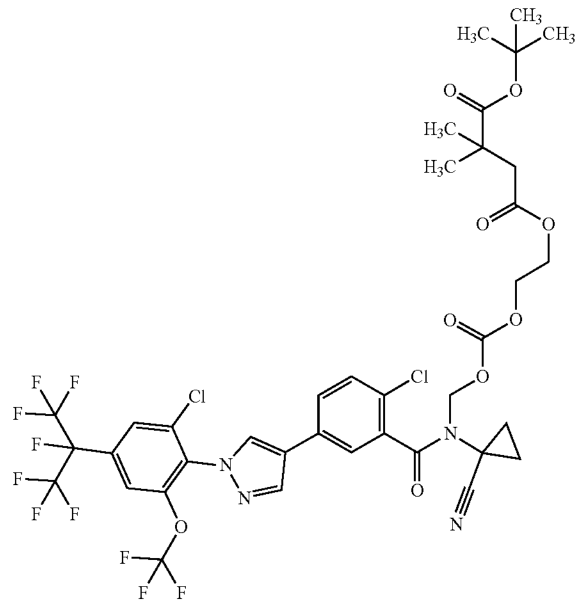 [SMILES: CC(C)(C)OC(=O)C(C)(C)CC(=O)OCCOC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (285 mg, 439 μmol) was dissolved in dry THF (10 mL) This solution was cooled to −45° C. on an acetone-dry ice bath. Potassium bis(trimethylsilyl)amide (1.4 mL, 0.50 M solution in toluene, 700 μmol) was added dropwise and the mixture was stirred 30 min. at −45° C. Then, a solution of sodium iodide (33 mg, 220 μmol) and 1-tert-butyl 4-(2-{[(chloromethoxy)carbonyl]oxy}ethyl) 2,2-dimethylbutanedioate (intermediate 29A, 227 mg, 98% purity, 659 μmol) in THF (4.0 mL) was added, the dry ice bath was removed and the mixture was stirred at room temperature for 90 min. The reaction mixture was poured into water and extracted with 3 portions of ethyl acetate. The combined organic extracts were dried over anhydrous sodium sulfate. The crude product was purified by preparative HPLC (RP C-18 10 μm, water-acetonitrile gradient with 0.01% TFA in both eluents, 90:10->5:95). 318 mg (100% purity, 76% yield) of the title compound were obtained.

LC-MS (method 3): $R_t$=2.74 min; MS (ESIpos): m/z=951 $[M+H]^+$ $^1$H-NMR (400 MHz, DMSO-d$^6$) δ [ppm]: −0.008 (0.48), 0.008 (0.44), 1.098 (10.35), 1.326 (16.00), 1.356 (3.74), 1.756 (0.99), 2.073 (0.53), 2.183 (0.41), 4.168 (1.32), 4.197 (0.89), 7.592 (0.58), 7.611 (0.67), 7.788 (1.00), 7.806 (0.85), 7.827 (0.69), 7.935 (1.73), 8.208 (1.98), 8.438 (1.58), 8.767 (1.29).

Intermediate 31A

Tert-Butyl (1S,2S)-2-hydroxycyclopentyl (2E)-but-2-enedioate

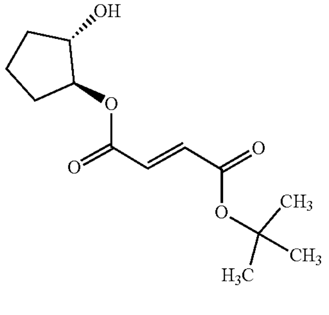 [SMILES: CC(C)(C)OC(=O)/C=C/C(=O)O[C@H]1CCC[C@@H]1O]

(1S,2S)-Cyclopentane-1,2-diol (2.68 g, 26.2 mmol) and N,N-diisopropylethylamine (2.7 ml, 16 mmol) were dissolved in DCM (25 mL). Then, a solution of tert-butyl (2E)-4-chloro-4-oxobut-2-enoate (intermediate 1A, 1.00 g, 5.25 mmol) in DCM (5 mL) was added dropwise at room temperature. The mixture was left stirring for 16 h. The reaction was then quenched with concentrated aqueous ammonium chloride and extracted with 3 portions of MTBE. Water was stripped off by filtration over a Chromabond PTS device and the solvent was distilled. The residue was purified by flash chromatography on silica gel (gradient cyclohexane/ethyl acetate 9:1-1:1) 270 mg (20% yield) of the title compound was isolated.

$^1$H-NMR (400 MHz, DMSO-d$^6$) δ [ppm]: 1.460 (16.00), 4.957 (0.94), 4.967 (0.91), 6.638 (4.27).

Intermediate 32A

Tert-Butyl (1S,2S)-2-{[(chloromethoxy)carbonyl]oxy}cyclopentyl (2E)-but-2-enedioate

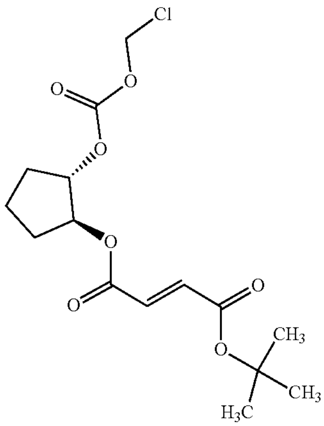 [SMILES: CC(C)(C)OC(=O)/C=C/C(=O)O[C@H]1CCC[C@@H]1OC(=O)OCCl]

tert-Butyl (1S,2S)-2-hydroxycyclopentyl (2E)-but-2-enedioate (intermediate 31A, 275 mg, 1.07 mmol) was dissolved in pyridine (10 mL) and the solution was cooled to 0° C. Chloromethyl carbonochloridate (190 μl, 2.1 mmol) was added dropwise and the mixture was stirred at room temperature over night. Then, the mixture was poured into water, the pH was adjusted to 4 by addition of 1M hydrochloric acid and the mixture was extracted with 3 portions of DCM. The combined organic layers were washed with 1M hydrochloric acid, water and brine. Residual water was stripped by filtration over a Chromabond PTS device, the solvent was distilled. The title compound (244 mg, 65% yield) was used without further purification.

$^1$H-NMR (400 MHz, DMSO-d$^6$) δ [ppm]: 1.464 (16.00), 1.734 (0.55), 1.744 (0.63), 1.753 (0.41), 5.890 (3.40), 6.666 (1.88), 6.677 (1.86).

Intermediate 33A

Tert-Butyl (1S,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)-oxy]cyclopentyl (2E)-but-2-enedioate

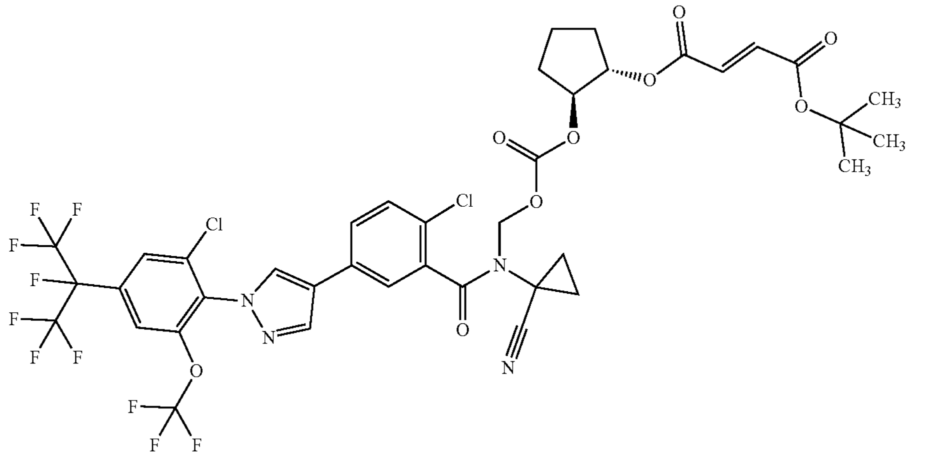 [SMILES: CC(C)(C)OC(=O)/C=C/C(=O)O[C@H]1CCC[C@@H]1OC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (199 mg, 308 μmol) was dissolved in dry THF (8 mL) This solution was cooled to −45° C. on an acetone-dry ice bath. Potassium bis(trimethylsilyl)amide (800 μL, 0.50 M solution in toluene, 400 μmol) was added dropwise and the mixture was stirred for 30 min. at −45° C. Then, a solution of sodium iodide (23 mg, 154 μmol) and tert-butyl (1S,2S)-2-{[(chloromethoxy)carbonyl]oxy}cyclopentyl (2E)-but-2-enedioate (intermediate 32A, 118 mg, 338 μmol) in THF (4.0 mL) was added, the dry ice bath was removed and the mixture was stirred at room temperature for 4 h. The reaction mixture was poured into concentrated aqueous ammonium chloride solution and extracted with 3 portions of ethyl acetate. The combined organic extracts were dried passing them over a Chromabond PTS device and evaporated. The crude product was purified by flash chromatography (silica gel, gradient DCM-DCM/ethyl acetate 1:1) and subsequently by preparative HPLC (RP C-18 10 μm, water-acetonitrile gradient with 0.01% TFA in both eluents, 90:10->5:95). 120 mg (41% yield) of the title compound were obtained.

LC-MS (method 3): $R_t$=2.83 min; MS (ESIpos): m/z=961 $[M+H]^+$ $^1$H-NMR (400 MHz, DMSO-$d^6$) δ [ppm]: 1.235 (0.66), 1.443 (16.00), 1.681 (0.41), 1.751 (0.43), 2.521 (0.65), 6.621 (1.79), 6.631 (1.85), 7.798 (0.73), 7.929 (0.62), 8.203 (0.66), 8.436 (0.70), 8.761 (0.47).

Intermediate 34A

Tert-Butyl (1S,2S)-2-{[(chloromethoxy)carbonyl]oxy}cyclopentyl Butanedioate

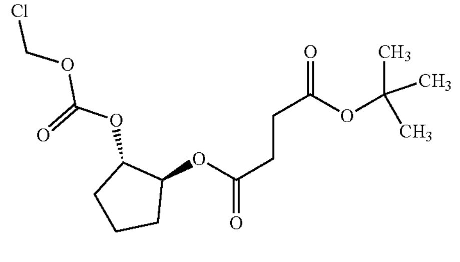 [SMILES: CC(C)(C)OC(=O)CCC(=O)O[C@H]1CCC[C@@H]1OC(=O)OCCl]

tert-Butyl (1S,2S)-2-{[(chloromethoxy)carbonyl]oxy}cyclopentyl (2E)-but-2-enedioate (intermediate 32A, 130 mg, 373 μmol) was dissolved in THF (5 mL) and 10% palladium on charcoal (39.7 mg, 10% purity, 37.3 μmol) was added. The mixture was hydrogenated at room temperature at ambient pressure over night. Then, the catalyst was filtered off and the filtrate was evaporated. The title compound (124 mg (95% yield) was used without further purification.

$^1$H-NMR (400 MHz, DMSO-$d^6$) δ [ppm]: 1.356 (0.45), 1.383 (16.00), 1.700 (0.43), 1.714 (0.69), 1.721 (0.41), 1.727 (0.58), 2.452 (0.51), 2.456 (0.55), 2.463 (0.86), 2.468 (0.72), 2.483 (0.92), 5.886 (3.56).

Intermediate 35A

Tert-Butyl (1S,2S)-2-[({[(2-chloro-5-{1-[2-chloro-4-(1,1,1,2,3,3,3-heptafluoropropan-2-yl)-6-(tri-fluoromethoxy)phenyl]-1H-pyrazol-4-yl}benzoyl)(1-cyanocyclopropyl)amino]methoxy}carbonyl)-oxy] cyclopentyl Butanedioate

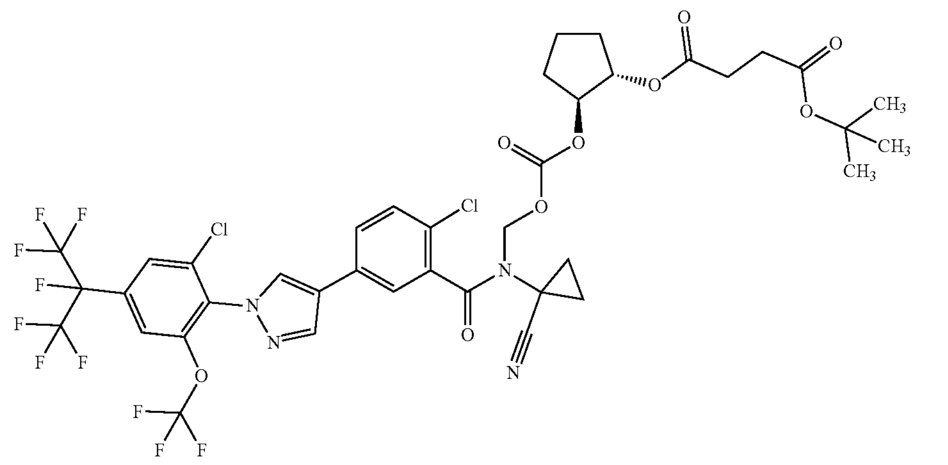 [SMILES: CC(C)(C)OC(=O)CCC(=O)O[C@H]1CCC[C@@H]1OC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (203 mg, 313 μmol) was dissolved in dry THF (8 mL) This solution was cooled to −45° C. on an acetone-dry ice bath. Potassium bis(trimethylsilyl)amide (813 μL, 0.50 M solution in toluene, 407 μmol) was added dropwise and the mixture was stirred for 30 min. at −45° C. Then, a solution of sodium iodide (23 mg, 154 μmol) and tert-butyl (1S,2S)-2-{[(chloromethoxy)carbonyl] oxy}cyclopentyl butanedioate (intermediate 34A, 120 mg, 344 μmol) in THF (4.0 mL) in THF (3 mL) was added, the dry ice bath was removed and the mixture was stirred at room temperature for 4 h. The reaction mixture was poured into concentrated aqueous ammonium chloride solution and extracted with 3 portions of ethyl acetate. The combined organic extracts were dried passing them over a Chromabond PTS device and evaporated. The crude product was purified by preparative HPLC (RP C-18 10 μm, water-acetonitrile gradient with 0.01% TFA in both eluents, 90:10->5:95). 100 mg (33% yield) of the title compound were obtained.

LC-MS (method 3): $R_t$=2.78 min; MS (ESIpos): m/z=963 $[M+H]^+$ $^1$H-NMR (500 MHz, DMSO-d$^6$) δ [ppm]: −0.022 (0.79), 1.235 (1.58), 1.354 (16.00), 1.650 (0.71), 1.753 (0.79), 1.963 (0.39), 2.424 (1.58), 2.435 (1.50), 4.955 (0.47), 7.586 (0.47), 7.603 (0.55), 7.799 (1.10), 7.819 (0.55), 7.934 (1.34), 8.208 (1.50), 8.211 (1.50), 8.442 (1.10), 8.760 (0.95).

Intermediate 36A

Tert-Butyl 2-hydroxyethyl Pentanedioate

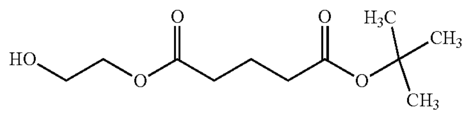 [SMILES: CC(C)(C)OC(=O)CCCC(=O)OCCO]

Ethane-1,2-diol (5.3 mL, 96 mmol) was dissolved in DCM (10 mL). and N,N-diisopropylethylamine (5.0 ml, 29 mmol) was added. Then, a solution of tert-butyl 5-chloro-5-oxopentanoate (CAS RN 2011712-15-3, 1.98 g, 9.58 mmol) in DCM (5 mL) was added under cooling with an ice bath. The reaction was left stirring over night, then poured into water and the pH was adjusted to 5-6 with 1M hydrochloric acid. The mixture was extracted with 2 portions of DCM, the combined organic extracts were briefly washed with concentrated aqueous sodium hydrogen carbonate, dried by passing through a Chromabond PTS device and evaporated. The residue was purified by chromatography over silica gel (gradient cyclohexane/ethyl acetate 80:20-50:50 giving 670 mg (30% yield) of the title compound.

$^1$H-NMR (400 MHz, DMSO-d$^6$) δ [ppm]: 1.395 (16.00), 1.706 (0.61), 1.725 (0.92), 1.743 (0.66), 2.215 (0.78), 2.234 (1.37), 2.252 (0.67), 2.308 (0.75), 2.327 (1.33), 2.345 (0.67), 3.546 (0.79), 3.559 (0.90), 3.572 (0.46), 4.008 (0.83), 4.021 (0.97), 4.034 (0.75), 4.772 (0.78).

Intermediate 37A

Tert-Butyl 2-{[(chloromethoxy)carbonyl]oxy}ethyl Pentanedioate

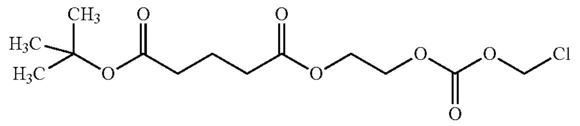 [SMILES: CC(C)(C)OC(=O)CCCC(=O)OCCOC(=O)OCCl]

tert-Butyl 2-hydroxyethyl pentanedioate (intermediate 36A, 640 mg, 2.76 mmol) was dissolved in pyridine (10 mL), chloromethyl carbonochloridate (490 µl, 5.5 mmol) was added dropwise and the mixture was stirred at room temperature over night. Then, the mixture was poured into 1M hydrochloric acid and the mixture was extracted with 3 portions of DCM. The combined organic layers were washed with 1M hydrochloric acid, water and concentrated aqueous sodium hydrogen carbonate solution, dried over magnesium sulfate and evaporated. The title compound (648 mg, 72% yield) was used without further purification.

$^1$H-NMR (400 MHz, DMSO-d$^6$) δ [ppm]: 1.392 (16.00), 1.701 (0.62), 1.720 (1.00), 1.738 (0.77), 2.210 (0.76), 2.229 (1.45), 2.247 (0.80), 2.322 (0.72), 2.340 (1.29), 2.358 (0.66), 4.256 (0.53), 4.267 (0.76), 4.272 (0.57), 4.278 (0.86), 4.383 (0.78), 4.389 (0.50), 4.394 (0.67), 4.405 (0.52), 5.901 (3.42).

Intermediate 38A

Tert-Butyl 2-[({[(2-chloro-5-{1-[2-chloro-4-(1,1,1,2,3,3,3-heptafluoropropan-2-yl)-6-(trifluoro-methoxy)phenyl]-1H-pyrazol-4-yl}benzoyl)(1-cyanocyclopropyl)amino]methoxy}carbonyl)oxy]-ethyl Pentanedioate

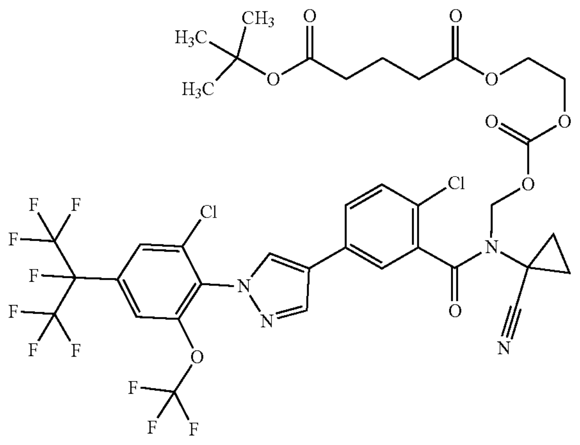 [SMILES: CC(C)(C)OC(=O)CCCC(=O)OCCOC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (300 mg, 462 µmol) was dissolved in dry THF (5 mL). This solution was cooled to −45° C. on an acetone-dry ice bath. Potassium bis(trimethylsilyl)amide (1.2 mL, 0.50 M solution in toluene, 600 µmol) was added dropwise and the mixture was stirred for 30 min. at −45° C. Then, a solution of sodium iodide (35 mg, 231 µmol) and tert-butyl 2-{[(chloromethoxy)carbonyl]oxy}ethyl pentanedioate (intermediate 37A, 180 mg, 554 µmol) in THF (3 mL) was added, the dry ice bath was removed and the mixture was stirred at room temperature over night. The reaction mixture was poured into concentrated aqueous ammonium chloride solution and extracted with 3 portions of ethyl acetate. The combined organic extracts were dried passing them over a Chromabond PTS device and evaporated. The crude product was purified by preparative HPLC (RP C-18 10 µm, water-acetonitrile gradient with 0.01% TFA in both eluents, 90:10->5:95). 155 mg (36% yield) were obtained.

LC-MS (method 3): $R_t$=2.69 min; MS (ESIpos): m/z=937 $[M+H]^+$ $^1$H-NMR (400 MHz, DMSO-d$^6$) δ [ppm]: 1.356 (0.65), 1.369 (16.00), 1.669 (0.42), 1.687 (0.60), 1.705 (0.46), 2.178 (0.46), 2.196 (0.83), 2.215 (0.41), 2.296 (0.54), 4.180 (0.46), 7.934 (0.61), 8.207 (0.68), 8.440 (0.54), 8.767 (0.43).

Intermediate 39A 1-tert-Butyl 1-(2-hydroxyethyl) cyclopropane-1,1-dicarboxylate

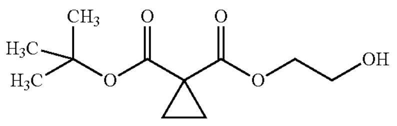 [SMILES: CC(C)(C)OC(=O)C1(C(=O)OCCO)CC1]

1-(tert-Butoxycarbonyl)cyclopropane-1-carboxylic acid (600 mg, 3.22 mmol) was dissolved in DCM (6.0 mL) and one drop of DMF was added. The solution was cooled to 0° C. and oxalic dichloride (560 µl, 6.4 mmol) was added dropwise. The cooling bath was removed and the reaction was left stirring at room temperature until the evolution of gas ceased. Volatiles were removed at room temperature under reduced pressure. The resulting acid chloride was dissolved in DCM (5 mL) and added to a solution of ethane-1,2-diol (1.8 mL, 32 mmol) and N,N-diisopropylethylamine (1.7 mL, 9.7 mmol) in DCM. The mixture was left stirring over night at room temperature and was then poured into water and pH was adjusted to 6-6 by addition of 1M hydrochloric acid. This mixture was extracted with 2 portions of DCM, the combined organic extracts were washed with concentrated aqueous solution of sodium hydrogen carbonate, passed over a Chromabond PTS device and evaporated. The crude product was purified by chromatography on silica gel (gradient cyclohexane/ethyl acetate 80:20-50:50) to give 450 mg (61% yield) of the title compound.

$^1$H-NMR (400 MHz, DMSO-d$^6$) δ [ppm]: 1.252 (0.80), 1.260 (1.68), 1.266 (0.91), 1.281 (0.95), 1.286 (1.65), 1.295 (0.71), 1.408 (16.00), 3.554 (0.44), 3.567 (0.95), 3.580 (1.02), 3.594 (0.46), 4.053 (0.94), 4.066 (1.13), 4.079 (0.81), 4.768 (0.43), 4.781 (0.85).

Intermediate 40A

1-tert-Butyl 1-(2-{[(chloromethoxy)carbonyl] oxy}ethyl) cyclopropane-1,1-dicarboxylate

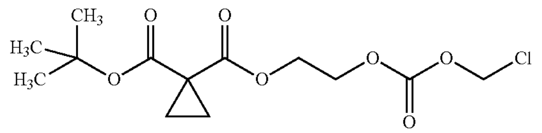 [SMILES: CC(C)(C)OC(=O)C1(C(=O)OCCOC(=O)OCCl)CC1]

1-tert-Butyl 1-(2-hydroxyethyl) cyclopropane-1,1-dicarboxylate (intermediate 39A, 445 mg, 1.93 mmol) was dissolved in pyridine (5.0 mL), chloromethyl carbonochloridate (340 μl, 3.9 mmol) was added dropwise and the mixture was stirred at room temperature over night. Then, the mixture was poured into 1M hydrochloric acid and the resulting mixture was extracted with 3 portions of DCM. The combined organic layers were washed with 1M hydrochloric acid, water and concentrated aqueous sodium hydrogen carbonate solution, dried over magnesium sulfate and evaporated. The title compound (648 mg, 72% yield) was used without further purification.

$^1$H-NMR (400 MHz, DMSO-d$^6$) δ [ppm]: 1.284 (3.08), 1.288 (2.98), 1.297 (0.63), 1.397 (16.00), 1.420 (1.60), 4.312 (0.60), 4.319 (0.70), 4.322 (0.77), 4.333 (0.97), 4.394 (0.94), 4.398 (0.71), 4.405 (0.74), 4.415 (0.53), 5.911 (3.59).

Intermediate 41A

1-tert-Butyl 1-{2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-ethyl} cyclopropane-1,1-dicarboxylate

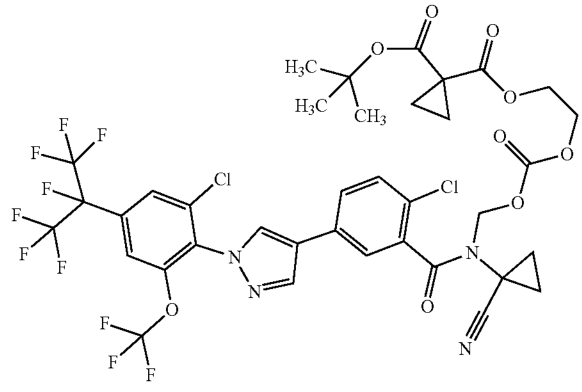 [SMILES: CC(C)(C)OC(=O)C1(C(=O)OCCOC(=O)OCN(C(=O)c2cc(-c3cnn(-c4c(Cl)cc(C(F)(C(F)(F)F)C(F)(F)F)cc4OC(F)(F)F)c3)ccc2Cl)C2(C#N)CC2)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (630 mg, 971 μmol) was dissolved in dry THF (20 mL). This solution was cooled to −45° C. on an acetone-dry ice bath. Potassium bis(trimethylsilyl)amide (2.5 mL, 0.50 M solution in toluene, 1.3 mmol) was added dropwise and the mixture was stirred for 30 min. at −45° C. Then, a solution of sodium iodide (73 mg, 485 μmol) and 1-tert-butyl 1-(2-{[(chloromethoxy)carbonyl]oxy}ethyl) cyclopropane-1,1-dicarboxylate (intermediate 40A, 470 mg, 1.46 mmol) in THF (3 mL) was added, the dry ice bath was removed and the mixture was stirred at room temperature over night. The reaction mixture was poured into water and extracted with 3 portions of ethyl acetate. The combined organic extracts were dried over anhydrous magnesium sulfate and evaporated. The crude product was purified by preparative HPLC (RP C-18 10 μm, water-acetonitrile gradient with 0.01% TFA in both eluents, 90:10->5:95). 570 mg (63% yield) of the title compound were obtained.

LC-MS (method 3): $R_t$=2.70 min; MS (ESIpos): m/z=935 $[M+H]^+$ $^1$H-NMR (400 MHz, DMSO-d$^6$) δ [ppm]: 1.245 (5.40), 1.324 (0.81), 1.356 (16.00), 1.758 (1.11), 4.235 (2.81), 7.592 (0.58), 7.612 (0.73), 7.791 (1.07), 7.807 (0.95), 7.829 (0.76), 7.935 (1.90), 8.209 (2.10), 8.213 (2.09), 8.443 (1.47), 8.766 (1.30).

Intermediate 42A

Tert-Butyl-4-hydroxycyclohexyl (2E)-but-2-enedioate (Mixture of Diastereomers)

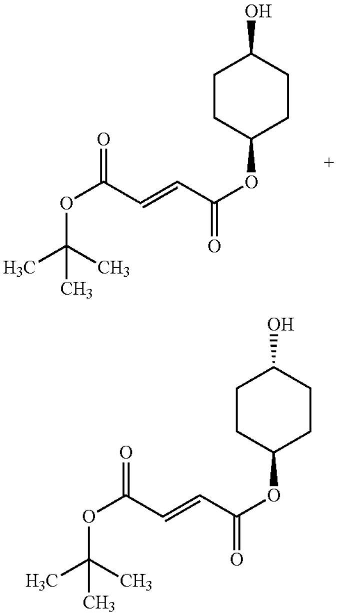

Cyclohexane-1,4-diol (mixture of cis and trans diastereomers, 23.23 g, 200 mmol) and N,N-diisopropylethylamine (5.23 mL, 30 mmol) were suspended in THF (100 mL). A solution of tert-butyl (2E)-4-chloro-4-oxobut-2-enoate (intermediate 1A, 1.91 g, 10.0 mmol) in THF (20 mL) was slowly added. Eventually, the reaction was quenched by addition of water and extracted with 3 portions of DCM. The combined organic extracts were dried over sodium sulfate, evaporated and purified by flash chromatography over silica gel (gradient cyclohexane-cyclohexane/ethyl acetate 3:2). The resulting product (1.60 g, 59% of theory) was obtained as a mixture of isomers.

LC-MS (method 2): $R_t$=0.89 min (58 area %) and 0.91 min (42 area %); MS (ESIpos): m/z=288 $[M+NH_4]^+$ Intermediate 43A Tert-Butyl Cis-4-hydroxycyclohexyl (2E)-but-2-enedioate

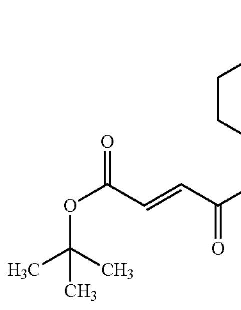

The product mixture of intermediate 42A (1.60 g, 5.92 mmol) was submitted to preparative SFC in order to separate the diasteromers. SFC conditions: column Chirapak AD-H (SFC) 5 μm, 250×30 mm; eluent: carbon dioxide/ethanol 7:3; pressure: 135 bar; eluent temperature: 38° C., cyclone temperature 40° C.; flow: 125 mL/min; UV detection at 210 nm.

The first peak ($R_t$=1.02 min) was collected and evaporated. This material was dissolved in DCM, filtered over a layer of diatomaceous earth and was eventually evaporated. Yield: 845 mg of the title compound. The stereochemistry was assigned by comparison to authentic (1r,4r)-isomer prepared from pure trans-cyclohexane-1,4-diol (intermediate 44A).

LC-MS (method 4): $R_t$=2.68 min; MS (ESIpos): m/z=288 $[M+NH_4]^+$ $^1$H-NMR (400 MHz, DMSO-d$^6$) δ [ppm]: 1.467 (16.00), 1.549 (0.57), 1.559 (0.73), 1.580 (0.45), 1.590 (0.58), 4.513 (0.84), 4.523 (0.83), 6.650 (2.12), 6.655 (2.11).

Intermediate 44A

Tert-Butyl Trans-4-hydroxycyclohexyl (2E)-but-2-enedioate

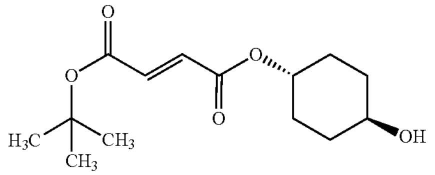 [SMILES: CC(C)(C)OC(=O)/C=C/C(=O)O[C@H]1CC[C@H](O)CC1]

From the preparative SFC separation described in intermediate 43A, the second peak ($R_t$=2.09 min) was collected. This material was dissolved in DCM, filtered over a layer of diatomaceous earth and was eventually evaporated. Yield: 365 mg of the title compound.

The stereochemistry was assigned by comparison with material prepared independently using commercially available trans-1,4-cyclohexanediol (CAS RN 6995-79-5): trans-Cyclohexane-1,4-diol (CAS RN 6995-79-5, 1.00 g, 8.61 mmol) and N,N-diisopropylethylamine (900 μl, 5.2 mmol) were dissolved in THF (20 mL) and a solution of tert-butyl (2E)-4-chloro-4-oxobut-2-enoate (intermediate 1A, 328 mg, 1.72 mmol) in THF (5 mL) was slowly added. Eventually, the reaction was quenched by addition of water and extracted with 3 portions of DCM. The combined organic extracts were dried over sodium sulfate, evaporated and purified by flash chromatography over silica gel (gradient cyclohexane-cyclohexane/ethyl acetate 1:1). 214 mg (46% yield) were isolated.

LC-MS (method 4): $R_t$=2.63 min; MS (ESIpos): m/z=288 $[M+NH_4]^+$ $^1$H-NMR (500 MHz, DMSO-d$^6$) δ [ppm]: 1.280 (0.56), 1.303 (0.62), 1.417 (0.73), 1.458 (16.00), 1.788 (0.54), 1.795 (0.57), 1.814 (0.49), 1.821 (0.46), 1.879 (0.57), 1.886 (0.55), 1.904 (0.50), 4.567 (1.04), 4.575 (0.91), 4.732 (0.42), 5.750 (0.62), 6.633 (2.89).

Intermediate 45A

Tert-Butyl Cis-4-{[(chloromethoxy)carbonyl]oxy}cyclohexyl (2E)-but-2-enedioate

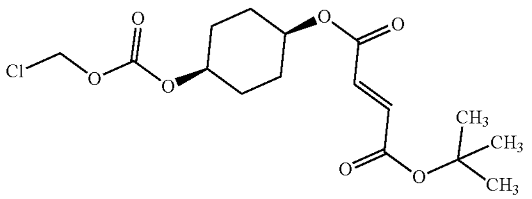 [SMILES: CC(C)(C)OC(=O)/C=C/C(=O)O[C@H]1CC[C@@H](OC(=O)OCCl)CC1]

tert-Butyl cis-4-hydroxycyclohexyl (2E)-but-2-enedioate (intermediate 43A, 210 mg, 777 μmol) was dissolved in pyridine (5.0 mL), chloromethyl carbonochloridate (100 μL, 1.2 mmol) was added and the mixture was stirred at room temperature for 45 min. Then, the solvent was distilled, the residue was dissolved in ethyl acetate (100 mL) and subsequently washed with, water and 3 portions of brine. The organic phase was dried over sodium sulfate and evaporated. The crude product was purified by flash chromatography on silica gel (gradient cyclohexane-cyclohexane ethyl acetate 4:1). 198 mg (100% purity, 70% yield) of the title compound were isolated.

$^1$H-NMR (400 MHz, DMSO-d$^6$) δ [ppm]: 1.466 (16.00), 1.736 (0.43), 1.749 (0.66), 1.758 (0.83), 1.767 (0.71), 1.785 (0.78), 1.796 (0.93), 1.811 (0.60), 5.901 (3.59), 6.675 (4.24).

Intermediate 46A

Tert-Butyl Cis-4-[({[(2-chloro-5-{1-[2-chloro-4-(1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-cyclohexyl (2E)-but-2-enedioate

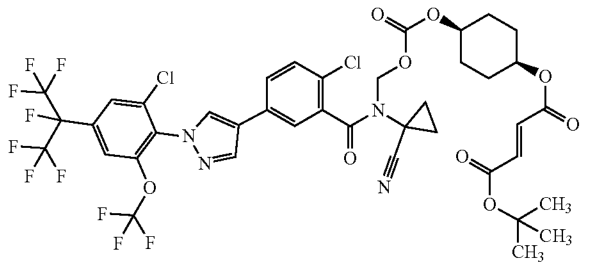 [SMILES: CC(C)(C)OC(=O)/C=C/C(=O)O[C@H]1CC[C@@H](OC(=O)OCN(C(=O)c2cc(-c3cnn(-c4c(Cl)cc(C(F)(C(F)(F)F)C(F)(F)F)cc4OC(F)(F)F)c3)ccc2Cl)C2(C#N)CC2)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (275 mg, 424 μmol) was dissolved in dry THF (8 mL). This solution was cooled to −45° C. on an acetone-dry ice bath. Potassium bis(trimethylsilyl)amide (1.4 mL, 0.50 M solution in toluene, 680 μmol) was added dropwise and the mixture was stirred for 30 min. at −45° C. Then, a solution of sodium iodide (32 mg, 212 μmol) and tert-butyl cis-4-{[(chloromethoxy)carbonyl]oxy}cyclohexyl (2E)-but-2-enedioate (intermediate 45A, 231 mg, 636 μmol) in THF (3 mL) was added, the dry ice bath was removed and the mixture was stirred at room temperature for 30 min. The reaction mixture was poured into water and extracted with 3 portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 325 mg (100% purity, 79% yield) of the title compound were obtained.

LC-MS (method 2): $R_t$=1.55 min; MS (ESIpos): m/z=975 $[M+H]^+$ $^1$H-NMR (400 MHz, DMSO-$d^6$) δ [ppm]: 1.452 (16.00), 1.691 (0.98), 1.762 (0.44), 3.518 (0.87), 6.653 (2.33), 7.802 (0.68), 7.923 (0.57), 8.196 (0.66), 8.453 (0.46), 8.776 (0.42).

Intermediate 47A

Tert-Butyl Cis-4-hydroxycyclohexyl butanedioate

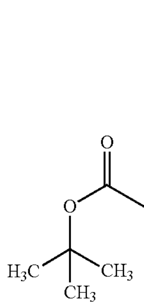

tert-Butyl cis-4-hydroxycyclohexyl (2E)-but-2-enedioate (intermediate 43A, 210 mg, 777 μmol) was dissolved in ethanol (10 mL) and hydrogenated at ambient pressure and room temperature in the presence of 10% palladium on activated charcoal (41 mg, 39 μmol) for 90 min. The mixture was filtered over a pad of diatomaceous earth and evaporated. The title compound (167 mg, 79% yield) was used without further purification.

$^1$H-NMR (400 MHz, DMSO-$d^6$) δ [ppm]: 1.384 (16.00), 1.504 (0.69), 1.522 (1.45), 2.444 (0.40), 4.477 (0.80), 4.487 (0.80).

Intermediate 48A

Tert-Butyl Cis-4-{[(chloromethoxy)carbonyl]oxy}cyclohexyl Butanedioate

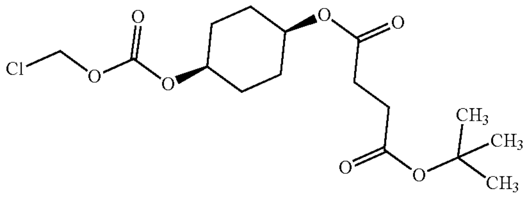 [SMILES: CC(C)(C)OC(=O)CCC(=O)O[C@H]1CC[C@@H](OC(=O)OCCl)CC1]

tert-Butyl cis-4-hydroxycyclohexyl butanedioate (intermediate 47A, 165 mg, 606 μmol) was dissolved in pyridine (7.0 mL), chloromethyl carbonochloridate (58 μl, 0.9 mmol) was added and the mixture was stirred at room temperature for 45 min. Then, the solvent was distilled, the residue was dissolved in ethyl acetate (100 mL) and subsequently washed with water and brine. The organic phase was dried over sodium sulfate and evaporated. The crude product was purified by flash chromatography on silica gel (gradient cyclohexane-cyclohexane ethyl acetate 3:1). 180 mg (100% purity, 81% yield) of the title compound were isolated.

$^1$H-NMR (400 MHz, DMSO-$d^6$) δ [ppm]: 1.382 (16.00), 1.664 (0.50), 1.679 (0.78), 1.691 (0.67), 1.702 (0.47), 1.743 (0.47), 1.760 (0.73), 1.772 (0.70), 2.454 (0.42), 2.457 (0.40), 2.461 (0.65), 2.469 (1.10), 2.479 (1.14), 5.894 (3.54).

Intermediate 49A

Tert-Butyl Cis-4-[({[(2-chloro-5-{1-[2-chloro-4-(1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-cyclohexyl Butanedioate

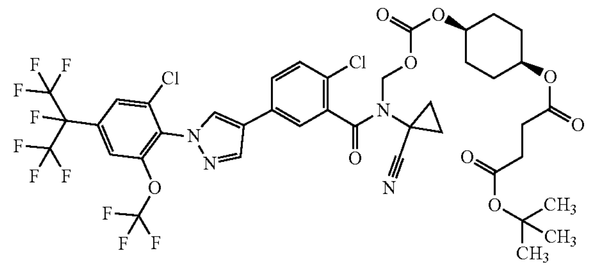

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (267 mg, 411 μmol) was dissolved in dry THF (8 mL). This solution was cooled to −45° C. on an acetone-dry ice bath. Potassium bis(trimethylsilyl)amide (1.1 ml, 0.50 M solution in toluene, 530 μmol) was added dropwise and the mixture was stirred for 30 min. at −45° C. Then, a solution of sodium iodide (31 mg, 206 μmol) and tert-butyl cis-4-{[(chloromethoxy)carbonyl]oxy}cyclohexyl (2E)-but-2-enedioate (intermediate 48A, 180 mg, 493 μmol) in THF (3 mL) was added, the dry ice bath was removed and the mixture was stirred at room temperature for 45 min. The reaction mixture was poured into water and extracted with 3 portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 277 mg (100% purity, 69% yield) of the title compound were obtained.

LC-MS (method 4): $R_t$=5.30 min; MS (ESIpos): m/z=977 $[M+H]^+$ $^1$H-NMR (400 MHz, DMSO-d$^6$) δ [ppm]: 1.356 (1.04), 1.369 (16.00), 1.633 (0.73), 1.662 (0.71), 1.761 (0.41), 2.442 (0.57), 2.449 (0.90), 2.462 (0.95), 2.470 (0.60), 2.476 (0.50), 7.800 (0.68), 7.934 (0.56), 8.208 (0.62), 8.212 (0.61), 8.448 (0.44), 8.772 (0.42).

Intermediate 50A

Tert-Butyl Trans-4-{[(chloromethoxy)carbonyl]oxy}cyclohexyl (2E)-but-2-enedioate

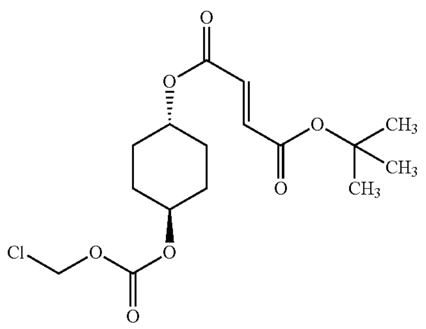 [SMILES: CC(C)(C)OC(=O)/C=C/C(=O)O[C@H]1CC[C@H](OC(=O)OCCl)CC1]

tert-butyl trans-4-hydroxycyclohexyl (2E)-but-2-enedioate (intermediate 44A, 210 mg, 777 μmol) was dissolved in pyridine (3.0 mL), chloromethyl carbonochloridate (120 μl, 1.2 mmol) was added and the mixture was stirred at room temperature for 1 h. Then, the solvent was distilled, the residue was dissolved in ethyl acetate (50 mL) and subsequently washed with water and brine. The organic phase was dried over sodium sulfate and evaporated. The crude product was purified by flash chromatography on silica gel (gradient cyclohexane-cyclohexane ethyl acetate 4:1). 237 mg (84% yield) of the title compound were isolated.

$^1$H-NMR (500 MHz, DMSO-d$^6$) δ [ppm]: 1.463 (16.00), 1.599 (0.86), 1.615 (0.87), 1.981 (0.42), 5.896 (3.73), 6.663 (4.43).

Intermediate 51A

Tert-butyl trans-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-cyclohexyl (2E)-but-2-enedioate

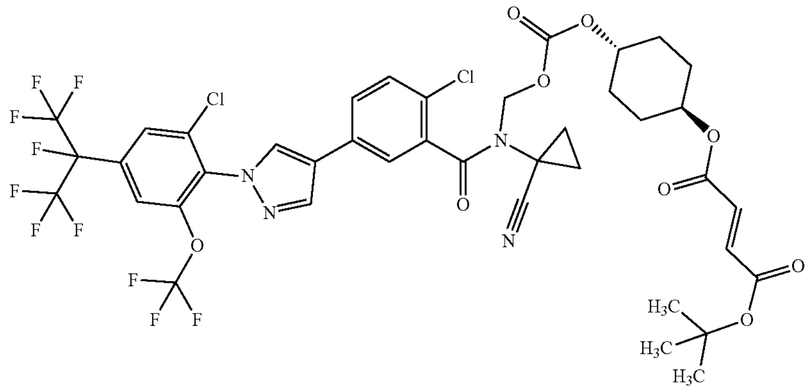 [SMILES: CC(C)(C)OC(=O)/C=C/C(=O)O[C@H]1CC[C@H](OC(=O)OCN(C(=O)c2cc(-c3cnn(-c4c(Cl)cc(C(F)(C(F)(F)F)C(F)(F)F)cc4OC(F)(F)F)c3)ccc2Cl)C2(C#N)CC2)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (162 mg, 250 μmol) was dissolved in dry THF (8 mL). This solution was cooled to −45° C. on an acetone-dry ice bath. Potassium bis(trimethylsilyl)amide (800 μL, 0.50 M solution in toluene, 400 μmol) was added dropwise and the mixture was stirred for 30 min. at −45° C. Then, a solution of sodium iodide (19 mg, 125 μmol) and tert-butyl trans-4-{[(chloromethoxy)carbonyl]oxy}cyclohexyl (2E)-but-2-enedioate (intermediate 50A, 136 mg, 375 μmol) in THF (3 mL) was added, the dry ice bath was removed and the mixture was stirred at room temperature for 30 min. The reaction mixture was poured into water and extracted with 3 portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 197 mg (81% of theory) of the title compound were obtained.

LC-MS (method 4): $R_t$=5.49 min; MS (ESIpos): m/z=975 $[M+H]^+$ $^1$H-NMR (600 MHz, DMSO-d$^6$) δ [ppm]: 1.459 (16.00), 1.502 (0.48), 3.392 (0.44), 5.757 (0.95), 6.641 (1.72), 7.804 (0.56), 7.929 (0.58), 8.206 (0.69), 8.461 (0.55), 8.779 (0.53).

Intermediate 52A

Tert-Butyl Cis-4-{[(chloromethoxy)carbonyl]oxy}cyclohexane-1-carboxylate

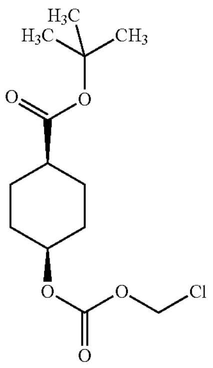 [SMILES: CC(C)(C)OC(=O)[C@H]1CC[C@@H](OC(=O)OCCl)CC1]

tert-Butyl cis-4-hydroxycyclohexane-1-carboxylate (CAS-RN 931110-79-1, 401 mg, 2.00 mmol) was dissolved in pyridine (6.5 mL), chloromethyl carbonochloridate (300 µl, 3.0 mmol) was added and the mixture was stirred at room temperature for 1 h. Then, the solvent was distilled, the residue was dissolved in ethyl acetate (50 mL) and subsequently washed with water and brine. The organic phase was dried over sodium sulfate and evaporated. The crude product was purified by flash chromatography on silica gel (gradient cyclohexane-cyclohexane ethyl acetate 4:1). 478 mg (82% yield) of the title compound were isolated.

$^1$H-NMR (600 MHz, DMSO-d$^6$) δ [ppm]: 1.397 (16.00), 1.639 (0.63), 1.646 (0.61), 1.654 (0.51), 5.887 (3.63).

Intermediate 53A

Tert-Butyl Cis-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-cyclohexane-1-carboxylate

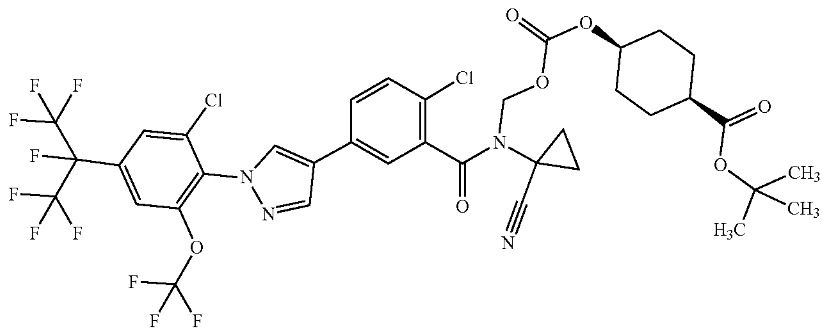 [SMILES: CC(C)(C)OC(=O)[C@H]1CC[C@@H](OC(=O)OCN(C(=O)c2cc(-c3cnn(-c4c(Cl)cc(C(F)(C(F)(F)F)C(F)(F)F)cc4OC(F)(F)F)c3)ccc2Cl)C2(C#N)CC2)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (162 mg, 250 µmol) was dissolved in dry THF (8 mL). This solution was cooled to −45° C. on an acetone-dry ice bath. Potassium bis(trimethylsilyl)amide (800 µL, 0.50 M solution in toluene, 400 µmol) was added dropwise and the mixture was stirred for 30 min. at −45° C. Then, a solution of sodium iodide (19 mg, 125 µmol) and tert-butyl cis-4-{[(chloromethoxy)carbonyl]oxy}cyclohexane-1-carboxylate (intermediate 52A, 110 mg, 375 µmol) in THF (3 mL) was added, the dry ice bath was removed and the mixture was stirred at room temperature for 30 min. The reaction mixture was poured into water and extracted with 3 portions of ethyl acetate. The combined organic extracts were dried over anhydrous sodium sulfate and evaporated. The crude product was purified by preparative HPLC (RP C-18 10 µm, water-acetonitrile gradient with 0.01% TFA in both eluents, 90:10->5:95). 196 mg (87 of theory) of the title compound were obtained. LC-MS (method 4): $R_t$=5.41 min; MS (ESIpos): m/z=905 [M+H]$^+$ $^1$H-NMR (600 MHz, DMSO-d$^6$) δ [ppm]: 1.234 (0.49), 1.358 (0.50), 1.375 (16.00), 1.395 (0.47), 1.400 (0.55), 1.591 (0.91), 1.605 (0.84), 1.660 (0.56), 1.762 (0.59), 7.813 (0.87), 7.932 (1.04), 8.209 (1.16), 8.452 (0.78), 8.777 (0.76).

Intermediate 54A

Tert-Butyl Trans-4-{[(chloromethoxy)carbonyl]oxy}cyclohexane-1-carboxylate

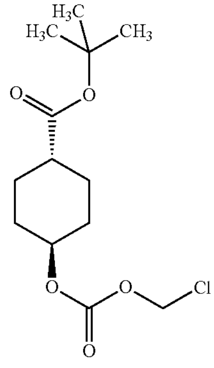 [SMILES: CC(C)(C)OC(=O)[C@H]1CC[C@H](OC(=O)OCCl)CC1]

tert-Butyl trans-4-hydroxycyclohexane-1-carboxylate (CAS RN 869193-57-7, 401 mg, 2.00 mmol) was dissolved in pyridine (6.5 mL), chloromethyl carbonochloridate (300 µl, 3.0 mmol) was added and the mixture was stirred at room temperature for 1 h. Then, the solvent was distilled, the residue was dissolved in ethyl acetate (50 mL) and subsequently washed with water and brine. The organic phase was dried over sodium sulfate and evaporated. The crude product was purified by flash chromatography on silica gel (gradient cyclohexane-cyclohexane ethyl acetate 4:1). 500 mg (85% yield) of the title compound were isolated.

$^1$H-NMR (600 MHz, DMSO-d$^6$) δ [ppm]: 1.389 (16.00), 1.413 (0.58), 1.429 (1.06), 1.446 (0.66), 1.984 (0.44), 5.881 (3.82).

Intermediate 55A

Tert-Butyl Trans-4-[({[(2-chloro-5-{1-[2-chloro-4-(1,1,1,2,3,3,3-heptafluoropropan-2-yl)-6-(trifluoromethoxy)phenyl]-1-pyrazol-4-yl}benzoyl)(1-cyanocyclopropyl)amino]methoxy}carbonyl)oxy]-cyclohexane-1-carboxylate

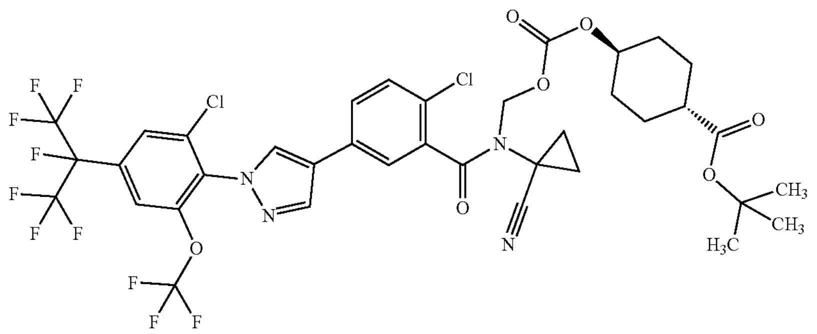 [SMILES: CC(C)(C)OC(=O)[C@H]1CC[C@H](OC(=O)OCN(C(=O)c2cc(-c3cnn(-c4c(Cl)cc(C(F)(C(F)(F)F)C(F)(F)F)cc4OC(F)(F)F)c3)ccc2Cl)C2(C#N)CC2)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (162 mg, 250 μmol) was dissolved in dry THF (8 mL). This solution was cooled to −45° C. on an acetone-dry ice bath. Potassium bis(trimethylsilyl)amide (800 μL, 0.50 M solution in toluene, 400 μmol) was added dropwise and the mixture was stirred for 30 min. at −45° C. Then, a solution of sodium iodide (19 mg, 125 μmol) and tert-butyl trans-4-{[(chloromethoxy)carbonyl]oxy}cyclohexane-1-carboxylate (intermediate 54A, 110 mg, 375 μmol) in THF (3 mL) was added, the dry ice bath was removed and the mixture was stirred at room temperature for 30 min. The reaction mixture was poured into water and extracted with 3 portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 191 mg (98% purity, 82% of theory) of the title compound were obtained.

LC-MS (method 4): $R_t$=5.44 min; MS (ESIpos): m/z=905 $[M+H]^+$ $^1$H-NMR (600 MHz, DMSO-d$^6$) δ [ppm]: 1.129 (0.53), 1.257 (0.72), 1.391 (13.61), 1.407 (2.06), 1.780 (0.74), 1.847 (0.61), 2.564 (16.00), 7.620 (0.48), 7.634 (0.53), 7.806 (0.79), 7.827 (0.56), 7.842 (0.50), 7.957 (1.20), 8.234 (1.26), 8.478 (0.93), 8.801 (0.92).

Intermediate 56A

Tert-Butyl {[(chloromethoxy)carbonyl]oxy}acetate

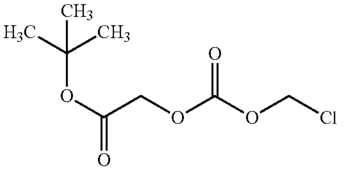

tert-Butyl hydroxyacetate (CAS-RN 50595-15-8, 264 mg, 2.00 mmol) was dissolved in pyridine (6.5 mL), chloromethyl carbonochloridate (300 μl, 3.0 mmol) was added and the mixture was stirred at room temperature for 1 h. Then, the solvent was distilled, the residue was dissolved in ethyl acetate (50 mL) and subsequently washed with water and brine. The organic phase was dried over sodium sulfate and evaporated. The crude product was purified by flash chromatography on silica gel (gradient cyclohexane-cyclohexane ethyl acetate 4:1). 430 mg (89% purity, 85% yield) of the title compound were isolated.

$^1$H-NMR (500 MHz, DMSO-d$^6$) δ [ppm]: 1.426 (2.11), 1.431 (16.00), 4.688 (3.87), 5.946 (4.12).

Intermediate 57A

Tert-Butyl [({[(2-chloro-5-{1-[2-chloro-4-(1,1,1,2,3,3,3-heptafluoropropan-2-yl)-6-(trifluorometh-oxy)phenyl]-1H-pyrazol-4-yl}benzoyl)(1-cyanocyclopropyl)amino]methoxy}carbonyl)oxy]acetate

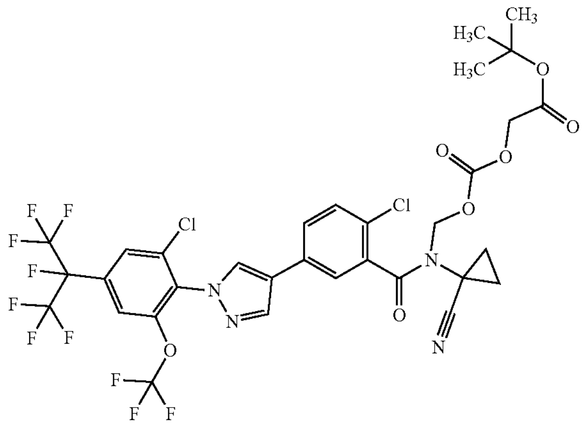 [SMILES: CC(C)(C)OC(=O)COC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluoropropan-2-yl)-6-(trifluoromethoxy)phenyl]-1H-pyrazol-4-yl}-N-(1-cyanocyclopropyl)benzamide (162 mg, 250 μmol) was dissolved in dry THF (8 mL). This solution was cooled to −45° C. on an acetone-dry ice bath. Potassium bis(trimethylsilyl)amide (800 μL, 0.50 M solution in toluene, 400 μmol) was added dropwise and the mixture was stirred for 30 min. at −45° C. Then, a solution of sodium iodide (19 mg, 125 μmol) and tert-butyl {[(chloromethoxy)carbonyl]oxy}acetate (intermediate 56A, 84.2 mg, 375 μmol) in THF (3 mL) was added, the dry ice bath was removed and the mixture was stirred at room temperature for 30 min. The reaction mixture was poured into water and extracted with 3 portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). of the title compound were obtained. 120 mg (57% yield) were isolated.

LC-MS (method 4): $R_t$=4.99 min; MS (ESIpos): m/z=837 $[M+H]^+$ $^1$H-NMR (600 MHz, DMSO-$d^6$) δ [ppm]: −0.022 (0.77), 1.235 (1.70), 1.357 (10.57), 1.364 (16.00), 1.417 (1.30), 1.504 (0.42), 1.767 (1.65), 2.184 (0.68), 4.491 (3.15), 6.872 (0.44), 7.604 (0.89), 7.618 (0.98), 7.782 (1.45), 7.813 (1.01), 7.826 (0.95), 7.939 (2.92), 8.214 (3.08), 8.440 (5.00), 8.760 (1.98).

Intermediate 58A

Tert-Butyl 4-{[(chloromethoxy)carbonyl]oxy}butanoate

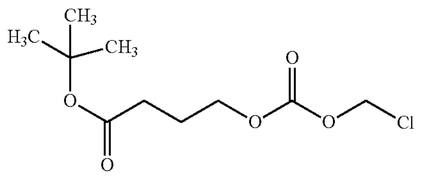 [SMILES: CC(C)(C)OC(=O)CCCOC(=O)OCCl]

tert-butyl 4-hydroxybutanoate (CAS RN 59854-12-5, 250 mg, 1.56 mmol) was dissolved in pyridine (5.1 mL). This solution was cooled to 0° C., chloromethyl carbonochloridate (240 μL, 2.4 mmol) was added and the mixture was stirred at room temperature over night. Then, the solvent was distilled, the residue was dissolved in ethyl acetate and subsequently washed with water and brine. The organic phase was dried over sodium sulfate and evaporated. The crude product was purified by flash chromatography on silica gel (gradient cyclohexane-cyclohexane ethyl acetate 4:1). 263 mg (67% yield) of the title compound were isolated. $^1$H-NMR (600 MHz, DMSO-$d^6$) δ [ppm]: 1.400 (16.00), 1.836 (0.69), 1.847 (1.06), 1.859 (0.73), 2.271 (0.87), 2.283 (1.65), 2.295 (0.78), 4.185 (0.85), 4.196 (1.73), 4.207 (0.83), 5.890 (3.93).

Intermediate 59A

Tert-butyl 4-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]butanoate

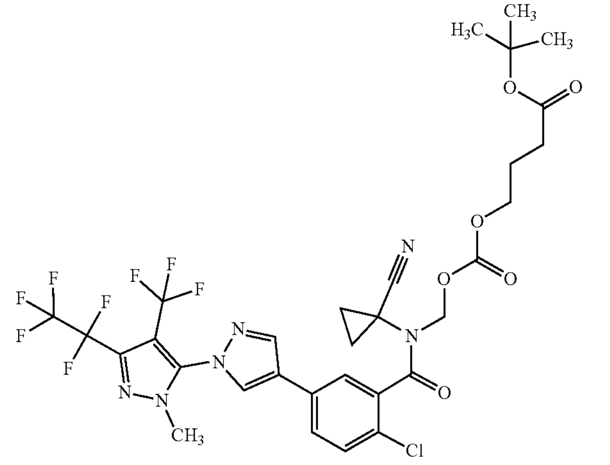 [SMILES: Cn1nc(C(F)(F)C(F)(F)F)c(C(F)(F)F)c1-n1cc(-c2ccc(Cl)c(C(=O)N(COC(=O)OCCCC(=O)OC(C)(C)C)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (292 mg, 528 μmol) was dissolved in dry THF (16 mL). This solution was cooled to −45° C. on an acetone-dry ice bath. Potassium bis(trimethylsilyl)amide (1.6 mL, 0.50 M solution in toluene, 840 μmol) was added dropwise and the mixture was stirred for 30 min. at −45° C. Then, a solution of sodium iodide (39.5 mg, 264 μmol) and tert-Butyl 4-{[(chloromethoxy)carbonyl]oxy}butanoate (intermediate 58A, 160 mg, 633 μmol) in THF (5.0 mL) was added, the dry ice bath was removed and the mixture was stirred at room temperature over night. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 231 mg (100% purity, 57% yield) of the title compound were obtained.

LC-MS (Method 4): $R_t$=4.80 min; MS (ESIpos): m/z=769 $[M+H]^+$ $^1$H-NMR (600 MHz, DMSO-$d^6$) δ [ppm]: 1.367 (16.00), 1.754 (1.69), 1.764 (1.54), 2.074 (1.78), 2.204 (0.77), 2.216 (1.32), 2.228 (0.72), 3.824 (7.66), 4.021 (0.65), 7.616 (0.65), 7.629 (0.72), 7.825 (1.06), 7.849 (0.68), 7.863 (0.64), 8.566 (1.34), 8.842 (1.30).

Intermediate 60A

Tert-Butyl 3-{[(chloromethoxy)carbonyl]oxy}-2,2-dimethylpropanoate

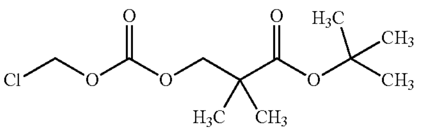 [SMILES: CC(C)(C)OC(=O)C(C)(C)COC(=O)OCCl]

tert-butyl 3-hydroxy-2,2-dimethylpropanoate (CAS RN 25307-76-0, 348 mg, 2.00 mmol) was dissolved in pyridine (7.0 mL). This solution was cooled to 0° C., chloromethyl carbonochloridate (240 μL, 3.0 mmol) was added and the mixture was stirred at room temperature over night. Then, the solvent was distilled, the residue was dissolved in ethyl acetate and subsequently washed with water and brine. The organic phase was dried over sodium sulfate and evaporated. The crude product was purified by flash chromatography on silica gel (gradient cyclohexane-cyclohexane ethyl acetate). 258 mg (48% yield) of the title compound were isolated.

$^1$H-NMR (400 MHz, DMSO-d$^6$) δ [ppm]: 1.118 (9.71), 1.371 (0.81), 1.378 (16.00), 4.194

Intermediate 61A

Tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]-2,2-dimethylpropanoate

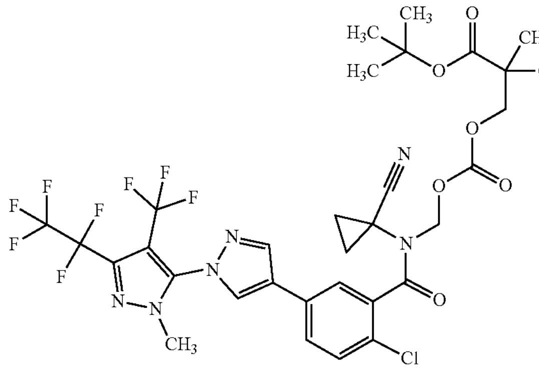

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (262 mg, 475 μmol) was dissolved in dry THF (15 mL). This solution was cooled to −45° C. on an acetone-dry ice bath. Potassium bis(trimethylsilyl)amide (1.5 mL, 0.50 M solution in toluene, 760 μmol) was added dropwise and the mixture was stirred for 30 min. at −45° C. Then, a solution of sodium iodide (35.6 mg, 237 μmol) and tert-butyl 3-{[(chloromethoxy)carbonyl]oxy}-2,2-dimethylpropanoate (intermediate 60A, 190 mg, 712 μmol)) in THF (5.0 mL) was added, the dry ice bath was removed and the mixture was stirred at room temperature over the weekend. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 166 mg (91% purity, 41% yield) of the title compound were obtained.

LC-MS (Method 4): $R_t$=5.02 min; MS (ESIpos): m/z=727 $[M+H]^+$ $^1$H-NMR (400 MHz, DMSO-d$^6$) δ [ppm]: −0.022 (0.59), −0.008 (3.30), 0.008 (3.41), 1.044 (9.00), 1.095 (2.59), 1.109 (0.96), 1.235 (0.98), 1.306 (1.20), 1.329 (16.00), 1.370 (5.59), 1.379 (2.07), 1.484 (0.42), 1.758 (1.21), 2.524 (1.26), 3.824 (11.37), 4.024 (1.01), 4.069 (0.85), 7.613 (0.75), 7.633 (0.91), 7.826 (1.30), 7.846 (1.05), 7.868 (0.89), 8.560 (1.75), 8.815 (1.78).

Intermediate 62A

Tert-Butyl Trans-4-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclohexyl (2E)-but-2-enedioate

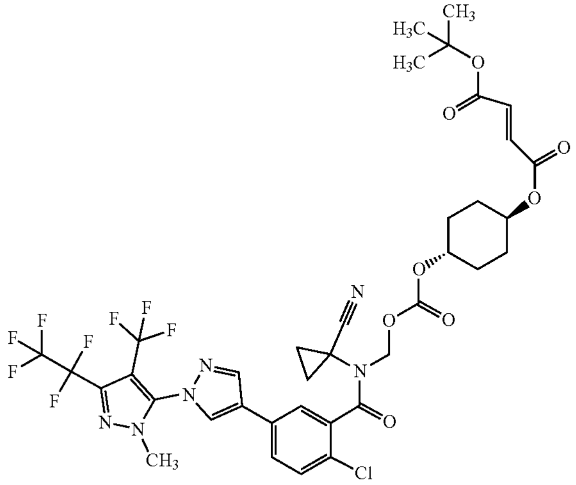 [SMILES: Cn1nc(C(F)(F)C(F)(F)F)c(C(F)(F)F)c1-n1cc(-c2ccc(Cl)c(C(=O)N(COC(=O)O[C@H]3CC[C@H](OC(=O)/C=C/C(=O)OC(C)(C)C)CC3)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (203 mg, 368 μmol) was dissolved in dry THF (9 mL). This solution was cooled to −45° C. on an acetone-dry ice bath. Potassium bis(trimethylsilyl)amide (1.1 mL, 0.50 M solution in toluene, 590 μmol) was added dropwise and the mixture was stirred for 30 min. at −45° C. Then, a solution of sodium iodide (27.5 mg, 184 μmol) and tert-butyl (1r,4r)-4-{[(chloromethoxy)carbonyl]oxy}cyclohexyl (2E)-but-2-enedioate (intermediate 50A, 200 mg, 551 μmol) in THF (4.0 mL) was added, the dry ice bath was removed and the mixture was stirred at room temperature over night. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 206 mg (100% purity, 64% yield) of the title compound were obtained.

LC-MS (Method 4): $R_t$=5.12 min: MS (ESIpos): m/z=879 $[M+H]^+$ $^1$H-NMR (400 MHz, DMSO-d$^6$) δ [ppm]: −0.008 (0.60), 0.008 (0.70), 1.157 (0.55), 1.175 (1.11), 1.193 (0.57), 1.234 (0.40), 1.458 (16.00), 1.504 (0.55), 1.767 (0.41), 1.856 (0.44), 1.988 (2.03), 3.823 (3.34), 4.021 (0.47), 4.039 (0.47), 6.638 (1.73), 7.840 (0.56), 8.579 (0.55), 8.844 (0.53).

Intermediate 63A

Tert-Butyl Trans-4-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl) amino]methoxy}carbonyl)oxy]cyclohexane-1-carboxylate and evaporated. The crude product was purified by preparative HPLC (RP C-18 10 μm, water-acetonitrile gradient with 0.01% TFA in both eluents, 90:10->5:95). 311 mg (98% purity, 66% yield) of the title compound were obtained.

LC-MS (Method 4): $R_t$=5.08 min; MS (ESIpos): m/z=809 $[M+H]^+$

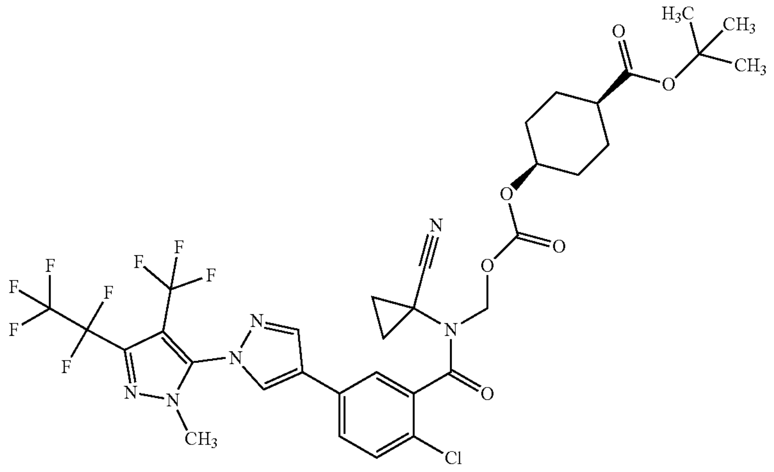 [SMILES: Cn1nc(C(F)(F)C(F)(F)F)c(C(F)(F)F)c1-n1cc(-c2ccc(Cl)c(C(=O)N(COC(=O)O[C@H]3CC[C@@H](C(=O)OC(C)(C)C)CC3)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (315 mg, 569 μmol) was dissolved in dry THF (16 mL). This solution was cooled to −45° C. on an acetone-dry ice bath. Potassium bis(trimethylsilyl)amide (1.8 mL, 0.50 M solution in toluene, 910 μmol) was added dropwise and the mixture was stirred for 30 min. at −45° C. Then, a solution of sodium iodide (42.7 mg, 285 μmol) and tert-butyl (1s,4s)-4-{[(chloromethoxy)carbonyl]oxy}cyclohexane-1-carboxylate (intermediate 52A, 250 mg, 854 μmol) in THF (5.0 mL) was added, the dry ice bath was removed and the mixture was stirred at room temperature for 2 h. The reaction mixture was poured into water and extracted with three portions of ethyl acetate. The combined organic extracts were dried over anhydrous sodium sulfate $^1$H-NMR (600 MHz, DMSO-d$^6$) δ [ppm]: 1.357 (1.18), 1.379 (16.00), 1.590 (0.86), 1.767 (0.56), 2.075 (1.06), 3.826 (5.33), 7.612 (0.43), 7.627 (0.48), 7.851 (1.16), 7.861 (0.58), 8.574 (0.95), 8.848 (0.92).

Intermediate 64A

Tert-Butyl Trans-4-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl) amino]methoxy}carbonyl)oxy]cyclohexane-1-carboxylate

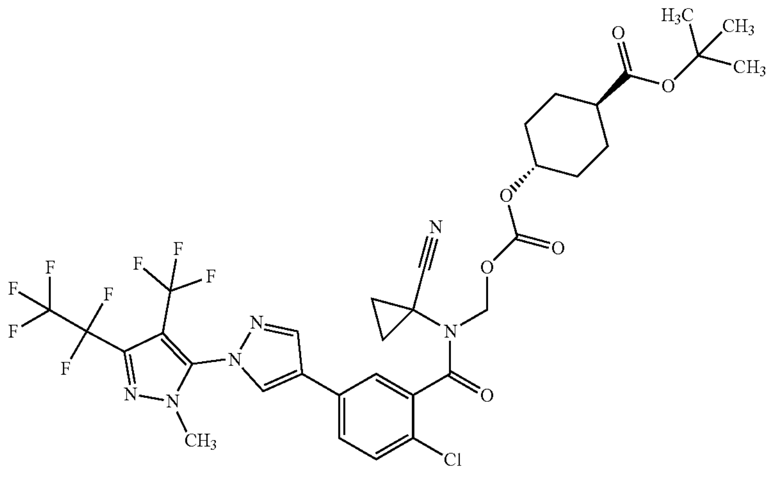 [SMILES: Cn1nc(C(F)(F)C(F)(F)F)c(C(F)(F)F)c1-n1cc(-c2ccc(Cl)c(C(=O)N(COC(=O)O[C@H]3CC[C@H](C(=O)OC(C)(C)C)CC3)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (189 mg, 342 μmol) was dissolved in dry THF (11 mL). This solution was cooled to −45° C. on an acetone-dry ice bath. Potassium bis(trimethylsilyl)amide (1.1 mL, 0.50 M solution in toluene, 550 μmol) was added dropwise and the mixture was stirred for 30 min. at −45° C. Then, a solution of sodium iodide (25.6 mg, 171 μmol) and tert-Butyl (1r,4r)-4-{[(chloromethoxy)carbonyl]oxy}cyclohexane-1-carboxylate (intermediate 54A, 150 mg, 512 μmol) in THF (3.0 mL) was added, the dry ice bath was removed and the mixture was stirred at room temperature over night. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 201 mg (100% purity, 73% yield) of the title compound were obtained.

LC-MS (Method 4): $R_t$=5.07 min; MS (ESIpos): m/z=809 $[M+H]^+$ $^1$H-NMR (600 MHz, DMSO-$d^6$) δ [ppm]: 1.234 (0.53), 1.335 (0.85), 1.358 (1.57), 1.370 (16.00), 1.765 (0.75), 1.824 (0.66), 2.075 (6.04), 3.370 (0.40), 3.828 (6.58), 7.623 (0.61), 7.637 (0.71), 7.827 (0.96), 7.850 (0.62), 7.865 (0.59), 8.579 (1.25), 8.847 (1.22).

Intermediate 65A

Tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]propyl (2E)-but-2-enedioate

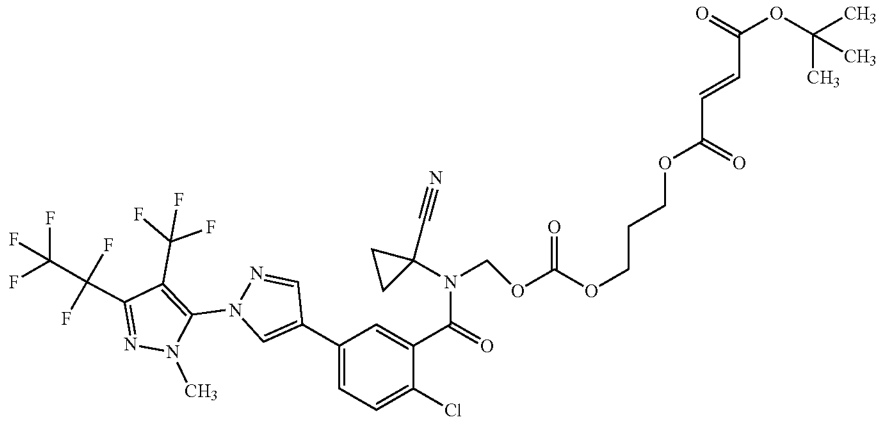 [SMILES: Cn1nc(C(F)(F)C(F)(F)F)c(C(F)(F)F)c1-n1cc(-c2ccc(Cl)c(C(=O)N(COC(=O)OCCCOC(=O)/C=C/C(=O)OC(C)(C)C)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (228 mg, 413 μmol) was dissolved in dry THF (16 mL). This solution was cooled to −45° C. on an acetone-dry ice bath. Potassium bis(trimethylsilyl)amide (1.3 mL, 0.50 M solution in toluene, 660 μmol) was added dropwise and the mixture was stirred for 30 min. at −45° C. Then, a solution of sodium iodide (31.0 mg, 207 μmol) and tert-Butyl 3-{[(chloromethoxy)carbonyl]oxy}propyl (2E)-but-2-enedioate (intermediate 6A, 200 mg, 620 μmol) in THF (4.0 mL) was added, the dry ice bath was removed and the mixture was stirred at room temperature at 2 h. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 202 mg (100% purity, 58% yield) of the title compound were obtained.

LC-MS (Method 4): $R_t$=4.85 min; MS (ESIpos): m/z=783 $[M+H]^+$ $^1$H-NMR (400 MHz, DMSO-$d^6$) δ [ppm]: 1.450 (16.00), 1.760 (0.45), 1.926 (0.42), 2.073 (0.68), 3.820 (3.80), 4.138 (0.56), 4.154 (0.67), 6.643 (1.46), 7.830 (0.49), 7.842 (0.41), 8.559 (0.63), 8.835 (0.60).

Intermediate 66A

Tert-Butyl 3-hydroxypropyl Butanedioate

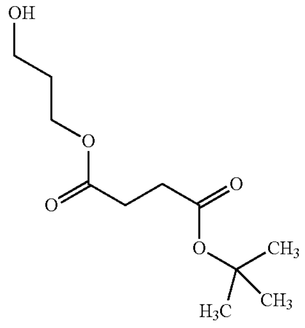 [SMILES: CC(C)(C)OC(=O)CCC(=O)OCCCO]

tert-Butyl 3-hydroxypropyl (2E)-but-2-enedioate (intermediate 5A, 450 mg, 1.95 mmol) was dissolved in ethanol (10 mL) under an argon atmosphere. 10% Palladium on charcoal (41.6 mg, 39.1 μmol) was added and the mixture was hydrogenated over night at ambient pressure at room temperature. The catalyst was then removed by filtration over a layer of diatomaceous earth and the solvent was distilled. 430 mg (95% yield) of the title compound were obtained.

$^1$H-NMR (400 MHz, DMSO-$d^6$) δ [ppm]: 1.384 (16.00), 1.685 (0.76), 1.701 (1.19), 1.717 (0.80), 2.438 (0.52), 2.440 (0.48), 2.445 (0.66), 2.453 (0.95), 2.454 (1.08), 2.467 (1.04), 2.477 (0.61), 2.484 (0.54), 3.427 (0.41), 3.443 (0.93), 3.456 (0.92), 4.049 (0.78), 4.065 (1.59), 4.082 (0.75), 4.484 (0.42), 4.496 (0.85).

Intermediate 67A

Tert-Butyl 3-{[(chloromethoxy)carbonyl]oxy}propyl butanedioate

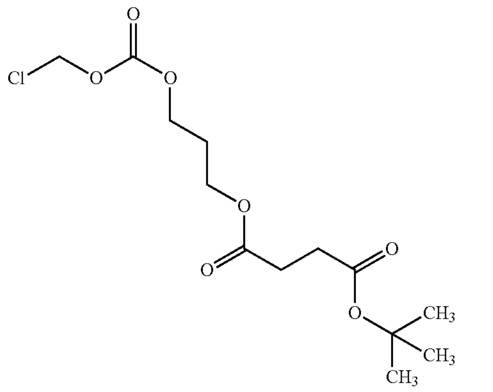 [SMILES: CC(C)(C)OC(=O)CCC(=O)OCCCOC(=O)OCCl]

tert-Butyl 3-hydroxypropyl butanedioate (intermediate 66A, 120 mg, 517 µmol) was dissolved in pyridine (4.0 mL). This solution was cooled to 0° C., chloromethyl carbonochloridate (69 µl, 770 µmol) was added and the mixture was stirred at room temperature for 2 h. Then, the solvent was distilled, the residue was dissolved in ethyl acetate and subsequently washed with water and brine. The organic phase was dried over sodium sulfate and evaporated. The crude product was purified by flash chromatography on silica gel (gradient cyclohexane-cyclohexane ethyl acetate 4:1). 144 mg (100% purity, 86% yield) of the title compound were isolated.

LC-MS (Method 4): $R_t$=3.09 min; MS (ESIpos): m/z=151 $[M+H]^+$ $^1$H-NMR (400 MHz, DMSO-$d^6$) δ [ppm]: 1.381 (16.00), 1.931 (0.71), 1.947 (1.08), 1.963 (0.73), 2.450 (0.62), 2.456 (0.65), 2.466 (1.08), 2.482 (1.11), 4.073 (0.74), 4.089 (1.51), 4.105 (0.72), 4.235 (0.76), 4.251 (1.58), 4.267 (0.75), 5.894 (3.71).

Intermediate 68A

Tert-Butyl 3-[({[{[2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]propyl Butanedioate

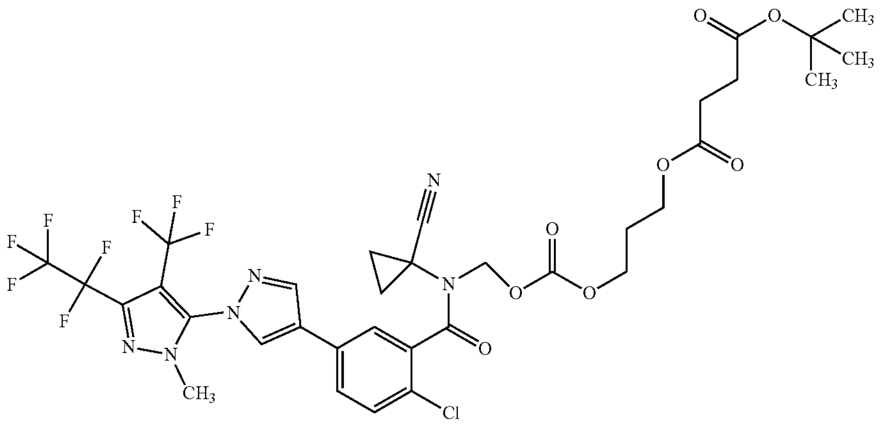 [SMILES: Cn1nc(C(F)(F)C(F)(F)F)c(C(F)(F)F)c1-n1cc(-c2ccc(Cl)c(C(=O)N(COC(=O)OCCCOC(=O)CCC(=O)OC(C)(C)C)C3(C#N)CC3)c2)cn1]

-

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (159 mg, 287 µmol) was dissolved in dry THF (9 mL). This solution was cooled to −45° C. on an acetone-dry ice bath. Potassium bis(trimethylsilyl)amide (900 µL, 0.50 M solution in toluene, 460 µmol) was added dropwise and the mixture was stirred for 30 min. at −45° C. Then, a solution of sodium iodide (21.5 mg, 144 µmol) and tert-Butyl 3-{[(chloromethoxy)carbonyl]oxy}propyl butanedioate (intermediate 67A, 140 mg, 431 µmol) in THF (2.0 mL) was added, the dry ice bath was removed and the mixture was stirred at room temperature for 3 h. The reaction mixture was poured into water and extracted with three portions of ethyl acetate. The combined organic extracts were dried over anhydrous sodium sulfate and evaporated. The crude product was purified by preparative HPLC (RP C-18 10 µm, water-acetonitrile gradient with 0.01% TFA in both eluents, 90:10->5:95). 196 mg (100% purity, 81% yield) of the title compound were obtained.

LC-MS (Method 4): $R_t$=4.71 min; MS (ESIpos): m/z=841 $[M+H]^+$

$^1$H-NMR (400 MHz, DMSO-$d^6$) δ [ppm]: 1.030 (6.03), 1.045 (6.10), 1.360 (16.00), 1.761 (0.67), 1.842 (0.45), 1.857 (0.64), 1.872 (0.48), 2.086 (2.40), 2.437 (1.36), 2.451 (1.24), 3.757 (0.42), 3.772 (0.56), 3.788 (0.43), 3.821 (5.60), 4.011 (0.50), 4.026 (0.88), 4.042 (0.56), 4.086 (0.65), 7.635 (0.47), 7.832 (0.72), 7.843 (0.60), 7.865 (0.43), 8.563 (0.91), 8.837 (0.91).

Intermediate 69A 1-tert-Butyl 1-{2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino] methoxy}carbonyl)oxy]ethyl} cyclopropane-1,1-dicarboxylate

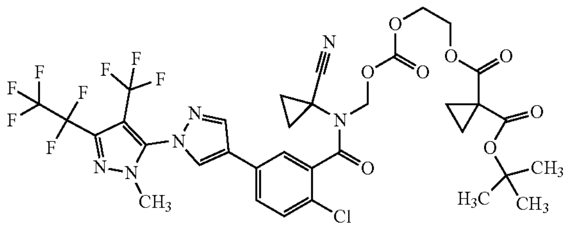 [SMILES: Cn1nc(C(F)(F)C(F)(F)F)c(C(F)(F)F)c1-n1cc(-c2ccc(Cl)c(C(=O)N(COC(=O)OCCOC(=O)C3(C(=O)OC(C)(C)C)CC3)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (171 mg, 310 μmol) was dissolved in dry THF (8 mL). This solution was cooled to −45° C. on an acetone-dry ice bath. Potassium bis(trimethylsilyl)amide (910 μL, 0.50 M solution in toluene, 500 μmol) was added dropwise and the mixture was stirred for 30 min. at −45° C. Then, a solution of sodium iodide (27.9 mg, 186 μmol) and 1-tert-Butyl 1-(2-{[(chloromethoxy)carbonyl]oxy}ethyl) cyclopropane-1,1-dicarboxylate (intermediate 40A, 150 mg, 465 μmol) in THF (3.0 mL) was added, the dry ice bath was removed and the mixture was stirred at room temperature for 3 h. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 180 mg (86% purity, 60% yield) of the title compound were obtained.

LC-MS (Method 4): $R_t$=4.77 min; MS (ESIpos): m/z=783 $[M+H]^+$

$^1$H-NMR (400 MHz, DMSO-$d^6$) δ [ppm]: 1.157 (0.80), 1.175 (1.60), 1.193 (0.88), 1.249 (6.35), 1.358 (16.00), 1.760 (1.22), 1.988 (2.93), 2.073 (1.87), 3.820 (11.25), 4.021 (0.72), 4.038 (0.73), 4.236 (3.37), 7.614 (0.71), 7.636 (0.88), 7.831 (1.26), 7.849 (0.99), 7.871 (0.84), 8.561 (1.70), 8.834 (1.60).

Intermediate 70A

Tert-Butyl 2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino] methoxy}carbonyl)oxy]ethyl Pentanedioate

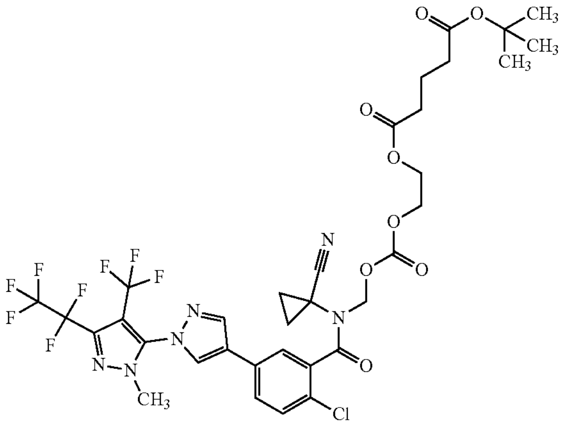 [SMILES: Cn1nc(C(F)(F)C(F)(F)F)c(C(F)(F)F)c1-n1cc(-c2ccc(Cl)c(C(=O)N(COC(=O)OCCOC(=O)CCCC(=O)OC(C)(C)C)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (238 mg, 431 μmol) was dissolved in dry THF (12 mL). This solution was cooled to −45° C. on an acetone-dry ice bath. Potassium bis(trimethylsilyl)amide (1.4 mL, 0.50 M solution in toluene, 690 μmol) was added dropwise and the mixture was stirred for 30 min. at −45° C. Then, a solution of sodium iodide (32.3 mg, 216 μmol) and tert-Butyl 2-{[(chloromethoxy)carbonyl]oxy}ethyl pentanedioate (intermediate 37A, 210 mg, 647 μmol) in THF (4.0 mL) was added, the dry ice bath was removed and the mixture was stirred at room temperature over night. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 201 mg (66% purity, 37% yield) of the title compound were obtained.

LC-MS (Method 4): $R_t$=4.75 min; MS (ESIpos): m/z=785 $[M+H]^+$

$^1$H-NMR (400 MHz, DMSO-$d^6$) δ [ppm]: 1.373 (16.00), 1.668 (0.43), 1.687 (0.62), 1.705 (0.49), 1.761 (0.42), 2.180 (0.44), 2.198 (0.82), 2.216 (0.44), 2.295 (0.59), 3.821 (3.64), 4.177 (0.53), 7.834 (0.44), 8.559 (0.60), 8.836 (0.55).

Intermediate 71A

Tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]-2,2-dimethylpropyl Butanedioate

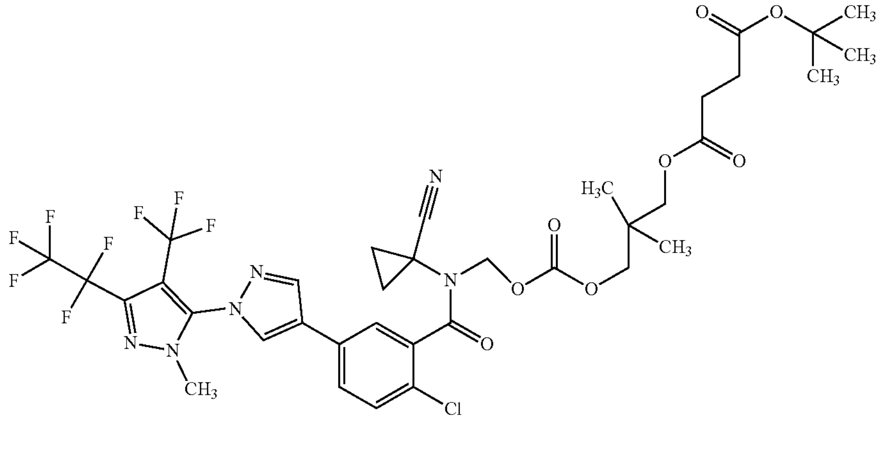 [SMILES: Cn1nc(C(F)(F)C(F)(F)F)c(C(F)(F)F)c1-n1cc(-c2ccc(Cl)c(C(=O)N(COC(=O)OCC(C)(C)COC(=O)CCC(=O)OC(C)(C)C)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (261 mg, 472 μmol) was dissolved in dry THF (12 mL). This solution was cooled to −45° C. on an acetone-dry ice bath. Potassium bis(trimethylsilyl)amide (1.4 mL, 0.50 M solution in toluene, 760 μmol) was added dropwise and the mixture was stirred for 30 min. at −45° C. Then, a solution of sodium iodide (35.4 mg, 236 μmol) and tert-Butyl 3-{[(chloromethoxy)carbonyl]oxy}-2,2-dimethylpropyl butanedioate (intermediate 14A, 250 mg, 709 μmol) in THF (4.0 mL) was added, the dry ice bath was removed and the mixture was stirred at room temperature for 1 h. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 349 mg (100% purity, 85% yield) of the title compound were obtained.

LC-MS (Method 4): $R_t$=4.98 min; MS (ESIpos): m/z=868 $[M+H]^+$ $^1$H-NMR (400 MHz, DMSO-d$^6$) δ [ppm]: 0.851 (1.90), 1.175 (0.72), 1.355 (7.00), 1.988 (1.27), 2.444 (0.47), 2.466 (0.44), 2.523 (0.41), 3.318 (16.00), 3.321 (15.00), 3.785 (0.54), 3.822 (2.61), 7.842 (0.55).

Intermediate 72A

Tert-Butyl [({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]acetate

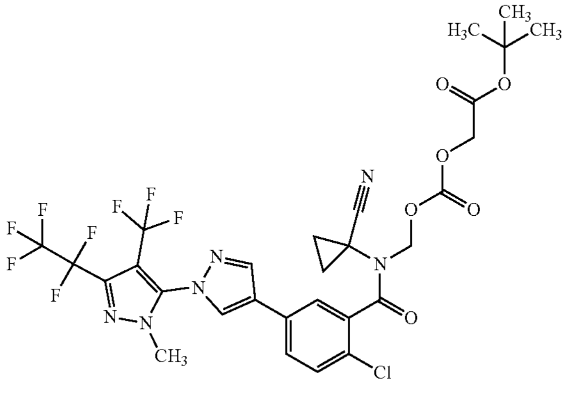 [SMILES: Cn1nc(C(F)(F)C(F)(F)F)c(C(F)(F)F)c1-n1cc(-c2ccc(Cl)c(C(=O)N(COC(=O)OCC(=O)OC(C)(C)C)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (246 mg, 445 μmol) was dissolved in dry THF (13 mL). This solution was cooled to −45° C. on an acetone-dry ice bath. Potassium bis(trimethylsilyl)amide (1.8 mL, 0.50 M solution in toluene, 710 μmol) was added dropwise and the mixture was stirred for 30 min. at −45° C. Then, a solution of sodium iodide (33.4 mg, 223 μmol) and tert-Butyl {[(chloromethoxy)carbonyl]oxy}acetate (intermediate 56A, 150 mg, 668 μmol) in THF (4.0 mL) was added, the dry ice bath was removed and the mixture was stirred at room temperature over night. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 230 mg (100% purity, 70% yield) of the title compound were obtained.

LC-MS (Method 4): $R_t$=4.65 min; MS (ESIpos): m/z=685 $[M+H]^+$ $^1$H-NMR (600 MHz, DMSO-$d^6$) δ [ppm]: 1.365 (16.00), 1.430 (1.20), 1.772 (1.41), 2.075 (0.41), 3.295 (0.63), 3.823 (13.60), 4.502 (3.21), 7.628 (0.89), 7.642 (0.99), 7.825 (1.45), 7.855 (0.91), 7.868 (0.87), 8.558 (3.53), 8.829 (2.26).

Intermediate 73A 1-tert-Butyl 1-methyl cyclopropane-1,1-dicarboxylate

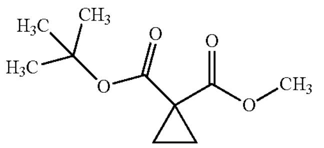

To a solution of tert-Butyl methyl malonate (CAS-RN: 42726-73-8, 35.00 g, 200.92 mmol) in N,N-dimethylformamide (350 mL), 1-bromo-2-chloroethane (40 ml, 401.84 mmol), potassium carbonate (69.42 g, 502.30 mmol) and 1-butyl-3-methyl-1H-imidazol-3-ium tetrafluoroborate (11.15 g, 50.32 mmol) was added with stirring at room temperature. After stirring for 48 h, the reaction mixture was diluted with water (800 mL) and extracted with diethyl ether (800 mL three times). The combined organic layers were washed with water (800 mL) and brine (800 mL), dried over anhydrous sodium sulfate and filtered. The filtrate was evaporated under reduced pressure to give 40 g (60% purity, 60% yield) of the title compound as a colourless oil.

$^1$H-NMR (300 MHz, DMSO-$d^6$) δ [ppm]: 1.175 (0.54), 1.260 (0.47), 1.271 (2.24), 1.278 (2.26), 1.289 (0.47), 1.369 (0.41), 1.379 (0.40), 1.398 (16.00), 1.408 (13.59), 1.989 (1.01), 2.891 (0.41), 3.387 (2.76), 3.639 (4.45), 3.652 (5.98).

Intermediate 74A 1-(tert-Butoxycarbonyl)cyclopropane-1-carboxylic Acid

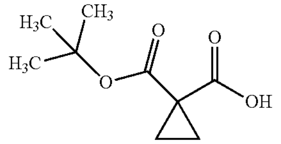

To a solution of 1-tert-Butyl 1-methyl cyclopropane-1,1-dicarboxylate (intermediate 73A, 40.00 g, 119.86 mmol) in a mixture of tetrahydrofuran (200 mL), methanol (100 mL) and water (100 mL), lithium hydroxide monohydrate (10.06 g, 239.72 mmol) was added. The mixture was stirred at room temperature for 2 h, then most of the solvents was removed by evaporation under vacuum, the residue was diluted with water (200 mL) and extracted with diethyl ether (200 mL three times). The aqueous layer was acidified to pH 2-3 with ice-cold 6 M hydrochloric acid and extracted with dichloromethane (2.0 L three times), dried over anhydrous sodium sulfate and filtered. The residue was concentrated under reduced pressure to give 12.00 g (95% purity, 51% yield) of the title compound as a colourless oil.

$^1$H-NMR (300 MHz, DMSO-$d^6$) δ [ppm]: 1.202 (0.43), 1.213 (1.95), 1.223 (2.00), 1.233 (0.52), 1.397 (16.00).

Intermediate 75A

Tert-Butyl 1-(hydroxymethyl)cyclopropane-1-carboxylate

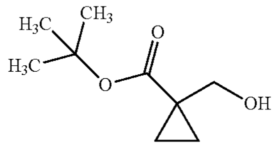

To a solution of 1-(tert-butoxycarbonyl)cyclopropane-1-carboxylic acid (Intermediate 74A, 12.80 g, 68.74 mmol), and triethylamine (13.91 g, 137.48 mmol) in tetrahydrofuran (160 mL), isobutyl chloroformate (11.74 g, 85.93 mmol) was added dropwise with stirring at 0° C. Stirring was maintained for 1 h, then the mixture was filtered and washed with tetrahydrofuran (20 mL). The filtrate was cooled to 0° C. and then a solution of sodium borohydride (5.20 g, 137.48 mmol) in 1-methyl-2-pyrrolidinone (20 ml) was added. The reaction mixture was stirred at room temperature for 2 h then diluted with ether (100 mL), washed with saturated sodium bicarbonate aqueous solution (200 ml), water (200 mL) and brine (200 mL). The combined organic layers were dried over anhydrous sodium sulfate and filtered. The filtrate was evaporated under reduced pressure. The residue was purified by column chromatography on silica gel (120 g, eluent: petroleum ether-ethyl acetate 20:1) to give 6.50 g (95% purity, 52% yield) of the title compound as colourless oil.

$^1$H-NMR (300 MHz, DMSO-$d^6$) δ [ppm]: 0.785 (0.92), 0.794 (1.35), 0.805 (0.61), 0.911 (0.57), 0.922 (1.34), 0.931 (0.88), 0.945 (0.40), 1.375 (16.00), 1.398 (0.50), 3.502 (1.55), 3.521 (1.64), 4.499 (0.48), 4.518 (1.00), 4.538 (0.48), 5.760 (0.80).

Intermediate 76A

Tert-Butyl 2-({[(chloromethoxy)carbonyl]oxy}methyl)-2-methylbutanoate

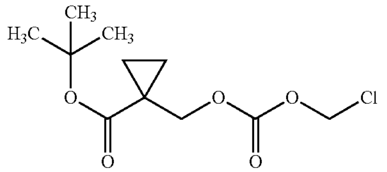 [SMILES: CC(C)(C)OC(=O)C1(COC(=O)OCCl)CC1]

tert-Butyl 2-(hydroxymethyl)-2-methylbutanoate (intermediate 75A, 377 mg, 2.00 mmol) was dissolved in pyridine (6.5 mL) and the solution was cooled to 0° C. Chloromethyl carbonochloridate (300 μL, 3.0 mmol) was added at once and the mixture was stirred at room temperature for 2 h. The solvent was evaporated. The residue was redissolved in ethyl acetate (50 mL) washed with water (20 mL) and brine (20 mL) dried over anhydrous sodium sulfate and evaporated. The crude product was purified by chromatography on silica gel (cyclohexane/ethyl acetate 4:1) to give 440 mg (100% purity, 78% yield) of the title compound.

$^1$H-NMR (600 MHz, DMSO-d$^6$) δ [ppm]: 0.985 (0.51), 0.992 (1.36), 0.997 (1.36), 1.004 (0.54), 1.129 (0.63), 1.135 (1.42), 1.140 (1.22), 1.147 (0.40), 1.374 (16.00), 4.290 (3.28), 5.905 (3.83)

Intermediate 77A

Tert-Butyl 1-{[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]methyl}cyclopropane-1-carboxylate

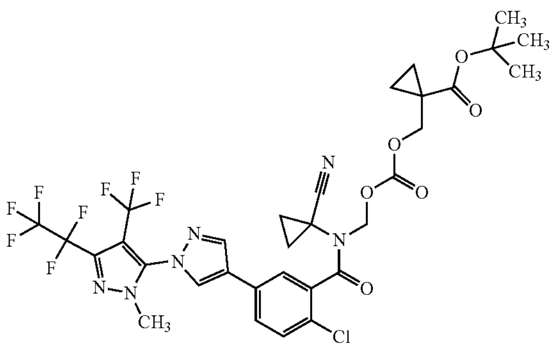 [SMILES: Cn1nc(C(F)(F)C(F)(F)F)c(C(F)(F)F)c1-n1cc(-c2ccc(Cl)c(C(=O)N(COC(=O)OCC3(C(=O)OC(C)(C)C)CC3)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (278 mg, 504 μmol) was dissolved in dry THF (16 mL). This solution was cooled to −45° C. on an acetone-dry ice bath. Potassium bis(trimethylsilyl)amide (1.6 mL, 0.50 M solution in toluene, 810 μmol) was added dropwise and the mixture was stirred for 30 min. at −45° C. Then, a solution of sodium iodide (37.7 mg, 236 μmol) and tert-Butyl 2-({[(chloromethoxy)carbonyl]oxy}methyl)-2-methylbutanoate (intermediate 76A, 200 mg, 756 μmol) in THF (5.0 mL) was added, the dry ice bath was removed and the mixture was stirred at room temperature over night. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 213 mg (100% purity, 54% yield) of the title compound were obtained.

LC-MS (Method 4): $R_t$=4.87 min; MS (ESIpos): m/z=781 [M+H]$^+$ $^1$H-NMR (600 MHz, DMSO-d$^6$) δ [ppm]: 0.913 (1.97), 1.085 (2.09), 1.235 (0.58), 1.318 (16.00), 1.368 (1.19), 1.761 (1.15), 2.075 (1.55), 3.374 (1.26), 3.824 (11.32), 4.118 (0.50), 4.154 (0.54), 7.619 (0.89), 7.633 (1.03), 7.844 (1.57), 7.852 (1.19), 7.866 (0.95), 8.568 (1.94), 8.838 (1.81).

Intermediate 78A

Tert-Butyl Trans-4-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclohexyl (2E)-but-2-enedioate

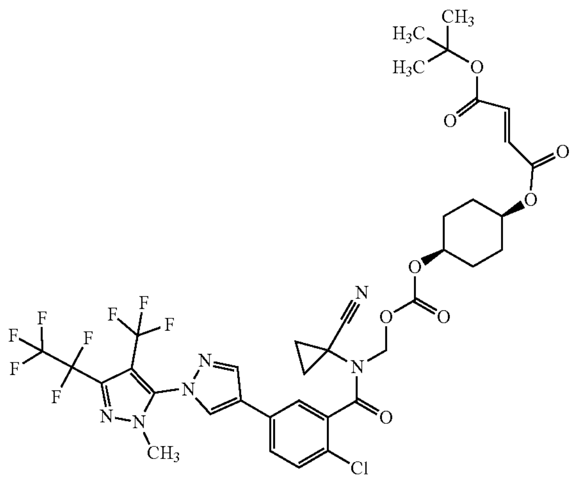 [SMILES: Cn1nc(C(F)(F)C(F)(F)F)c(C(F)(F)F)c1-n1cc(-c2ccc(Cl)c(C(=O)N(COC(=O)O[C@H]3CC[C@@H](OC(=O)/C=C/C(=O)OC(C)(C)C)CC3)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (120 mg, 217 μmol) was dissolved in dry THF (7 mL). This solution was cooled to −45° C. on an acetone-dry ice bath. Potassium bis(trimethylsilyl)amide (800 μL, 0.50 M solution in toluene, 350 μmol) was added dropwise and the mixture was stirred for 30 min. at −45° C. Then, a solution of sodium iodide (19.5 mg, 130 μmol) and tert-Butyl (1S,4S)-4-{[(chloromethoxy)carbonyl]oxy}cyclohexyl (2E)-but-2-enedioate (intermediate 45A, 118 mg, 326 μmol)) in THF (2.0 mL) was added, the dry ice bath was removed and the mixture was stirred at room temperature over night. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 120 mg (100% purity, 63% yield) of the title compound were obtained.

LC-MS (Method 4): $R_t$=5.07 min; MS (ESIpos): m/z=879 [M+H]$^+$ $^1$H-NMR (400 MHz, DMSO-d$^6$) δ [ppm]: −0.022 (0.60), −0.008 (1.01), 0.008 (1.09), 1.234 (1.46), 1.356 (0.79), 1.457 (16.00), 1.685 (1.04), 1.767 (0.57), 2.073 (4.31), 2.086 (0.45), 3.816 (3.69), 6.652 (1.84), 7.843 (0.62). 8.572 (0.58). 8.847 (0.56).

Intermediate 79A

Tert-Butyl 2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino] methoxy}carbonyl)oxy]ethyl Butanedioate

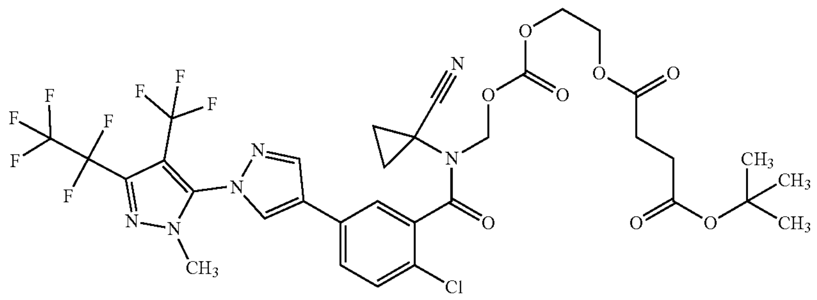 [SMILES: Cn1nc(C(F)(F)C(F)(F)F)c(C(F)(F)F)c1-n1cc(-c2ccc(Cl)c(C(=O)N(COC(=O)OCCOC(=O)CCC(=O)OC(C)(C)C)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (111 mg, 200 μmol) was dissolved in dry THF (6 mL). This solution was cooled to −45° C. on an acetone-dry ice bath. Potassium bis(trimethylsilyl)amide (640 μL, 0.50 M solution in toluene, 320 μmol) was added dropwise and the mixture was stirred for 30 min. at −45° C. Then, a solution of sodium iodide (18 mg, 120 μmol) and tert-Butyl 2-{[(chloromethoxy)carbonyl]oxy}ethyl butanedioate (intermediate 9A, 93 mg, 300 μmol)) in THF (2.0 mL) was added, the dry ice bath was removed and the mixture was stirred at room temperature for 45 min. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 132 mg (100% purity, 80% yield) of the title compound were obtained.

LC-MS (Method 4): $R_t$=4.75 min; MS (ESIpos): m/z=827 $[M+H]^+$ $^1$H-NMR (400 MHz, DMSO-d$^6$) δ [ppm]: −0.008 (0.44), 0.008 (0.50), 1.235 (0.40), 1.356 (16.00), 1.385 (0.59), 1.763 (0.67), 2.416 (0.87), 2.431 (1.09), 2.459 (0.91), 2.474 (0.91), 3.441 (1.82), 4.184 (0.96), 4.212 (0.65), 7.615 (0.40), 7.636 (0.50), 7.838 (0.79), 7.868 (0.47), 8.562 (1.02), 8.837 (0.97).

Intermediate 80A

Tert-Butyl 2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino] methoxy}carbonyl)oxy]ethyl (2E)-but-2-enedioate

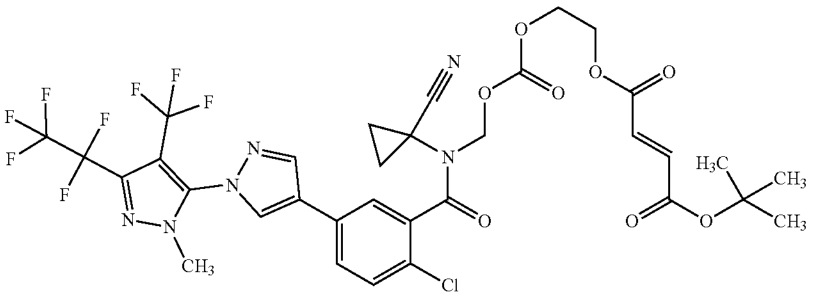 [SMILES: Cn1nc(C(F)(F)C(F)(F)F)c(C(F)(F)F)c1-n1cc(-c2ccc(Cl)c(C(=O)N(COC(=O)OCCOC(=O)/C=C/C(=O)OC(C)(C)C)C3(C#N)CC3)c2)cn1]

2-Chloro-N-(1-cyanocyclopropyl)-5-[2'-methyl-5'-(pentafluoroethyl)-4'-(trifluoromethyl)-2'H-[1,3'-bipyrazol]-4-yl]benzamide (75.0 mg, 136 μmol) was dissolved in dry THF (4 mL). This solution was cooled to −45° C. on an acetone-dry ice bath. Potassium bis(trimethylsilyl)amide (400 μL, 0.50 M solution in toluene, 220 μmol) was added dropwise and the mixture was stirred for 30 min. at −45° C. Then, a solution of sodium iodide (10.2 mg, 67.8 μmol) and tert-Butyl 2-{[(chloromethoxy)carbonyl]oxy}ethyl (2E)-but-2-enedioate (intermediate 3A, 62.8 mg, 204 μmol) in THF (2.0 mL) was added, the dry ice bath was removed and the mixture was stirred at room temperature for 1 h. The reaction mixture was poured into water and extracted with three portions of ethyl acetate. The combined organic extracts were dried over anhydrous sodium sulfate and evaporated. The crude product was purified by preparative HPLC (RP C-18 10 μm, water-acetonitrile gradient with 0.01% TFA in both eluents, 90:10->5:95). 75.7 mg (100% purity, 68% yield) of the title compound were obtained.

LC-MS (Method 4): $R_t$=4.85 min; MS (ESIpos): m/z=825 $[M+H]^+$

Intermediate 81A

Tert-Butyl 1-{[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]methyl}cyclopropane-1-carboxylate

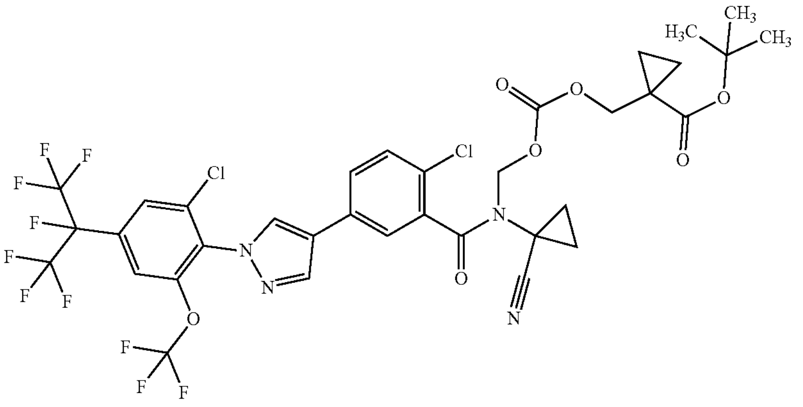 [SMILES: CC(C)(C)OC(=O)C1(COC(=O)OCN(C(=O)c2cc(-c3cnn(-c4c(Cl)cc(C(F)(C(F)(F)F)C(F)(F)F)cc4OC(F)(F)F)c3)ccc2Cl)C2(C#N)CC2)CC1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (162 mg, 250 μmol) was dissolved in dry THF (6.0 mL) This solution was cooled to −45° C. on an acetone-dry ice bath. Potassium bis(trimethylsilyl)amide (800 μL, 0.50 M solution in toluene, 400 μmol) was added dropwise and the mixture was stirred 30 min. at −45° C. Then, sodium iodide (18.7 mg, 125 μmol) and a solution of tert-Butyl 2-({[(chloromethoxy)carbonyl]oxy}methyl)-2-methylbutanoate (intermediate 76A, 105 mg, 375 μmol) in THF (2.0 mL) was added, the dry ice bath was removed and the mixture was stirred at room temperature for 60 min. The reaction mixture was evaporated. The crude product was purified by preparative HPLC (RP C-18 10 μm water-acetonitrile gradient with 0.01% TFA in both eluents, 90:10->5:95). 205 mg (100% purity, 93% yield) of the title compound were obtained.

LC-MS (Method 4): $R_t$=5.25 min; MS (ESIneg): m/z=920 $[M-H]^-$ $^1$H-NMR (500 MHz, DMSO-$d^6$) δ [ppm]: 0.913 (1.92), 1.078 (2.08), 1.162 (1.60), 1.176 (3.19), 1.190 (1.66), 1.234 (0.56), 1.313 (16.00), 1.357 (4.37), 1.757 (1.28), 1.990 (5.95), 2.185 (0.49), 4.009 (0.50), 4.023 (1.43), 4.038 (1.42), 4.052 (0.51), 4.120 (0.57), 4.150 (0.59), 7.596 (0.82), 7.612 (0.98), 7.809 (2.54), 7.826 (0.98), 7.943 (2.24), 8.220 (2.52), 8.454 (2.00), 8.772 (1.80).

Intermediate 82A

Tert-Butyl 3-{[(chloromethoxy)carbonyl]oxy}propanoate

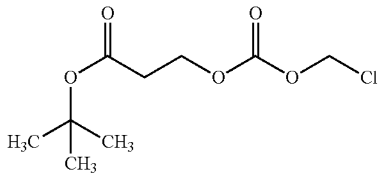

tert-Butyl 3-hydroxypropanoate (CAS-RN: 59854-11-4, 590 μl, 4.0 mmol) was dissolved in pyridine (13.0 mL) and the solution was cooled to 0° C. Chloromethyl carbonochloridate (610 μL, 6.0 mmol) was added at once and the mixture was stirred at room temperature for 2 h. The solvent was evaporated. The residue was redissolved in ethyl acetate (50 mL), washed with water (20 mL) and brine (20 mL) dried over anhydrous sodium sulfate and evaporated. The crude product was purified by chromatography on silica gel (cyclohexane/ethyl acetate 4:1) to give 768 mg (80% of theory) of the title compound.

$^1$H-NMR (500 MHz, DMSO-$d^6$) δ [ppm]: 1.402 (16.00), 2.619 (0.78), 2.631 (1.48), 2.643 (0.80), 4.337 (0.80), 4.349 (1.48), 4.361 (0.77), 5.897 (3.97).

Intermediate 83A

Tert-Butyl 3-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]propanoate

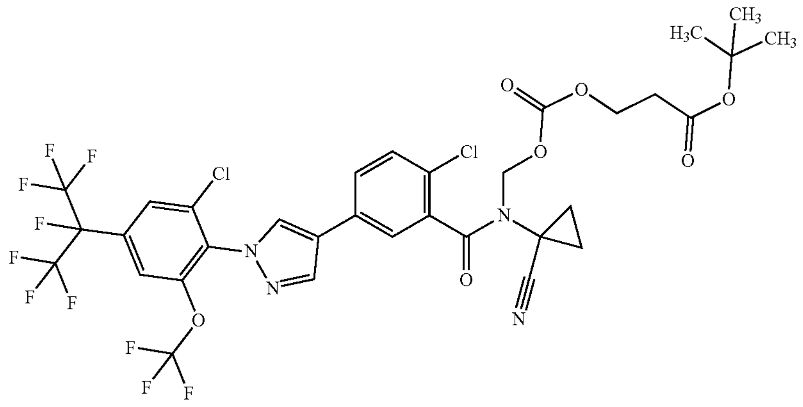 [SMILES: CC(C)(C)OC(=O)CCOC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (162 mg, 250 μmol) was dissolved in dry THF (6.0 mL) This solution was cooled to −45° C. on an acetone-dry ice bath. Potassium bis(trimethylsilyl)amide (800 μL, 0.50 M solution in toluene, 400 μmol) was added dropwise and the mixture was stirred 30 min. at −45° C. Then, sodium iodide (18.7 mg, 125 μmol) and a solution of tert-Butyl 3-{[(chloromethoxy)carbonyl]oxy}propanoate (intermediate 82A, 89.5 mg, 375 μmol) in THF (2.0 mL) was added, the dry ice bath was removed and the mixture was stirred at room temperature for 60 min. The reaction mixture evaporated. The crude product was purified by preparative HPLC (RP C-18 10 μm water-acetonitrile gradient with 0.01% TFA in both eluents, 90:10->5:95). 198 mg (100% purity, 93% yield) of the title compound were obtained.

LC-MS (Method 4): $R_t$=5.10 min; MS (ESIneg): m/z=849 $[M-H]^-$ $^1$H-NMR (500 MHz, DMSO-$d^6$) δ [ppm]: 1.234 (0.54), 1.360 (16.00), 1.757 (1.05), 2.077 (0.83), 2.184 (0.45), 2.524 (0.86), 4.181 (0.62), 7.596 (0.68), 7.613 (0.79), 7.785 (1.08), 7.813 (0.76), 7.830 (0.70), 7.942 (1.84), 8.217 (2.09), 8.220 (2.05), 8.451 (1.54), 8.771 (1.42).

Intermediate 84A

Tert-Butyl 4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]butanoate

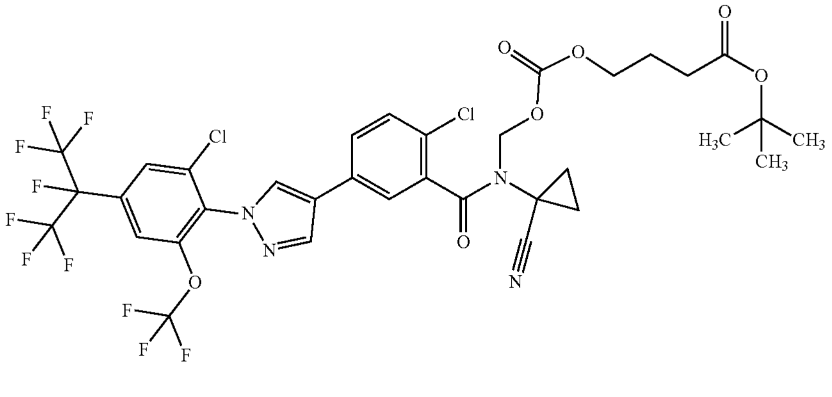 [SMILES: CC(C)(C)OC(=O)CCCOC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (162 mg, 250 μmol) was dissolved in dry THF (6.0 mL) This solution was cooled to −45° C. on an acetone-dry ice bath. Potassium bis(trimethylsilyl)amide (800 μL, 0.50 M solution in toluene, 400 μmol) was added dropwise and the mixture was stirred 30 min. at −45° C. Then, sodium iodide (18.7 mg, 125 μmol) and a solution of tert-Butyl 4-{[(chloromethoxy)carbonyl]oxy}butanoate (intermediate 58A, 94.8 mg, 375 μmol) in THF (2.0 mL) was added, the dry ice bath was removed and the mixture was stirred at room temperature for 60 min. The reaction mixture was evaporated. The crude product was purified by preparative HPLC (RP C-18 10 μm water-acetonitrile gradient with 0.01% TFA in both eluents, 90:10->5:95). 196 mg (100% purity, 91% yield) of the title compound were obtained.

LC-MS (Method 4): $R_t$=5.19 min; MS (ESIpos): m/z=865 $[M+H]^+$ $^1$H-NMR (500 MHz, DMSO-d$^6$) δ [ppm]: 1.234 (0.53), 1.365 (16.00), 1.756 (1.66), 2.202 (0.65), 2.216 (1.11), 2.231 (0.61), 4.023 (0.62), 7.592 (0.54), 7.609 (0.63), 7.789 (0.91), 7.807 (0.65), 7.823 (0.56), 7.941 (1.34), 8.216 (1.50), 8.451 (1.18), 8.779 (1.11).

Intermediate 85A

Tert-Butyl (1R,2R)-2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl) amino]methoxy}carbonyl)oxy]cyclopentyl butanedioate

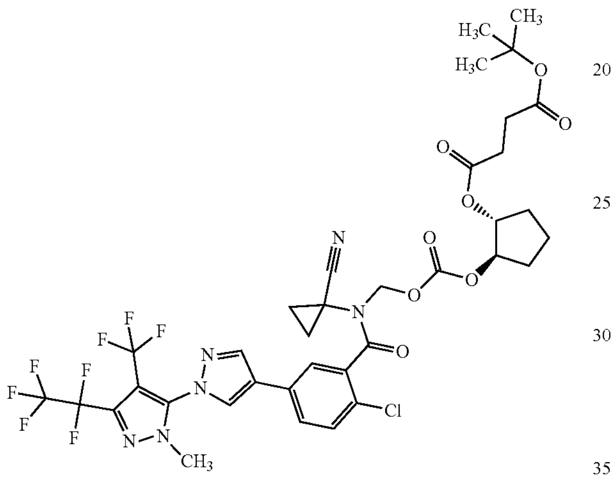

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (105 mg, 190 μmol) was dissolved in dry THF (6.0 mL) This solution was cooled to −45° C. on an acetone-dry ice bath. Potassium bis(trimethylsilyl)amide (600 μL, 0.50 M solution in toluene, 300 μmol) was added dropwise and the mixture was stirred 30 min. at −45° C. Then, sodium iodide (14.2 mg, 95 μmol) and a solution of tert-Butyl (1R,2R)-2-{[(chloromethoxy)carbonyl]oxy}cyclopentyl butanedioate (intermediate 34A, 100 mg, 285 μmol) in THF (2.0 mL) was added, the dry ice bath was removed and the mixture was stirred at room temperature for a night. The reaction mixture was poured into water and extracted with three portions of ethyl acetate. The combined organic extracts were dried over anhydrous sodium sulfate and evaporated. The crude product was purified by preparative HPLC (RP C-18 10 μm water-acetonitrile gradient with 0.01% TFA in both eluents, 90:10->5:95). 87.1 mg (95% purity, 50% yield) of the title compound were obtained.

LC-MS (Method 4): $R_t$=5.05 min; MS (ESIpos): m/z=867 $[M+H]^+$ $^1$H-NMR (600 MHz, DMSO-d$^6$) δ [ppm]: 1.236 (0.45), 1.357 (16.00), 1.382 (0.41), 1.655 (0.49), 1.757 (0.55), 2.085 (4.91), 2.183 (0.77), 2.423 (1.20), 2.438 (0.96), 2.500 (11.24), 3.821 (5.47), 5.746 (3.10), 6.871 (0.49), 7.832 (0.60), 7.843 (0.47), 8.556 (0.70), 8.826 (0.67).

Intermediate 86A

Tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino] methoxy}carbonyl)oxy]-2,2-dimethylpropyl (2E)-but-2-enedioate

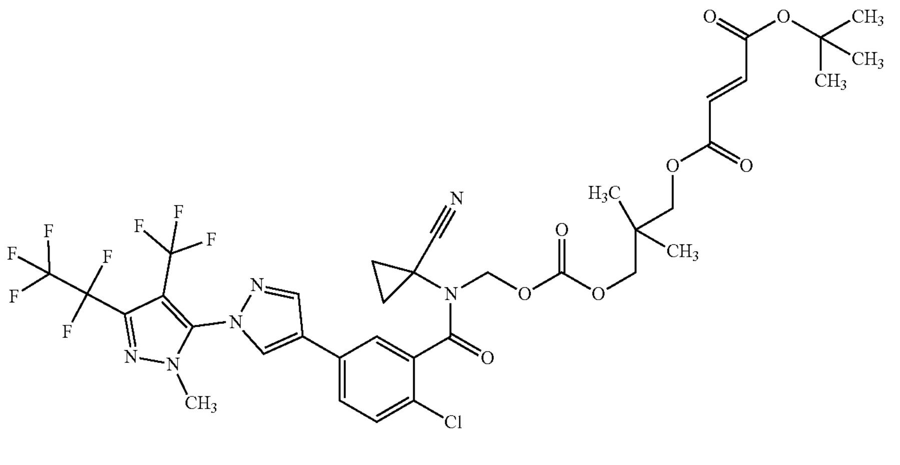 [SMILES: Cn1nc(C(F)(F)C(F)(F)F)c(C(F)(F)F)c1-n1cc(-c2ccc(Cl)c(C(=O)N(COC(=O)OCC(C)(C)COC(=O)/C=C/C(=O)OC(C)(C)C)C3(C#N)CC3)c2)cn1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (210 mg, 380 μmol) was dissolved in dry THF (10 mL) This solution was cooled to −45° C. on an acetone-dry ice bath. Potassium bis(trimethylsilyl)amide (900 μL, 0.50 M solution in toluene, 600 μmol) was added dropwise and the mixture was stirred 30 min. at −45° C. Then, sodium iodide (28.5 mg, 190 μmol) and a solution of tert-Butyl 3-{[(chloromethoxy)carbonyl]oxy}-2, 2-dimethylpropyl (2E)-but-2-enedioate (intermediate 12A, 200 mg, 570 μmol) in THF (2.0 mL) was added, the dry ice bath was removed and the mixture was stirred at room temperature over night. The reaction mixture was poured into water and extracted with three portions of ethyl acetate. The combined organic extracts were dried over anhydrous sodium sulfate and evaporated. The crude product was purified by preparative HPLC (RP C-18 10 μm water-acetonitrile gradient with 0.01% TFA in both eluents, 90:10->5:95). 295 mg (100% purity, 89% yield) of the title compound were obtained.

LC-MS (Method 4): $R_t$=5.12 min; MS (ESIpos): m/z=811 $[M+H]^+$ $^1$H-NMR (400 MHz, DMSO-d$^6$) δ [ppm]: −0.008 (0.93), 0.008 (1.01), 0.887 (2.51), 1.356 (1.22), 1.453 (16.00), 2.073 (5.27), 3.438 (1.10), 3.821 (3.53), 3.911 (1.18), 6.654 (1.00), 7.840 (0.73), 8.556 (0.55), 8.828 (0.50).

Intermediate 87A 1-tert-Butyl 4-{2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]ethyl} 2,2-dimethylbutanedioate

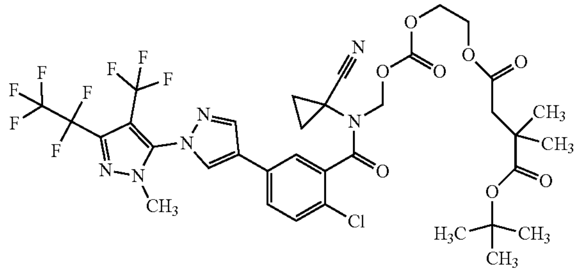 [SMILES: Cn1nc(C(F)(F)C(F)(F)F)c(C(F)(F)F)c1-n1cc(-c2ccc(Cl)c(C(=O)N(COC(=O)OCCOC(=O)CC(C)(C)C(=O)OC(C)(C)C)C3(C#N)CC3)c2)cn1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (97.9 mg, 177 μmol) was dissolved in dry THF (5.0 mL) This solution was cooled to −45° C. on an acetone-dry ice bath. Potassium bis(trimethylsilyl)amide (560 μL, 0.50 M solution in toluene, 280 μmol) was added dropwise and was added 30 min. at −45° C. Then, sodium iodide (13.3 mg, 88.6 μmol) and a solution of 1-tert-Butyl 4-(2-{[(chloromethoxy)carbonyl]oxy}ethyl) 2,2-dimethylbutanedioate (intermediate 29A, 90.0 mg, 266 μmol) in THF (2.0 mL) was added, the dry ice bath was removed and the mixture was stirred at room temperature over night. 1-tert-Butyl 4-(2-{[(chloromethoxy)carbonyl]oxy}ethyl) 2,2-dimethylbutanedioate (intermediate 29A, 30.0 mg, 88.7 μmol) was added and was added. The reaction mixture was poured into water and extracted with three portions of ethyl acetate. The combined organic extracts were dried over anhydrous sodium sulfate and evaporated. The crude product was purified by preparative HPLC (RP C-18 10 μm water-acetonitrile gradient with 0.01% TFA in both eluents, 90:10->5:95). 56.2 mg (100% purity, 37% yield) of the title compound were obtained.

LC-MS (Method 4): $R_t$ =4.93 min; MS (ESIpos): m/z=855 $[M+H]^+$ $^1$H-NMR (600 MHz, DMSO-d$^6$) δ [ppm]: 1.143 (2.13), 1.228 (2.13), 1.239 (3.20), 1.912 (4.27), 2.392 (3.20), 2.430 (5.33), 2.619 (3.20), 2.660 (5.33), 3.338 (4.27), 3.353 (5.33), 3.362 (3.20), 3.388 (16.00), 3.494 (14.93), 3.512 (6.40), 7.023 (2.13), 7.108 (2.13), 7.193 (2.13).

Intermediate 88A

Benzyl 3-{[(chloromethoxy)carbonyl]oxy}-2,2-dimethylpropanoate

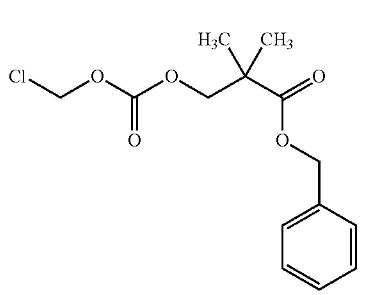 [SMILES: CC(C)(COC(=O)OCCl)C(=O)OCc1ccccc1]

Benzyl 3-hydroxy-2,2-dimethylpropanoate (CAS-RN: 17701-61-0,417 mg, 2.00 mmol) was dissolved in pyridine (7.5 mL) and the solution was cooled to 0° C. Chloromethyl carbonochloridate (270 μL, 3.0 mmol) was added at once and the mixture was stirred at room temperature for 16 h. The solvent was evaporated. The residue was redissolved in ethyl acetate (50 mL) washed with water (20 mL) and brine (20 mL) dried over anhydrous sodium sulfate and evaporated. The crude product was purified by chromatography on silica gel (cyclohexane/ethyl acetate 5:1) to give 230 mg (100% purity, 38% yield) of the title compound.

LC-MS (Method 2): $R_t$ =1.07 min; MS (ESIpos): m/z=301 $[M+H]^+$ $^1$H-NMR (400 MHz, DMSO-d$^6$) δ [ppm]: −0.008 (0.53), 0.008 (0.63), 1.195 (16.00), 4.263 (5.41), 5.122 (4.61), 5.875 (6.25), 7.322 (1.17), 7.340 (2.99), 7.360 (1.79), 7.375 (1.15).

Intermediate 89A

Benzyl 3-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-2,2-dimethylpropanoate

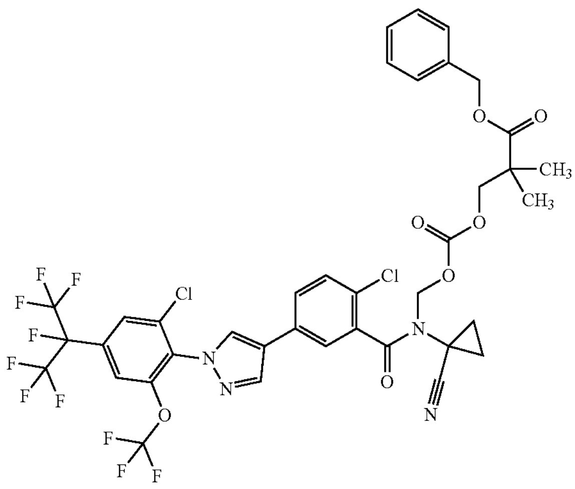 [SMILES: CC(C)(COC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1)C(=O)OCc1ccccc1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (331 mg, 510 μmol) was dissolved in dry THF (15 mL) This solution was cooled to −45° C. on an acetone-dry ice bath. Potassium bis(trimethylsilyl)amide (1.6 mL, 0.50 M solution in toluene, 820 μmol) was added dropwise and was added 30 min. at −45° C. Then, sodium iodide (38.2 mg, 255 μmol) and a solution of benzyl 3-{[(chloromethoxy)carbonyl]oxy}-2,2-dimethylpropanoate (intermediate 88A, 230 mg, 765 μmol) in THF (2 ml) was added, the dry ice bath was removed and the mixture was stirred at room temperature for 90 min. The reaction mixture was poured into water and extracted with three portions of ethyl acetate. The combined organic extracts were dried over anhydrous sodium sulfate and evaporated. The crude product was purified by preparative HPLC (RP C-18 10 μm water-acetonitrile gradient with 0.01% TFA in both eluents, 90:10->5:95). 435 mg (99% purity, 92% yield) of the title compound were obtained.

LC-MS (Method 3): $R_t$=2.72 min; MS (ESIpos): m/z=913 $[M+H]^+$ $^1$H-NMR (400 MHz, DMSO-d$^6$) δ [ppm]: −0.008 (3.58), 0.008 (2.47), 1.122 (16.00), 1.157 (2.02), 1.175 (2.57), 1.193 (1.74), 1.235 (1.44), 1.356 (3.95), 1.490 (0.69), 1.644 (0.62), 1.754 (2.39), 1.988 (2.13), 2.184 (0.50), 2.328 (0.69), 2.524 (2.36), 2.670 (0.76), 4.021 (0.56), 4.039 (0.62), 4.098 (2.12), 5.070 (6.65), 5.240 (0.53), 5.374 (0.55), 7.301 (7.10), 7.313 (5.22), 7.328 (3.15), 7.579 (1.35), 7.600 (1.58), 7.772 (2.32), 7.800 (1.93), 7.820 (1.60), 7.934 (3.98), 8.206 (4.50), 8.422 (4.34), 8.704 (4.44).

Intermediate 90A

Tert-Butyl (1S,2S)-2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclopentyl (2E)-but-2-enedioate

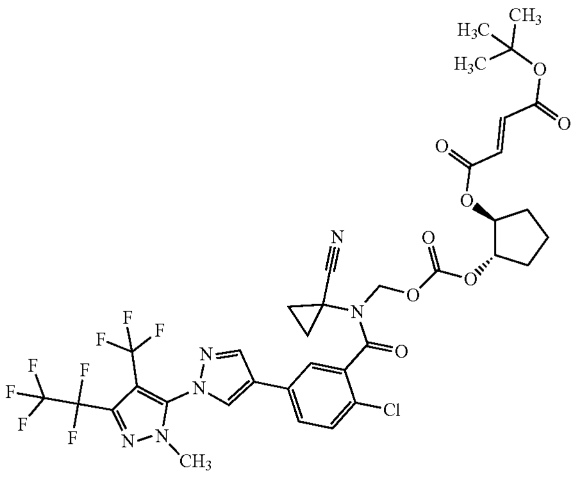 [SMILES: Cn1nc(C(F)(F)C(F)(F)F)c(C(F)(F)F)c1-n1cc(-c2ccc(Cl)c(C(=O)N(COC(=O)O[C@H]3CCC[C@@H]3OC(=O)/C=C/C(=O)OC(C)(C)C)C3(C#N)CC3)c2)cn1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (87.1 mg, 157 μmol) was dissolved in dry THF (6.0 mL) This solution was cooled to −45° C. on an acetone-dry ice bath. Potassium bis(trimethylsilyl)amide (600 μL, 0.50 M solution in toluene, 250 μmol) was added dropwise and was added 30 min. at −45° C. Then, sodium iodide (11.8 mg, 78.7 μmol) and a solution of tert-Butyl (1S,2S)-2-{[(chloromethoxy)carbonyl]oxy}cyclopentyl (2E)-but-2-enedioate (intermediate 32A, 82.4 mg, 236 μmol) THF (2.0 ml) was added, the dry ice bath was removed and the mixture was stirred at room temperature over night. The reaction mixture was poured into water and extracted with three portions of ethyl acetate. The combined organic extracts were dried over anhydrous sodium sulfate and evaporated. The crude product was purified by preparative HPLC (RP C-18 10 μm water-acetonitrile gradient with 0.01% TFA in both eluents, 90:10->5:95). 57.6 mg (42% yield) of the title compound were obtained.

LC-MS (Method 4): $R_t$=5.19 min; MS (ESIpos): m/z=809 $[M+H]^+$ $^1$H-NMR (400 MHz, DMSO-d$^6$) δ [ppm]: −0.008 (0.41), 0.008 (0.46), 1.235 (0.76), 1.356 (3.04), 1.447 (16.00), 1.462 (1.49), 1.675 (0.48), 1.759 (0.52), 2.183 (0.41), 3.820 (4.01), 5.754 (4.57), 6.622 (0.82), 6.632 (0.97), 7.839 (0.85), 8.557 (0.59), 8.831 (0.57).

Intermediate 91A

Tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]propanoate

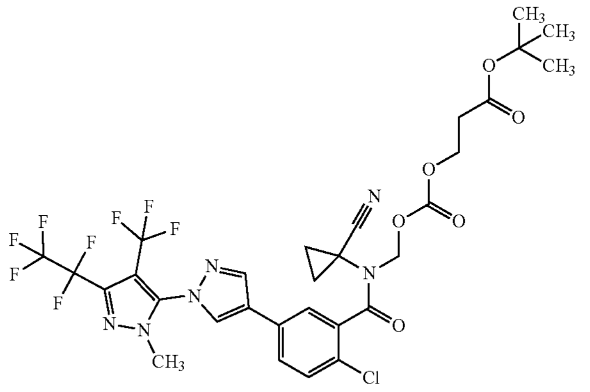 [SMILES: Cn1nc(C(F)(F)C(F)(F)F)c(C(F)(F)F)c1-n1cc(-c2ccc(Cl)c(C(=O)N(COC(=O)OCCC(=O)OC(C)(C)C)C3(C#N)CC3)c2)cn1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (276 mg, 500 μmol) was dissolved in dry THF (12.0 mL) This solution was cooled to −45° C. on an acetone-dry ice bath. Potassium bis(trimethylsilyl)amide (1.6 mL, 0.50 M solution in toluene, 800 μmol) was added dropwise and was added 30 min. at −45° C. Then, sodium iodide (37.5 mg, 250 μmol) and a solution of tert-Butyl 3-{[(chloromethoxy)carbonyl]oxy}propanoate (intermediate 82A, 179 mg, 750 μmol) THF (4 ml) was added, the dry ice bath was removed and the mixture was stirred at room temperature over night. The reaction mixture was poured into water and extracted with three portions of ethyl acetate. The combined organic extracts were dried over anhydrous sodium sulfate and evaporated. The crude product was purified by preparative HPLC (RP C-18 10 μm water-acetonitrile gradient with 0.01% TFA in both eluents, 90:10->5:95). 254 mg (100% purity, 67% yield) of the title compound were obtained.

LC-MS (Method 4): $R_t$=4.70 min; MS (ESIpos): m/z=699 $[M+H]^+$ $^1$H-NMR (600 MHz, DMSO-d$^6$) δ [ppm]: 1.365 (16.00), 1.758 (1.31), 2.071 (4.24), 3.822 (11.81), 4.183 (0.88), 7.616 (0.74), 7.630 (0.85), 7.818 (1.23), 7.854 (0.94), 7.868 (0.93), 8.556 (1.65), 8.827 (1.62).

Intermediate 92A

Tert-Butyl 1-{2-chloro-5-[2'-methyl-5'-(pentafluoroethyl)-4'-(trifluoromethyl)-2'H-[1,3'-bipyrazol]-4-yl]phenyl}-2-(1-cyanocyclopropyl)-11,11-dimethyl-1,5-dioxo-4,6,9-trioxa-2-azadodecan-12-oate

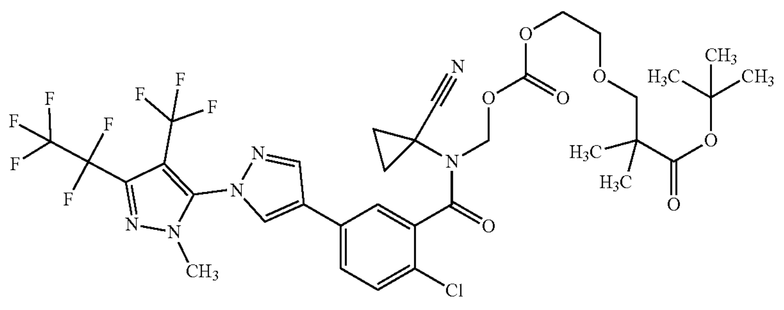 [SMILES: Cn1nc(C(F)(F)C(F)(F)F)c(C(F)(F)F)c1-n1cc(-c2ccc(Cl)c(C(=O)N(COC(=O)OCCOCC(C)(C)C(=O)OC(C)(C)C)C3(C#N)CC3)c2)cn1]

2-Chloro-5-{1-[2-chloro-4-(1,1,1,2,3,3,3-heptafluorpropan-2-yl)-6-(trifluormethoxy)phenyl]-1H-pyrazol-4-yl}-N-(1-cyanocyclopropyl)benzamide (138 mg, 250 μmol) was dissolved in dry THF (5.5 mL) This solution was cooled to −45° C. on an acetone-dry ice bath. Potassium bis(trimethylsilyl)amide (650 μL, 0.50 M solution in toluene, 330 μmol) was added dropwise and was added 30 min. at −45° C. Then, sodium iodide (18.7 mg, 125 μmol) and a solution of tert-Butyl 3-(2-{[(chloromethoxy)carbonyl]oxy}ethoxy)-2,2-dimethylpropanoate (intermediate 23A, 93.2 mg, 300 μmol) THF (2.0 ml) was added, the dry ice bath was removed and the mixture was stirred at room temperature for 30 min. The reaction mixture evaporated. The crude product was purified by preparative HPLC (RP C-18 10 μm water-acetonitrile gradient with 0.01% TFA in both eluents, 90:10->5:95). 110 mg (100% purity, 53% yield) of the title compound were obtained.

LC-MS (Method 4): $R_t$=5.15 min; MS (ESIpos): m/z=771 [M+H-C4H8]+$^+$ $^1$H-NMR (600 MHz, DMSO-d$^6$) δ [ppm]: 0.005 (0.68), 1.001 (10.40), 1.041 (2.96), 1.043 (3.10), 1.236 (0.57), 1.335 (16.00), 1.357 (6.04), 1.374 (4.82), 1.376 (3.88), 1.755 (1.20), 2.183 (0.59), 2.515 (0.76), 2.518 (0.74), 2.521 (0.68), 3.267 (0.76), 3.271 (0.48), 3.329 (3.16), 3.359 (0.65), 3.369 (0.78), 3.376 (0.59), 3.537 (1.72), 3.819 (14.82), 4.113 (0.87), 5.247 (0.59), 7.614 (0.74), 7.628 (0.87), 7.815 (1.24), 7.850 (0.87), 7.863 (0.83), 8.552 (1.72), 8.826 (1.63).

Synthesis of Example Compounds According to the Present Invention

Example Compound 1

(11E)-1-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-1,5,10-trioxo-4,6,9-trioxa-2-azatridec-11-en-13-oic Acid

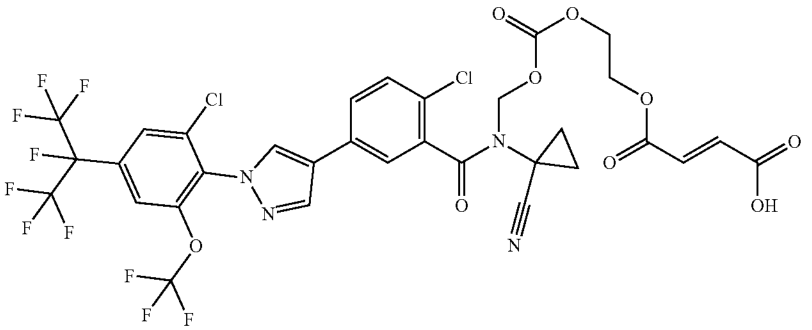 [SMILES: N#CC1(N(COC(=O)OCCOC(=O)/C=C/C(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl 2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]ethyl (2E)-but-2-enedioate (intermediate 4A, 105 mg, 114 μmol) was dissolved in 30% TFA in DCM (11 mL) and stirred at ambient temperature for 45 min. The volatiles were evaporated and the residue was purified by preparative HPLC (RP C-18 10 μm acetonitrile-water gradient with 0.01% TFA in both eluents, 10:90->95:5) and eventually by flash chromatography over silica gel eluted consecutively with cyclohexane, cyclohexane/ethyl acetate 4:1, ethyl acetate and finally ethyl acetate/methanol 10:1. The title compound was isolated in a yield of 56 mg (57% of theory).

LC-MS (method 2): $R_t$=1.26 min; MS (ESIpos): m/z=865 [M+H]$^+$ $^1$H-NMR (400 MHz, DMSO-d$^6$) δ [ppm]: −0.149 (1.74), −0.008 (16.00), 0.008 (11.78), 0.146 (1.48), 0.853 (0.63), 1.183 (0.78), 1.235 (3.59), 1.259 (1.56), 1.298 (0.78), 1.337 (0.81), 1.352 (0.85), 1.504 (1.96), 1.643 (1.89), 1.756 (6.78), 2.328 (1.41), 2.367 (1.07), 2.670 (1.44), 2.710 (0.96), 4.311

(11.48), 5.273 (1.44), 5.409 (1.48), 6.621 (1.48), 6.661 (10.11), 6.675 (13.67), 6.715 (2.04), 7.583 (3.30), 7.603 (4.07), 7.799 (9.78), 7.823 (4.70), 7.928 (11.37), 8.204 (11.96), 8.441 (10.78), 8.764 (7.52), 11.201 (0.52), 13.223 (1.63).

Example Compound 2

(12E)-1-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-1,5,11-trioxo-4,6,10-trioxa-2-azatetradec-12-en-14-oic Acid

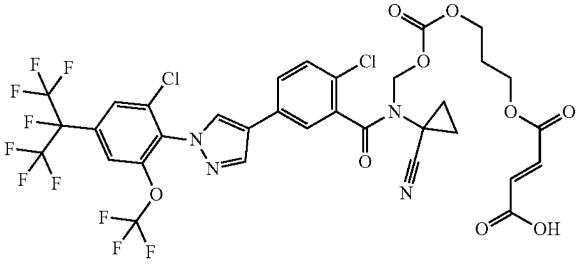 [SMILES: N#CC1(N(COC(=O)OCCCOC(=O)/C=C/C(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl 3-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino] methoxy}carbonyl)oxy]propyl (2E)-but-2-enedioate (intermediate 7A, 60.0 mg, 64.1 μmol) was dissolved in 30% TFA in DCM (3.0 mL) and stirred at ambient temperature for 15 min. The volatiles were evaporated and the residue was purified by preparative HPLC (RP C-18 10 μm acetonitrile-water gradient with 0.01% TFA in both eluents, 10:90->95:5). 38.0 mg (64% yield) of the title compound were obtained.

LC-MS (method 4): $R_t$=4.34 min; MS (ESIpos): m/z=879 $[M+H]^+$ $^1$H-NMR (500 MHz, DMSO-$d^6$) δ [ppm]: −0.120 (0.56), 1.235 (1.78), 1.490 (2.29), 1.655 (1.95), 1.756 (8.08), 1.930 (7.19), 2.363 (1.39), 2.637 (1.28), 4.123 (6.58), 4.159 (10.37), 5.254 (1.56), 5.405 (1.67), 6.638 (1.90), 6.670 (15.33), 6.679 (16.00), 6.710 (2.01), 7.589 (4.40), 7.605 (5.24), 7.790 (8.59), 7.803 (6.63), 7.820 (5.30), 7.927 (13.60), 8.201 (15.00), 8.443 (10.98), 8.766 (9.59), 13.209 (0.78).

Example Compound 3

1-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-1,5,10-trioxo-4,6,9-trioxa-2-azatridecan-13-oic Acid

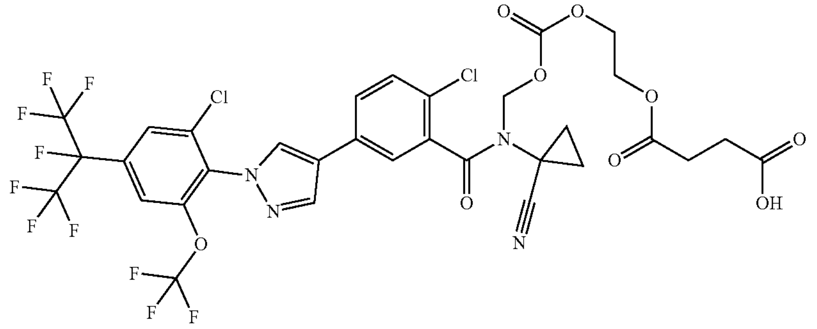 [SMILES: N#CC1(N(COC(=O)OCCOC(=O)CCC(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl 2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino] methoxy}carbonyl)oxy]ethyl butanedioate (intermediate 10A, 100 mg, 108 μmol) was dissolved in 30% TFA in DCM (5.0 mL) and stirred at ambient temperature for 15 min. The volatiles were evaporated and the residue was purified by preparative HPLC (RP C-18 10 μm acetonitrile-water gradient with 0.01% TFA in both eluents, 10:90->95:5). 78.0 mg (95% purity, 79% yield) of the title compound were obtained.

LC-MS (method 4): $R_t$=4.20 min; MS (ESIpos): m/z=867 $[M+H]^+$ $^1$H-NMR (400 MHz, DMSO-$d^6$) δ [ppm]: −0.149 (0.42), −0.022 (0.86), −0.008 (3.63), 0.008 (2.88), 1.235 (1.93), 1.513 (2.33), 1.647 (2.07), 1.761 (8.31), 2.323 (0.89), 2.328 (1.12), 2.367 (1.10), 2.441 (11.63), 2.454 (15.22), 2.473 (12.55), 2.670 (1.10), 2.710 (0.99), 3.540 (1.05), 3.552 (0.99), 3.566 (0.78), 4.018 (0.47), 4.030 (0.44), 4.183 (11.61), 4.363 (0.89), 5.279 (1.65), 5.403 (1.75), 7.556 (0.44), 7.592 (4.26), 7.612 (5.25), 7.758 (0.84), 7.801 (11.92), 7.824 (5.73), 7.936 (14.56), 8.209 (16.00), 8.213 (15.61), 8.446 (12.94), 8.770 (10.75), 12.198 (0.81).

Example Compound 4

(12E)-1-(2-chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-8,8-dimethyl-1,5,11-trioxo-4,6,10-trioxa-2-azatetradec-12-en-14-oic Acid

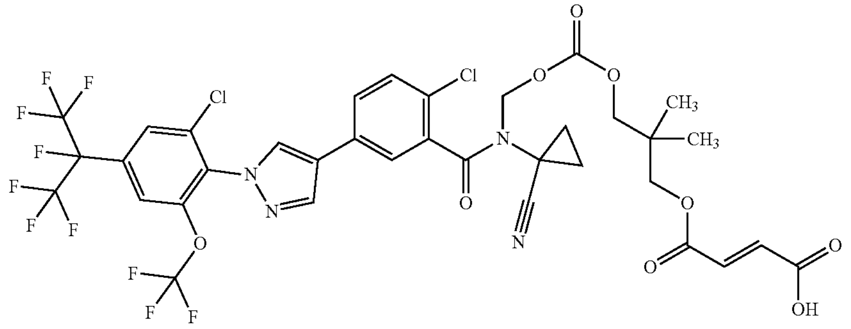 [SMILES: CC(C)(COC(=O)/C=C/C(=O)O)COC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

tert-Butyl 3-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-2,2-dimethylpropyl (2E)-but-2-enedioate (intermediate 13A, 298 mg, 309 μmol) was dissolved in 30% TFA in DCM (15 mL) and stirred at ambient temperature for 25 min. The volatiles were evaporated and the residue was purified by preparative HPLC (RP C-18 10 μm acetonitrile-water gradient with 0.01% TFA in both eluents, 10:90->95:5). 204 mg (100% purity, 73% yield) of the title compound were obtained.

LC-MS (method 4): $R_t$=4.60 min; MS (ESIpos): m/z=907 $[M+H]^+$ $^1$H-NMR (400 MHz, DMSO-d$^6$) δ [ppm]: −0.008 (2.25), 0.888 (16.00), 1.235 (0.89), 1.751 (2.55), 2.073 (13.35), 2.328 (1.35), 2.367 (0.82), 2.670 (1.53), 2.710 (0.97), 3.915 (7.86), 5.399 (0.64), 6.688 (12.63), 7.577 (1.40), 7.599 (1.79), 7.800 (3.96), 7.930 (4.29), 8.203 (5.10), 8.439 (4.13), 8.753 (3.27), 13.206 (1.89).

Example Compound 5

1-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-8,8-dimethyl-1,5,11-trioxo-4,6,10-trioxa-2-azatetradecan-14-oic Acid

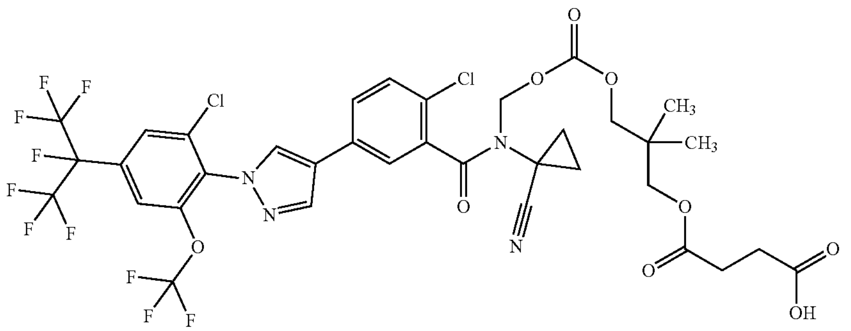 [SMILES: CC(C)(COC(=O)CCC(=O)O)COC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1]

tert-Butyl 3-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-2,2-dimethylpropyl butanedioate (intermediate 15A, 325 mg, 337 μmol) was dissolved in 30% TFA in DCM (16 mL) and stirred at ambient temperature for 10 min. The volatiles were evaporated and the residue was purified by preparative HPLC (RP C-18 10 μm acetonitrile-water gradient with 0.01% TFA in both eluents, 10:90->95:5). 237 mg (77% yield) of the title compound were obtained.

LC-MS (method 4): $R_t$=4.54 min; MS (ESIpos): m/z=909 $[M+H]^+$

$^1$H-NMR (400 MHz, DMSO-d[6]) δ [ppm]: −0.008 (2.76), 0.008 (1.95), 0.848 (16.00), 1.234 (0.49), 1.501 (0.70), 1.757 (2.59), 2.073 (8.11), 2.328 (1.65), 2.366 (1.08), 2.463 (4.81), 2.670 (1.68), 2.710 (1.05), 3.784 (4.59), 3.867 (2.84), 5.404 (0.59), 7.585 (1.35), 7.606 (1.62), 7.803 (4.27), 7.938 (4.38), 8.210 (5.05), 8.443 (3.68), 8.760 (3.19), 12.197 (2.14).

Example Compound 6

(2E)-4-({(rel 1R,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl}oxy)-4-oxobut-2-enoic Acid

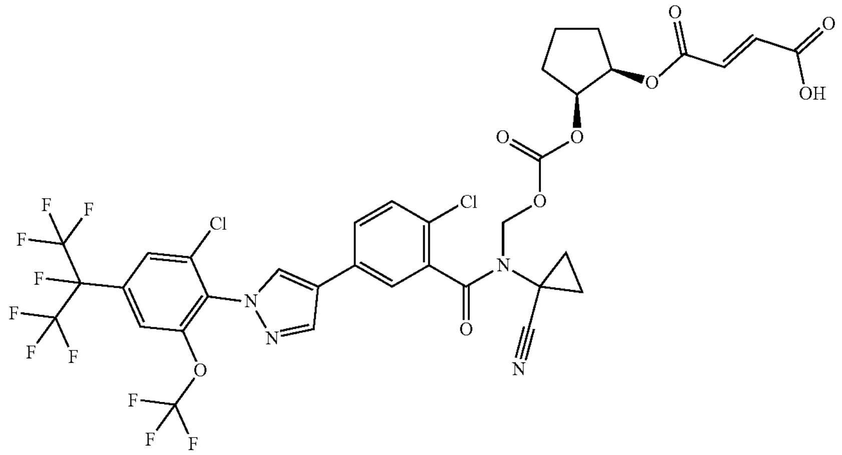 [SMILES: N#CC1(N(COC(=O)O[C@H]2CCC[C@H]2OC(=O)/C=C/C(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl (rel 1R,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl (2E)-but-2-enedioate (intermediate 18A, 455 mg, 473 μmol) was dissolved in in DCM (10 mL) and TFA (1.8 mL) was added. The mixture was stirred at ambient temperature for 1 h. The volatiles were evaporated and the residue was purified by preparative HPLC (RP C-18 10 μm acetonitrile-water gradient with 0.01% TFA in both eluents, 10:90->95:5). 135 mg (100% purity, 32% yield) of the title compound were obtained.

LC-MS (method 2): $R_t$=1.34 min; MS (ESIpos): m/z=905 $[M+H]^+$

$^1$H-NMR (400 MHz, DMSO-d[6]) δ [ppm]: −0.149 (0.57), −0.008 (4.30), 0.008 (3.38), 0.146 (0.39), 1.029 (0.75), 1.235 (1.80), 1.459 (3.38), 1.547 (4.12), 1.742 (13.68), 1.958 (4.30), 2.073 (1.10), 2.328 (1.36), 2.367 (1.71), 2.524 (4.08), 2.671 (1.36), 2.711 (1.58), 4.944 (3.59), 5.110 (4.82), 5.244 (1.75), 6.632 (10.43), 7.568 (4.34), 7.587 (5.35), 7.790 (15.30), 7.810 (6.44), 7.934 (14.73), 8.209 (16.00), 8.432 (15.39), 8.741 (9.60), 13.189 (2.81).

Example Compound 7

4-({(rel 1R,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl}oxy)-4-oxobutanoic Acid

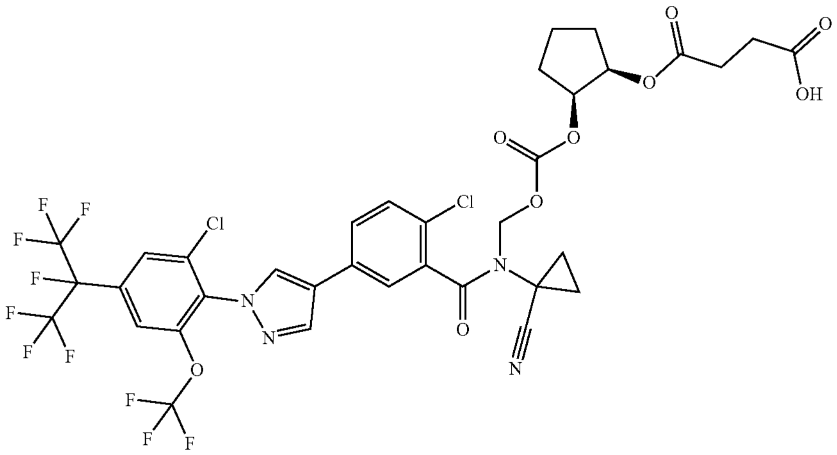 [SMILES: N#CC1(N(COC(=O)O[C@H]2CCC[C@H]2OC(=O)CCC(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl (rel 1R,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl butanedioate (intermediate 20A, 515 mg, 534 μmol) was dissolved in DCM (10 mL) and TFA (2.1 mL) was added. The mixture was stirred at ambient temperature for 20 min. The volatiles were evaporated and the residue was purified by preparative HPLC (RP C-18 10 μm acetonitrile-water gradient with 0.01% TFA in both eluents, 10:90->95:5). 300 mg (98% purity, 61% yield) of the title compound were obtained.

LC-MS (method 3): $R_t$=2.41 min; MS (ESIpos): m/z=907 $[M+H]^+$ $^1$H-NMR (400 MHz, DMSO-d$^6$) δ [ppm]: −0.008 (1.23), 0.008 (1.36), 1.218 (1.44), 1.235 (0.94), 1.283 (3.94), 1.509 (4.09), 1.628 (4.47), 1.693 (5.07), 1.758 (8.98), 1.908 (4.09), 2.074 (2.64), 2.671 (0.76), 2.711 (0.65), 4.874 (2.93), 4.996 (3.70), 5.277 (1.31), 7.588 (4.05), 7.609 (5.11), 7.802 (12.66), 7.820 (6.24), 7.936 (13.33), 8.211 (14.70), 8.405 (0.96), 8.444 (11.48), 8.759 (9.61), 12.165 (16.00).

Example Compound 8

1-(2-chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-11,11-dimethyl-1,5-dioxo-4,6,9-trioxa-2-azadodecan-12-oic Acid

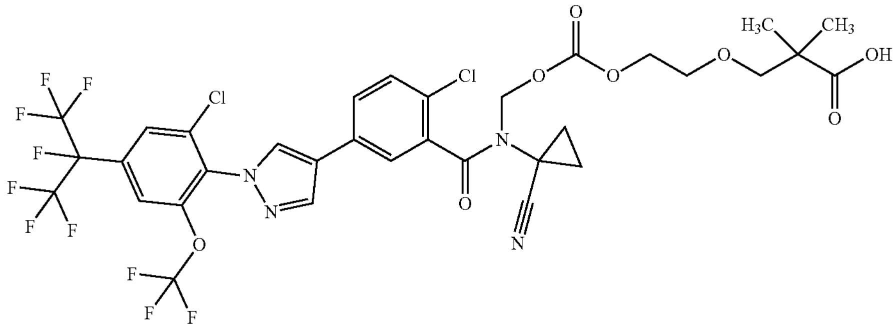 [SMILES: CC(C)(COCCOC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1)C(=O)O]

tert-Butyl 1-(2-chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-11,11-dimethyl-1,5-dioxo-4,6,9-trioxa-2-azadodecan-12-oate (intermediate 24A, 195 mg, 211 μmol) was dissolved in 30% TFA in DCM (10 mL) and stirred for 5 min at room temperature. Volatiles were evaporated under vacuum at ambient temperature. The residue was purified by preparative HPLC (RP C-18 10 μm acetonitrile-water gradient with 0.01% TFA in both eluents, 10:90->95:5). 152 mg (83% yield) of the title compound were isolated.

LC-MS (method 4): $R_t$=4.57 min; MS (ESIpos): m/z=867 $[M+H]^+$ $^1$H-NMR (400 MHz, DMSO-d$^6$) δ [ppm]: 1.027 (5.86), 1.758 (0.71), 3.340 (16.00), 3.360 (2.50), 3.546 (0.85), 4.115 (0.46), 7.611 (0.45), 7.794 (0.72), 7.802 (0.70), 7.824 (0.46), 7.937 (1.16), 8.213 (1.28), 8.444 (1.07), 8.768 (0.88).

Example Compound 9

1-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-12,12-dimethyl-1,5,10-trioxo-4,6,9-trioxa-2-azatridecan-13-oic Acid

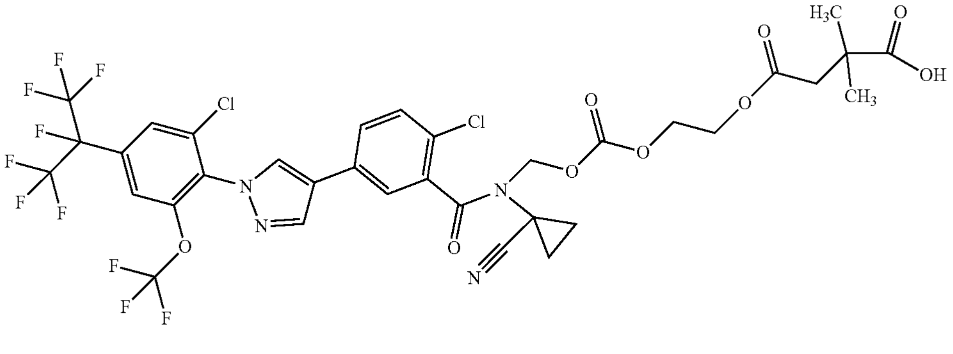 [SMILES: CC(C)(CC(=O)OCCOC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1)C(=O)O]

1-tert-Butyl 4-{2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]ethyl} 2,2-dimethylbutanedioate (intermediate 30A, 310 mg, 100% purity, 326 μmol) was dissolved in 30% TFA in DCM (16 mL) and stirred for 10 min at room temperature. Volatiles were evaporated and the residue was purified by preparative HPLC (RP C-18 10 μm acetonitrile-water gradient with 0.01% TFA in both eluents, 10:90->95:5). 207 mg (71% yield) of the title compound were obtained.

LC-MS (method 4): $R_t$=4.43 min; MS (ESIpos): m/z=895 $[M+H]^+$ $^1$H-NMR (500 MHz, DMSO-$d^6$) δ [ppm]: −0.120 (0.63), −0.007 (7.27), 0.006 (4.39), 0.116 (0.58), 1.127 (16.00), 1.168 (1.12), 1.512 (0.48), 1.660 (0.43), 1.760 (1.88), 2.362 (0.42), 2.636 (0.45), 3.541 (1.40), 4.157 (2.46), 4.200 (1.25), 7.593 (1.01), 7.609 (1.16), 7.793 (1.88), 7.805 (1.58), 7.822 (1.24), 7.935 (3.31), 8.208 (3.72), 8.441 (2.73), 8.769 (2.32).

Example Compound 10

(2E)-4-({(1S,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl}oxy)-4-oxobut-2-enoic Acid

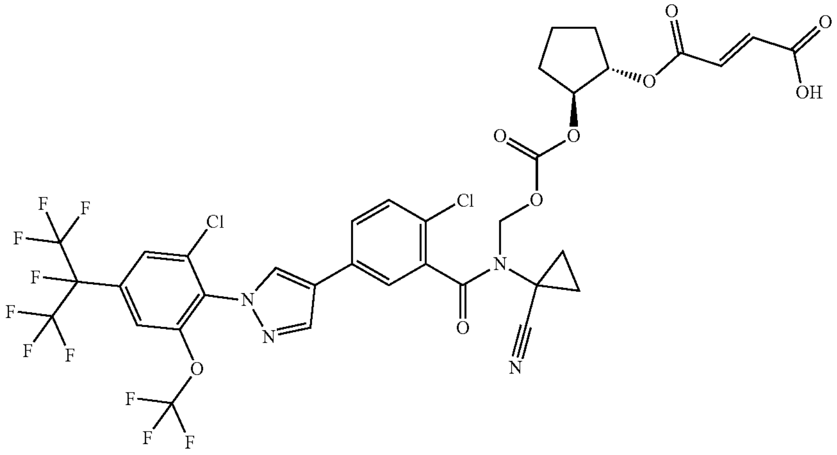 [SMILES: N#CC1(N(COC(=O)O[C@H]2CCC[C@@H]2OC(=O)/C=C/C(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl (1S,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl (2E)-but-2-enedioate (intermediate 33A, 120 mg, 125 μmol) was dissolved in DCM (5.0 mL) and TFA (480 μL) was added. The mixture was stirred at room temperature for 1 h. Then, another 480 μL of TFA were added and stirring was continued for 45 min. The solvent was distilled at room temperature under vacuum and the residue was purified by preparative HPLC (RP C-18 10 μm acetonitrile-water gradient with 0.01% TFA in both eluents, 10:90->95:5). 58.0 mg (51% yield) of the title compound were obtained.

LC-MS (method 3): $R_t$=2.46 min; MS (ESIpos): m/z=905 $[M+H]^+$ $^1$H-NMR (400 MHz, DMSO-d6) δ[ppm]: −0.149 (1.27), −0.008 (9.64), 0.008 (10.30), 0.146 (1.15), 1.141 (1.33), 1.235 (2.85), 1.465 (2.61), 1.501 (2.30), 1.673 (8.42), 1.754 (9.70), 2.025 (4.55), 2.328 (1.70), 2.367 (2.36), 2.670 (1.64), 2.710 (2.36), 4.883 (3.33), 5.067 (4.30), 5.277 (1.45), 5.384 (1.39), 6.583 (5.09), 6.622 (13.39), 6.669 (16.00), 6.709 (6.00), 7.583 (4.00), 7.603 (4.97), 7.799 (14.30), 7.820 (5.82), 7.931 (12.73), 8.204 (13.94), 8.442 (13.33), 8.762 (9.27), 13.231 (1.45).

Example Compound 11

4-({(1S,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl}oxy)-4-oxobutanoic Acid

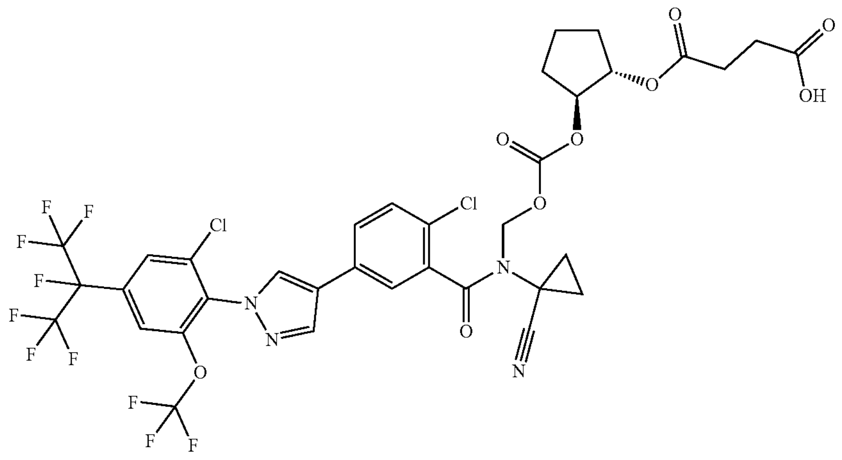 [SMILES: N#CC1(N(COC(=O)O[C@H]2CCC[C@@H]2OC(=O)CCC(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl (1S,2S)-2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclopentyl butanedioate (intermediate 35A, 100 mg, 104 μmol) was dissolved in DCM (5.0 mL) and TFA (1.0 mL) was added. The mixture was stirred at room temperature for 30 min, then volatiles were evaporated at room temperature under vacuum. The crude product was purified by preparative HPLC (RP C-18 10 μm acetonitrile-water gradient with 0.01% TFA in both eluents, 10:90->95:5). 66 mg (70% yield) of the title compound were obtained.

LC-MS (method 3): $R_t$=2.41 min; MS (ESIpos): m/z=907 $[M+H]^+$ $^1$H-NMR (400 MHz, DMSO-$d^6$) δ [ppm]: −0.008 (2.67), 0.008 (3.56), 1.235 (0.89), 1.567 (2.67), 1.646 (4.44), 1.755 (4.44), 1.953 (2.67), 2.330 (1.78), 2.368 (2.67), 2.445 (16.00), 2.672 (1.78), 2.712 (1.78), 3.071 (0.89), 3.105 (0.89), 3.229 (1.78), 3.489 (0.89), 3.643 (0.89), 3.664 (0.89), 4.279 (0.89), 4.791 (1.78), 4.955 (2.67), 5.389 (0.89), 7.585 (2.67), 7.606 (2.67), 7.799 (6.22), 7.823 (2.67), 7.936 (7.11), 8.209 (8.00), 8.442 (6.22), 8.759 (5.33).

Example Compound 12

1-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-2-(1-cyanocyclopropyl)-1,5,10-trioxo-4,6,9-trioxa-2-azatetradecan-14-oic Acid

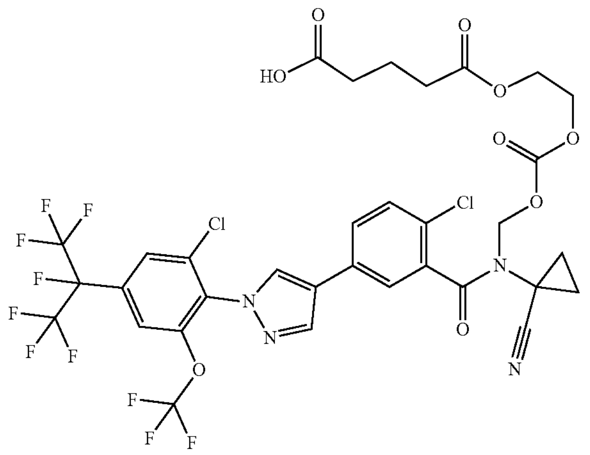 [SMILES: N#CC1(N(COC(=O)OCCOC(=O)CCCC(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl 2-[({[(2-chloro-5-{1-[2-chloro-4-(1,1,1,2,3,3,3-heptafluoropropan-2-yl)-6-(trifluoromethoxy)phenyl]-

1H-pyrazol-4-yl}benzoyl)(1-cyanocyclopropyl)amino] methoxy}carbonyl)oxy]ethyl pentanedioate (intermediate 38A, 150 mg, 160 μmol) was dissolved in DCM (5.0 mL) and TFA (2.0 mL) was added. The mixture was stirred at room temperature for 10 min, then volatiles were evaporated at room temperature under vacuum. The crude product was purified by preparative HPLC (RP C-18 10 μm acetonitrile-water gradient with 0.01% TFA in both eluents, 10:90->95:5). 79 mg (56% yield) of the title compound were obtained.

LC-MS (method 3): $R_t$=2.34 min; MS (ESIpos): m/z=881 $[M+H]^+$ $^1$H-NMR (400 MHz, DMSO-d$^6$) δ [ppm]: −0.149 (0.83), 0.008 (6.71), 0.146 (0.91), 1.044 (0.61), 1.235 (1.59), 1.508 (2.69), 1.681 (9.25), 1.699 (12.06), 1.718 (9.78), 1.756 (7.51), 2.073 (4.51), 2.203 (8.87), 2.221 (16.00), 2.240 (7.85), 2.293 (6.10), 2.311 (10.65), 2.328 (7.70), 2.366 (1.97), 2.670 (1.97), 2.709 (1.67), 3.409 (8.80), 4.177 (9.52), 4.216 (6.26), 4.590 (0.76), 5.175 (1.21), 5.272 (1.52), 5.404 (1.71), 7.557 (1.25), 7.588 (4.09), 7.608 (5.04), 7.757 (2.35), 7.794 (8.95), 7.823 (5.12), 7.935 (13.95), 8.209 (15.32), 8.442 (11.79), 8.767 (9.21), 12.058 (1.97).

Example Compound 13

1-[10-(2-Chloro-5-{1-[2-chloro-4-(1,1,1,2,3,3,3-heptafluoropropan-2-yl)-6-(trifluoromethoxy)phenyl]-1H-pyrazol-4-yl}phenyl)-9-(1-cyanocyclopropyl)-6,10-dioxo 2,5,7-trioxa-9-azadecanan-1-oyl] cyclopropane-1-carboxylic Acid

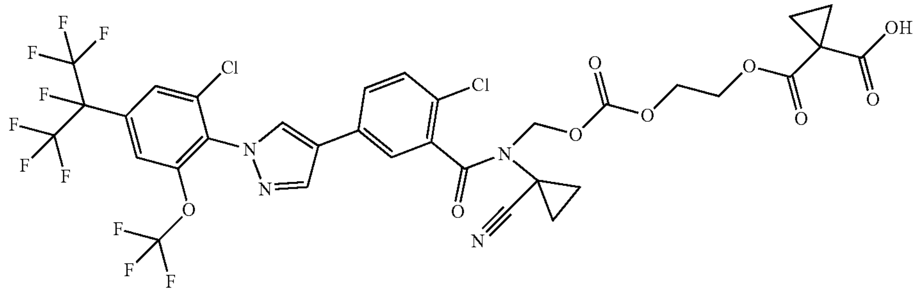 [SMILES: N#CC1(N(COC(=O)OCCOC(=O)C2(C(=O)O)CC2)C(=O)c2cc(-c3cnn(-c4c(Cl)cc(C(F)(C(F)(F)F)C(F)(F)F)cc4OC(F)(F)F)c3)ccc2Cl)CC1]

1-tert-Butyl 1-{2-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino] methoxy}carbonyl)oxy]ethyl} cyclopropane-1,1-dicarboxylate (intermediate 41 A, 570 mg, 609 μmol) was dissolved in DCM (10 mL) and TFA (2.0 mL) was added. The mixture was stirred at room temperature for 10 min, then volatiles were evaporated at room temperature under vacuum. The crude product was purified by preparative HPLC (RP C-18 10 μm acetonitrile-water gradient with 0.01% TFA in both eluents, 10:90->95:5). 365 mg (66% yield) of the title compound were obtained.

LC-MS (method 3): $R_t$=2.39 min; MS (ESIpos): m/z=879 $[M+H]^+$ $^1$H-NMR (400 MHz, DMSO-d$^6$) δ [ppm]: 1.280 (16.00), 1.505 (0.86), 1.648 (0.73), 1.762 (2.91), 2.073 (0.50), 2.328 (0.52), 2.670 (0.53), 4.226 (6.88), 5.277 (0.61), 5.395 (0.64), 7.591 (1.44), 7.611 (1.82), 7.802 (3.23), 7.826 (1.95), 7.936 (5.09), 8.212 (5.51), 8.446 (4.38), 8.767 (3.48), 12.780 (0.99).

Example Compound 14

(2E)-4-({cis-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy] cyclohexyl}oxy)-4-oxobut-2-enoic Acid

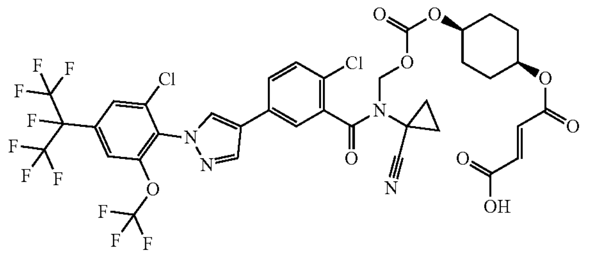 [SMILES: N#CC1(N(COC(=O)O[C@H]2CC[C@@H](OC(=O)/C=C/C(=O)O)CC2)C(=O)c2cc(-c3cnn(-c4c(Cl)cc(C(F)(C(F)(F)F)C(F)(F)F)cc4OC(F)(F)F)c3)ccc2Cl)CC1]

tert-Butyl cis-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino] methoxy}carbonyl)oxy]cyclohexyl (2E)-but-2-enedioate (intermediate 46A, 320 mg, 328 μmol) was dissolved in 30% TFA in DCM (16 mL) and the mixture was stirred at ambient temperature for 25 min. The solvent was distilled, the residue was taken up in acetonitrile and purified by preparative HPLC (RP C-18 10 μm acetonitrile:water+0.01% TFA 10:90->95:5). Fractions containing the desired product were combined and freeze-dried to give 215 mg (71% yield) of the title compound.

LC-MS (method 4): $R_t$=4.57 min; MS (ESIpos): m/z=919 $[M+H]^+$ $^1$H-NMR (400 MHz, DMSO-d$^6$) δ [ppm]: −0.008 (3.46), 0.008 (3.26), 1.234 (0.64), 1.697 (11.46), 1.764 (4.98), 2.073 (1.23), 2.328 (2.39), 2.366 (1.39), 2.670 (2.23), 2.710 (1.35), 3.472 (14.21), 4.595 (1.71), 4.850 (2.19), 5.261 (0.84), 6.643 (0.88), 6.683 (16.00), 6.688 (15.20), 6.727 (0.84), 7.593 (2.11), 7.614 (2.43), 7.802 (7.68), 7.821 (3.18), 7.924 (6.29), 8.196 (7.44), 8.452 (5.13), 8.775 (4.74), 13.181 (0.64).

Example Compound 15

4-({cis-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexyl}oxy)-4-oxobutanoic Acid

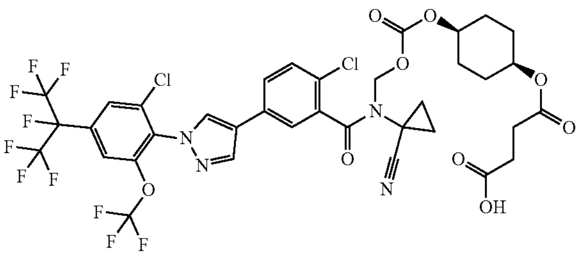 [SMILES: N#CC1(N(COC(=O)O[C@H]2CC[C@@H](OC(=O)CCC(=O)O)CC2)C(=O)c2cc(-c3cnn(-c4c(Cl)cc(C(F)(C(F)(F)F)C(F)(F)F)cc4OC(F)(F)F)c3)ccc2Cl)CC1]

tert-Butyl cis-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexyl butanedioate (intermediate 49A, 273 mg, 279 μmol) was dissolved in 30% TFA in DCM (14 mL) and the mixture was stirred at ambient temperature for 15 min. The solvent was distilled, the residue was taken up in acetonitrile and purified by preparative HPLC (RP C-18 10 μm acetonitrile:water+0.01% TFA 10:90->95:5). Fractions containing the desired product were combined and freeze-dried to give 255 mg (99% yield) of the title compound.

LC-MS (method 4): $R_t$=4.50 min; MS (ESIpos): m/z=921 $[M+H]^+$ $^1$H-NMR (400 MHz, DMSO-d$^6$) δ [ppm]: −0.149 (0.62), −0.008 (5.28), 0.008 (4.78), 0.146 (0.62), 1.234 (0.45), 1.505 (1.28), 1.663 (9.81), 1.762 (5.48), 2.073 (2.23), 2.323 (2.10), 2.327 (2.89), 2.332 (2.23), 2.366 (1.20), 2.443 (2.27), 2.467 (15.05), 2.473 (16.00), 2.523 (8.99), 2.665 (2.47), 2.670 (3.34), 2.674 (2.52), 2.710 (1.40), 4.566 (2.02), 4.725 (2.72), 5.262 (0.91), 5.410 (0.95), 7.592 (2.27), 7.614 (2.76), 7.801 (8.74), 7.820 (3.59), 7.937 (7.55), 8.210 (8.29), 8.214 (8.29), 8.451 (6.06), 8.773 (5.65), 12.184 (1.36).

Example Compound 16

(2E)-4-({trans-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexyl}oxy)-4-oxobut-2-enoic Acid

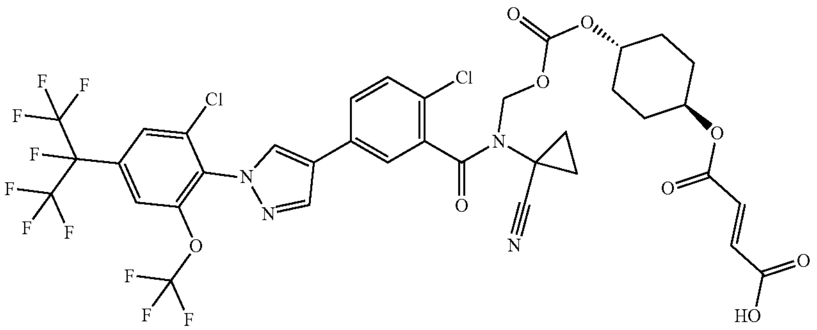 [SMILES: N#CC1(N(COC(=O)O[C@H]2CC[C@H](OC(=O)/C=C/C(=O)O)CC2)C(=O)c2cc(-c3cnn(-c4c(Cl)cc(C(F)(C(F)(F)F)C(F)(F)F)cc4OC(F)(F)F)c3)ccc2Cl)CC1]

tert-Butyl trans-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexyl (2E)-but-2-enedioate (intermediate 51A, 192 mg, 197 μmol) was dissolved in 30% TFA in DCM (19 mL) and the mixture was stirred at ambient temperature for 30 min. The solvent was distilled, the residue was taken up in acetonitrile and purified by preparative HPLC (RP C-18 10 μm acetonitrile:water+0.01% TFA 10:90->95:5). Fractions containing the desired product were combined and freeze-dried to give 133 mg (73% of theory) of the title compound.

LC-MS method 4): $R_t$=4.56 min; MS (ESIpos): m/z=919 $[M+H]^+$ $^1$H-NMR (500 MHz, DMSO-d6) δ[ppm]: −0.007 (3.06), 0.006 (2.21), 1.234 (0.72), 1.511 (9.00), 1.654 (2.19), 1.766 (7.12), 1.860 (7.44), 2.365 (0.55), 2.639 (0.54), 4.561 (3.25), 4.806 (3.40), 5.262 (1.65), 5.408 (1.74), 6.636 (2.45), 6.668 (15.70), 6.679 (16.00), 6.710 (2.42), 7.601 (5.00), 7.617 (5.79), 7.805 (13.70), 7.823 (5.29), 7.941 (10.76), 8.214 (12.49), 8.464 (10.82), 8.704 (0.47), 8.784 (10.72).

Example Compound 17

Cis-4-[({[(2-Chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexane-1-carboxylic Acid

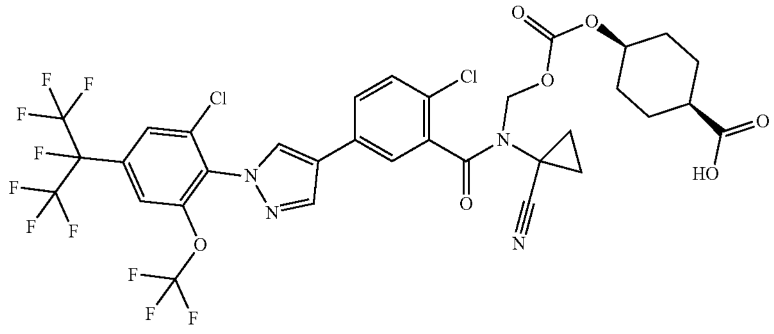 [SMILES: N#CC1(N(COC(=O)O[C@H]2CC[C@@H](C(=O)O)CC2)C(=O)c2cc(-c3cnn(-c4c(Cl)cc(C(F)(C(F)(F)F)C(F)(F)F)cc4OC(F)(F)F)c3)ccc2Cl)CC1]

tert-Butyl cis-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexane-1-carboxylate (intermediate 53A, 190 mg, 210 μmol) was dissolved in 30% TFA in DCM (19 mL) and the mixture was stirred at ambient temperature for 10 min. The solvent was distilled, the residue was taken up in acetonitrile and purified by preparative HPLC (RP C-18 10 μm acetonitrile:water+0.01% TFA 10:90->95:5). Fractions containing the desired product were combined and freeze-dried to give 110 mg (62% yield) of the title compound.

LC-MS (method 4): $R_t$=4.47 min; MS (ESIpos): m/z=849 $[M+H]^+$ $^1$H-NMR (500 MHz, DMSO-$d^6$) δ [ppm]: −0.022 (0.83), 0.006 (1.66), 1.234 (1.39), 1.275 (0.53), 1.491 (2.58), 1.605 (16.00), 1.648 (8.81), 1.673 (8.69), 1.763 (9.17), 2.297 (3.65), 2.361 (0.73), 2.638 (0.56), 4.637 (4.73), 4.805 (0.50), 5.252 (1.82), 5.392 (1.89), 7.589 (5.24), 7.607 (5.98), 7.814 (13.64), 7.944 (13.72), 8.217 (15.39), 8.457 (12.23), 8.776 (11.73), 12.133 (0.48).

Example Compound 18

Trans-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexane-1-carboxylic Acid

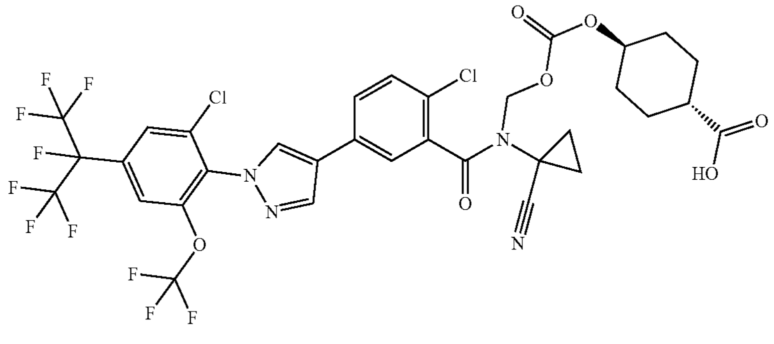 [SMILES: N#CC1(N(COC(=O)O[C@H]2CC[C@H](C(=O)O)CC2)C(=O)c2cc(-c3cnn(-c4c(Cl)cc(C(F)(C(F)(F)F)C(F)(F)F)cc4OC(F)(F)F)c3)ccc2Cl)CC1]

tert-Butyl trans-4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]cyclohexane-1-carboxylate (intermediate 55A, 189 mg, 209 μmol) was dissolved in 30% TFA in DCM (19 mL) and the mixture was stirred at ambient temperature for 10 min. The solvent was distilled, the residue was taken up in acetonitrile and purified by preparative HPLC (RP C-18 10 μm acetonitrile:water+0.01% TFA 10:90->95:5). Fractions containing the desired product were combined and freeze-dried to give 121 mg (94% purity, 64% yield) of the title compound.

LC-MS (method 4): $R_t$=4.48 min; MS (ESIpos): m/z=849 $[M+H]^+$ $^1$H-NMR (600 MHz, DMSO-$d^6$) δ [ppm]: −0.022 (0.75), 0.005 (1.63), 1.190 (0.66), 1.234 (1.15), 1.360 (8.78), 1.454 (2.90), 1.659 (2.14), 1.759 (9.21), 1.863 (8.45), 2.033 (0.88), 2.075 (1.12), 2.167 (3.86), 2.387 (1.15), 2.426 (1.45), 2.518 (3.02), 2.521 (3.23), 2.524 (3.17), 2.615 (1.03), 2.655 (1.09), 4.398 (3.71), 4.573 (0.54), 5.241 (1.96), 5.389 (2.05), 7.563 (0.69), 7.577 (1.03), 7.599 (6.37), 7.613 (7.00), 7.760 (1.39), 7.785 (10.20), 7.806 (6.97), 7.820 (6.13), 7.940 (14.97), 8.215 (16.00), 8.454 (13.74), 8.778 (13.13), 12.109 (0.78).

Example Compound 19

[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]acetic Acid

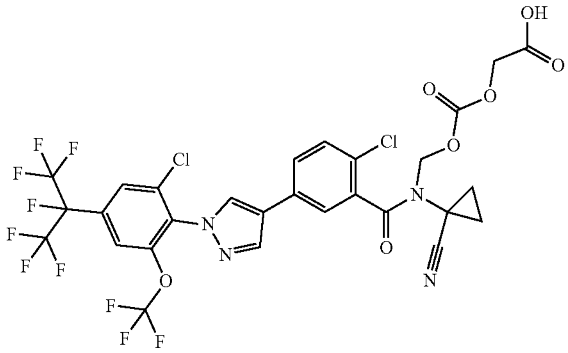 [SMILES: N#CC1(N(COC(=O)OCC(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl [({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl) oxy]acetate (intermediate 57A, 115 mg, 137 μmol) was dissolved in 30% TFA in DCM (19 mL) and the mixture was stirred at ambient temperature for 10 min. The solvent was distilled, the residue was taken up in acetonitrile and purified by preparative HPLC (RP C-18 10 μm acetonitrile:water+0.01% TFA 10:90->95:5). Fractions containing the desired product were combined and freeze-dried to give 34.0 mg (97% purity, 31% yield) of the title compound.

LC-MS (method 4): $R_t$=4.18 min; MS (ESIpos): m/z=781 $[M+H]^+$ $^1$H-NMR (500 MHz, DMSO-$d^6$) δ [ppm]: −0.120 (1.08), 0.117 (0.99), 1.170 (0.48), 1.184 (0.97), 1.198 (0.48), 1.234 (0.97), 1.516 (2.26), 1.658 (1.97), 1.767 (9.02), 4.204 (0.50), 4.218 (0.54), 4.475 (1.18), 4.524 (16.00), 4.688 (1.39), 5.210 (0.93), 5.312 (1.82), 5.444 (1.93), 7.539 (0.44), 7.603 (4.58), 7.619 (5.41), 7.689 (0.62), 7.780 (7.71), 7.808 (5.37), 7.824 (4.85), 7.947 (14.20), 8.223 (15.38), 8.321 (0.39), 8.444 (15.83), 8.771 (12.83), 13.240 (1.08).

Example 20

4-[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]butanoic Acid

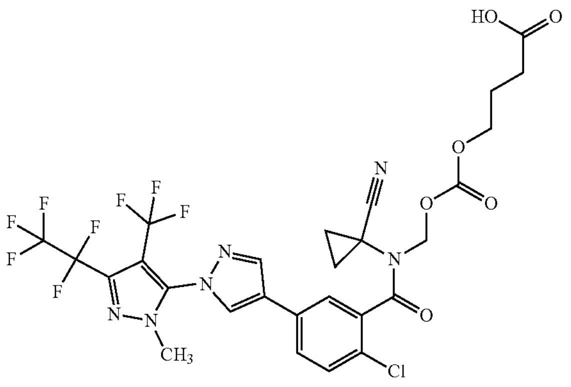 [SMILES: Cn1nc(C(F)(F)C(F)(F)F)c(C(F)(F)F)c1-n1cc(-c2ccc(Cl)c(C(=O)N(COC(=O)OCCCC(=O)O)C3(C#N)CC3)c2)cn1]

tert-Butyl 4-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]butanoate (intermediate 59A, 230 mg, 299 μmol) was dissolved in 30% TFA in DCM (10 mL) and the mixture was stirred at ambient temperature for 7 min. The solvent was distilled, the residue was taken up in acetonitrile and purified by preparative HPLC (RP C-18 10 μm acetonitrile:water+0.01% TFA 10:90->95:5). The crude product was purified by flash chromatography on silica gel (gradient cyclohexane-cyclohexane ethyl acetate 2:1-ethyl acetate methanol 80:20). 60.9 mg (100% purity, 29% yield) of the title compound were isolated.

LC-MS (Method 4): $R_t$=3.89 min; MS (ESIpos): m/z=713 $[M+H]^+$ $^1$H-NMR (600 MHz, DMSO-$d^6$) δ [ppm]: 1.500 (0.44), 1.760 (2.79), 2.242 (1.98), 3.820 (16.00), 4.037 (1.23), 7.613 (0.94), 7.627 (1.05), 7.825 (1.70), 7.843 (1.21), 7.858 (1.12), 8.557 (2.18), 8.830 (2.26).

Example 21

3-[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]-2,2-dimethylpropanoic Acid

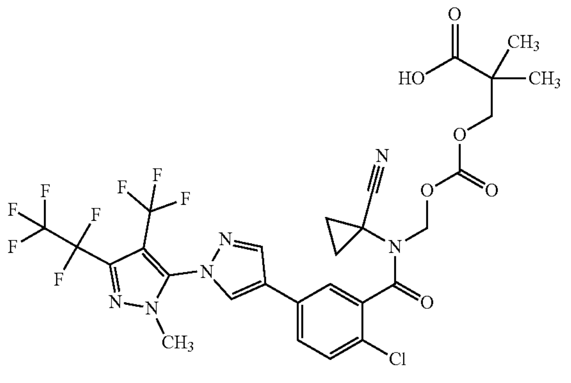 [SMILES: Cn1nc(C(F)(F)C(F)(F)F)c(C(F)(F)F)c1-n1cc(-c2ccc(Cl)c(C(=O)N(COC(=O)OCC(C)(C)C(=O)O)C3(C#N)CC3)c2)cn1]

tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]-2,2-dimethylpropanoate (intermediate 61A, 160 mg, 204 μmol) was dissolved in 30% TFA in DCM (8 mL) and the mixture was stirred at ambient temperature for 5 min. The solvent was distilled, the residue was taken up in acetonitrile and purified by preparative HPLC (RP C-18 10 μm acetonitrile:water+0.01% TFA 10:90->95:5). 78.3 mg (100% purity, 53% yield) of the title compound were isolated.

LC-MS (Method 4): $R_t$=4.10 min; MS (ESIpos): m/z=727 $[M+H]^+$ $^1$H-NMR (400 MHz, DMSO-$d^6$) δ [ppm]: −0.008 (0.47), 0.008 (0.47), 1.034 (0.97), 1.064 (12.20), 1.145 (0.70), 1.493 (0.48), 1.644 (0.43), 1.762 (1.81), 2.524 (1.47), 3.823 (16.00), 4.035 (1.24), 7.612 (1.00), 7.632 (1.26), 7.841 (2.64), 7.864 (1.27), 8.564 (2.70), 8.828 (2.75).

Example 22

Trans (2E)-4-({-4-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclohexyl}oxy)-4-oxobut-2-enoic Acid

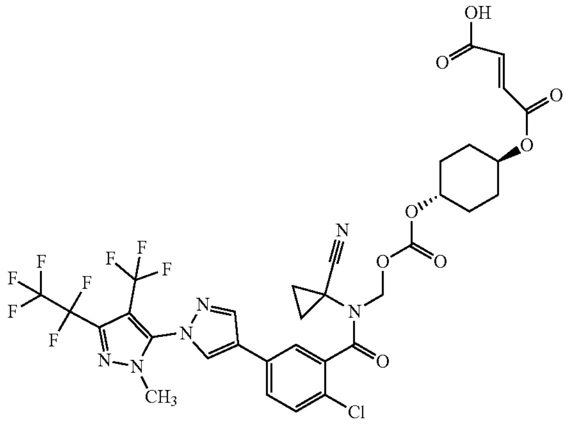 [SMILES: Cn1nc(C(F)(F)C(F)(F)F)c(C(F)(F)F)c1-n1cc(-c2ccc(Cl)c(C(=O)N(COC(=O)O[C@H]3CC[C@H](OC(=O)/C=C/C(=O)O)CC3)C3(C#N)CC3)c2)cn1]

tert-Butyl trans-4-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclohexyl (2E)-but-2-enedioate (intermediate 62A, 188 mg, 214 μmol) was dissolved in 30% TFA in DCM (15 mL) and the mixture was stirred at ambient temperature for 15 min. The solvent was distilled, the residue was taken up in acetonitrile and purified by preparative HPLC (RP C-18 10 μm acetonitrile:water+0.01% TFA 10:90->95:5). 125 mg (100% purity, 71% yield) were isolated.

LC-MS (Method 4): $R_1$=4.11 min; MS (ESIpos): m/z=823 $[M+H]^+$ $^1$H-NMR (400 MHz, DMSO-$d^6$) δ [ppm]: −0.149 (1.71), 0.008 (16.00), 0.146 (1.67), 1.236 (1.47), 1.511 (6.79), 1.766 (5.25), 1.863 (5.63), 2.328 (0.85), 2.366 (1.19), 2.670 (1.02), 2.710 (1.26), 3.431 (8.97), 4.560 (2.15), 4.810 (2.39), 5.255 (1.16), 5.400 (1.19), 6.626 (1.16), 6.666 (10.85), 6.676 (11.39), 6.715 (1.23), 7.621 (3.17), 7.641 (3.92), 7.841 (7.23), 7.866 (3.72), 8.577 (7.03), 8.844 (7.03), 13.178 (0.89).

Example 23

Cis-4-[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclohexane-1-carboxylic Acid

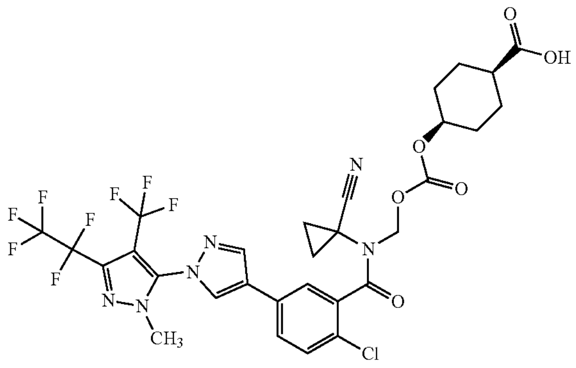 [SMILES: Cn1nc(C(F)(F)C(F)(F)F)c(C(F)(F)F)c1-n1cc(-c2ccc(Cl)c(C(=O)N(COC(=O)O[C@H]3CC[C@@H](C(=O)O)CC3)C3(C#N)CC3)c2)cn1]

tert-butyl cis-4-[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclohexane-1-carboxylate (intermediate 63A, 300 mg, 371 μmol) was dissolved in 30% TFA in DCM (15 mL) and the mixture was stirred at ambient temperature for 15 min. The solvent was distilled, the residue was taken up in acetonitrile and purified by preparative HPLC (RP C-18 10 μm acetonitrile:water+0.01% TFA 10:90->95:5). 51.4 mg (100% purity, 18% yield) of the title compound were obtained.

LC-MS (Method 4): $R_t$=4.07 min; MS (ESIpos): m/z=753 $[M+H]^+$ $^1$H-NMR (600 MHz, DMSO-$d^6$) δ [ppm]: 1.489 (0.54), 1.609 (2.64), 1.643 (1.72), 1.677 (1.68), 1.767 (1.77), 2.301 (0.79), 3.824 (16.00), 4.636 (1.05), 5.399 (0.41), 7.613 (1.19), 7.628 (1.36), 7.849 (3.12), 8.573 (2.84), 8.842 (2.82).

Example 24

Trans-4-[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclohexane-1-carboxylic Acid

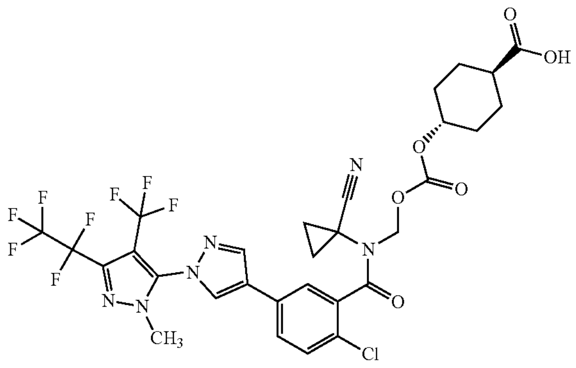 [SMILES: Cn1nc(C(F)(F)C(F)(F)F)c(C(F)(F)F)c1-n1cc(-c2ccc(Cl)c(C(=O)N(COC(=O)O[C@H]3CC[C@H](C(=O)O)CC3)C3(C#N)CC3)c2)cn1]

tert-Butyl trans-4-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclohexane-1-carboxylate (intermediate 64A, 200 mg, 247 μmol) was dissolved in 30% TFA in DCM (10 mL) and the mixture was stirred at ambient temperature for 5 min. The solvent was distilled, the residue was taken up in acetonitrile and purified by preparative HPLC (RP C-18 10 μm acetonitrile:water+0.01% TFA 10:90->95:5). 53.1 mg (100% purity, 29% yield) of the title compound were obtained.

LC-MS (Method 4): $R_t$=4.04 min; MS (ESIpos): m/z=753 $[M+H]^+$ $^1$H-NMR (600 MHz, DMSO-$d^6$) δ [ppm]: 1.360 (1.47), 1.461 (0.56), 1.655 (0.41), 1.763 (1.63), 1.861 (1.32), 2.172 (0.75), 3.823 (16.00), 4.393 (0.69), 7.624 (1.30), 7.638 (1.48), 7.825 (2.02), 7.847 (1.26), 7.863 (1.15), 8.576 (2.69), 8.845 (2.67).

Example 25

(12E)-1-{2-Chloro-5-[2'-methyl-5'-(pentafluoroethyl)-4'-(trifluoromethyl)-2'H-[1,3'-bipyrazol]-4-yl]phenyl}-2-(1-cyanocyclopropyl)-1,5,11-trioxo-4,6,10-trioxa-2-azatetradec-12-en-14-oic Acid

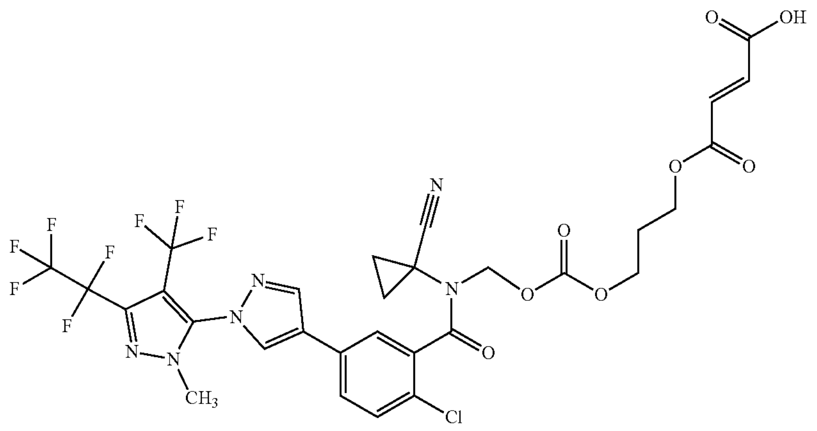 [SMILES: Cn1nc(C(F)(F)C(F)(F)F)c(C(F)(F)F)c1-n1cc(-c2ccc(Cl)c(C(=O)N(COC(=O)OCCCOC(=O)/C=C/C(=O)O)C3(C#N)CC3)c2)cn1]

- tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]propyl (2E)-but-2-enedioate (intermediate 65A, 200 mg, 238 μmol) was dissolved in 30% TFA in DCM (12 mL) and the mixture was stirred at ambient temperature for 10 min. The solvent was distilled, the residue was taken up in acetonitrile and purified by preparative HPLC (RP C-18 10 μm acetonitrile:water+0.01% TFA 10:90->95:5). 8.10 mg (100% purity, 4% yield) of the title compound were obtained.

LC-MS (Method 4): $R_t$=4.00 min; MS (ESIpos): m/z=783 $[M+H]^+$ $^1$H-NMR (500 MHz, DMSO-$d^6$) δ [ppm]: −0.120 (0.72), −0.007 (7.75), 0.006 (5.08), 0.116 (0.66), 1.225 (1.22), 1.236 (1.36), 1.259 (0.63), 1.285 (0.81), 1.297 (0.83), 1.337 (0.74), 1.494 (0.46), 1.760 (1.58), 1.908 (0.98), 1.917 (1.05), 1.929 (1.49), 1.941 (1.10), 2.040 (1.53), 2.358 (0.42), 2.362 (0.61), 2.365 (0.42), 2.518 (0.85), 2.522 (0.59), 2.632 (0.42), 2.635 (0.61), 2.639 (0.41), 3.820 (16.00), 4.124 (1.36), 4.144 (1.64), 4.156 (2.17), 6.622 (0.46), 6.653 (1.90), 6.674 (2.34), 6.706 (0.68), 7.612 (0.98), 7.628 (1.14), 7.829 (1.68), 7.843 (1.31), 7.860 (1.03), 8.560 (2.30), 8.834 (2.17).

Example 26

1-{2-Chloro-5-[2'-methyl-5'-(pentafluoroethyl)-4'-(trifluoromethyl)-2'H-[1,3'-bipyrazol]-4-yl]phenyl}-2-(1-cyanocyclopropyl)-1,5,11-trioxo-4,6,10-trioxa-2-azatetradecan-14-oic Acid

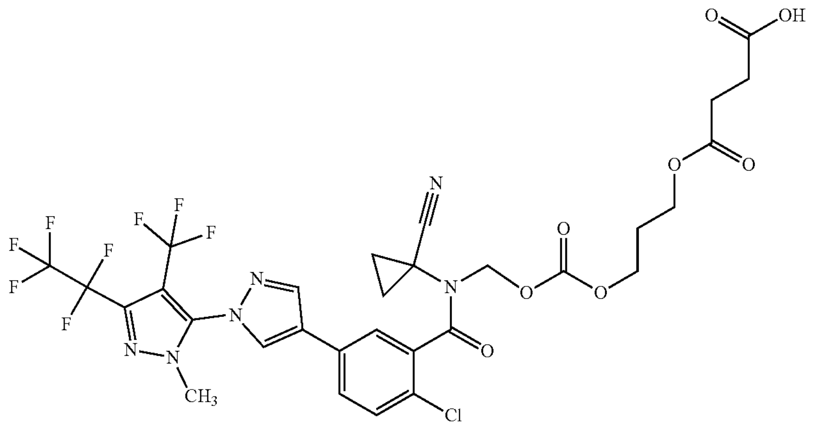 [SMILES: Cn1nc(C(F)(F)C(F)(F)F)c(C(F)(F)F)c1-n1cc(-c2ccc(Cl)c(C(=O)N(COC(=O)OCCCOC(=O)CCC(=O)O)C3(C#N)CC3)c2)cn1]

tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]propyl butanedioate (intermediate 68A, 190 mg, 226 μmol) was dissolved in 30% TFA in DCM (10 mL) and the mixture was stirred at ambient temperature for 5 min. The solvent was distilled, the residue was taken up in acetonitrile and purified by preparative HPLC (RP C-18 10 μm acetonitrile: water+0.01% TFA 10:90->95:5). 36.1 mg (100% purity, 20% yield) of the title compound were obtained.

LC-MS (Method 4): $R_t$=3.96 min; MS (ESIpos): m/z=785 $[M+H]^+$ $^1H$-NMR (600 MHz, DMSO-$d^6$) δ [ppm]: 1.397 (0.45), 1.491 (0.52), 1.664 (0.46), 1.765 (1.77), 1.847 (1.27), 1.857 (1.82), 1.867 (1.36), 2.426 (0.45), 2.456 (3.27), 2.467 (3.22), 2.575 (0.52), 3.822 (16.00), 4.027 (2.34), 4.036 (1.52), 4.090 (1.44), 5.249 (0.40), 5.405 (0.42), 7.620 (1.13), 7.634 (1.29), 7.832 (1.98), 7.847 (1.31), 7.861 (1.22), 8.568 (2.47), 8.839 (2.62).

Example 27

1-[10-{2-Chloro-5-[2'-methyl-5'-(pentafluoroethyl)-4'-(trifluoromethyl)-2'H-[1,3'-bipyrazol]-4-yl]phenyl}-9-(1-cyanocyclopropyl)-6,10-dioxo-2,5,7-trioxa-9-azadecanan-1-oyl]cyclopropane-1-carboxylic Acid

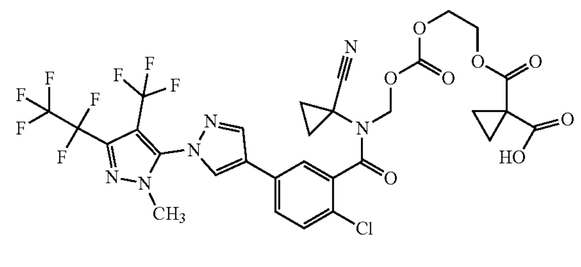 [SMILES: Cn1nc(C(F)(F)C(F)(F)F)c(C(F)(F)F)c1-n1cc(-c2ccc(Cl)c(C(=O)N(COC(=O)OCCOC(=O)C3(C(=O)O)CC3)C3(C#N)CC3)c2)cn1]

tert-Butyl 2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]ethyl ethyl(methyl)propanedioate (intermediate 69A, 167 mg, 195 μmol) was dissolved in 30% TFA in DCM (15 mL) and the mixture was stirred at ambient temperature for 5 min. The solvent was distilled, the residue was taken up in acetonitrile and purified by preparative HPLC (RP C-18 10 μm acetonitrile:water+0.01% TFA 10:90->95:5). 24.6 mg (100% purity, 16% yield) of the title compound were obtained.

LC-MS (Method 4): $R_t$=4.03 min; MS (ESIpos): m/z=783 $[M+H]^+$ $^1H$-NMR (500 MHz, DMSO-$d^6$) δ [ppm]: −0.120 (0.79), −0.006 (9.82), 0.006 (6.98), 0.117 (0.79), 1.280 (7.07), 1.397 (2.03), 1.492 (0.48), 1.646 (0.50), 1.765 (1.75), 2.362 (0.64), 2.635 (0.69), 3.545 (0.50), 3.820 (16.00), 4.227 (3.99), 5.886 (0.43), 7.616 (0.98), 7.633

Example 28

1-{2-Chloro-5-[2'-methyl-5'-(pentafluoroethyl)-4'-(trifluoromethyl)-2'H-[1,3'-bipyrazol]-4-yl]phenyl}-2-(1-cyanocyclopropyl)-1,5,10-trioxo-4,6,9-trioxa-2-azatetradecan-14-oic Acid

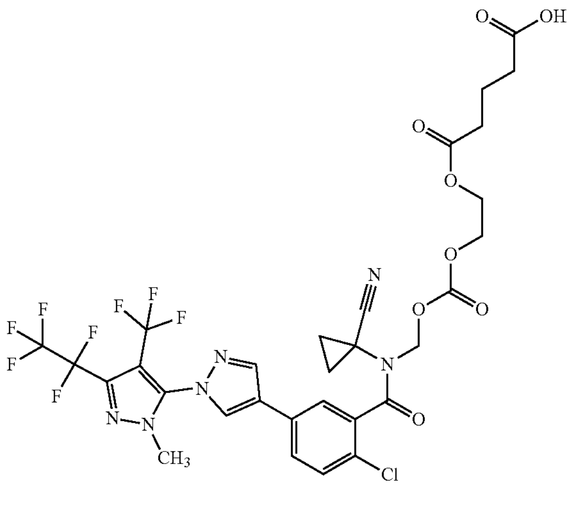 [SMILES: Cn1nc(C(F)(F)C(F)(F)F)c(C(F)(F)F)c1-n1cc(-c2ccc(Cl)c(C(=O)N(COC(=O)OCCOC(=O)CCCC(=O)O)C3(C#N)CC3)c2)cn1]

tert-Butyl 2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]ethyl pentanedioate (intermediate 70A, 200 mg, 238 μmol) was dissolved in 30% TFA in DCM (12 mL) and the mixture was stirred at ambient temperature for 5 min. The solvent was distilled, the residue was taken up in acetonitrile and purified by preparative HPLC (RP C-18 10 μm acetonitrile:water+0.01% TFA 10:90->95:5). 131 mg (100% purity, 70% yield) of the title compound were obtained.

LC-MS (Method 4): $R_t$=3.84 min; MS (ESIpos): m/z=785 $[M+H]^+$ $^1$H-NMR (400 MHz, DMSO-d$^6$) δ [ppm]: 1.372 (0.41), 1.503 (0.58), 1.681 (1.89), 1.699 (2.52), 1.717 (1.98), 1.736 (1.17), 1.762 (1.78), 2.205 (1.76), 2.223 (3.23), 2.241 (1.68), 2.290 (1.30), 2.309 (2.32), 2.327 (1.62), 2.366 (0.46), 3.821 (16.00), 4.177 (2.15), 4.220 (1.47), 7.612 (0.96), 7.632 (1.15), 7.791 (0.40), 7.835 (2.02), 7.866 (1.14), 8.561 (2.51), 8.834 (2.41).

Example 29

1-{2-Chloro-5-[2'-methyl-5'-(pentafluoroethyl)-4'-(trifluoromethyl)-2'H-[1,3'-bipyrazol]-4-yl]phenyl}-2-(1-cyanocyclopropyl)-8,8-dimethyl-1,5,11-trioxo-4,6,10-trioxa-2-azatetradecan-14-oic Acid

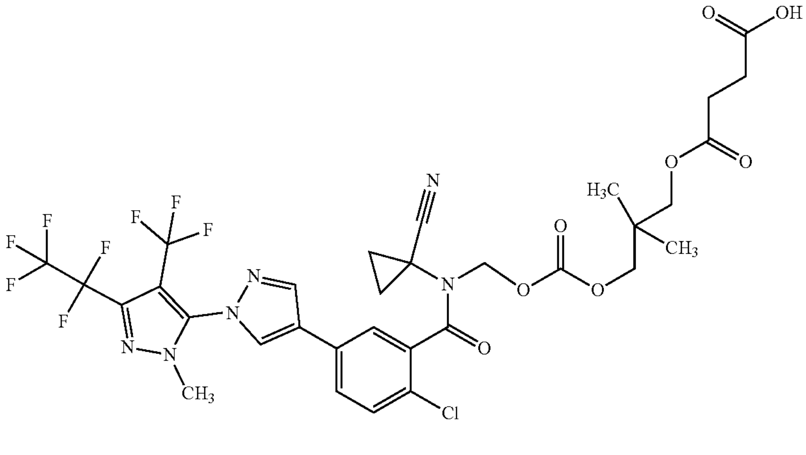 [SMILES: Cn1nc(C(F)(F)C(F)(F)F)c(C(F)(F)F)c1-n1cc(-c2ccc(Cl)c(C(=O)N(COC(=O)OCC(C)(C)COC(=O)CCC(=O)O)C3(C#N)CC3)c2)cn1]

tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]-2,2-dimethylpropyl butanedioate (intermediate 71A, 300 mg, 345 μmol) was dissolved in 30% TFA in DCM (16 mL) and the mixture was stirred at ambient temperature for 15 min. The solvent was distilled, the residue was taken up in acetonitrile and purified by preparative HPLC (RP C-18 10 μm acetonitrile:water+0.01% TFA 10:90->95:5). 91.1 mg (100% purity, 32% yield) of the title compound were obtained.

LC-MS (Method 4): $R_t$=4.13 min; MS (ESIpos): m/z=813 $[M+H]^+$ $^1$H-NMR (400 MHz, DMSO-d$^6$) δ [ppm]: −0.008 (0.62), 0.008 (0.76), 0.851 (10.99), 0.934 (0.59), 1.500 (0.44), 1.762 (1.66), 2.463 (2.83), 3.785 (3.21), 3.822 (16.00), 3.866 (1.89), 7.610 (0.90), 7.631 (1.11), 7.842 (3.25), 7.860 (1.33), 8.563 (2.40), 8.831 (2.28).

Example 30

[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]acetic Acid

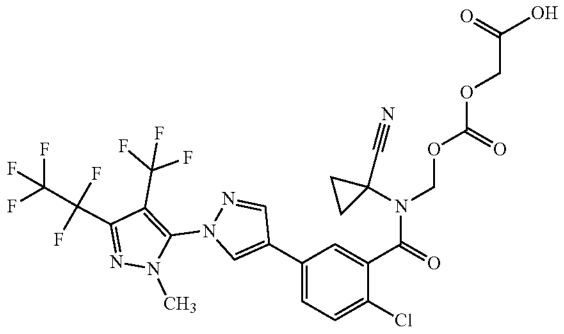 [SMILES: Cn1nc(C(F)(F)C(F)(F)F)c(C(F)(F)F)c1-n1cc(-c2ccc(Cl)c(C(=O)N(COC(=O)OCC(=O)O)C3(C#N)CC3)c2)cn1]

tert-Butyl [({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]acetate (intermediate 72A, 230 mg, 310 μmol) was dissolved in 30% TFA in DCM (15 mL) and the mixture was stirred at ambient temperature for 10 min. The solvent was distilled, the residue was taken up in acetonitrile and purified by preparative HPLC (RP C-18 10 μm acetonitrile:water+0.01% TFA 10:90->95:5). The crude product was purified by flash chromatography on silica gel (gradient cyclohexane-cyclohexane ethyl acetate 4:1). 45.3 mg (100% purity, 21% yield) of the title compound were isolated.

LC-MS (Method 4): $R_t$=3.82 min; MS (ESIneg): m/z=683 $[M-H]^-$ $^1$H-NMR (400 MHz, DMSO-d$^6$) δ [ppm]: −0.008 (1.75), 0.008 (1.76), 1.512 (0.46), 1.682 (0.44), 1.766 (1.61), 2.328 (0.41), 2.524 (1.93), 2.670 (0.45), 3.818 (16.00), 3.906 (0.42), 4.533 (2.86), 7.621 (0.78), 7.643 (0.97), 7.815 (1.45), 7.846 (1.05), 7.869 (0.96), 8.551 (4.10), 8.569 (0.45), 8.824 (4.02).

Example 31

1-{[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]methyl}cyclopropane-1-carboxylic Acid

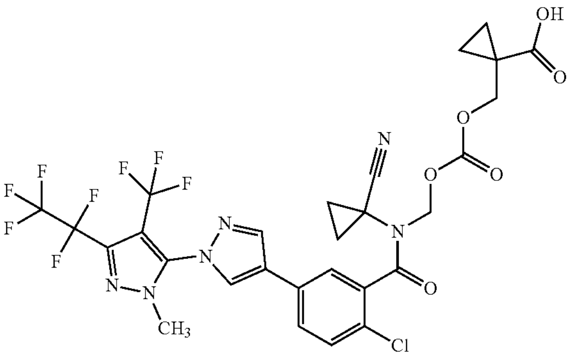 [SMILES: Cn1nc(C(F)(F)C(F)(F)F)c(C(F)(F)F)c1-n1cc(-c2ccc(Cl)c(C(=O)N(COC(=O)OCC3(C(=O)O)CC3)C3(C#N)CC3)c2)cn1]

tert-Butyl 1-{[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]methyl}cyclopropane-1-carboxylate (intermediate 77A, 210 mg, 269 μmol) was dissolved in 30% TFA in DCM (9.0 mL) and the mixture was stirred at ambient temperature for 7 min. The solvent was distilled, the residue was taken up in acetonitrile and purified by preparative HPLC (RP C-18 10 μm acetonitrile:water+0.01% TFA 10:90->95:5). The crude product was purified by flash chromatography on silica gel (gradient cyclohexane-cyclohexane ethyl acetate 4:1). 62 mg (100% purity, 32% yield) of the title compound were isolated.

LC-MS (Method 4): $R_t$=3.99 min; MS (ESIpos): m/z=725 $[M+H]^+$ $^1$H-NMR (400 MHz, DMSO-d$^6$) δ [ppm]: −0.008 (0.54), 0.008 (0.58), 0.921 (2.34), 1.117 (2.55), 1.491 (0.54), 1.659 (0.45), 1.759 (1.82), 3.823 (16.00), 4.153 (0.70), 7.613 (1.00), 7.634 (1.26), 7.833 (2.10), 7.864 (1.19), 8.565 (2.97), 8.835 (2.83).

Example 32

Cis-(2E)-4-({-4-[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclohexyl}oxy)-4-oxobut-2-enoic Acid

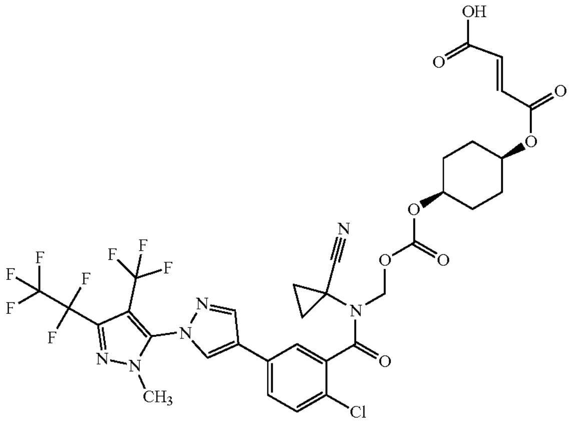 [SMILES: Cn1nc(C(F)(F)C(F)(F)F)c(C(F)(F)F)c1-n1cc(-c2ccc(Cl)c(C(=O)N(COC(=O)O[C@H]3CC[C@@H](OC(=O)/C=C/C(=O)O)CC3)C3(C#N)CC3)c2)cn1]

tert-Butyl (1S,4S)-4-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclohexyl (2E)-but-2-enedioate (intermediate 78A, 73 mg, 83 μmol) was dissolved in 30% TFA in DCM (7.0 mL) and the mixture was stirred at ambient temperature for 10 min. The solvent was distilled, the residue was taken up in acetonitrile and purified by preparative HPLC (RP C-18 10 μm acetonitrile:water+0.01% TFA 10:90->95:5). 39.5 mg (100% purity, 58% yield) of the title compound were isolated.

LC-MS (Method 4): $R_t$=4.10 min; MS (ESIpos): m/z=823 $[M+H]^+$ $^1$H-NMR (400 MHz, DMSO-d$^6$) δ [ppm]: −0.149 (0.40), −0.022 (0.42), −0.008 (3.14), 0.008 (3.57), 1.235 (0.86), 1.457 (0.99), 1.467 (0.55), 1.506 (0.53), 1.695 (4.74), 1.767 (2.39), 3.568 (0.44), 3.818 (16.00), 4.584 (0.83), 4.857 (0.94), 6.684 (5.76), 6.687 (5.79), 7.619 (1.04), 7.639 (1.25), 7.845 (3.70), 7.865 (1.33), 8.574 (2.46), 8.845 (2.38).

Example 33

1-{2-chloro-5-[2'-methyl-5'-(pentafluoroethyl)-4'-(trifluoromethyl)-2'H-[1,3'-bipyrazol]-4-yl]phenyl}-2-(1-cyanocyclopropyl)-1,5,10-trioxo-4,6,9-trioxa-2-azatridecan-13-oic Acid

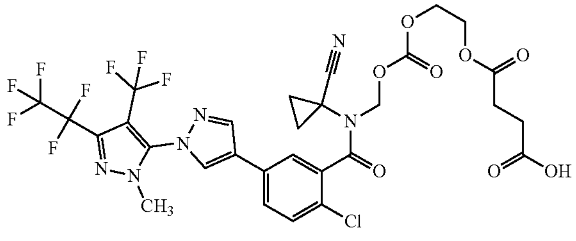 [SMILES: Cn1nc(C(F)(F)C(F)(F)F)c(C(F)(F)F)c1-n1cc(-c2ccc(Cl)c(C(=O)N(COC(=O)OCCOC(=O)CCC(=O)O)C3(C#N)CC3)c2)cn1]

tert-Butyl 2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]ethyl butanedioate (intermediate 79A, 130 mg, 157 μmol) was dissolved in 30% TFA in DCM (15.0 mL) and the mixture was stirred at ambient temperature for 10 min. The solvent was distilled, the residue was taken up in acetonitrile and purified by preparative HPLC (RP C-18 10 μm acetonitrile:water+0.01% TFA 10:90->95:5). 109 mg (95% purity, 86% yield) of the title compound were isolated.

LC-MS (Method 4): $R_t$=3.96 min; MS (ESIpos): m/z=771 $[M+H]^+$ $^1$H-NMR (400 MHz, DMSO-$d^6$) δ [ppm]: 1.501 (0.48), 1.669 (0.43), 1.767 (1.73), 2.444 (2.28), 2.455 (3.01), 2.473 (2.80), 3.822 (16.00), 4.184 (2.35), 4.213 (1.52), 7.617 (0.96), 7.637 (1.19), 7.843 (2.31), 7.868 (1.18), 8.564 (2.63), 8.837 (2.53).

Example 34

(11E)-1-{2-Chloro-5-[2'-methyl-5'-(pentafluoroethyl)-4'-(trifluoromethyl)-2'H-[1,3'-bipyrazol]-4-yl]phenyl}-2-(1-cyanocyclopropyl)-1,5,10-trioxo-4,6,9-trioxa-2-azatridec-11-en-13-oic Acid

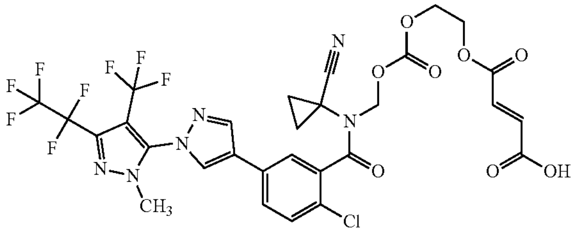 [SMILES: Cn1nc(C(F)(F)C(F)(F)F)c(C(F)(F)F)c1-n1cc(-c2ccc(Cl)c(C(=O)N(COC(=O)OCCOC(=O)/C=C/C(=O)O)C3(C#N)CC3)c2)cn1]

tert-Butyl 2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]ethyl (2E)-but-2-enedioate (intermediate 80A, 74.0 mg, 89.7 μmol) was dissolved in 30% TFA in DCM (7.4 mL) and the mixture was stirred at ambient temperature for 5 min. The solvent was distilled, the residue was taken up in acetonitrile and purified by preparative HPLC (RP C-18 10 μm acetonitrile:water+0.01% TFA 10:90->95:5). 54.9 mg (94% purity, 69% yield) of the title compound were isolated.

LC-MS (Method 4): $R_t$=4.01 min; MS (ESIpos): m/z=769 $[M+H]^+$ $^1$H-NMR (400 MHz, DMSO-$d^6$) δ [ppm]: −0.008 (1.28), 0.008 (1.19), 1.496 (0.55), 1.683 (0.50), 1.758 (1.64), 2.323 (0.73), 2.327 (1.00), 2.332 (0.77), 2.366 (0.89), 2.523 (3.51), 2.665 (0.68), 2.670 (0.93), 2.674 (0.71), 2.710 (0.75), 3.820 (16.00), 4.309 (3.05), 6.665 (2.39), 6.672 (2.67), 7.603 (1.09), 7.625 (1.12), 7.839 (2.55), 7.861 (1.12), 8.556 (2.62), 8.833 (2.23), 13.218 (0.52).

Example 35

1-{[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]methyl}cyclopropane-1-carboxylic Acid

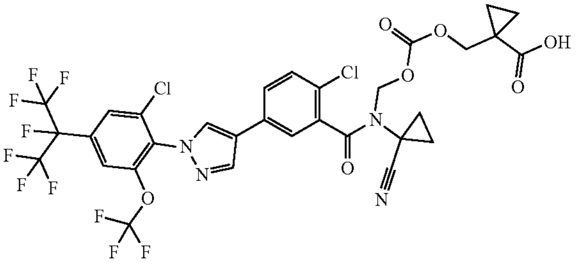 [SMILES: N#CC1(N(COC(=O)OCC2(C(=O)O)CC2)C(=O)c2cc(-c3cnn(-c4c(Cl)cc(C(F)(C(F)(F)F)C(F)(F)F)cc4OC(F)(F)F)c3)ccc2Cl)CC1]

tert-Butyl 1-{[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]methyl}cyclopropane-1-carboxylate (intermediate 81A, 200 mg, 228 μmol) was dissolved in 30% TFA in DCM (20.0 mL) and the mixture was stirred at ambient temperature for 15 min. The solvent was distilled, the residue was taken up in acetonitrile and purified by preparative HPLC (RP C-18 10 μm acetonitrile:water+0.01% TFA 10:90->95:5). 135 mg (95% purity, 68% yield) of the title compound were isolated.

LC-MS (Method 4): $R_t$=4.43 min; MS (ESIpos): m/z=821 $[M+H]^+$ $^1$H-NMR (400 MHz, DMSO-$d^6$) δ [ppm]: 0.008 (1.67), 0.921 (10.12), 1.114 (11.51), 1.186 (1.08), 1.234 (1.08), 1.501 (2.38), 1.640 (1.98), 1.754 (8.17), 2.328 (0.96), 2.367 (1.08), 2.670 (0.99), 2.711 (1.15), 4.167 (2.60), 4.275 (1.08), 5.265 (1.67), 5.395 (1.73), 7.589 (4.33), 7.609 (5.32), 7.795 (10.58), 7.820 (5.45), 7.935 (14.42), 8.210 (16.00), 8.446 (13.80), 8.763 (11.91), 12.471 (1.33).

Example 36

3-[({[(2-Chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]propanoic Acid

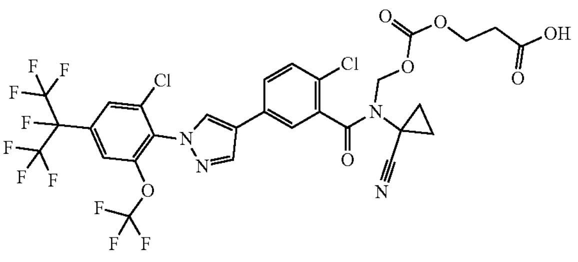 [SMILES: N#CC1(N(COC(=O)OCCC(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl 3-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]propanoate (intermediate 83A, 192 mg, 225 μmol) was dissolved in 30% TFA in DCM (19 mL) and the mixture was stirred at ambient temperature for 15 min. The solvent was distilled, the residue was taken up in acetonitrile and purified by preparative HPLC (RP C-18 10 μm acetonitrile:water+0.01% TFA 10:90->95:5). 134 mg (100% purity, 75% yield) of the title compound were isolated.

LC-MS (Method 4): $R_t$=4.28 min; MS (ESIpos): m/z=795 $[M+H]^+$ $^1$H-NMR (400 MHz, DMSO-$d^6$) δ [ppm]: 1.235 (0.79), 1.505 (2.52), 1.638 (2.12), 1.756 (8.75), 2.073 (12.12), 2.328 (0.62), 2.367 (0.65), 2.671 (1.31), 2.711 (0.76), 4.191 (5.65), 4.345 (0.86), 5.163 (0.47), 5.271 (1.76), 5.386 (1.85), 7.558 (0.47), 7.594 (4.25), 7.614 (5.32), 7.783 (7.52), 7.805 (6.74), 7.826 (5.60), 7.935 (14.80), 8.208 (16.00), 8.211 (15.98), 8.446 (13.07), 8.768 (12.06), 12.416 (1.42).

Example 37

4-[({[(2-Chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]butanoic Acid

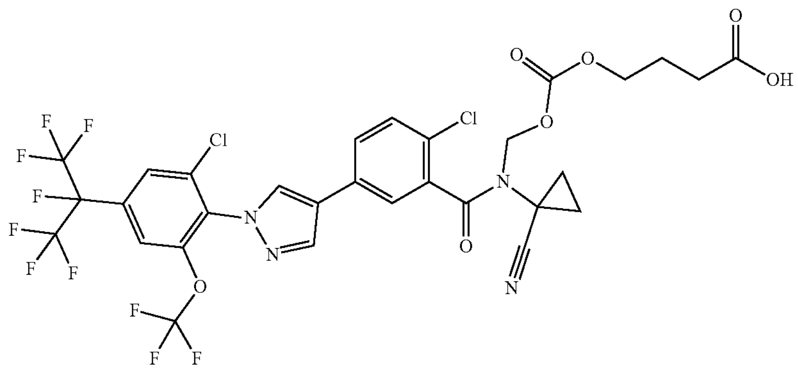 [SMILES: N#CC1(N(COC(=O)OCCCC(=O)O)C(=O)c2cc(-c3cnn(-c4c(Cl)cc(C(F)(C(F)(F)F)C(F)(F)F)cc4OC(F)(F)F)c3)ccc2Cl)CC1]

tert-Butyl 4-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]butanoate (intermediate 84A, 190 mg, 220 μmol) was dissolved in 30% TFA in DCM (19 mL) and the mixture was stirred at ambient temperature for 10 min. The solvent was distilled, the residue was taken up in acetonitrile and purified by preparative HPLC (RP C-18 10 μm acetonitrile:water+0.01% TFA 10:90->95:5). 139 mg (96% purity, 75% yield) of the title compound were isolated.

LC-MS (Method 4): $R_t$=4.33 min; MS (ESIpos): m/z=809 $[M+H]^+$ $^1$H-NMR (400 MHz, DMSO-$d^6$) δ [ppm]: 1.234 (0.62), 1.508 (2.36), 1.639 (2.19), 1.755 (13.94), 1.768 (14.21), 2.226 (6.06), 2.244 (10.41), 2.261 (6.12), 2.329 (1.14), 2.367 (0.63), 2.671 (0.52), 2.711 (0.48), 4.036 (6.76), 4.185 (0.78), 5.257 (1.74), 5.380 (1.83), 7.590 (4.72), 7.610 (5.76), 7.793 (9.88), 7.822 (5.85), 7.935 (14.31), 8.209 (16.00), 8.446 (12.78), 8.770 (11.49), 12.122 (0.66).

Example 38

4-({(1R,2R)-2-[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclopentyl}oxy)-4-oxobutanoic Acid

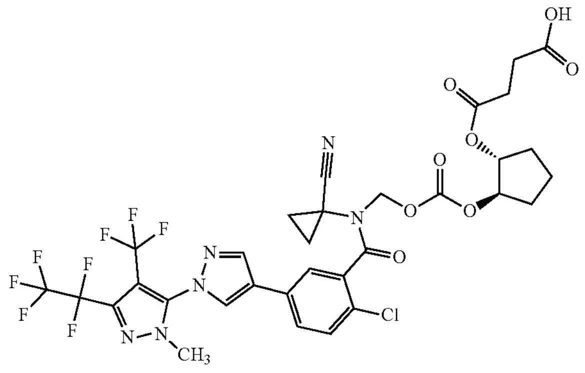

tert-Butyl (1R,2R)-2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclopentyl butanedioate (intermediate 85A, 87.0 mg, 100 μmol) was dissolved in 30% TFA in DCM (8.0 mL) and the mixture was stirred at ambient temperature for 5 min. The solvent was distilled, the residue was taken up in acetonitrile and purified by preparative HPLC (RP C-18 10 μm acetonitrile:water+0.01% TFA 10:90->95:5). 32.3 mg (100% purity, 40% yield) of the title compound were isolated.

LC-MS (Method 4): $R_t$=4.16 min; MS (ESIpos): m/z=811 $[M+H]^+$ $^1$H-NMR (600 MHz, DMSO-d$^6$) δ [ppm]: 1.236 (0.46), 1.320 (0.89), 1.651 (1.39), 1.756 (1.73), 1.966 (0.89), 2.085 (0.46), 2.384 (1.39), 2.422 (2.03), 2.449 (4.39), 2.517 (2.36), 2.611 (0.93), 2.652 (0.84), 3.266 (2.32), 3.820 (16.00), 4.791 (0.68), 4.950 (0.89), 7.611 (0.93), 7.626 (1.10), 7.831 (1.60), 7.859 (1.14), 8.557 (1.90), 8.826 (1.90), 12.182 (0.84).

Example 39

(12E)-1-{2-chloro-5-[2'-methyl-5'-(pentafluoroethyl)-4'-(trifluoromethyl)-2'H-[1,3'-bipyrazol]-4-yl]phenyl}-2-(1-cyanocyclopropyl)-8,8-dimethyl-1,5,11-trioxo-4,6,10-trioxa-2-azatetradec-12-en-14-oic Acid

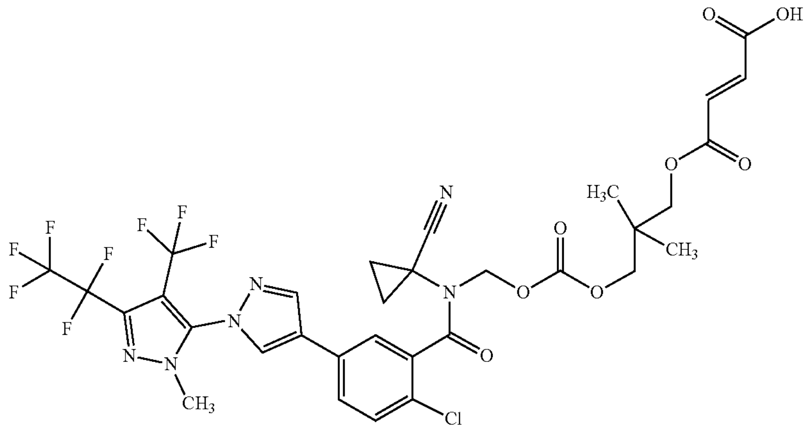 [SMILES: Cn1nc(C(F)(F)C(F)(F)F)c(C(F)(F)F)c1-n1cc(-c2ccc(Cl)c(C(=O)N(COC(=O)OCC(C)(C)COC(=O)/C=C/C(=O)O)C3(C#N)CC3)c2)cn1]

tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]-2,2-dimethylpropyl (2E)-but-2-enedioate (intermediate 86A, 280 mg, 323 μmol) was dissolved in 30% TFA in DCM (16 mL) and the mixture was stirred at ambient temperature for 15 min. The solvent was distilled, the residue was taken up in acetonitrile and purified by preparative HPLC (RP C-18 10 μm acetonitrile:water+0.01% TFA 10:90->95:5). 88.2 mg (100% purity, 34% yield) of the title compound were isolated.

LC-MS (Method 4): $R_t$=4.18 min; MS (ESIpos): m/z=811 $[M+H]^+$ $^1$H-NMR (600 MHz, DMSO-d$^6$) δ [ppm]: 0.892 (12.63), 0.925 (0.51), 0.982 (0.62), 1.379 (0.40), 1.483 (0.45), 1.668 (0.40), 1.759 (1.55), 2.521 (0.46), 3.823 (16.00), 3.915 (5.04), 6.687 (5.15), 7.604 (1.07), 7.619 (1.19), 7.843 (3.36), 7.854 (1.45), 8.561 (2.50), 8.830 (2.39).

Example 40

1-{2-Chloro-5-[2'-methyl-5'-(pentafluoroethyl)-4'-(trifluoromethyl)-2'H-[1,3'-bipyrazol]-4-yl]phenyl}-2-(1-cyanocyclopropyl)-12,12-dimethyl-1,5,10-trioxo-4,6,9-trioxa-2-azatridecan-13-oic Acid

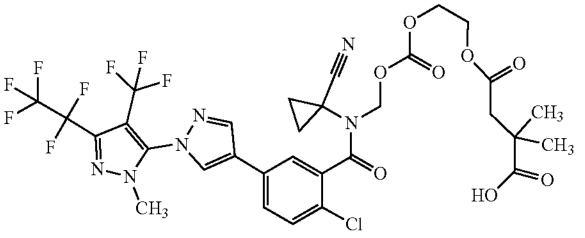

1-tert-Butyl 4-{2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]ethyl} 2,2-dimethylbutanedioate (intermediate 87A, 55.3 mg, 64.7 μmol) was dissolved in 30% TFA in DCM (5 mL) and the mixture was stirred at ambient temperature for 5 min. The solvent was distilled, the residue was taken up in acetonitrile and purified by preparative HPLC (RP C-18 10 μm acetonitrile:water+0.01% TFA 10:90->95:5). 10.9 mg (100% purity, 21% yield) of the title compound were isolated.

LC-MS (Method 4): $R_t$=4.07 min; MS (ESIpos): m/z=799 $[M+H]^+$ $^1$H-NMR (600 MHz, DMSO-d$^6$) δ [ppm]: −0.022 (0.51), 0.843 (0.46), 0.855 (0.88), 0.866 (0.41), 1.129 (14.61), 1.167 (0.78), 1.237 (3.81), 1.490 (0.53), 1.671 (0.42), 1.769 (1.56), 3.824 (16.00), 4.158 (2.44), 4.216 (0.82), 5.254 (0.41), 5.416 (0.41), 7.623 (1.28), 7.637 (1.49), 7.840 (2.01), 7.854 (1.28), 7.868 (1.12), 8.572 (2.76), 8.845 (2.61).

Example 41

3-[({[(2-Chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-2,2-dimethylpropanoic Acid

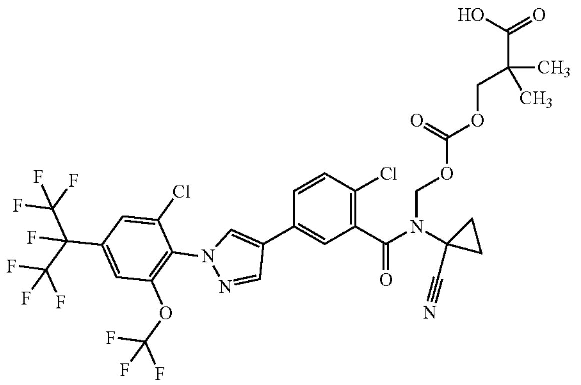 [SMILES: CC(C)(COC(=O)OCN(C(=O)c1cc(-c2cnn(-c3c(Cl)cc(C(F)(C(F)(F)F)C(F)(F)F)cc3OC(F)(F)F)c2)ccc1Cl)C1(C#N)CC1)C(=O)O]

Benzyl 3-[({[(2-chloro-5-{1-[2-chloro-4-(1,1,1,2,3,3,3-heptafluoropropan-2-yl)-6-(trifluoromethoxy)phenyl]-1H-pyrazol-4-yl}benzoyl)(1-cyanocyclopropyl)amino]methoxy}carbonyl)oxy]-2,2-dimethylpropanoate (intermediate 89A, 415 mg, 454 μmol) was dissolved in ethyl acetate (200 mL) under an argon atmosphere. 10% Palladium on charcoal (22.0 mg) was added and the mixture was hydrogenated over 6 h at ambient pressure at room temperature. The catalyst was then removed by filtration over a layer of diatomaceous earth and the solvent was distilled. The crude product was purified by preparative HPLC (RP C-18 10 μm water-acetonitrile gradient with 0.01% TFA in both eluents, 90:10->5:95). 299 mg (100% purity, 80% yield) of the title compound were obtained.

LC-MS (Method 4): $R_t$=4.54 min; MS (ESIpos): m/z=823 $[M+H]^+$ $^1$H-NMR (400 MHz, DMSO-$d^6$) δ [ppm]: 1.017 (4.00), 1.063 (16.00), 1.235 (0.82), 1.513 (0.87), 1.640 (0.77), 1.756 (3.11), 3.363 (1.74), 4.037 (1.81), 5.277 (0.68), 5.400 (0.59), 7.588 (1.42), 7.608 (1.78), 7.762 (0.76), 7.801 (4.81), 7.822 (2.28), 7.935 (4.90), 8.213 (5.67), 8.446 (4.01), 8.755 (4.30).

Example 42

(2E)-4-({(1S,2S)-2-[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclopentyl}oxy)-4-oxobut-2-enoic Acid

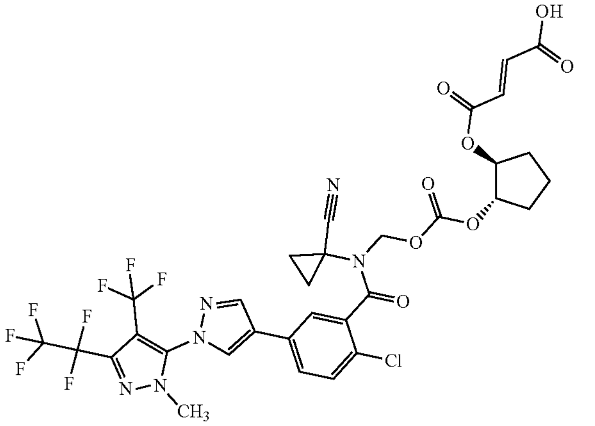

tert-Butyl (1S,2S)-2-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]cyclopentyl (2E)-but-2-enedioate (intermediate 90A, 57.6 mg, 66.6 μmol) was dissolved in 30% TFA in DCM (6 mL) and the mixture was stirred at ambient temperature for 8 min. The solvent was distilled, the residue was taken up in acetonitrile and purified by preparative HPLC (RP C-18 10 μm acetonitrile:water+0.01% TFA 10:90->95:5). 27.1 mg (100% purity, 50% yield) of the title compound were isolated.

LC-MS (Method 4): $R_t$=4.21 min; MS (ESIpos): m/z=809 $[M+H]^+$ $^1$H-NMR (600 MHz, DMSO-$d^6$) δ [ppm]: 1.236 (0.46), 1.494 (0.43), 1.643 (1.35), 1.694 (1.37), 1.756 (1.86), 2.033 (0.85), 2.070 (0.66), 2.572 (0.40), 3.820 (16.00), 4.884 (0.65), 5.065 (0.80), 6.612 (0.70), 6.638 (1.67), 6.674 (1.68), 6.699 (0.77), 7.606 (0.90), 7.619 (1.06), 7.835 (1.83), 7.856 (1.23), 8.554 (2.09), 8.825 (1.88).

Example 43

3-[({[{2-Chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]propanoic Acid

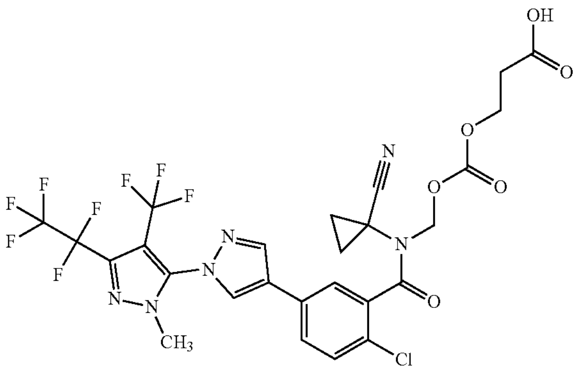 [SMILES: Cn1nc(C(F)(F)C(F)(F)F)c(C(F)(F)F)c1-n1cc(-c2ccc(Cl)c(C(=O)N(COC(=O)OCCC(=O)O)C3(C#N)CC3)c2)cn1]

tert-Butyl 3-[({[{2-chloro-5-[2'-methyl-5'-(pentafluoroethyl)-4'-(trifluoromethyl)-2'H-[1,3'-bipyrazol]-4-yl]benzoyl}(1-cyanocyclopropyl)amino]methoxy}carbonyl)oxy]propanoate (intermediate 91A, 250 mg, 331 μmol) was dissolved in 30% TFA in DCM (12 mL) and the mixture was stirred at ambient temperature for 8 min. The solvent was distilled, the residue was taken up in acetonitrile and purified by preparative HPLC (RP C-18 10 μm acetonitrile:water+0.01% TFA 10:90->95:5). The crude product was purified by flash chromatography on silica gel (gradient cyclohexane: ethyl acetate 2:1->ethyl acetate: methanol 4:1). 42.9 mg (100% purity, 19% yield) of the title compound were isolated.

LC-MS (Method 4): $R_t$=3.85 min; MS (ESIpos): m/z=699 $[M+H]^+$ $^{1}$H-NMR (600 MHz, DMSO-$d^6$) δ [ppm]: 1.494 (1.33), 1.650 (1.10), 1.759 (4.94), 2.085 (16.00), 2.344 (0.66), 2.355 (0.41), 2.384 (0.45), 2.423 (0.73), 2.613 (0.57), 2.652 (1.15), 3.421 (6.26), 3.598 (0.49), 3.608 (0.83), 3.619 (0.50), 3.697 (0.41), 3.807 (2.81), 4.191 (2.93), 4.348 (0.56), 5.259 (0.89), 5.393 (0.98), 7.618 (2.64), 7.631 (3.04), 7.787 (0.65), 7.820 (4.69), 7.850 (3.42), 7.864 (3.28), 8.557 (6.79), 8.830 (7.19), 12.411 (0.42).

Example 44

1-{2-Chloro-5-[2'-methyl-5'-(pentafluoroethyl)-4'-(trifluoromethyl)-2'H-[1,3'-bipyrazol]-4-yl]phenyl}-2-(1-cyanocyclopropyl)-11,11-dimethyl-1,5-dioxo-4,6,9-trioxa-2-azadodecan-12-oic Acid

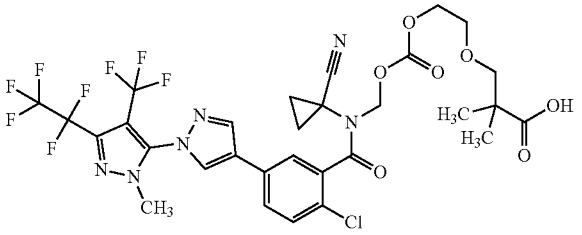 [SMILES: Cn1nc(C(F)(F)C(F)(F)F)c(C(F)(F)F)c1-n1cc(-c2ccc(Cl)c(C(=O)N(COC(=O)OCCOCC(C)(C)C(=O)O)C3(C#N)CC3)c2)cn1]

tert-Butyl 1-{2-chloro-5-[2'-methyl-5'-(pentafluoroethyl)-4'-(trifluoromethyl)-2'H-[1,3'-bipyrazol]-4-yl]phenyl}-2-(1-cyanocyclopropyl)-11,11-dimethyl-1,5-dioxo-4,6,9-trioxa-2-azadodecan-12-oate (intermediate 92A, 108 mg, 131 μmol) was dissolved in 30% TFA in DCM (11 mL) and the mixture was stirred at ambient temperature for 10 min. The solvent was distilled, the residue was taken up in acetonitrile and purified by preparative HPLC (RP C-18 10 μm acetonitrile:water+0.01% TFA 10:90->95:5). 80.0 mg (100% purity, 79% yield) of the title compound were isolated.

LC-MS (Method 4): $R_t$=4.24 min; MS (ESIpos): m/z=771 $[M+H]^+$ $^{1}$H-NMR (600 MHz, DMSO-$d^6$) δ [ppm]: 0.005 (0.68), 1.029 (10.00), 1.076 (1.10), 1.760 (1.36), 2.515 (0.65), 2.518 (0.72), 2.521 (0.57), 2.572 (0.51), 3.391 (0.96), 3.548 (1.76), 3.819 (16.00), 4.119 (0.85), 7.615 (0.76), 7.628 (0.87), 7.826 (1.26), 7.847 (0.95), 7.861

Physicochemical and Biological Examples: Assessment of Prodrug Stability and Release of Parent Compound Preparation of the PBS buffer solution pH 7.4:90 g sodium chloride, 13.61 g potassium dihydrogen phosphate, 83.35 g 1M aqueous sodium hydroxide were dissolved in water. More water was added up to a total volume of 1 L. This solution was diluted 1:10 with water. Eventually, pH was adjusted to pH 7.4 by the addition of phosphoric acid.

Citric acid buffer solution pH 3.0: commercially available citric acid buffer (pH 3) from Fluka (art. No 31046) was used containing 8.47 g of citric acid, 3.49 g of sodium chloride and 0.82 g of sodium hydroxide.

Physicochemical and Biological Examples

Assessment of Prodrug Stability and Release of Parent Compound

Preparation of the PBS buffer solution pH 7.4:90 g sodium chloride, 13.61 g potassium dihydrogen phosphate, 83.35 g 1M aqueous sodium hydroxide were dissolved in water. More water was added up to a total volume of 1 L. This solution was diluted 1:10 with water. Eventually, pH was adjusted to pH 7.4 by the addition of phosphoric acid.

Citric acid buffer solution pH 3.0: commercially available citric acid buffer (pH 3) from Fluka (art. No 31046) was used containing 8.47 g of citric acid, 3.49 g of sodium chloride and 0.82 g of sodium hydroxide.

Biological Example B1

Measurement of Solubility in Buffer at pH 6.5

2-4 mg of the test compound are dissolved in DMSO to reach a concentration of 50 g/L (solution A). To 10 μl of this solution 960 μl PBS buffer pH 6.5 are added (final concentration: 515 μg/l); the mixture is shaken for 24 h at rt in a 96 well plate. An aliquot is centrifuged at 42000 rpm für 30 min. The supernatant is diluted with acetonitrile/water (8:2) 1:10 and 1:1000 resp. This diluted samples are analyzed by LC-MSMS. Results are provided in Table 0, below.

Calibration: 10 μl of solution A are diluted with 823 μl DMSO (final concentration: 600 μg/ml), which is further diluted with acetonitrile/water 8:2 by a factor of 100 (provides solution B).

The calibration curve is obtained from solution B by further diluting with acetonitrile/water 8:2 with target concentrations of 1.2-12-60-600 ng/ml and injecting these four solutions for MS measurement.

MS method optimization: Solution B is utilized for MS method optimization.

PBS-Puffer: 6.18 g sodium chloride and 3.96 g sodium dihydrogen phosphate are dissolved in 1 L aqua dist., the pH is adjusted to 6.5 with 1N sodium hydroxide.

LC and MS Conditions:

LC-MSMS optimization: The following configurations were used for optimization

AB Sciex TRIPLE QUAD 4500, Agilent 1260 Infinity (G1312B), degasser (G4225A), column oven (G1316C and G1316A), CTC Analytics PAL injection system HTS-xt Eluent A: 0.5 ml formic acid (50% strength)/L water, Eluent B: 0.5 ml formic acid (50% strength)/L acetonitrile

| time [min] | flow [µl/min] | % B |
|---|---|---|
| 0.00 | 200 | 70 |
| 0.08 | 200 | 70 |
| 0.09 | 25 | 70 |
| 0.60 | 25 | 70 |
| 0.65 | 200 | 70 |
| 1.10 | 200 | 70 |

Autosampler: without auto inject ahead setting; column: stainless steel capillary, oven temperature: 22° C.; flow rate: flow gradient, injected volume: 2 µL.

Waters Quattro Micro MS, Agilent 1100 (G1312A), degasser (G1322A), column oven (G1316A), CTC Analytics PAL injection system HTS, eluents as above

| time [min] | flow [µl/min] | % B |
|---|---|---|
| 0.00 | 250 | 70 |
| 1.50 | 250 | 70 |

Autosampler with auto inject ahead setting; column: stainless steel capillary, oven temperature: 22° C., flow rate: flow gradient, injected volume: 5 µL.

MS method: Flow Injection Analysis (FIA) for optimization ("MS-OPTI"); ionization mode ABSciex- MS: ESI-pos/neg, Waters-MS: ESI-pos HPLC Method for MSMS Quantification:

The following conditions were used for quantification:

Eluent A, B as above

ABSciex-MS

| time [min] | % A | % B |
|---|---|---|
| 0 | 90 | 10 |
| 0.5 | 5 | 95 |
| 0.84 | 5 | 95 |
| 0.85 | 90 | 10 |
| 1.22 | 90 | 10 |

Autosampler without auto inject ahead setting, column: Waters OASIS HLB, 2,1×20 mm, 25µ, column temperature: 30° C., flow rate: 2.5 mL/min, injected volume: 2 µl, Splitter (before MS) 1:20.

Waters-MS

Gradient as above

Autosampler: with auto inject ahead setting, column: stainless steel capillary, column: Waters OASIS HLB, 2,1×20 mm, 25µ, column temperature: 30° C., flow rate: 2.5 mL/min, injected volume: 5 µL, Splitter (before MS) 1:20, MS method: Multiple Reaction Monitoring (MRM).

TABLE 0

Solubility of example compounds at pH 6.5

| Example No | mg/mL |
|---|---|
| 1 | 5 |
| 2 | 4 |
| 3 | 6 |
| 4 | 2 |
| 5 | 2 |
| 6 | 4 |
| 7 | 3 |
| 8 | 1 |
| 9 | 5 |
| 10 | 3 |
| 11 | 2 |
| 12 | 3 |
| 13 | 7 |
| 14 | 19 |
| 15 | 1 |
| 16 | 2 |
| 17 | 2 |
| 18 | 3 |
| 19 | 42 |
| 20 | 212 |
| 21 | 136 |
| 22 | 17 |
| 23 | 50 |
| 24 | 57 |
| 25 | 98 |
| 26 | 96 |
| 27 | 147 |
| 28 | 76 |
| 29 | 35 |
| 30 | 398 |
| 31 | 168 |
| 32 | 41 |
| 35 | 8 |
| 36 | 16 |
| 37 | 7 |
| 38 | 37 |
| 39 | 43 |
| 40 | 43 |
| 41 | 4 |
| 42 | 38 |

Biological Example B2

Measurement of Stability of Prodrugs in Buffer at pH 7.4

Measurement 0.15 mg of the test compound were dissolved in 0.1 mL dimethylsulfoxide and 0.4 mL acetonitrile. For complete dissolution, the HPLC vial with the sample solution was shaken and treated with ultrasound. Then, 1.0 mL of PBS buffer solution pH 7.4 was added and the sample was vortexed. The sample solution was analysed by HPLC (method 8) to determine the amount of the test compound at a particular time over a period of 24 h at 37° C. The peak areas, given as percentage of total area, are used for quantification. In addition, the reaction mixture was analysed by method 9 (HPLC-MS) at the final timepoint.

TABLE 1

Stability of Example Compounds at pH 7.4

| Example Compound No. | % Recovery after 24 h |
|---|---|
| 1 | 100 |
| 2 | 98 |
| 3 | 99 |
| 4 | 99 |
| 5 | 99 |
| 6 | 98 |
| 7 | 99 |

TABLE 1-continued

| Stability of Example Compounds at pH 7.4 | |
|---|---|
| Example Compound No. | % Recovery after 24 h |
| 8 | 98 |
| 9 | 98 |
| 10 | 100 |
| 11 | 100 |
| 12 | 95 |
| 13 | 92 |
| 14 | 100 |
| 15 | 98 |
| 16 | 100 |
| 17 | 100 |
| 18 | 100 |
| 19 | 95 |
| 20 | 83 |
| 21 | 99 |
| 22 | 100 |
| 23 | 100 |
| 24 | 100 |
| 25 | 100 |
| 26 | 100 |
| 27 | 90 |
| 28 | 95 |
| 29 | 100 |
| 30 | 96 |
| 31 | 99 |
| 32 | 100 |
| 33 | 96 |
| 34 | 96 |
| 35 | 100 |
| 36 | 98 |
| 37 | 84 |
| 38 | 98 |
| 39 | 99 |
| 40 | 97 |
| 41 | 99 |
| 42 | 99 |
| 43 | 98 |

Biological Example B3

Measurement of Release of Parent Compound in Rat Plasma 1 mg of the test compound was dissolved in 0.5 mL acetonitrile/dimethylsulfoxide 9:1. For complete dissolution the HPLC vial was shaken and treated with ultrasound. 20 µl of this solution were added to 1 mL of rat (Li-heparin plasma, Hannover-Janvier rat, RjHan male) with vortexing at a temperature of 37° C. Aliquots (100 µL each) were taken at 0.17, 0.5, 1, 1.5, 2 and 4 hours. Each aliquot was transferred to a vial containing 300 µL of acetonitrile/citric acid buffer pH 3 8:2. These solutions were centrifuged at 5000 rpm for 10 minutes. The supernatant was analysed by HPLC (Method 8) to determine the amount of the test compound. In addition, the reaction mixture was analysed by method 9 (HPLC-MS) at the final timepoint. Both decrease of the prodrug concentration and increase of parent compound concentration were monitored. All data is given as percent area of the prodrug at to.

Parent compound A means 2-Chlor-5-{1-[2-chlor-4-(1,1,1,2,3,3,3-heptafluorpropan-2-yl)-6-(trifluormethoxy)phenyl]-1H-pyrazol-4-yl}-N-(1-cyanocyclopropyl)benzamide (CAS-RN 1771742-44-9).

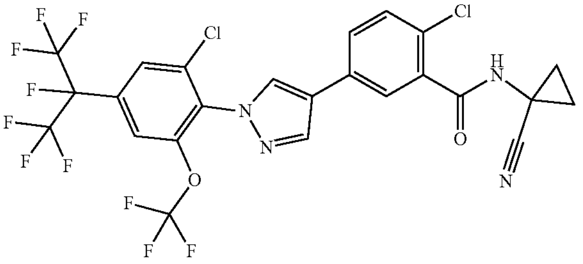 [SMILES: N#CC1(NC(=O)c2cc(-c3cnn(-c4c(Cl)cc(C(F)(C(F)(F)F)C(F)(F)F)cc4OC(F)(F)F)c3)ccc2Cl)CC1]

Parent compound B means 2-chloro-N-(1-cyanocyclopropyl)-5-[2'-methyl-5'-(pentafluoroethyl)-4'-(trifluoromethyl)-2'H-[1,3'-bipyrazol]-4-yl]benzamide (CAS-RN 1621436-41-6)

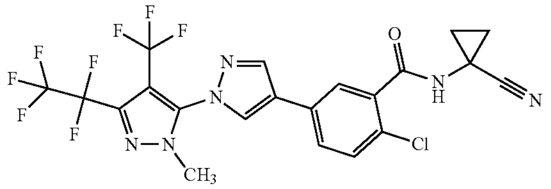 [SMILES: Cn1nc(C(F)(F)C(F)(F)F)c(C(F)(F)F)c1-n1cc(-c2ccc(Cl)c(C(=O)NC3(C#N)CC3)c2)cn1]

TABLE 2

| Degradation of prodrugs in rat plasma: and release of parent drug | | | | | | | | |
|---|---|---|---|---|---|---|---|---|
| Example | % Recovery of prodrug at different time points | | | | | | Parent | % Parent Drug |
| No | 0.17 h | 0.5 h | 1 h | 1.5 h | 2 h | 4 h | Drug | 4 h |
| 1 | 12 | 0 | 0 | 0 | 0 | 0 | A | 74 |
| 2 | 26 | 0 | 0 | 0 | 0 | 0 | A | 73 |
| 3 | 37 | 0 | 0 | 0 | 0 | 0 | A | 104 |
| 4 | 0 | 0 | 0 | 0 | 0 | 0 | A | 99 |
| 5 | 0 | 0 | 0 | 0 | 0 | 0 | A | 102 |
| 6 | 49 | 33 | 22 | 19 | 7 | 0 | A | 78 |
| 7 | 44 | 27 | 12 | 0 | 0 | 0 | A | 99 |
| 8 | 30 | 0 | 0 | 0 | 0 | 0 | A | 110 |
| 9 | 26 | 0 | 0 | 0 | 0 | 0 | A | 99 |
| 10 | 50 | 7 | 0 | 0 | 0 | 0 | A | 76 |
| 11 | 74 | 41 | 18 | 10 | 0 | 0 | A | 101 |
| 12 | 9 | 0 | 0 | 0 | 0 | 0 | A | 107 |
| 14 | 0 | 0 | 0 | 0 | 0 | 0 | A | 99 |
| 15 | 0 | 0 | 0 | 0 | 0 | 0 | A | 102 |
| 16 | 37 | 13 | 0 | 0 | 0 | 0 | A | 92 |
| 17 | 41 | 16 | 6 | 0 | 0 | 0 | A | 100 |
| 18 | 78 | 52 | 33 | 23 | 16 | 5 | A | 95 |
| 19 | 97 | 97 | 96 | 96 | 94 | 95 | A | 10 |
| 21 | 0 | 0 | 0 | 0 | 0 | 0 | B | 114 |
| 22 | 35 | 0 | 0 | 0 | 0 | 0 | B | 74 |
| 23 | 0 | 0 | 0 | 0 | 0 | 0 | B | 102 |
| 24 | 65 | 41 | 22 | 12 | 0 | 0 | B | 100 |
| 25 | 9 | 0 | 0 | 0 | 0 | 0 | B | 72 |
| 26 | 36 | 0 | 0 | 0 | 0 | 0 | B | 101 |
| 28 | 0 | 0 | 0 | 0 | 0 | 0 | B | 99 |
| 29 | 0 | 0 | 0 | 0 | 0 | 0 | B | 103 |
| 30 | 96 | 95 | 93 | 88 | 89 | 70 | B | 29 |
| 31 | 5 | 0 | 0 | 0 | 0 | 0 | B | 101 |
| 32 | 0 | 0 | 0 | 0 | 0 | 0 | B | 100 |
| 33 | 26 | 0 | 0 | 0 | 0 | 0 | B | 102 |
| 34 | 25 | 0 | 0 | 0 | 0 | 0 | B | 64 |
| 35 | 63 | 29 | 10 | 3 | 0 | 0 | A | 99 |
| 36 | 90 | 78 | 67 | 56 | 48 | 28 | A | 75 |
| 38 | 36 | 18 | 0 | 0 | 0 | 0 | B | 104 |
| 39 | 0 | 0 | 0 | 0 | 0 | 0 | B | 81 |
| 40 | 0 | 0 | 0 | 0 | 0 | 0 | B | 99 |
| 41 | 25 | 0 | 0 | 0 | 0 | 0 | A | 107 |
| 42 | 27 | 5 | 0 | 0 | 0 | 0 | B | 84 |
| 43 | 69 | 38 | 20 | 8 | 4 | 0 | B | 101 |

Biological Example B4

Measurement of Release of Parent Compound in Dog Plasma 1 mg of the test compound was dissolved in 0.5 mL acetonitrile/dimethylsulfoxide 9:1. For complete dissolution the HPLC vial was shaken and treated with ultrasound. 20 µl of this solution were added to 1 mL of dog plasma (Beagle) under vortexing at a temperature of 37° C. Aliquots (100 µL each) were taken at 0.17, 0.5, 1, 1.5, 2 and 4 hours. Each aliquot was transferred to a vial containing 300 µL of acetonitrile/citric acid buffer pH 3 80:20. These solutions were centrifuged at 5000 rpm for 10 minutes. The supernatant was analysed by HPLC (Method 8) to determine the amount of the test compound. In addition, the reaction mixture was analysed by method 9 (HPLC-MS) at the final timepoint.

Both decrease of the prodrug concentration and increase of parent compound concentration were monitored. All data is given as percent area of the prodrug at $t_0$.

TABLE 3

Degradation of prodrugs in dog plasma

| Example Compound No. | % Recovery at indicated time points 0.17 h | 0.5 h | 1 h | 1.5 h | 2 h | 4 h | Parent Drug | % Parent Drug 4 h |
|---|---|---|---|---|---|---|---|---|
| 1 | 100 | 100 | 100 | 88 | 82 | 54 | A | 32 |

Biological Example B5

Evaluation of Pharmacokinetics (In Vivo)

To evaluate the pharmacokinetics of test substances in vivo, these test substances are dissolved in appropriate formulation vehicles (ethanol, dimethyl sulfoxide, PEG400, glycerol formal etc.), or mixtures thereof. The test substances are then administered to rats or dogs intravenously, orally or subcutaneously. The intravenous application is performed as bolus. Administered doses range usually between 0.1 to 5 mg/kg, however, doses for subcutaneous and oral administration can exceed this range up to doses of 30 mg/kg. Blood samples are retrieved via a catheter, exsanguination or venous puncture in vials containing appropriate anticoagulants, such as lithium heparinate or potassium EDTA. Plasma is generated from the blood via centrifugation. Blood samples are taken over an appropriate time interval, usually lasting up to 144 h after administration. If necessary, samples from later time points can also be taken. If possible, time points are chosen so that the initial absorption phase, the maximum plasma concentration (Cmax), and exposure within a certain time interval (AUC (0-t)) are described. Furthermore, it is possible to also retrieve organ-, tissue- and urine samples. The quantitative measurement of the test substances in the samples is performed using calibration curves in the respective matrices. The protein content of the samples is precipitated using acetonitrile or methanol. Thereafter, the samples are separated using HPLC in combination with reversed phase chromatography columns. The HPLC system is coupled to a triple quadrupole mass spectrometer via an electrospray interface. The evaluation of the plasma concentration/time profiles are afterwards evaluated using a validated pharmacokinetics evaluation program.

Exposure of parent compound A within a certain time interval displayed as AUC(0-t) in tables 4-6 was used to assess conversion of prodrug to drug and absorption of prodrug compared to parent in vivo, respectively. Comparison of exposures after intravenous administration of parent compound A and prodrugs showed the amount of prodrug which was converted into parent. Comparison of exposures after subcutaneous or oral administration of parent and prodrugs additionally showed altered absorption characteristics of prodrugs compared to parent. Relative bioavailability ($F_{rel}$) was used to describe the exposure of parent after prodrug administration compared to the exposure of parent after direct administration of compound A which was normalised to 100%.

TABLE 4

AUC of parent compound A after intravenous administration of example prodrugs and after intravenous administration of parent compound A

| | Units | Concentration of Parent Compound A | | | | | |
|---|---|---|---|---|---|---|---|
| after admin. of | | Parent Compound A | Example Compound 4 | Example Compound 3 | Example Compound 1 | Parent Compound A | Example Compound 1 |
| Admin Route | | iv bolus | | | | | |
| Species | | Rat | | | | Dog | |
| $AUC(0\text{-}144\ h)_{norm}$ | kg · h/L | 11 | 5.4 | 5.6 | 8.5 | | |
| $AUC(0\text{-}72\ h)_{norm}$ | kg · h/L | | | | | 6.0 | 4.6 |
| after admin. of | | Example 6 | | | | | |
| Admin Route | | iv bolus | Example 8 | Example 17 | Example 18 | | |
| Species | | | | Rat | | | |
| $AUC(0\text{-}144\ h)_{norm}$ | kg · h/L | | | 7.1 | | | |
| $AUC(0\text{-}72\ h)_{norm}$ | kg · h/L | 5.1 | 4.4 | 4.1 | | | |
| after admin. of | | Example 6 | | | | | |

TABLE 5

AUC of parent compound A after subcutaneous administration of example prodrugs and after subcutaneous administration of parent compound A

| | Units | Concentration of Parent Compound A | | | | | |
|---|---|---|---|---|---|---|---|
| after admin. of | | Parent Compound A | Example Compound 4 | Example Compound 3 | Example Compound 1 | Parent Compound A | Example Compound 1 |
| Admin Route | | sc | | | | | |
| Species | | Rat | | | | Dog | |
| AUC(0-144 h)$_{norm}$ | kg · h/L | 1.7 | 6.8 | 3.8 | 6.4 | | |
| AUC(0-384 h)$_{norm}$ | kg · h/L | | | | | 1.0 | 17 |
| $F_{rel}$* | % | 100 | 413 | 233 | 387 | 100 | 1688 |
| after admin. of | | Example 6 | Example 8 | Example 17 | Example 18 | Example 18** | |
| Admin Route | | sc | | | | | |
| Species | | Rat | | | | Dog | |
| AUC(0-144 h)$_{norm}$ | kg · h/L | 9.0 | 2.2 | 3.1 | 5.6 | | |
| AUC(0-384 h)$_{norm}$ | kg · h/L | | | | | 11.8 | |
| $F_{rel}$* | % | 526 | 127 | 184 | 329 | 1178 | |

*$F_{rel}$ calculated based on AUC(0-t)norm

**Test substance was dissolved in triacetin

TABLE 6

AUC of parent compound A after oral administration of example prodrugs and after oral administration of parent compound A

| after admin. of | Units | Concentration of Parent Compound A: Example Compound 1 | Concentration of Parent Compound A: Parent compound A |
|---|---|---|---|
| Admin Route | | po | |
| Species | | Rat | |
| Dose Admin | | 20 | |
| Unit Dose Admin | | mg/kg | |
| AUC(0-24)$_{norm}$ | kg · h/L | 1.4 | 0.37 |
| F* | % | 54 | 14 |

*F calculated based on AUC(0-24)$_{norm}$

Biological Example B6

Measurement of the Antiparasitic Activity after Administration of a Prodrug to Rats Compounds were dissolved in the appropriate volume of glycerol formal (p.a.) just before application to the animals (dose volume was adjusted to 0.03 mL/kg bodyweight). 5 rats per group were either injected intraperitoneally or subcutaneously.

Rats were infested with 30 *Dermacentor variabilis* nymphs on study days −2, 7, 14, 21, 28, 35 and 30 adult *Ctenocephalides* fleas on study days −1, 8, 15, 22, 29, 36.

Parasite counts were performed on study days 2, 9, 16, 23, 30, 37.

Percent efficacy was calculated as arithmetic mean parasite numbers as life attached tick numbers and live flea numbers of the respective study group in comparison to parasite counts on a placebo-treated control group. Infestation of groups with less than 75% efficacy on two consecutive counting occasions will terminated for the respective parasite.

Both SC prodrug treatments (example 1 and example 4) are superior in their flea and tick efficacy on rats over the parent drug also injected subcutaneously.

TABLE 7

In-vivo Efficacy of parent compound A and prodrug examples formulations applied i.p. or sc in rats

| Example | Dose mg/kg] | Applicat. type | Parasite | SD2 | SD9 | SD16 | SD23 | SD30 | SD37 | SD42 |
|---|---|---|---|---|---|---|---|---|---|---|
| Parent Compound A | 10 | ip | CF A | 84 | 68 | 71 | na | na | na | na |
| | | | DV N | 96 | 87 | 83 | 93 | 53 | 32 | na |
| | | sc | CF A | 53 | 44 | na | na | na | na | na |
| | | | DV N | 72 | 61 | na | na | na | na | na |
| Example Compound 1 | 13.33 | sc | CF A | 100 | 100 | 100 | 99 | 81 | 75 | 79 |
| | | | DV N | 99 | 100 | 100 | 100 | 77 | 90 | 81 |
| Example Compound 2 | 13.98 | sc | CF A | 99 | 93 | 99 | 97 | 66 | 76 | 69 |
| | | | DV N | 98 | 98 | 96 | 99 | 99 | 97 | 82 |
| Example 3 | 13.36 | sc | CF A | 97 | 97 | 93 | 86 | 76 | 72 | na |
| | | | DV N | 99 | 99 | 100 | 77 | 57 | 49 | na |
| Example 4 | 13.98 | sc | CF A | 99 | 93 | 99 | 97 | 66 | 76 | na |
| | | | DV N | 98 | 98 | 96 | 99 | 99 | 97 | na |

TABLE 7-continued

| In-vivo Efficacy of parent compound A and prodrug examples formulations applied i.p. or sc in rats | | | | | | | | | | |
|---|---|---|---|---|---|---|---|---|---|---|
| Example | Dose mg/kg] | Applicat. type | Parasite | SD2 | SD9 | SD16 | SD23 | SD30 | SD37 | SD42 |
| Example 6 | 13.95 | sc | CF A | 100 | 100 | 94 | 73 | 59 | 100 | na |
| | | | DV N | 100 | 100 | 100 | 78 | 58 | 31 | na |
| Example 7 | 13.98 | sc | CF A | 100 | 98 | 99 | 91 | 86 | 66 | na |
| | | | DV N | 99 | 100 | 96 | 98 | 89 | 46 | na |
| Example 18 | 13.08 | sc | CF A | 100 | 97 | 94 | 82 | 76 | 75 | na |
| | | | DV N | 100 | 100 | 100 | 82 | 74 | 47 | na |
| Example 35 | 13.65 | sc | CF A | 100 | 100 | 98 | 87 | 70 | 49 | na |
| | | | DV N | 100 | 99 | 80 | 97 | 80 | 53 | na |
| Example 36 | 13.25 | sc | CF A | no data | 100 | 93 | 99 | 80 | 67 | na |
| | | | DV N | no data | 96 | 88 | 99 | 89 | 68 | na |

CF = Ctenocphalides felis;
DV = Dermacentor variabilis;
A = adult; N = nymph

Biological Example B7

Measurement of the Antiparasitic Activity after Administration of a Prodrug to Dogs Compounds were dissolved in the appropriate volume of glycerol formal (p.a.) just before application to the animals (dose volume was adjusted to 0.1 ml/kg bodyweight). Dogs were were injected intravenously respective subcutaneously (see table 8 for details).

Dogs were infested with ectoparasites according to table on study 1 day prior to counting for fleas, 2 days prior to counting for RS, IR, DV ticks and 3 days prior to counting for AA ticks. For this purpose, dogs were placed in an individually labeled box with grid windows. The ticks were released onto the back of the dogs and were allowed to disperse and move into the hair without disturbance. The dog remained in the box for approximately 120 minutes with the lid closed and the light switched off in the room. For flea infestations, flea containers were opened in the animal's cage and fleas were applied on the dog's back between the shoulders.

Parasite counts were performed as indicated in Table 8. Tick counts including removal of *I. ricinus, R. sanguineus* and *D. variabilis* were conducted 48(±4) hours after the infestation. Tick counts including removal of *A. americanum* were conducted 72(±4) hours after the infestation. Flea counts were conducted 24(±4) hours after the infestation.

On each parasite assessment day percent efficacy was calculated as arithmetic mean parasite numbers as life attached and live free tick numbers and live flea numbers of the respective study group in comparison to parasite counts on a placebo non-treated control group.

Based on the results of these infestations a five months efficacy of the prodrug "1" against *D. variabilis* as least sensitive species could be reached.

TABLE 8

| In-vivo Efficacy of parent and prodrug formulations applied iv or sc in dogs | | | | | | | | | | |
|---|---|---|---|---|---|---|---|---|---|---|
| Com- | treat- | Dose | | Para- | % Efficacy in study month | | | | | |
| pound | ment | [mg/kg] | Study | site | 1 | 2 | 3 | 4 | 5 | 6 |
| A | iv | 2 × 5 | 1 | CF | 100 | 100 | 100 | 100 | 100 | 100 |
| A | iv | 2 × 5 | 1 | DV | 98 | 99 | 100 | 95 | 98 | 84 |

TABLE 8-continued

| In-vivo Efficacy of parent and prodrug formulations applied iv or sc in dogs | | | | | | | | | | |
|---|---|---|---|---|---|---|---|---|---|---|
| Com- | treat- | Dose | | Para- | % Efficacy in study month | | | | | |
| pound | ment | [mg/kg] | Study | site | 1 | 2 | 3 | 4 | 5 | 6 |
| A | iv | 2 × 5 | 1 | IR | 100 | 100 | 100 | 100 | 98 | 98 |
| A | iv | 2 × 5 | 1 | RS | 100 | 100 | 100 | 100 | 100 | 99 |
| A | iv | 2 × 5 | 2 | AA | 100 | 99 | 99 | 99 | 95 | 98 |
| A | sc | 5 | 3 | DV | | | | | | 19 |
| A | sc | 5 | 3 | IR | | | | | | 3 |
| A | sc | 5 | 3 | RS | | | | | | 50 |
| A | sc | 5 | 3 | AA | | | | | | 90 |
| 1 | sc | 13.33 (=10 parent) | 4 | DV | | | | 96 | 100 | 77 |

The invention claimed is:

1. A compound of formula (I)

(I)

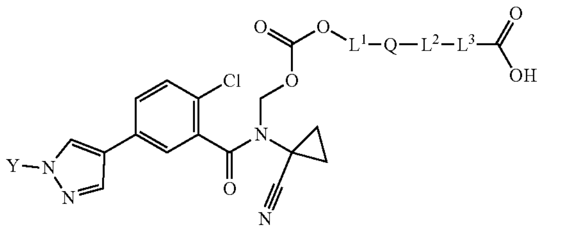

wherein

Q is O or absent;

$L^1$ is linear $C_2$-$C_4$ alkanediyl, which is optionally substituted with one or more groups independently selected from the group consisting of halogen, $C_1$-$C_4$ alkyl and $C_3$-$C_6$ cycloalkyl, wherein two $C_1$-$C_4$-alkyl substituents may form a ring together with the carbon atom to which they are bonded; or is a moiety $(CH_2)_n$—X—$(CH_2)_m$ wherein n and m are independently 0, 1 or 2 and X is $C_3$-$C_7$-cycloalkanediyl, which is optionally substituted with $C_1$-$C_4$ alkyl; or $L^1$ is absent;

with the proviso that in the case of $L^1$ being absent, Q is also absent;

$L^2$ is C═O or absent, $L^3$ is linear $C_1$-$C_4$ alkanediyl, which is optionally substituted with one or more groups independently selected from the group consisting of $C_1$-$C_4$ alkyl, $C_3$-$C_6$ cycloalkyl and halogen, wherein two $C_1$-$C_4$-alkyl substituents may form a ring together with the carbon atom to which they are bonded; or is a group $(CH_2)_n$—(CH═CH)—$CH_2)_m$, which is optionally substituted with up to 2 groups independently selected from the group consisting of $C_1$-$C_4$ alkyl, $C_3$-$C_5$ cycloalkyl and halogen, wherein n and m are independently 0, 1 or 2; or is $C_3$-$C_7$-cycloalkanediyl, which is optionally substituted with one or more groups independently selected from the group consisting of $C_1$-$C_4$-alkyl and halogen;

Y is selected from $T^1$ $T^1$

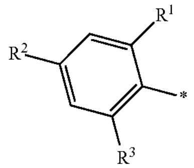

wherein $R^1$, $R^2$ and $R^3$ are each independently selected from the group consisting of hydrogen, halogen, cyano, nitro, linear or branched $C_1$-$C_6$-alkyl, $C_3$-$C_6$-cycloalkyl, $C_1$-$C_6$-alkoxy, linear or branched halogen-substituted $C_1$-$C_6$-alkyl, halogen-substituted $C_1$-$C_6$-alkoxy, halogen substituted $C_3$-$C_6$-cycloalkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, N—$C_1$-$C_3$-alkoxy-$C_1$-$C_4$-alkylamino and 1-pyrrolidinyl or $T^2$ $T^2$

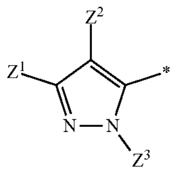

wherein $Z^1$ and $Z^2$ are each independently selected from the group consisting of hydrogen, halogen, cyano, nitro, linear or branched $C_1$-$C_6$-alkyl, $C_3$-$C_6$-cycloalkyl, $C_1$-$C_6$-alkoxy, $C_1$-$C_6$-alkylcarbonyl, halogen-substituted linear or branched $C_1$-$C_6$-alkyl, halogen-substituted $C_1$-$C_6$-alkoxy, halogen substituted $C_3$-$C_6$-cycloalkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, N—$C_1$-$C_3$-alkoxy-$C_1$-$C_4$-alkylamino and 1-pyrrolidinyl; and $Z^3$ represents hydrogen or linear $C_1$-$C_6$-alkyl, $C_3$-$C_6$-cycloalkyl, $C_2$-$C_6$-alkenyl, $C_2$-$C_6$-alkynyl, aryl or heteroaryl, which may independently of one another be substituted with 1 to 5 substituents selected from the group consisting of hydroxy, halogen, cyano, nitro, amino, $C_1$-$C_3$-alkyl, $C_1$-$C_3$-alkoxy, hydroxycarbonyl, alkoxycarbonyl, alkylcarbamoyl, cycloalkylcarbamoyl and phenyl or a salt thereof.

2. The compound according to claim 1, wherein

Q is O;

$L^2$ is C═O;

$L^3$ is a group $(CH_2)_n$—(CH═CH)—$CH_2)_m$, which is optionally substituted with up to 2 groups independently selected from the group consisting of $C_1$-$C_4$ alkyl, $C_3$-$C_5$ cycloalkyl and halogen, wherein n and m are independently 0, 1 or 2;

or a salt thereof.

3. The according to claim 1, wherein

Q is O;

$L^2$ is C═O;

$L^3$ is a group $(CH_2)_n$—(CH═CH)—$CH_2)_m$, wherein n and m are 0;

or a salt thereof.

4. The compound according to claim 1, wherein

Q is O $L^2$ is C═O $L^3$ is linear $C_1$-$C_4$ alkanediyl, which is optionally substituted with one or more groups independently selected from the group consisting of $C_1$-$C_4$ alkyl, $C_3$-$C_6$ cycloalkyl and halogen, wherein two $C_1$-$C_4$-alkyl substituents may form a ring together with the carbon atom to which they are bonded; and or a salt thereof.

5. The compound according to claim 1, wherein

Q is O;

$L^2$ is absent;

$L^3$ is linear $C_1$-$C_4$ alkanediyl, which is optionally substituted with one or more groups independently selected from the group consisting of $C_1$-$C_4$ alkyl, $C_3$-$C_6$ cycloalkyl and halogen, wherein two $C_1$-$C_4$-alkyl substituents may form a ring together with the carbon atom to which they are bonded; and or a salt thereof.

6. The compound according to claim 1, wherein $L^1$, $L^2$ and Q are absent;

or a salt thereof.

7. The compound according to claim 1, wherein one or more of the following conditions apply Q is O;

and/or $L^1$ is linear $C_2$-$C_4$ alkanediyl, which is optionally substituted with one or more $C_1$-$C_4$ alkyl groups, wherein two $C_1$-$C_4$-alkyl substituents may form a ring together with the carbon atom to which they are bonded and/or $L^2$ is C═O and/or $L^3$ is a group $(CH_2)_n$—(CH═CH)—$CH_2)_m$, which is optionally substituted with up to 2 groups independently selected from the group consisting of $C_1$-$C_4$ alkyl, $C_3$-$C_5$ cycloalkyl and halogen, wherein n and m are independently 0, 1 or 2 or a salt thereof.

8. The compound according to claim 1, wherein

Y is selected from $T^1$ $T^1$

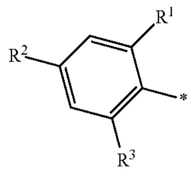

wherein $R^1$, $R^2$ and $R^3$ are each independently selected from the group consisting of hydrogen, halogen, linear or branched $C_1$-$C_3$-alkyl, $C_3$-$C_6$-cycloalkyl, $C_1$-$C_3$-alkoxy, linear or branched halogen-substituted $C_1$-$C_3$-alkyl, halogen-substituted $C_1$-$C_3$-alkoxy, halogen substituted $C_3$-$C_6$-cycloalkyl, and 1-pyrrolidinyl, or $T^2$ $T^2$

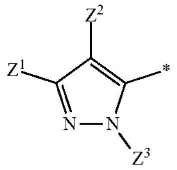

wherein $Z^1$ represents linear or branched $C_1$-$C_3$-alkyl, $C_3$-$C_6$-cycloalkyl, $C_1$-$C_3$-alkoxy, which may independently of one another be substituted with 1 to 5 substituents selected from the group consisting of hydroxy, halogen, cyano, nitro, $C_1$-$C_3$-alkyl, and $C_1$-$C_3$-alkoxy, $Z^2$ represents halogen, cyano, nitro, amino, or linear or branched $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, which may independently of one another be substituted with 1 to 5 substituents selected from the group consisting of hydroxy, halogen, cyano, nitro, $C_1$-$C_3$-alkyl, and $C_1$-$C_3$-alkoxy;

and $Z^3$ represents hydrogen or linear or branched $C_1$-$C_6$-alkyl, $C_3$-$C_6$-cycloalkyl, $C_2$-$C_6$-alkenyl, $C_2$-$C_6$-alkynyl, aryl or hetaryl, which may independently of one another be substituted with 1 to 5 substituents selected from the group consisting of hydroxy, halogen, cyano, nitro, $C_1$-$C_3$-alkyl, and $C_1$-$C_3$-alkoxy;

or a salt thereof.

9. The compound according to claim 1, wherein

Y is selected from $T^1$ $T^1$

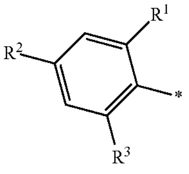

wherein $R^1$ is halogen;

$R^2$ is linear or branched $C_1$-$C_3$-alkyl substituted with 1 to 7 halogen; and $R^3$ is $C_1$-$C_3$-alkoxy substituted with 1 to 3 halogen;

or $T^2$ $T^2$

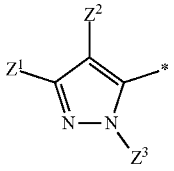

wherein $Z^1$ represents linear or branched $C_1$-$C_3$-alkyl or $C_3$-$C_6$-cycloalkyl, substituted with 1 to halogen substituents;

$Z^2$ represents linear or branched $C_1$-$C_3$-alkyl substituted with 1 to 3 halogen substituents, or $Z^2$ represents nitro, methylsulphanyl, methylsulphinyl, methylsulphonyl, fluorine, chlorine, bromine, iodine; and $Z^3$ represents hydrogen or linear or branched $C_1$-$C_6$-alkyl, linear or branched $C_1$-$C_6$-alkyl;

or a salt thereof.

10. The compound according to claim 1, wherein T1 is represented by one of the following groups T1-1, T1-2 or T1-3:

T1-1

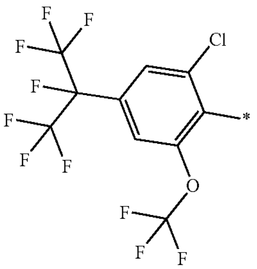

T1-2

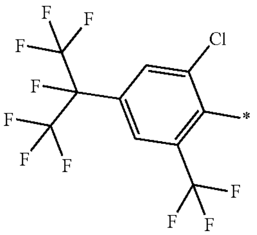

T2-1

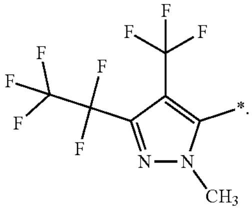

11. A pharmaceutical composition comprising the compound according to claim 1.

12. The pharmaceutical composition according to claim 11, further comprising at least one component selected from the group consisting of pharmaceutically acceptable auxiliaries, excipients, solvents and additional pharmaceutically active agents.

13. The pharmaceutical composition according to claim 12 which is formulated for use in subcutaneous or oral application.

14. A method for controlling one or more parasites on animals comprising administering to the animals the compound of claim 1 or a pharmaceutical composition thereof.

15. A process for preparing the compound according to claim 1 comprising reacting a compound (A)

(A)

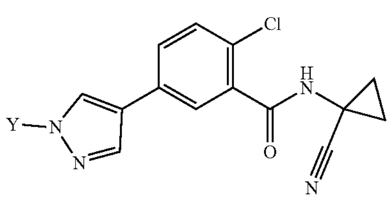

with a group (B)

(B)

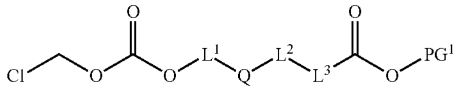

wherein $PG^1$ represents a protecting group or hydrogen to form the compounds according to formula (I), and wherein in cases wherein $PG^1$ is not hydrogen, deprotection is carried out to form the compounds (I);

wherein the process further comprises preparing the group (B) by i) reacting a compound (IIa) with a compound (IIIa) to form compound (Va), wherein $PG^2$ is a protecting group or hydrogen, and wherein in cases wherein $PG^2$ is not hydrogen (Va) is obtained by selectively cleaving $PG^2$:

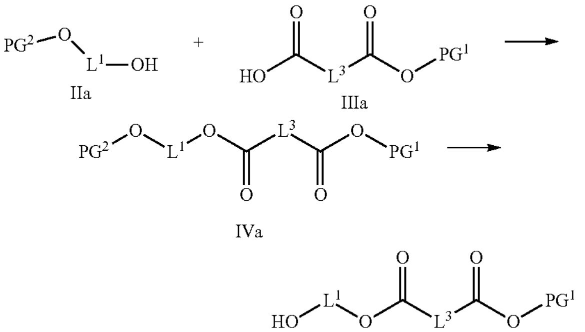

IIa IIIa IVa Va wherein $PG^1$ represents a protecting group or hydrogen; or ii) reacting a compound (VI) with compound (IIIb) to form compound (Vb), wherein $PG^2$ is a protecting group or hydrogen, and wherein in cases wherein $PG^2$ is not hydrogen (Vb) is obtained by selectively cleaving $PG^2$:

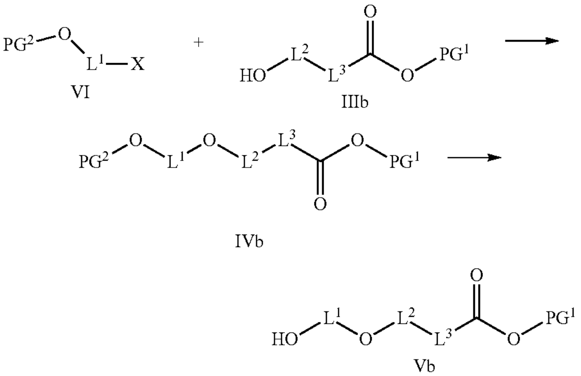

VI IIIb IVb Vb and wherein $PG^1$ represents a protecting group or hydrogen.

16. An intermediate compound according to formula (B), (B)

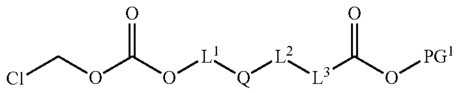

(B)

wherein

Q is O;

$L^2$ is C=O;

$L^1$ is linear $C_2$-$C_4$ alkanediyl, which is optionally substituted with one or more groups independently selected from the group consisting of halogen, $C_1$-$C_4$ alkyl and $C_3$-$C_6$ cycloalkyl, wherein two $C_1$-$C_4$-alkyl substituents may form a ring together with the carbon atom to which they are bonded; or is a moiety $(CH_2)_n$—X—$(CH_2)_m$ wherein n and m are independently 0, 1 or 2 and X is $C_3$-$C_7$-cycloalkanediyl, which is optionally substituted with $C_1$-$C_4$ alkyl; or $L^1$ is absent;

with the proviso that in the case of $L^1$ being absent, Q is also absent;

$L^3$ is linear $C_1$-$C_4$ alkanediyl, which is optionally substituted with one or more groups independently selected from the group consisting of $C_1$-$C_4$ alkyl, $C_3$-$C_6$ cycloalkyl and halogen, wherein two $C_1$-$C_4$-alkyl substituents may form a ring together with the carbon atom to which they are bonded; or is a group $(CH_2)_n$—(CH=CH)—$CH_2)_m$, which is optionally substituted with up to 2 groups independently selected from the group consisting of $C_1$-$C_4$ alkyl, $C_3$-$C_5$ cycloalkyl and halogen, wherein n and m are independently 0, 1 or 2; or is $C_3$-$C_7$-cycloalkanediyl, which is optionally substituted with one or more groups independently selected from the group consisting of $C_1$-$C_4$-alkyl and halogen;

PG[1] represents a tert-butyl group or according to formula (C), (C)

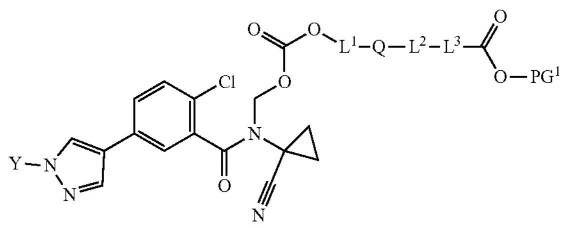

wherein

Q is O or absent;

$L^1$ is linear $C_2$-$C_4$ alkanediyl, which is optionally substituted with one or more groups independently selected from the group consisting of halogen, $C_1$-$C_4$ alkyl and $C_3$-$C_6$ cycloalkyl, wherein two $C_1$-$C_4$-alkyl substituents may form a ring together with the carbon atom to which they are bonded; or is a moiety $(CH_2)_n$—X—$(CH_2)_m$ wherein n and m are independently 0, 1 or 2 and X is $C_3$-$C_7$-cycloalkanediyl, which is optionally substituted with $C_1$-$C_4$ alkyl; or $L^1$ is absent;

with the proviso that in the case of $L^1$ being absent, Q is also absent;

$L^2$ is C═O or absent, $L^3$ is linear $C_1$-$C_4$ alkanediyl, which is optionally substituted with one or more groups independently selected from the group consisting of $C_1$-$C_4$ alkyl, $C_3$-$C_6$ cycloalkyl and halogen, wherein two $C_1$-$C_4$-alkyl substituents may form a ring together with the carbon atom to which they are bonded; or is a group $(CH_2)_n$—(CH═CH)—$CH_2)_m$, which is optionally substituted with up to 2 groups independently selected from the group consisting of $C_1$-$C_4$ alkyl, $C_3$-$C_5$ cycloalkyl and halogen, wherein n and m are independently 0, 1 or 2; or is $C_3$-$C_7$-cycloalkanediyl, which is optionally substituted with one or more groups independently selected from the group consisting of $C_1$-$C_4$-alkyl and halogen;

Y is selected from $T^1$ $T^1$

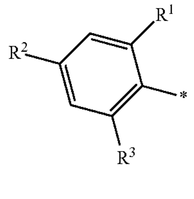

wherein $R^1$, $R^2$ and $R^3$ are each independently selected from the group consisting of hydrogen, halogen, cyano, nitro, linear or branched $C_1$-$C_6$-alkyl, $C_3$-$C_6$-cycloalkyl, $C_1$-$C_6$-alkoxy, linear or branched halogen-substituted $C_1$-$C_6$-alkyl, halogen-substituted $C_1$-$C_6$-alkoxy, halogen substituted $C_3$-$C_6$-cycloalkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, N—$C_1$-$C_3$-alkoxy-$C_1$-$C_4$-alkylamino and 1-pyrrolidinyl or $T^2$ $T^2$

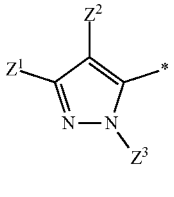

wherein $Z^1$ and $Z^2$ are each independently selected from the group consisting of hydrogen, halogen, cyano, nitro, linear or branched $C_1$-$C_6$-alkyl, $C_3$-$C_6$-cycloalkyl, $C_1$-$C_6$-alkoxy, $C_1$-$C_6$-alkylcarbonyl, halogen-substituted linear or branched $C_1$-$C_6$-alkyl, halogen-substituted $C_1$-$C_6$-alkoxy, halogen substituted $C_3$-$C_6$-cycloalkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino, N—$C_1$-$C_3$-alkoxy-$C_1$-$C_4$-alkylamino and 1-pyrrolidinyl; and $Z^3$ represents hydrogen or linear $C_1$-$C_6$-alkyl, $C_3$-$C_6$-cycloalkyl, $C_2$-$C_6$-alkenyl, $C_2$-$C_6$-alkynyl, aryl or hetaryl, which may independently of one another be substituted with 1 to 5 substituents selected from the group consisting of hydroxy, halogen, cyano, nitro, amino, $C_1$-$C_3$-alkyl, $C_1$-$C_3$-alkoxy, hydroxycarbonyl, alkoxycarbonyl, alkylcarbamoyl, cycloalkylcarbamoyl and phenyl and wherein PG[1] represents a tert-butyl group.

17. The compound according to claim 7, wherein n and m are 0.

18. The compound according to claim 8, wherein $R^1$, $R^2$ and $R^3$ are each independently selected from the group consisting of halogen, linear or branched halogen-substituted $C_1$-$C_3$-alkyl, and halogen-substituted $C_1$-$C_3$-alkoxy;

$Z^1$ represents linear or branched $C_1$-$C_3$-alkyl or $C_3$-$C_6$-cycloalkyl, which may independently of one another be substituted with 1 to 5 halogen substituents;

$Z^2$ represents linear or branched $C_1$-$C_3$-alkyl, which may be substituted with 1 to 5 halogen substituents, optionally with 1 to 3 halogen substituents; and/or $Z^3$ represents hydrogen or linear or branched $C_1$-$C_6$-alkyl which may be substituted with 1 to 5 substituents selected from the group consisting of hydroxy, halogen, $C_1$-$C_3$-alkyl, and $C_1$-$C_3$-alkoxy.

19. The compound according to claim 18, wherein $Z^2$ represents trifluormethyl, or $Z^2$ represents nitro, methylsulphanyl, methylsulphinyl, methylsulphonyl, fluorine, chlorine, bromine, or iodine.

20. The compound according to claim 9, wherein Y is $T^1$ $T^1$

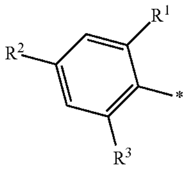

wherein $R^1$ is selected from the group consisting of fluorine, bromine or chlorine;

$R^2$ is linear or branched $C_1$-$C_3$-alkyl substituted with 1 to 7 fluorine; and/or $R^3$ is $C_1$-$C_3$-alkoxy substituted with 1 to 3 fluorine.

21. The compound according to claim 19, wherein $R^1$ is chlorine;

$R^2$ is $CF_3$, $C_2F_5$ or $C_3F_7$; and/or $R^3$ is $OCF_3$, $O_2F_5$ or $OC_3F_7$.

22. The compound according to claim 9, wherein Y is $T^2$ $T^2$

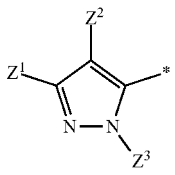

wherein $Z^1$ represents trifluoromethyl, 1-chlorocyclopropyl, 1-fluorocyclopropyl or pentafluoroethyl;

$Z^2$ represents nitro, methylsulphanyl, methylsulphinyl, methylsulphonyl, fluorine, chlorine, bromine, iodine, or linear or branched $C_1$-$C_3$-alkyl substituted with 1 to 3 fluorine;

and/or $Z^3$ represents hydrogen, methyl, ethyl, or n-propyl.

23. The compound according to claim 21, wherein $Z^1$ represents trifluoromethyl or pentafluoroethyl; and/or $Z^2$ represents trifluoromethyl.

24. The product according to claim 14, wherein the parasites are insects or arachnids on companion animals.

* * * * *